United States Patent
Zetterberg et al.

(10) Patent No.: US 12,410,207 B2
(45) Date of Patent: Sep. 9, 2025

(54) GALACTOSIDE INHIBITOR OF GALECTINS

(71) Applicant: GALECTO BIOTECH AB, Copenhagen (DK)

(72) Inventors: Fredrik Zetterberg, Askim (SE); Kristoffer Peterson, Lund (SE)

(73) Assignee: GALECTO BIOTECH AB, Copenhagen (DK)

( * ) Notice: Subject to any disclaimer, the term of this patent is extended or adjusted under 35 U.S.C. 154(b) by 757 days.

(21) Appl. No.: 17/624,663

(22) PCT Filed: Jul. 3, 2020

(86) PCT No.: PCT/EP2020/068831
§ 371 (c)(1),
(2) Date: Jan. 4, 2022

(87) PCT Pub. No.: WO2021/004538
PCT Pub. Date: Jan. 7, 2021

(65) Prior Publication Data
US 2022/0281909 A1    Sep. 8, 2022

(30) Foreign Application Priority Data

Jul. 3, 2019 (EP) .................................. 19184150
Feb. 24, 2020 (EP) .................................. 20159106
Apr. 6, 2020 (EP) .................................. 20168148

(51) Int. Cl.
C07H 19/052    (2006.01)
C07H 19/24    (2006.01)

(52) U.S. Cl.
CPC .......... C07H 19/052 (2013.01); C07H 19/24 (2013.01)

(58) Field of Classification Search
None
See application file for complete search history.

(56) References Cited

FOREIGN PATENT DOCUMENTS

WO    2016120403 A1    8/2016
WO    WO-2018011094 A1 *    1/2018    ......... A61K 31/7056

OTHER PUBLICATIONS

International Search Report issued on Oct. 21, 2020 in corresponding International Application No. PCT/EP2020/068831; 5 pages.
Salameh B A et al., "Thiodigalactoside Derivatives as High Affinity Galectin-3 Inhibitors", Bioorganic & Medical Chemistry, vol. 18, No. 14, Jul. 15, 2020, pp. 5367-5378, XP027263501.

* cited by examiner

Primary Examiner — Traviss C McIntosh, III
(74) Attorney, Agent, or Firm — Maier & Maier, PLLC

(57) ABSTRACT

A D-galactopyranose compound of formula (1)

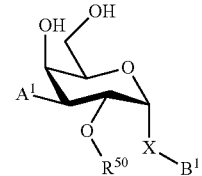

wherein
the pyranose ring is α-D-galactopyranose, and these compounds are high affinity galectin-3 inhibitors. Also, pharmaceutical compositions including these compounds. Further, a method for treatment of a disorder relating to the binding of a galectin-3 to a ligand, such as inflammation, in a mammal, such as a human, wherein a therapeutically effective amount of at least one of these compounds is administered to a mammal in need of the treatment.

16 Claims, 1 Drawing Sheet

GALACTOSIDE INHIBITOR OF GALECTINS

FIELD

The present invention relates to novel compounds, the use of said compounds as medicament and for the manufacture of a medicament for the treatment of inter alia cancers; fibrosis; scarring; keloid formation; aberrant scar formation; surgical adhesions; pathological angiogenesis; eye diseases; HIV-1 diseases; inflammation or transplant rejection in mammals. Furthermore, some compounds have potential to pass the blood brain barrier and has a potential for being treatment for CNS conditions. In addition some compounds have suitability as oral drugs. The invention also relates to pharmaceutical compositions comprising said novel compounds.

BACKGROUND

Galectins are proteins with a characteristic carbohydrate recognition domain (CRD) (Leffler et al., 2004). This is a tightly folded β-sandwich of about 130 amino acids (about 15 kDa) with the two defining features 1) a β-galactose binding site and 2) sufficient similarity in a sequence motif of about seven amino acids, most of which (about six residues) make up the β-galactose binding site. However, sites adjacent to the β-galactose site are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004).

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Lepur et al., 2012). These were the first discovered galectins and are abundant in many tissues.

There are now over 5700 publications on galectins in PubMed, with most, as mentioned above, about galectins-1 (>1400) and -3 (>2800). Strong evidence suggests roles for galectins in e.g. inflammation and cancer, and development (Blidner et al., 2015, Ebrahim et al., 2014).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004; Arthur et al., 2015). They can also function in all these compartments; for galectin-3, solid evidence published in well respected journals support roles in RNA splicing in the nucleus, inhibition of apoptosis in the cytosol, accumulation around disrupted vesicles, association with microtubule organizing center of cilia, and a variety of extracellular effects on cell signaling and adhesion (Elola et al. 2015, Funasaka et al., 2014, Aits et al., 2015, Clare et al., 2014). Other galectins also may act in the cytosol by enhancing apoptosis and regulating the cell cycle and differentiation in certain cells. Most galectins act also extracellularly by cross-linking glycoproteins (e.g. laminin, integrins, and IgE receptors) possibly forming supramolecular ordered arrays (Elola et al., 2015) and may thereby modulate cell adhesion and induce intracellular signals. Related to this, recent years have seen the emergence of a molecular mechanism of these galectin functions involving a formation of microdomains (lattices) within membranes, (Elola et al., 2015) which in turn affects intracellular trafficking and cell surface presentation of glycoprotein receptors. This has been documented in cell culture, in null mutant mice, and animals treated with galectin or galectin inhibitors. (Johannes, L.; Jacob, R.; Leffler, H. Galectins at a Glance. *J. Cell. Sci.* 2018, 131 (9), jcs208884.).

Potential Therapeutic Use of Galectin-3 Inhibitors

Galectin-3 has been implicated in diverse phenomena and, hence, inhibitors may have multiple uses (Blanchard et al., 2014). It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation

A pro-inflammatory role of galectin-3 is indicated by its induction in cells at inflammatory sites, a variety of effects on immune cells (e.g. oxidative burst in neutrophils and chemotaxis in monocytes), and decrease of the inflammatory response, mainly in neutrophils and macrophages, in null mutant mice (Blidner et al., 2015, Arthur et al., 2015). Importantly, recent studies have identified galectin-3 as a key rate-limiting factor in macrophage M2 differentiation and myofibroblast activation, which influences the development of fibrosis (Mackinnon et al., 2008; Mackinnon et al., 2012, Li et al., 2014).

Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of certain receptors (Elola et al., 2015), such as the TGF-β receptor (MacKinnon, 2012), which in turn regulates alternative macrophage differentiation into M2 macrophages and myofibroblast activation.

Hence, as galectin-3 is a good candidate for being an endogenous enhancer of TGF-β signaling and alternative macrophage differentiation and myofibroblast activation, galectin-3 inhibitors may be very useful in treating fibrosis and adverse tissue remodeling.

Treatment of Cancer

A large number of immunohistochemical studies show changed expression of certain galectins in cancer (Thijssen et al, 2015; Ebrahim et al., 2014) and for example galectin-3 is now an established histochemical marker of thyroid cancer. The direct evidence for a role of galectin-3 in cancer comes mainly from mouse models. In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. Further, recent evidence have shown that galectin-3 plays a critical role in the tumor microenvironment (Ruvolo, 2015). Galectin-3 is also believed to regulate the interaction between the tumor cells and immune cells, such as T-lymphocytes (T-cells), and inhibition of galectin-3 has been shown to restore T-cell activity (Demotte et al. 2010, Kouo et al. 2015, Menero et al. 2015). From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Blanchard et al., 2015).

Also other galectins are frequently over-expressed in low differentiated cancer cells, or induced in specific cancer types (Thijssen et al, 2015; Ebrahim et al. 2014). Galectin-1 induces apoptosis in activated T-cells and has a remarkable immunosuppressive effect on autoimmune disease in vivo (Blidner et al., 2015). Therefore, the over-expression of these galectins in cancers might help the tumor to defend itself against the T-cell response raised by the host.

Null mutant mice for galectins-1, -3, -7 and -9 have been established and are healthy and reproduce apparently normally in animal house conditions. However, further studies have revealed subtle phenotypes under different type of challenge, mainly in function of immune cells (Blidner et al., 2015), but also other cells types (Viguier et al., 2014). The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Treatment of Angiogenesis

Vascular endothelial growth factors (VEGFs) signaling through VEGF receptor-2 (VEGFR-2) is the primary angiogenic pathway. Studies have been published demonstrating that both galectin-1 (Gal-1) and galectin-3 (Gal-3) are important modulators for VEGF/VEGFR-2 signaling pathway (Croci et al., 2014). It has also been published that a galectin inhibitor, TDX, is expected have efficacy against pathological angiogenesis. (Chen 2012)

Known Inhibitors

Natural Ligands

Solid phase binding assays and inhibition assays have identified a number of saccharides and glycoconjugates with the ability to bind galectins (reviewed by Leffler, 2001 and Leffler et al., 2004). All galectins bind lactose with a $K_d$ of 0.5-1 mM. The affinity of D-galactose is 50-100 times lower. N-Acetyllactosamine and related disaccharides bind about as well as lactose, but for certain galectins, they can bind either worse or up to 10 times better. The best small saccharide ligands for galectin-3 were those carrying blood group A-determinants attached to lactose or LacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1 (Leffler and Barondes, 1986). A modified plant pectin polysaccharide has been reported to bind galectin-3 (Pienta et al., 1995).

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. A chemically modified form of citrus pectin (Platt and Raz, 1992) that inhibits galectin-3 shows anti-tumor activity in vivo (Pienta et al., 1995; Nangia-Makker et al., 2002).

Cluster molecules having up to four lactose moieties showed a strong multivalency effect when binding to galectin-3, but not to galectin-1 and galectin-5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules.

Thiodigalactoside is known to be a synthetic and hydrolytically stable, yet polar inhibitor, approximately as efficient as N-acetyllactosamine (Leffler and Barondes, 1986). N-Acetyllactosamine derivatives carrying aromatic amides or substituted benzyl ethers at C-3' have been demonstrated to be highly efficient inhibitors of galectin-3, with unprecedented $IC_{50}$ values as low as 4.8 µM, which is a 20-fold improvement in comparison with the natural N-acetyllactosamine disaccharide (Sörme et al., 2002; Sörme et al., 2003b). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed, (Cumpstey et al., 2005b; Cumpstey et al., 2008; Salameh et al., 2010; WO/2005/113569 and US2007185041; WO/2005/113568, U.S. Pat. No. 7,638,623 B2, T. Delaine, 2016, ChemBioChem 10.1002/cbic.201600285)) which lack 0-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach at 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamido- and ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

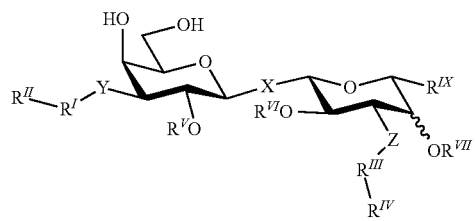

as described in WO/2005/113568, and

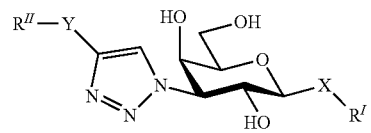

as described in WO/2005/113569, in which $R^1$ can be a D-galactose.

In recently published US20140099319, WO2014067986 and (T. Delaine, 2016, ChemBioChem 10.1002/cbic.201600285) are disclosed a compound of formula

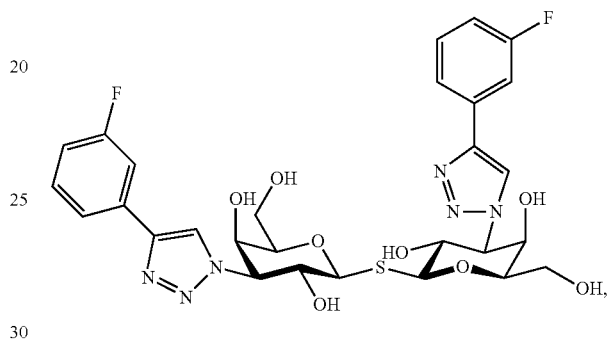

having fluorine (F) in the meta position on both the phenyl rings in relation to the triazole rings. This compound has been shown to be a promising drug candidate for lung fibrosis, and in particular is very selective on galectin-3 with high affinity.

A series of small C1 or C1 and C3-substituted galactopyranosides have been disclosed showing affinity towards galectin-3 and 1. The beta-D-galactopyranosides were reported as having affinity in the same range or less than lactose, which has a Kd of about 91 µM towards galectin-3 and 190 µM towards galectin-1. (Giguere, D et. al. 2011, 2008, 2006).

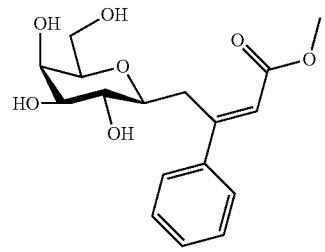

Gal-1 313 µM
Gal-3 >5000

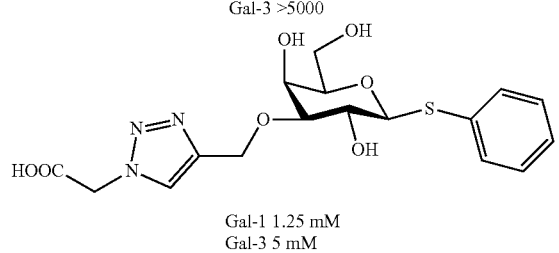

Gal-1 1.25 mM
Gal-3 5 mM

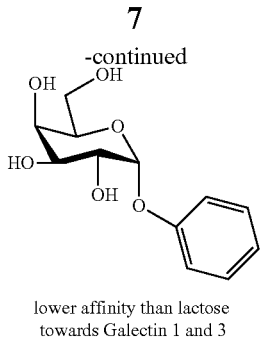

lower affinity than lactose
towards Galectin 1 and 3

There is no disclosure or mentioning of corresponding alpha-anomers having affinity towards galectin-3 or galectin-1 better than lactose.

SUMMARY

The compounds of the present invention are novel α-D-galactopyranose compounds that unexpectedly have shown high affinity for galectin-3 and some are galectin-1 inhibitors and still some are combined galectin-1 and -3 inhibitors and are considered novel potent drug candidates. Some compounds have good systemic uptake in in vitro and in vivo ADME studies and are suitable for oral treatment. Some compounds also pass the BBB and are suitable for inhibition of galectin 1 and/or 3 in CNS.

In a broad aspect the present invention relates to a D-galactopyranose compound of formula (1)

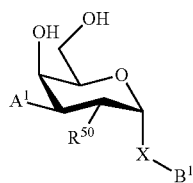

wherein
the pyranose ring is α-D-galactopyranose,
$A^1$ is $R^1$—Z,
Wherein
Z is a five membered heterocycle having at least one heteroatom selected from O, S, and N, except 1,2,3-triazole and is attached to the α-D-galactopyranose;
$R^1$ is selected from a) an aryl, such as phenyl or naphthyl, optionally substituted with a group selected from a halogen; CN; —COOH; —CONR$^{6a}$R$^{7a}$, wherein R$^{6a}$ and R$^{7a}$ are independently selected from H, $C_{1-3}$ alkyl, cyclopropyl, and iso-propyl, or R$^{6a}$ and R$^{7a}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; NR$^{8a}$R$^{9a}$, wherein R$^{8a}$ and R$^{9a}$ are independently selected from H, $C_{1-3}$ alkyl and isopropyl; OH; and R$^{10a}$—CONH— wherein R$^{10a}$ is selected from $C_{1-3}$ alkyl and cyclopropyl; b) a heterocycle, such as heteroaryl or heterocycloalkyl, optionally substituted with a group selected from a halogen; a spiro heterocycle; CN; —COOH; —CONR$^{12a}$R$^{13a}$ wherein R$^{12a}$ and R$^{13a}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; NR$^{14a}$R$^{15a}$, wherein R$^{14a}$ and R$^{15a}$ are independently selected from H, $C_{1-3}$ alkyl, cyclopropyl and isopropyl, C(=O)—R$^{21a}$, wherein R$^{21a}$ is selected from H and $C_{1-3}$ alkyl; OH; and R$^{16a}$—CONH— wherein R$^{16a}$ is selected from $C_{1-3}$ alkyl and cyclopropyl;

X is selected from S, SO, $SO_2$, O, C=O, and CR$^{2b}$R$^{3b}$ wherein R$^{2b}$ and R$^{3b}$ are independently selected from hydrogen, OH, or halogen;

$B^1$ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and R$^{4b}$—CONH— wherein R$^{4b}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and R$^{5b}$—CONH— wherein R$^{5b}$ is selected from $C_{1-3}$ alkyl and cyclopropyl; b) an aryl, such as phenyl or naphthyl, optionally substituted with a group selected from a halogen; CN; a spiro heterocycle, such as N-(2-oxa)-6-azaspiro[3.3]heptanyl; $C_2$-alkynyl; —COOH; —CONR$^{6b}$R$^{7b}$, wherein R$^{6b}$ and R$^{7b}$ are independently selected from H, $C_{1-3}$ alkyl, cyclopropyl, and iso-propyl, or R$^{6b}$ and R$^{7b}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; NR$^{8b}$R$^{9b}$, wherein R$^{8b}$ and R$^{9b}$ are independently selected from H, $C_{1-3}$ alkyl and isopropyl; OH; a heterocycle optionally substituted with a $C_{1-3}$ alkyl optionally substituted with a OH; and R$^{10b}$—CONH— wherein R$^{10b}$ is selected from $C_{1-3}$ alkyl and cyclopropyl; c) a $C_{5-7}$ cycloalkyl, optionally substituted with a substituent selected from a halogen, $C_2$-alkynyl, CN, methyl optionally substituted with a F, $OCH_3$ optionally substituted with a F, $OCH_2CH_3$ optionally substituted with a F, OH, and R$^{11b}$—CONH— wherein R$^{11b}$ is selected from $C_{1-3}$ alkyl and cyclopropyl; and d) a heterocycle, such as heteroaryl or heterocycloalkyl, optionally substituted with a group selected from a halogen; a spiro heterocycle, such as N-(2-oxa)-6-azaspiro[3.3]heptanyl; $C_2$-alkynyl; CN; —COOH; —CONR$^{12b}$R$^{13b}$, wherein R$^{12b}$ and R$^{13b}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; NR$^{14b}$R$^{15b}$, wherein R$^{14b}$ and R$^{15b}$ are independently selected from H, $C_{1-3}$ alkyl and isopropyl; OH; a heterocycle optionally substituted with a $C_{1-3}$ alkyl optionally substituted with a OH; and R$^{16b}$—CONH— wherein R$^{16b}$ is selected from $C_{1-3}$ alkyl and cyclopropyl; e) a $C_{1-6}$ alkyl or branched $C_{3-6}$ alkyl; f) $C_{2-6}$ alkynyl;

$R^{50}$ is selected from the group consisting of a) H, b) OH, c) $OC_{1-6}$ alkyl optionally substituted with one or more halogen, phenyl, phenyl substituted with one or more groups selected form OH and halogen, CN, $OR^{17b}$, $NR^{18b}R^{19b}$, and $CONH_2$, wherein $R^{17b}$ is selected from the group consisting of H, CN, a halogen, methyl optionally substituted with a F, $OCH_3$ optionally substituted with a F, $OCH_2CH_3$ optionally substituted with a F, OH, and $R^{20b}$—CONH— wherein $R^{20b}$ is selected from $C_{1-3}$ alkyl and cyclopropyl, $R^{18b}$ is selected from the group consisting of H, CN, a halogen, methyl optionally substituted with a F, $OCH_3$ optionally substituted with a F, $OCH_2CH_3$ optionally substituted with a F, OH, and $R^{21b}$—CONH— wherein $R^{21b}$ is selected from $C_{1-3}$ alkyl and cyclopropyl, and $R^{19b}$ is selected from the group consisting of H, CN, a halogen, methyl optionally substituted with a F, $OCH_3$ optionally substituted with a F, $OCH_2CH_3$ optionally substituted with a F, OH, and $R^{22b}$—CONH— wherein $R^{22b}$ is selected from $C_{1-3}$ alkyl and cyclopropyl, d) branched $OC_{3-6}$ alkyl optionally substituted with one or more halogen, CN, $OR^{23b}$, $NR^{24b}R^{25b}$, and $CONH_2$, wherein $R^{23b}$ is selected from the group consisting of H, CN, a halogen, methyl optionally substituted with a F, $OCH_3$ optionally substituted with a F, $OCH_2CH_3$ optionally substituted with a F, OH, and $R^{26b}$—CONH— wherein $R^{26b}$ is selected from $C_{1-3}$ alkyl and cyclopropyl, $R^{24b}$ is selected from the group consisting of H, CN, a halogen, methyl optionally substituted with a F, $OCH_3$ optionally substituted with a F, $OCH_2CH_3$ optionally substituted with a F, OH, and $R^{27b}$—CONH— wherein $R^{27b}$ is selected from $C_{1-3}$ alkyl and cyclopropyl, and $R^{25b}$ is selected from the group consisting of H, CN, a halogen, methyl optionally substituted with a F, $OCH_3$ optionally substituted with a F, $OCH_2CH_3$ optionally substituted with a F, OH, and $R^{28}$—CONH— wherein $R^{28}$ is selected from $C_{1-3}$ alkyl and cyclopropyl, and e) cyclic $OC_{3-6}$ alkyl optionally substituted with one or more halogen, CN, $OR^{29}$, $NR^{30}R^{31}$, and $CONH_2$, wherein $R^{29}$ is selected from the group consisting of H, CN, a halogen, methyl optionally substituted with a F, $OCH_3$ optionally substituted with a F, $OCH_2CH_3$ optionally substituted with a F, OH, and $R^{32}$—CONH— wherein $R^{32}$ is selected from $C_{1-3}$ alkyl and cyclopropyl, $R^{30}$ is selected from the group consisting of H, CN, a halogen, methyl optionally substituted with a F, $OCH_3$ optionally substituted with a F, $OCH_2CH_3$ optionally substituted with a F, OH, and $R^{33}$—CONH— wherein $R^{33}$ is selected from $C_{1-3}$ alkyl and cyclopropyl, and $R^{31}$ is selected from the group consisting of H, CN, a halogen, methyl optionally substituted with a F, $OCH_3$ optionally substituted with a F, $OCH_2CH_3$ optionally substituted with a F, OH, and $R^{34}$—CONH— wherein $R^{34}$ is selected from $C_{1-3}$ alkyl and cyclopropyl; or a pharmaceutically acceptable salt or solvate thereof.

In a further aspect the present invention concerns a D-galactopyranose compound of formula (1)

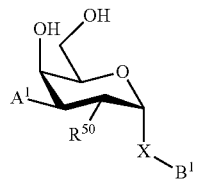

wherein
the pyranose ring is α-D-galactopyranose,
$A^1$ is $R^1$—Z,
Wherein
Z is a five membered heterocycle having at least one heteroatom selected from O, S, and N, except 1,2,3-triazole and is attached to the α-D-galactopyranose;
$R^1$ is selected from a) an aryl, such as phenyl or naphthyl, optionally substituted with a group selected from a halogen; CN; —COOH; —$CONR^{6a}R^{7a}$, wherein $R^{6a}$ and $R^{7a}$ are independently selected from H, $C_{1-3}$ alkyl, cyclopropyl, and iso-propyl, or $R^{6a}$ and $R^{7a}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{8a}R^{9a}$, wherein $R^{8a}$ and $R^{9a}$ are independently selected from H, $C_{1-3}$ alkyl and isopropyl; OH; and $R^{10a}$—CONH— wherein $R^{10a}$ is selected from $C_{1-3}$ alkyl and cyclopropyl; b) a heterocycle, such as heteroaryl or heterocycloalkyl, optionally substituted with a group selected from a halogen; a spiro heterocycle; CN; —COOH; —$CONR^{12a}R^{13a}$, wherein $R^{12}$ and $R^{13a}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{14a}R^{15a}$, wherein $R^{14a}$ and $R^{15a}$ are independently selected from H, $C_{1-3}$ alkyl, cyclopropyl and isopropyl, C(=O)—$R^{21a}$, wherein $R^{21a}$ is selected from H and $C_{1-3}$ alkyl; OH; and $R^{16a}$—CONH— wherein $R^{16a}$ is selected from $C_{1-3}$ alkyl and cyclopropyl;
X is selected from S, SO, $SO_2$, O, C=O, and $CR^{2b}R^{3b}$ wherein $R^{2b}$ and $R^{3b}$ are independently selected from hydrogen, OH, or halogen;
$B^1$ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and $R^{4b}$—CONH— wherein $R^{4b}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and $R^{5b}$—CONH— wherein $R^{5b}$ is selected from $C_{1-3}$ alkyl and cyclopropyl; b) an aryl, such as phenyl or naphthyl, optionally substituted with a group selected from a halogen; CN; $C_2$-alkynyl; —COOH; —$CONR^{6b}R^{7b}$, wherein $R^{6b}$ and $R^{7b}$ are independently selected from H, $C_{1-3}$ alkyl, cyclopropyl, and iso-propyl, or $R^{6b}$ and $R^{7b}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{8b}R^{9b}$, wherein $R^{8b}$ and $R^{9b}$ are independently selected from H, $C_{1-3}$ alkyl and isopropyl; OH; and $R^{19b}$—CONH— wherein $R^{19b}$ is selected from $C_{1-3}$ alkyl and cyclopropyl; c) a $C_{5-7}$ cycloalkyl, optionally substituted with a substituent selected from a halogen, $C_2$-alkynyl, CN, methyl optionally substituted with a F, $OCH_3$ optionally substituted with a F, $OCH_2CH_3$ optionally substituted with a F, OH, and $R^{11b}$—CONH— wherein $R^{11b}$ is selected from $C_{1-3}$ alkyl and cyclopropyl; and d) a heterocycle, such as heteroaryl or heterocycloalkyl, optionally substituted with a group selected from a halogen; a spiro heterocycle, such as N-(2-oxa)-6-azaspiro[3.3]heptanyl; $C_2$-alkynyl; CN; —COOH; —CONR$^{12b}$R$^{13b}$, wherein R$^{12b}$ and R$^{13b}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; NR$^{14b}$R$^{15b}$, wherein R$^{14b}$ and R$^{15b}$ are independently selected from H, $C_{1-3}$ alkyl and isopropyl; OH; and R$^{16b}$—CONH— wherein R$^{16b}$ is selected from $C_{1-3}$ alkyl and cyclopropyl; e) a $C_{1-6}$ alkyl or branched $C_{3-6}$ alkyl; f) $C_{2-6}$ alkynyl;

$R^{50}$ is selected from the group consisting of a) H, b) OH, c) $OC_{1-6}$ alkyl optionally substituted with one or more halogen, phenyl, phenyl substituted with one or more groups selected form OH and halogen, CN, OR$^{17b}$, NR$^{18b}$R$^{19b}$, and CONH$_2$, wherein R$^{17b}$ is selected from the group consisting of H, CN, a halogen, methyl optionally substituted with a F, $OCH_3$ optionally substituted with a F, $OCH_2CH_3$ optionally substituted with a F, OH, and R$^{20b}$—CONH— wherein R$^{20b}$ is selected from $C_{1-3}$ alkyl and cyclopropyl, R$^{18b}$ is selected from the group consisting of H, CN, a halogen, methyl optionally substituted with a F, $OCH_3$ optionally substituted with a F, $OCH_2CH_3$ optionally substituted with a F, OH, and R$^{21b}$—CONH— wherein R$^{21b}$ is selected from $C_{1-3}$ alkyl and cyclopropyl, and R$^{19b}$ is selected from the group consisting of H, CN, a halogen, methyl optionally substituted with a F, $OCH_3$ optionally substituted with a F, $OCH_2CH_3$ optionally substituted with a F, OH, and R$^{22b}$—CONH— wherein R$^{22b}$ is selected from $C_{1-3}$ alkyl and cyclopropyl, d) branched $OC_{3-6}$ alkyl optionally substituted with one or more halogen, CN, OR$^{23b}$, NR$^{24b}$R$^{25b}$, and CONH$_2$, wherein R$^{23b}$ is selected from the group consisting of H, CN, a halogen, methyl optionally substituted with a F, $OCH_3$ optionally substituted with a F, $OCH_2CH_3$ optionally substituted with a F, OH, and R$^{26b}$—CONH— wherein R$^{26b}$ is selected from $C_{1-3}$ alkyl and cyclopropyl, R$^{24b}$ is selected from the group consisting of H, CN, a halogen, methyl optionally substituted with a F, $OCH_3$ optionally substituted with a F, $OCH_2CH_3$ optionally substituted with a F, OH, and R$^{27b}$—CONH— wherein R$^{27b}$ is selected from $C_{1-3}$ alkyl and cyclopropyl, and R$^{25b}$ is selected from the group consisting of H, CN, a halogen, methyl optionally substituted with a F, $OCH_3$ optionally substituted with a F, $OCH_2CH_3$ optionally substituted with a F, OH, and R$^{28}$—CONH— wherein R$^{28}$ is selected from $C_{1-3}$ alkyl and cyclopropyl, and e) cyclic $OC_{3-6}$ alkyl optionally substituted with one or more halogen, CN, OR$^{29}$, NR$^{30}$R$^{31}$, and CONH$_2$, wherein R$^{29}$ is selected from the group consisting of H, CN, a halogen, methyl optionally substituted with a F, $OCH_3$ optionally substituted with a F, $OCH_2CH_3$ optionally substituted with a F, OH, and R$^{32}$—CONH— wherein R$^{32}$ is selected from $C_{1-3}$ alkyl and cyclopropyl, R$^{30}$ is selected from the group consisting of H, CN, a halogen, methyl optionally substituted with a F, $OCH_3$ optionally substituted with a F, $OCH_2CH_3$ optionally substituted with a F, OH, and R$^{33}$—CONH— wherein R$^{33}$ is selected from $C_{1-3}$ alkyl and cyclopropyl, and R$^{31}$ is selected from the group consisting of H, CN, a halogen, methyl optionally substituted with a F, $OCH_3$ optionally substituted with a F, $OCH_2CH_3$ optionally substituted with a F, OH, and R$^{34}$—CONH— wherein R$^{34}$ is selected from $C_{1-3}$ alkyl and cyclopropyl; or a pharmaceutically acceptable salt or solvate thereof.

In an embodiment Z is selected from 1,2,4-triazolyl, oxazolyl, oxadiazolyl, isoxazolyl, dioxolyl, dithiolyl, thiazolyl, isothiazolyl, furanyl, thiophen, pyrrolyl, imidazolyl, or pyrazolyl such as

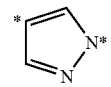

wherein the asterix on the carbon is linked to R1 and the Asterix on the nitrogen is attached to the α-D-galactopyranose. In another embodiment Z is an oxadiazolyl.

In a further embodiment $R^1$ is phenyl optionally substituted with a group selected from CN, OH, NH$_2$, F, Br, Cl, I, methyl optionally substituted with a fluorine (F), and $OCH_3$ optionally substituted with a F, and $SCH_3$ optionally substituted with a F.

In a further embodiment $R^1$ is phenyl substituted with a group selected from F, Cl, and methyl. Typically, $R^1$ is phenyl substituted with one, two or three, such as two or three, selected from F, Cl, and methyl.

In a still further embodiment $R^1$ is selected from a five or six membered heteroaromatic ring, optionally substituted with a group selected from Br; F; Cl; I; OH; CN; NR$^{14a}$R$^{15a}$, wherein R$^{14a}$ and R$^{15a}$ are independently selected from H, $C_{1-3}$ alkyl, cyclopropyl and isopropyl, C(=O)—R$^{21a}$, wherein R$^{21a}$ is selected from H and $C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; $OC_{1-3}$ alkyl optionally substituted with a F; and $SC_{1-3}$ alkyl optionally substituted with a F. preferably $R^1$ is a pyridinyl, optionally substituted with a group selected from OH, NH$_2$, CN, Br, Cl, I, F, methyl optionally substituted with a F, $OCH_3$ optionally substituted with a F, and $SCH_3$ optionally substituted with a F; or a pyrimidyl, optionally substituted with a group selected from H, CN, Br, Cl, I, F, methyl optionally substituted with a F, $OCH_3$ optionally substituted with a F, and $SCH_3$ optionally substituted with a F.

In a further embodiment $R^1$ is oxazolyl, such as oxazol-2-yl.

In a further embodiment $R^1$ is imidazolyl.

In a further embodiment $R^1$ is pyrazolyl.

In a further embodiment $R^1$ is a five or six membered heteroaromatic ring selected from the group consisting of formulas 2 to 9, wherein the asterix * indicates the carbon atom of the heteroaromatic ring that is covalently attached to the Z substituent:

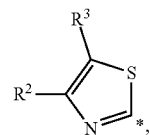

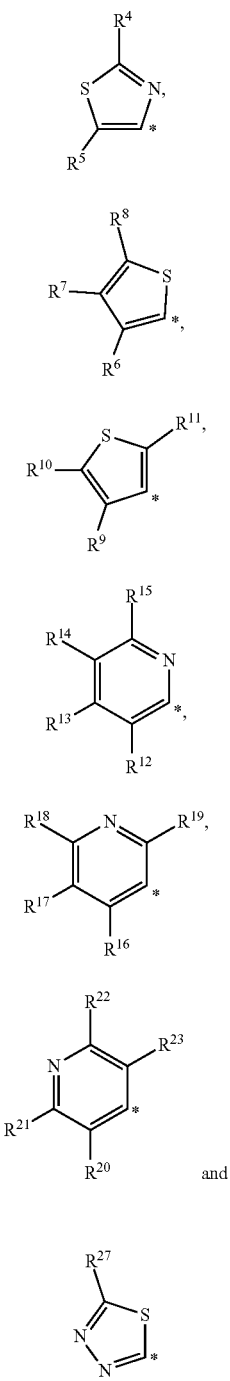

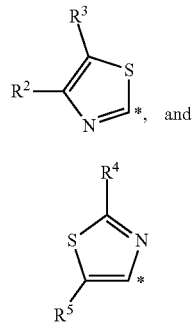

wherein R² to R²³ and R²⁷ are independently selected from H; halogen; OH; CN; SH; S—$C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; $OC_{1-3}$ alkyl optionally substituted with a F; $NR^{24}R^{25}$, wherein $R^{24}$ is selected from H, and $C_{1-3}$ alkyl, and $R^{25}$ is selected from H, $C_{1-3}$ alkyl, and $COR^{26}$, wherein $R^{26}$ is selected from H, and $C_{1-3}$ alkyl. Preferably, $R^1$ is selected from the group consisting of wherein R² is selected from the group consisting of OH, methyl and halogen, preferably F, Cl and Br;

R³ is selected from the group consisting of hydrogen, $C_{1-6}$ alkyl and halogen;

R⁴ is selected from the group consisting of OH, NH₂ and halogen, preferably F, Cl, and Br;

R⁵ is selected from the group consisting of hydrogen, $C_{1-6}$ alkyl and halogen.

In a still further embodiment X is selected from S, SO, SO₂, and O, such as S, SO, and SO₂, preferably S.

In a further embodiment B1 is selected from a heteroaryl, optionally substituted with a group selected from a halogen; CN; methyl optionally substituted with a F; and a heteroaryl. Preferably B1 is selected from a pyridinyl, optionally substituted with a group selected from a Cl, Br, CN; methyl; CF₃; pyridin; pyrimidin; oxazol; and thiazol.

In a further embodiment B1 is selected from a heteroaryl, optionally substituted with a group selected from a halogen; CN; ethynyl; methyl optionally substituted with a F; and a heterocycle optionally substituted with a $C_{1-3}$ alkyl optionally substituted with a OH. Preferably, B1 is selected from a pyridinyl, optionally substituted with a group selected from a Cl, Br, CN, methyl, CF₃, azetidinyl; azetidinyl substituted with a CH₂OH; pyridinyl, pyrimidinyl, oxazolyl, and thiazolyl.

In a still further embodiment B1 is selected from a phenyl, optionally substituted with a group selected from a halogen; and $C_{1-3}$ alkyl, optionally substituted with a F.

In a still further embodiment B1 is selected from a phenyl substituted with a group selected from a halogen, CN, and $C_{1-3}$ alkyl, optionally substituted with a F. Typically, B1 is selected from a phenyl substituted with one, two or three, such as one or two, selected from a Cl, F, Br, CN, Methyl, and CF₃.

In a further embodiment B1 is selected from a phenyl, optionally substituted with a group selected from a halogen, CN, $C_{1-3}$ alkyl, optionally substituted with a F, and $CONR^{6b}R^{7b}$, wherein $R^{6b}$ and $R^{7b}$ are independently selected from H, $C_{1-3}$ alkyl, cyclopropyl, and iso-propyl, or $R^{6b}$ and $R^{7b}$ together with the nitrogen may form a heterocycloalkyl.

In a further embodiment $R^{50}$ is selected from H, $C_{1-4}$ alkyl, such as methyl, ethyl, or isopropyl, $C_{1-4}$ alkyl substituted with at least one from the group consisting of phenyl and phenyl substituted with one or more groups selected form OH and halogen. In a typical embodiment $R^{50}$ is selected from OH.

In a further embodiment $R^{50}$ is $OC_{1-6}$ alkyl, such as methoxy.

In a further embodiment the compound of formula (1) is selected from any one of:

3-Chlorophenyl 3-deoxy-3-[4-(3-fluorophenyl)-1H-1,2-pyrazol-1-yl]-1-thio-α-D-galactopyranoside,
5-Chloropyridin-3-yl 3-[4-(4-chloro-3,5-difluorophenyl)-1H-1,2-pyrazol-1-yl]-3-deoxy-1-thio-α-D-galactopyranoside,
5-Chloropyridin-3-yl 3-deoxy-3-[4-(3,4,5-trifluorophenyl)-1H-1,2-pyrazol-1-yl]-1-thio-α-D-galactopyranoside, and
5-Chloropyridin-3-yl 3-deoxy-3-[4-(3,5-difluoro-4-methylphenyl)-1H-1,2-pyrazol-1-yl]-1-thio-α-D-galactopyranoside; or a pharmaceutically acceptable salt or solvate thereof.

In a further embodiment the compound of formula (1) is selected from any one of
5-Bromopyridin-3-yl 3-deoxy-3-[4-(3,4,5-trifluorophenyl)-1H-1,2-pyrazol-1-yl]-1-thio-α-D-galactopyranoside,
5-Bromopyridin-3-yl 3-[4-(4-chloro-3,5-difluorophenyl)-1H-1,2-pyrazol-1-yl]-3-deoxy-1-thio-α-D-galactopyranoside,
5-Ethynylpyridin-3-yl 3-[4-(4-chloro-3,5-difluorophenyl)-1H-1,2-pyrazol-1-yl]-3-deoxy-1-thio-α-D-galactopyranoside,
5-Chloro-2-cyanophenyl 3-[4-(4-chloro-3,5-difluorophenyl)-1H-1,2-pyrazol-1-yl]-3-deoxy-1-thio-α-D-galactopyranoside,
2-(N-Azetidinyl-carbonyl)-5-chlorophenyl 3-[4-(4-chloro-3,5-difluorophenyl)-1H-1,2-pyrazol-1-yl]-3-deoxy-1-thio-α-D-galactopyranoside,
2-(N-Azetidinyl-carbonyl)-5-chlorophenyl 3-deoxy-3-[4-(3,4,5-trifluorophenyl)-1H-1,2-pyrazol-1-yl]-1-thio-α-D-galactopyranoside,
5-Chloro-2-cyanophenyl 3-deoxy-3-[4-(3,4,5-trifluorophenyl)-1H-1,2-pyrazol-1-yl]-1-thio-α-D-galactopyranoside,
5-Chloro-2-cyanopyridin-3-yl 3-deoxy-3-[4-(3,4,5-trifluorophenyl)-1H-1,2-pyrazol-1-yl]-1-thio-α-D-galactopyranoside,
5-Chloro-2-cyanopyridin-3-yl 3-[4-(4-chloro-3,5-difluorophenyl)-1H-1,2-pyrazol-1-yl]-3-deoxy-1-thio-α-D-galactopyranoside,
5-Chloro-2-methylpyridin-3-yl 3-deoxy-3-[4-(3,4,5-trifluorophenyl)-1H-1,2-pyrazol-1-yl]-1-thio-α-D-galactopyranoside,
5-Bromo-2-cyanopyridin-3-yl 3-deoxy-3-[4-(3,4,5-trifluorophenyl)-1H-1,2-pyrazol-1-yl]-1-thio-α-D-galactopyranoside,
2-Cyano-5-ethynylpyridin-3-yl 3-deoxy-3-[4-(3,4,5-trifluorophenyl)-1H-1,2-pyrazol-1-yl]-1-thio-α-D-galactopyranoside,
5-Chloropyridin-3-yl 3-[4-(4-chloro-3-fluorophenyl)-1H-1,2-pyrazol-1-yl]-3-deoxy-1-thio-α-D-galactopyranoside,
5-Chloropyridin-3-yl 3-deoxy-3-[4-(6-fluoropyridin-2-yl)-1H-1,2-pyrazol-1-yl]-1-thio-α-D-galactopyranoside,
5-Chloropyridin-3-yl 3-deoxy-3-[4-(5-fluoropyridin-2-yl)-1H-1,2-pyrazol-1-yl]-1-thio-α-D-galactopyranoside,
5-Chloropyridin-3-yl 3-deoxy-3-[4-(4-fluoropyridin-2-yl)-1H-1,2-pyrazol-1-yl]-1-thio-α-D-galactopyranoside,
5-Chloropyridin-3-yl 3-deoxy-3-[4-(1H-1,2-pyrazol-3-yl)-1H-1,2-pyrazol-1-yl]-1-thio-α-D-galactopyranoside,
5-Chloropyridin-3-yl 3-deoxy-3-[4-(1-methyl-1,2-pyrazol-3-yl)-1H-1,2-pyrazol-1-yl]-1-thio-α-D-galactopyranoside,
5-Chloropyridin-3-yl 3-deoxy-3-[4-(1H-imidazol-2-yl)-1H-1,2-pyrazol-1-yl]-1-thio-α-D-galactopyranoside,
5-Chloropyridin-3-yl 3-deoxy-3-[4-(oxazol-2-yl)-1H-1,2-pyrazol-1-yl]-1-thio-α-D-galactopyranoside,
5-Chloropyridin-3-yl 3-deoxy-3-[4-(thiazol-4-yl)-1H-1,2-pyrazol-1-yl]-1-thio-α-D-galactopyranoside,
5-Chloropyridin-3-yl 3-deoxy-3-[4-(thiazol-2-yl)-1H-1,2-pyrazol-1-yl]-1-thio-α-D-galactopyranoside,
5-Chloropyridin-3-yl 3-[4-(4-chlorothiazol-2-yl)-1H-1,2-pyrazol-1-yl]-3-deoxy-1-thio-α-D-galactopyranoside,
5-Bromopyridin-3-yl 3-[4-(4-chlorothiazol-2-yl)-1H-1,2-pyrazol-1-yl]-3-deoxy-1-thio-α-D-galactopyranoside,
5-Chloro-2-cyanophenyl 3-[4-(4-chlorothiazol-2-yl)-1H-1,2-pyrazol-1-yl]-3-deoxy-1-thio-α-D-galactopyranoside,
5-Chloro-2-cyanopyridin-3-yl 3-[4-(4-chlorothiazol-2-yl)-1H-1,2-pyrazol-1-yl]-3-deoxy-1-thio-α-D-galactopyranoside,
5-Chloropyridin-3-yl 3-deoxy-3-[4-(2-hydroxythiazol-4-yl)-1H-1,2-pyrazol-1-yl]-1-thio-α-D-galactopyranoside,
5-Chloropyridin-3-yl 3-deoxy-3-[4-(3,4,5-trifluorophenyl)-1H-1,2-pyrazol-1-yl]-2-O-methyl-1-thio-α-D-galactopyranoside,
5-Bromopyridin-3-yl 3-deoxy-3-[4-(3,4,5-trifluorophenyl)-1H-1,2-pyrazol-1-yl]-2-O-methyl-1-thio-α-D-galactopyranoside,
5-Ethynylpyridin-3-yl 3-deoxy-3-[4-(3,4,5-trifluorophenyl)-1H-1,2-pyrazol-1-yl]-2-O-methyl-1-thio-α-D-galactopyranoside,
5-Chloro-2-cyanopyridin-3-yl 3-deoxy-3-[4-(3,4,5-trifluorophenyl)-1H-1,2-pyrazol-1-yl]-2-O-methyl-1-thio-α-D-galactopyranoside; or a pharmaceutically acceptable salt or solvate thereof.

In a still further embodiment the compound of formula (1) is selected from any one of:
3-Chlorophenyl 3-deoxy-3-[4-(3-fluorophenyl)-1H-1,2-pyrazol-1-yl]-1-thio-α-D-galactopyranoside,
5-Chloropyridin-3-yl 3-[4-(4-chloro-3,5-difluorophenyl)-1H-1,2-pyrazol-1-yl]-3-deoxy-1-thio-α-D-galactopyranoside,
5-Chloropyridin-3-yl 3-deoxy-3-[4-(3,4,5-trifluorophenyl)-1H-1,2-pyrazol-1-yl]-1-thio-α-D-galactopyranoside,
5-Chloropyridin-3-yl 3-deoxy-3-[4-(3,5-difluoro-4-methylphenyl)-1H-1,2-pyrazol-1-yl]-1-thio-α-D-galactopyranoside,
5-Bromopyridin-3-yl 3-deoxy-3-[4-(3,4,5-trifluorophenyl)-1H-1,2-pyrazol-1-yl]-1-thio-α-D-galactopyranoside,
5-Bromopyridin-3-yl 3-[4-(4-chloro-3,5-difluorophenyl)-1H-1,2-pyrazol-1-yl]-3-deoxy-1-thio-α-D-galactopyranoside,
5-Ethynylpyridin-3-yl 3-[4-(4-chloro-3,5-difluorophenyl)-1H-1,2-pyrazol-1-yl]-3-deoxy-1-thio-α-D-galactopyranoside,
5-Chloro-2-cyanophenyl 3-[4-(4-chloro-3,5-difluorophenyl)-1H-1,2-pyrazol-1-yl]-3-deoxy-1-thio-α-D-galactopyranoside,
2-(N-Azetidinyl-carbonyl)-5-chlorophenyl 3-[4-(4-chloro-3,5-difluorophenyl)-1H-1,2-pyrazol-1-yl]-3-deoxy-1-thio-α-D-galactopyranoside,
2-(N-Azetidinyl-carbonyl)-5-chlorophenyl 3-deoxy-3-[4-(3,4,5-trifluorophenyl)-1H-1,2-pyrazol-1-yl]-1-thio-α-D-galactopyranoside,
5-Chloro-2-cyanophenyl 3-deoxy-3-[4-(3,4,5-trifluorophenyl)-1H-1,2-pyrazol-1-yl]-1-thio-α-D-galactopyranoside,
5-Chloro-2-cyanopyridin-3-yl 3-deoxy-3-[4-(3,4,5-trifluorophenyl)-1H-1,2-pyrazol-1-yl]-1-thio-α-D-galactopyranoside,
5-Chloro-2-cyanopyridin-3-yl 3-[4-(4-chloro-3,5-difluorophenyl)-1H-1,2-pyrazol-1-yl]-3-deoxy-1-thio-α-D-galactopyranoside,
5-Chloro-2-methylpyridin-3-yl 3-deoxy-3-[4-(3,4,5-trifluorophenyl)-1H-1,2-pyrazol-1-yl]-1-thio-α-D-galactopyranoside, 5-Bromo-2-cyanopyridin-3-yl 3-deoxy-3-[4-(3,4,5-trifluorophenyl)-1H-1,2-pyrazol-1-yl]-1-thio-α-D-galactopyranoside, 2-Cyano-5-ethynylpyridin-3-yl 3-deoxy-3-[4-(3,4,5-trifluorophenyl)-1H-1,2-pyrazol-1-yl]-1-thio-α-D-galactopyranoside, 5-Chloropyridin-3-yl 3-[4-(4-chloro-3-fluorophenyl)-1H-1,2-pyrazol-1-yl]-3-deoxy-1-thio-α-D-galactopyranoside, 5-Chloropyridin-3-yl 3-deoxy-3-[4-(6-fluoropyridin-2-yl)-1H-1,2-pyrazol-1-yl]-1-thio-α-D-galactopyranoside, 5-Chloropyridin-3-yl 3-deoxy-3-[4-(5-fluoropyridin-2-yl)-1H-1,2-pyrazol-1-yl]-1-thio-α-D-galactopyranoside, 5-Chloropyridin-3-yl 3-deoxy-3-[4-(4-fluoropyridin-2-yl)-1H-1,2-pyrazol-1-yl]-1-thio-α-D-galactopyranoside, 5-Chloropyridin-3-yl 3-deoxy-3-[4-(1H-1,2-pyrazol-3-yl)-1H-1,2-pyrazol-1-yl]-1-thio-α-D-galactopyranoside, 5-Chloropyridin-3-yl 3-deoxy-3-[4-(1-methyl-1,2-pyrazol-3-yl)-1H-1,2-pyrazol-1-yl]-1-thio-α-D-galactopyranoside, 5-Chloropyridin-3-yl 3-deoxy-3-[4-(1H-imidazol-2-yl)-1H-1,2-pyrazol-1-yl]-1-thio-α-D-galactopyranoside, 5-Chloropyridin-3-yl 3-deoxy-3-[4-(oxazol-2-yl)-1H-1,2-pyrazol-1-yl]-1-thio-α-D-galactopyranoside, 5-Chloropyridin-3-yl 3-deoxy-3-[4-(thiazol-4-yl)-1H-1,2-pyrazol-1-yl]-1-thio-α-D-galactopyranoside, 5-Chloropyridin-3-yl 3-deoxy-3-[4-(thiazol-2-yl)-1H-1,2-pyrazol-1-yl]-1-thio-α-D-galactopyranoside, 5-Chloropyridin-3-yl 3-[4-(4-chlorothiazol-2-yl)-1H-1,2-pyrazol-1-yl]-3-deoxy-1-thio-α-D-galactopyranoside, 5-Bromopyridin-3-yl 3-[4-(4-chlorothiazol-2-yl)-1H-1,2-pyrazol-1-yl]-3-deoxy-1-thio-α-D-galactopyranoside, 5-Chloro-2-cyanophenyl 3-[4-(4-chlorothiazol-2-yl)-1H-1,2-pyrazol-1-yl]-3-deoxy-1-thio-α-D-galactopyranoside, 5-Chloro-2-cyanopyridin-3-yl 3-[4-(4-chlorothiazol-2-yl)-1H-1,2-pyrazol-1-yl]-3-deoxy-1-thio-α-D-galactopyranoside, 5-Chloropyridin-3-yl 3-deoxy-3-[4-(2-hydroxythiazol-4-yl)-1H-1,2-pyrazol-1-yl]-1-thio-α-D-galactopyranoside, 5-Chloropyridin-3-yl 3-deoxy-3-[4-(3,4,5-trifluorophenyl)-1H-1,2-pyrazol-1-yl]-2-O-methyl-1-thio-α-D-galactopyranoside, 5-Bromopyridin-3-yl 3-deoxy-3-[4-(3,4,5-trifluorophenyl)-1H-1,2-pyrazol-1-yl]-2-O-methyl-1-thio-α-D-galactopyranoside, 5-Ethynylpyridin-3-yl 3-deoxy-3-[4-(3,4,5-trifluorophenyl)-1H-1,2-pyrazol-1-yl]-2-O-methyl-1-thio-α-D-galactopyranoside, 5-Chloro-2-cyanopyridin-3-yl 3-deoxy-3-[4-(3,4,5-trifluorophenyl)-1H-1,2-pyrazol-1-yl]-2-O-methyl-1-thio-α-D-galactopyranoside, 5-Chloropyridin-3-yl 3-deoxy-3-[4-(3,4,5-trifluorophenyl)-1H-1,3-imidazol-1-yl]-1-thio-α-D-galactopyranoside, 5-Chloro-[3,3-bis(hydroxymethyl)azetidin-1-yl]pyridin-3-yl 3-deoxy-3-[4-(3,4,5-trifluorophenyl)-1H-1,2-pyrazol-1-yl]-1-thio-α-D-galactopyranoside, 5-Chloropyridin-3-yl 3-deoxy-3-[3-(3,4,5-trifluorophenyl)-1H-1,2-pyrazol-1-yl]-1-thio-α-D-galactopyranoside, 3,4-Dichlorophenyl 3-deoxy-3-[4-(3,4,5-trifluorophenyl)-oxazol-2-yl]-1-thio-α-D-galactopyranoside, 3,4-Dichlorophenyl 3-deoxy-3-[4-(3,4,5-trifluorophenyl)-thiazol-2-yl]-1-thio-α-D-galactopyranoside, 3,4-Dichlorophenyl 3-deoxy-3-[5-(3,4,5-trifluorophenyl)-1,3,4-oxadiazol-2-yl]-1-thio-α-D-galactopyranoside, 3,4-Dichlorophenyl 3-deoxy-3-[4-(2-hydroxythiazol-4-yl)-1H-1,2-pyrazol-1-yl]-2-O-methyl-1-thio-α-D-galactopyranoside, 5-Chloro-2-cyanophenyl 3-[4-(4-chloro-3,5-difluorophenyl)-1H-1,2-pyrazol-1-yl]-3-deoxy-2-O-methyl-1-thio-α-D-galactopyranoside, 5-Chloro-2-cyanophenyl 3-deoxy-3-[4-(3,4,5-trifluorophenyl)-1H-1,2-pyrazol-1-yl]-2-O-methyl-1-thio-α-D-galactopyranoside, and 5-Chloro-2-cyanophenyl 3-deoxy-3-[4-(2-hydroxythiazol-4-yl)-1H-1,2-pyrazol-1-yl]-2-O-methyl-1-thio-α-D-galactopyranoside; or a pharmaceutically salt or solvate thereof.

In a further aspect the present invention relates to a compound of formula (1) for use as a medicine.

In a still further aspect, the present invention relates to a pharmaceutical composition comprising the compound of any one of the previous claims and optionally a pharmaceutically acceptable additive, such as a carrier and/or excipient.

In a further aspect the present invention relates to a compound of formula (1) of the present invention for use in a method for treating a disorder relating to the binding of a galectin, such as galectin 1 and/or galectin 3, to a ligand in a mammal, such as a human. In a further embodiment the disorder is selected from the group consisting of inflammation; Inflammation induced thrombosis; Atopic dermatitis; Acute coronary syndrome; fibrosis, such as pulmonary fibrosis, liver fibrosis, kidney fibrosis, ophthalmological fibrosis and fibrosis of the skin and heart; local fibrosis such as Dupuytren's disease and Peyronie's disease; fibrotic complications of other therapies such as coronary stents, bile duct stents, cerebral artery stents, ureter stents; scleroderma; scarring; keloid formation; covid-19; acute lung injury; ARDS; viral pneumonitis, aberrant scar formation; surgical adhesions; septic shock; cancer, such as colorectal cancer, other gastrointestinal carcinomas such as pancreatic cancer, gastric cancer, biliary tract cancer, lung cancers, mesothelioma, female cancers like breast cancer, ovarian cancer, uterine cancer, cancer of the cervix uteri, cancer of the salpingx, cerebral cancers such as medulloblastomao, glioma, meningioma, sarcomas of the bones and muscles and other sarcomas, leukemias and lymphomas, such as T-cell lymphomas; transplant rejection; metastasising cancers; ageing; Dementia; Alzheimers; TGFbeta driven bone disease such as osteogenesis imperfecta; Pulmonary hypertension; autoimmune diseases, such as psoriasis, rheumatoid arthritis, Rheumatoid lung; Crohn's disease, ulcerative colitis, ankylosing spondylitis, systemic lupus erythematosus; viral infections such as influenza virus, HIV, Herpes virus, Coronaviruses, Hepatitis C; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases; diabetes; type I diabetes; type 2 diabetes; insulin resistens; obesity; Marfans syndrome; Loeys-Dietz syndrome; nephropathy; Diastolic HF; fibrotic lung complications of aPD1 and other CPI therapies; asthma and other interstitial lung diseases, including Hermansky-Pudlak syndrome, liver disorders, such as non-alcoholic steatohepatitis or non-alcoholic fatty liver disease; uterine disease such as uterine fibroids and uterine or cervical fibrosis.

In a still further aspect the present invention relates to a method for treatment of a disorder relating to the binding of a galectin, such as galectin 1 and/or galectin 3, to a ligand in a mammal, such as a human, wherein a therapeutically effective amount of at least one compound of formula (1) of the present invention is administered to a mammal in need of said treatment. In a further embodiment the disorder is selected from the group consisting of inflammation; Inflammation induced thrombosis; Atopic dermatitis; Acute coronary syndrome; fibrosis, such as pulmonary fibrosis, liver fibrosis, kidney fibrosis, ophthalmological fibrosis and fibrosis of the skin and heart; local fibrosis such as Dupuytren's disease and Peyronie's disease; fibrotic complications of other therapies such as coronary stents, bile duct stents, cerebral artery stents, ureter stents; scleroderma; scarring; keloid formation; covid-19; acute lung injury; ARDS; viral pneumonitis, aberrant scar formation; surgical adhesions; septic shock; cancer, such as colorectal cancer, other gastrointestinal carcinomas such as pancreatic cancer, gastric cancer, biliary tract cancer, lung cancers, mesothelioma, female cancers like breast cancer, ovarian cancer, uterine cancer, cancer of the cervix uteri, cancer of the salpingx, cerebral cancers such as medulloblastomao, glioma, meningioma, sarcomas of the bones and muscles and other sarcomas, leukemias and lymphomas, such as T-cell lymphomas; transplant rejection; metastasising cancers; ageing; Dementia; Alzheimers; TGFbeta driven bone disease such as osteogenesis imperfecta; Pulmonary hypertension; autoimmune diseases, such as psoriasis, rheumatoid arthritis, Rheumatoid lung; Crohn's disease, ulcerative colitis, ankylosing spondylitis, systemic lupus erythematosus; viral infections such as influenza virus, HIV, Herpes virus, Coronaviruses, Hepatitis C; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases; diabetes; type I diabetes; type 2 diabetes; insulin resistens; obesity; Marfans syndrome; Loeys-Dietz syndrome; nephropathy; Diastolic HF; fibrotic lung complications of aPD1 and other CPI therapies; asthma and other interstitial lung diseases, including Hermansky-Pudlak syndrome, liver disorders, such as non-alcoholic steatohepatitis or non-alcoholic fatty liver disease; uterine disease such as uterine fibroids and uterine or cervical fibrosis.

Another aspect of the present invention concerns combination therapy involving administering a compound of formula (I) of the present invention together with a therapeutically active compound different from the compound of formula (I) (interchangeable with "a different therapeutically active compound"). In one embodiment the present invention relates to a combination of a compound of formula (I) and a different therapeutically active compound for use in treatment of a disorder relating to the binding of a galectin-1 and/or -3 to a ligand in a mammal Such disorders are disclosed below.

In an embodiment of the present invention, a therapeutically effective amount of at least one compound of formula (I) of the present invention is administered to a mammal in need thereof in combination with a different therapeutically active compound. In a further embodiment, said combination of a compound of formula (I) together with a different therapeutically active compound is administered to a mammal suffering from a disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; type 2 diabetes; insulin resistens; obesity; Diastolic HF; asthma and other interstitial lung diseases, including Hermansky-Pudlak syndrome, mesothelioma; liver disorders, such as non-alcoholic steatohepatitis or non-alcoholic fatty liver disease.

A non-limiting group of cancers given as examples of cancers that may be treated, managed and/or prevented by administration of a compound of formula (I) in combination with a different therapeutically active compound is selected from: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In some aspects of the present invention, the administration of at least one compound of formula (I) of the present invention and at least one additional therapeutic agent demonstrates therapeutic synergy. In some aspects of the methods of the present invention, a measurement of response to treatment observed after administering both at least one compound of formula (I) of the present invention and the additional therapeutic agent is improved over the same measurement of response to treatment observed after administering either the at least one compound of formula (I) of the present invention or the additional therapeutic agent alone.

A further aspect of the present invention concerns combination therapy involving administering a compound of formula (I) of the present invention together with an antifibrotic compound different form the compound of formula (I) to a mammal in need thereof. In a further embodiment, such anti-fibrotic compound may be selected from the following non-limiting group of anti-fibrotic compounds: pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, PAT-1251 and PBI-4050.

A still further aspect of the present invention concerns combination therapy involving administering a compound of formula (I) in combination with a further conventional cancer treatment such as chemotherapy or radiotherapy, or treatment with immunostimulating substances, gene therapy, treatment with antibodies and treatment using dendritic cells, or mRNA based therapeutics including mRNA based cancer vaccines, and/or virus based cancer vaccines, to a mammal in need thereof.

In an embodiment the compound of formula (I) is administered together with at least one additional therapeutic agent selected from an antineoplastic chemotherapy agent. In a further embodiment, the antineoplastic chemotherapeutic agent is selected from: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In a further embodiment of the present invention, the further conventional cancer treatment includes radiation therapy. In some embodiments, radiation therapy includes localized radiation therapy delivered to the tumor. In some embodiments, radiation therapy includes total body irradiation.

In other embodiments of the present invention the further cancer treatment is selected from the group of immunostimulating substances e.g. cytokines and antibodies. Such cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In some embodiments of the present invention the compound of formula (I) is administered together with at least one additional therapeutic agent selected from a checkpoint inhibitor. In some embodiments of the invention, the checkpoint inhibitor is acting on one or more of the following, non-limiting group of targets: CEACAM1, galectin-9, TIM3, CD80, CTLA4, PD-1, PD-L1, HVEM, BTLA, CD160, VISTA, B7-H4, B7-2, CD155, CD226, TIGIT, CD96, LAG3, GITF, OX40, CD137, CD40, IDO, and TDO, kyneurenine antagonists. These are known targets and some of these targets are described in Melero et al., Nature Reviews Cancer (2015). Examples of check point inhibitors administered together with the compound of formula (1) are Anti-PD-1: Nivolumab, Pembrolizumab, Cemiplimab. Anti-PD-L1: Atezolizumab, Avelumab, Durvalumab and one Anti-CTLA-4: Ipilimumab. Each one of these check point inhibitors can be made the subject of an embodiment in combination with any one of the compounds of formula (1).

In some embodiments of the present invention the compound of formula (I) is administered together with at least one additional therapeutic agent selected from an inhibitor of indoleamine-2,3-dioxygenase (IDO).

In some embodiments of the present invention the compound of formula (I) is administered together with at least one additional therapeutic agent selected from one or more inhibitors of the CTLA4 pathway. In some embodiments, the inhibitor of the CTLA4 pathway is selected from one or more antibodies against CTLA4.

In some embodiments of the present invention the compound of formula (I) is administered together with at least one additional therapeutic agent selected from one or more inhibitors of the PD-1/PD-L pathway. In some embodiments, the one or more inhibitors of the PD-1/PD-L pathway are selected from one or more antibodies or antibody fragments against PD-1, PD-L1, and/or PD-L2, or other ways by which an anti-PD1 antibodies can be induced such as mRNA based introduction of genetic material which sets forth in-body production of anti-PD1 or anti-PDL1 antibodies or fragments of such antibodies.

In a still further aspect the present invention relates to a process of preparing a compound of formula II or a pharmaceutically acceptable salt or solvate thereof comprising the step a1 where $R^1$, X, $B^1$, $L^1$ and Z are defined as above under formula 1;

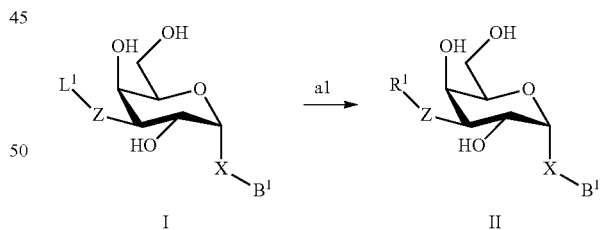

a1) Reacting a compound formula I, $L^1$-Z such as wherein $L^1$ is defined as bromine or iodine, with a boronic acid or borinate of the formula such as $R^1$—$B(OH)_2$ or 4,4,5,5-tetramethyl-1,3,2-dioxaborolane-$R^1$ in the presence of a metalloorganic catalyst such as Pd(dppf)Cl$_2$ and a base such as potassium carbonate in solvents such as dioxane and water optionally at elevated temperature to give a compound of the formula II.

In a still further aspect the present invention relates to a process of preparing a compound of formula II or a pharmaceutically acceptable salt or solvate thereof comprising the steps a2-a7 where $B^1$, Z, X are defined as above under formula 1;

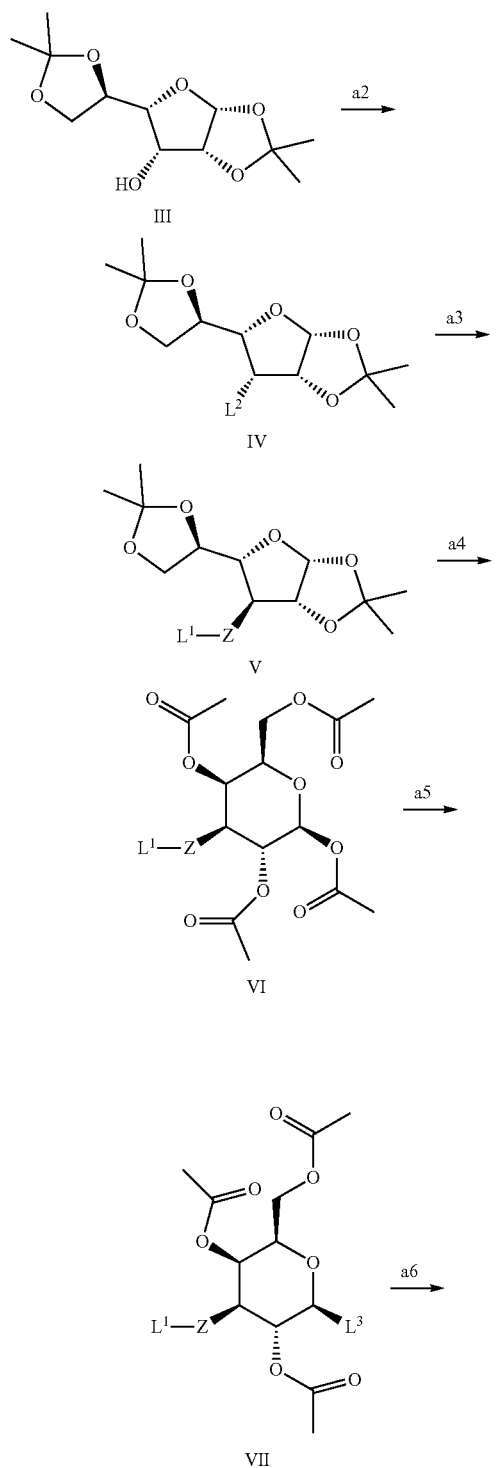

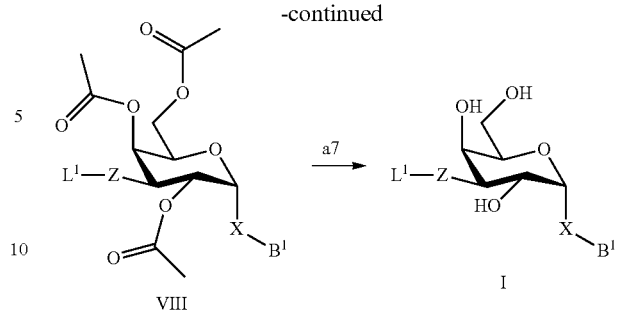

a2) Reacting a compound of formula III with a reagent such as trifluoromethanesulphonic anhydride to give a compound of the formula IV wherein $L^2$ is a leaving group such as a triflate.

a3) Reacting a compound of formula IV with a compound of the formula $L^1$-Z, such as

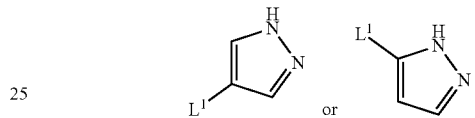

wherein $L^1$ is defined as a halide such as bromine or iodine, in the presence of a base such as $CsCO_3$ in a solvent such as DMF to give a compound of formula V a4) Reacting a compound of formula V with TFA and water while removing the water by azeotropic distillation to give a product which is further reacted with acetic anhydride, an organic base such as triethylamine TEA in a solvent such as ethanol to give a compound of formula VI.

a5) Reacting a compound of the formula VI with a reagent such as dichloromethylmethylether or $PCl_5$ in the presence of a lewis acid such as $BF_3Et_2O$ in an inert solvent such as dichloromethane or chloroform to give a compound of formula VII wherein $L^3$ is defined as a halogen such as chlorine.

a6) Reacting a compound of the formula VII with a reagent such as $B^1$—X—H such as $B^1$—S—H in the presence of a base like sodium hydride in an inert solvent such as DMF to give a compound formula VIII.

a7) Reacting a compound of formula VIII with a base such as sodium methoxide in a solvent such as methanol to give a compound of formula I.

In a still further aspect the present invention relates to a process of preparing a compound of formula II or a pharmaceutically acceptable salt or solvate thereof comprising the step a8 where $A^1$, $B^1$ and X are defined as above under formula 1;

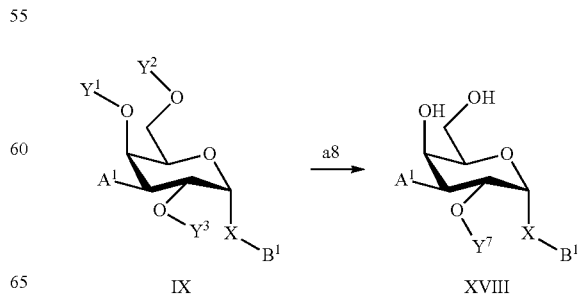

a8) Reacting a compound of formula IX wherein $Y^{1-3}$ are defined as acetates with a base such as sodium methoxide in a solvent such as methanol to give a compound of formula XVIII wherein $Y^7$ is a hydrogen; optionally reacting a compound of formula IX wherein $Y^1$ and $Y^2$ together form a benzylidene and Y3 is an alkyl such as methyl with an acid such as TFA to give a compound of formula XVIII wherein $Y^7$ is an alkyl such as methyl.

In a still further aspect the present invention relates to a process of preparing a compound of formula XII or a pharmaceutically acceptable salt or solvate thereof comprising the step a9-a11 where $A^1$, $B^1$ and X are defined as above under formula 1. $L^1$ is defined as bromine or iodine;

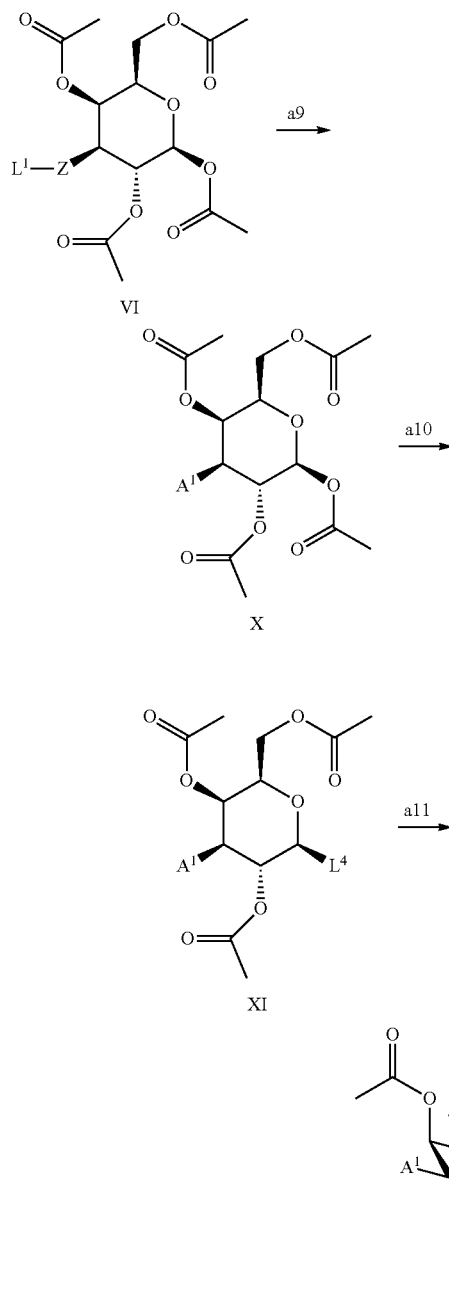

a9) Reacting a compound formula VI, wherein $L^1$-Z such as

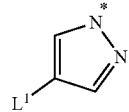

with a boronic acid or borinate of the formula such as $R^1$—$B(OH)_2$ or 4,4,5,5-tetramethyl-1,3,2-dioxaborolane-$R^1$ in the presence of a metalloorganic catalyst such as Pd(dppf)Cl$_2$ and a base such as potassium carbonate in solvents such as dioxane and water optionally at elevated temperature to give a compound of the formula X.

a10) Reacting a compound of the formula X with a reagent such as dichloromethylmethylether or PCl$_5$ in the presence of a lewis acid such as BF$_3$Et$_2$O in an inert solvent such as dichloromethane or chloroform to give a compound of formula XI wherein $L^4$ is defined as a halogen such as chlorine.

a11) Reacting a compound of formula XI with a reagent such as $B^1$—X—H such as $B^1$—S—H in the presence of a base like sodium hydride in an inert solvent such as DMF to give a compound of formula XII.

In a still further aspect the present invention relates to a process of preparing a compound of formula XII or a pharmaceutically acceptable salt or solvate thereof comprising the step a12-a13 where $A^1$, $B^1$ and X are defined as above under formula 1. $L^1$ is defined as bromine or iodine;

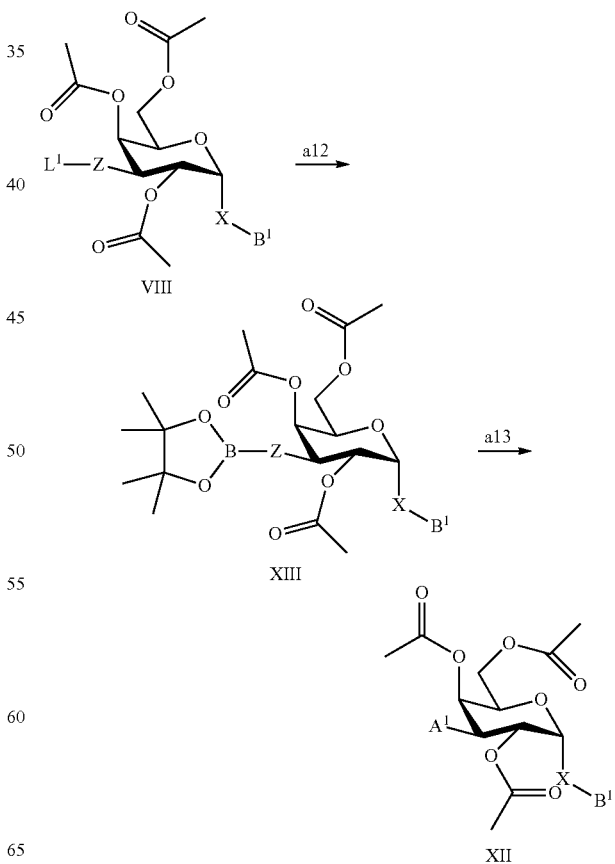

a12) Reacting a compound of the formula VIII $L^1$-Z such as

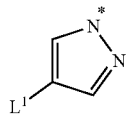

with bis(pinacolato)diboron in the presence of a metalloorganic reagent such as Pd(dppf)Cl$_2$ and a base such as potassium acetate in a solvent such as DMSO to give a compound of formula XIII.

a13) Reacting a compound of formula XIII with a compound of formula $R^1$-$L^5$ wherein $L^5$ is a halide such as Cl, Br or I in the presence of a metalloorganic reagent such as tetrakis(triphenylphosphine)palladium in a solvent such as toluene in the presence of a base such as Na$_2$CO$_3$ to give a compound of formula XII. $L^1$ is defined as bromine or iodine, In a still further aspect the present invention relates to a process of preparing a compound of formula XIII or a pharmaceutically acceptable salt or solvate thereof comprising the step a14-a16 where $B^1$ and X are defined as above under formula 1. $L^1$ is defined as bromine or iodine;

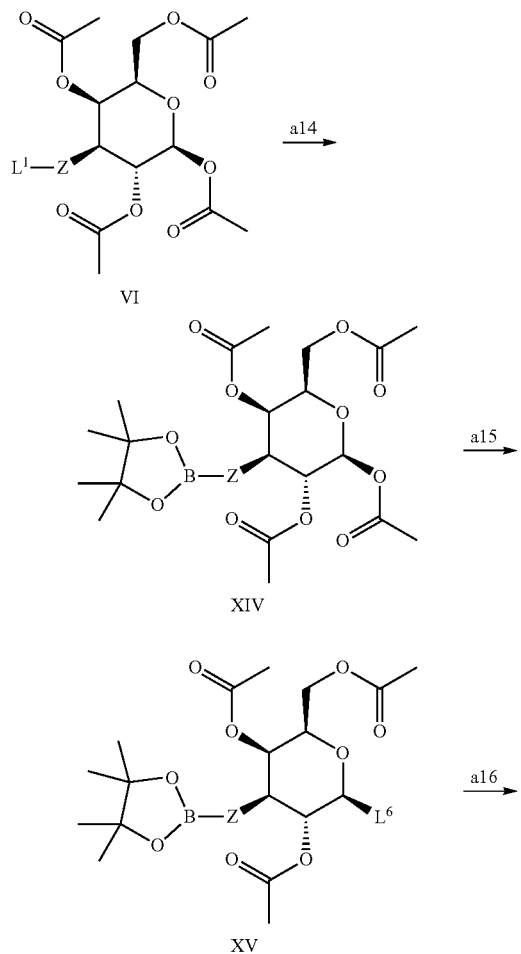

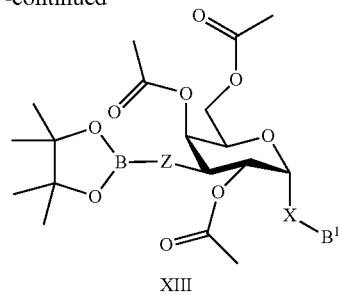

a14) Reacting a compound of formula VI wherein $L^1$-Z is defined as

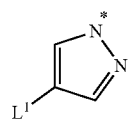

with bis(pinacolato)diboron in the presence of a metalloorganic reagent such as Pd(dppf)Cl$_2$ and a base such as potassium acetate in a solvent such as DMF to give a compound of formula XIV.

a15) Reacting a compound of formula XIV with a reagent such as dichloromethylmethylether or PCl$_5$ in the presence of a lewis acid such as BF$_3$Et$_2$O in an inert solvent such as dichloromethane or chloroform to give a compound of formula XV wherein $L^6$ is defined as a halogen such as chlorine.

a16) Reacting a compound of formula XV with a reagent such as $B^1$—X—H such as $B^1$—S—H in the presence of a base like sodium hydride in an inert solvent such as DMF to give a compound of formula XIII In a still further aspect the present invention relates to a process of preparing a compound of formula XIII or a pharmaceutically acceptable salt or solvate thereof comprising the step a17-a18 where $A^1$, $B^1$ and X are defined as above under formula 1. $L^1$ is defined as bromine or iodine;

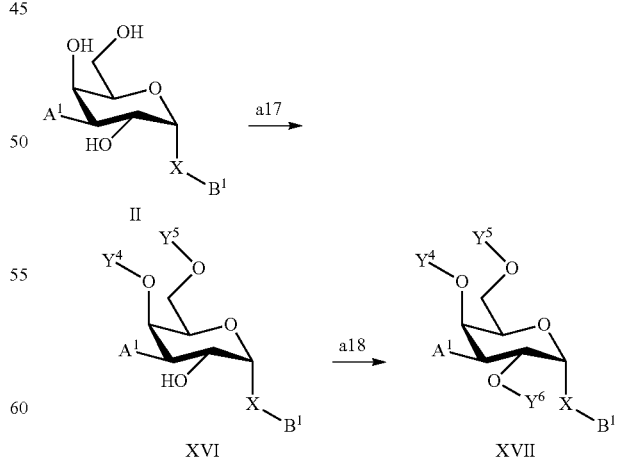

a17) Reacting a compound of formula II with benzaldehyde dimethylacetal and methanesulfonic acid to give a compound of formula XVI wherein $Y^5$ and $Y^5$ together form a protective group such as benzylidene.

a18) Reacting a compound of formula XVI wherein $Y^5$ and $Y^5$ together form a protective group such as benzylidene with an alkyl halide such as iodomethane in the presence of a base such as sodium hydride in a solvent such as DMF to give a compound of formula XVII wherein $Y^5$ and $Y^5$ together form a protective group such as benzylidene and $Y^6$ is a methyl.

In a still further aspect the present invention relates to a process of preparing a compound of formula XXI or a pharmaceutically acceptable salt or solvate thereof comprising the step a19-a20 where $R^1$, X and $B^1$ is defined as above under formula 1;

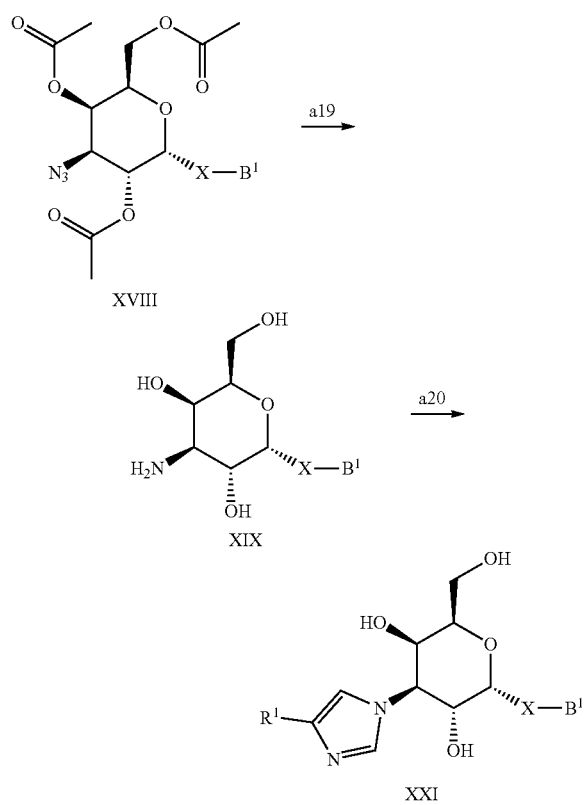

XVIII

XIX

XXI a19) Reacting a compound of the formula XVIII with sodium methoxide in methanol to give a product which is further reacted with 1,3-Propanedithiol and an organic base such as triethyl amine in a solvent such as methanol to give a compound of formula XIX.

a20) Reacting a compound of the formula

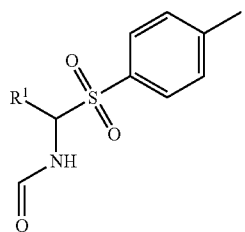

with phosphorous(V)oxylchloride in a solvent such as dimethoxyethane followed by addition of triethylamine to give an intermediate product A.

Reacting the compound of the formula XIX with oxoacetic acid and a base such as potassium carbonate in DMF followed by reaction with product A to give a compound of formula XXI.

In a still further aspect the present invention relates to a process of preparing a compound of formula XXIV or a pharmaceutically acceptable salt or solvate thereof comprising the step a21-a23 where $B^1$, Z and X are defined as above under formula 1. $L^1$ is defined as bromine or iodine;

In a still further aspect the present invention relates to a process of preparing a compound of formula XIII or a pharmaceutically acceptable salt or solvate thereof comprising the step a21-a23 where $B^1$ X and Z are defined as above under formula 1. $L^1$ is defined as bromine or iodine, $Y^7$ and $Y^8$ together form a protective group such as benzylidene and $Y^9$ is an alkyl group such as methyl;

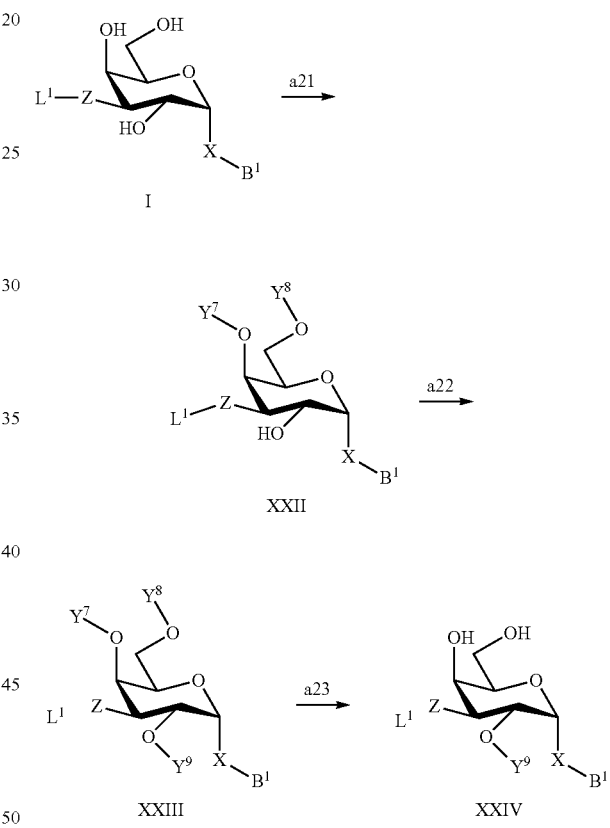

I

XXII

XXIII

XXIV a21) Reacting a compound of formula I with benzaldehyde dimethylacetal and methanesulfonic acid to give a compound of formula XXII.

a22) Reacting a compound of formula XXII with an alkyl halide such as iodomethane in the presence of a base such as sodium hydride in a solvent such as DMF to give a compound of formula XXIII.

a23) Reacting a compound of formula XXIII with an acid such as TFA to give a compound of formula XXIV.

In a still further aspect the present invention relates to a process of preparing a compound of formula XXXIII or a pharmaceutically acceptable salt or solvate thereof comprising the step a24-a31 wherein $R^1$ and $B^1$ is defined as under formula 1;

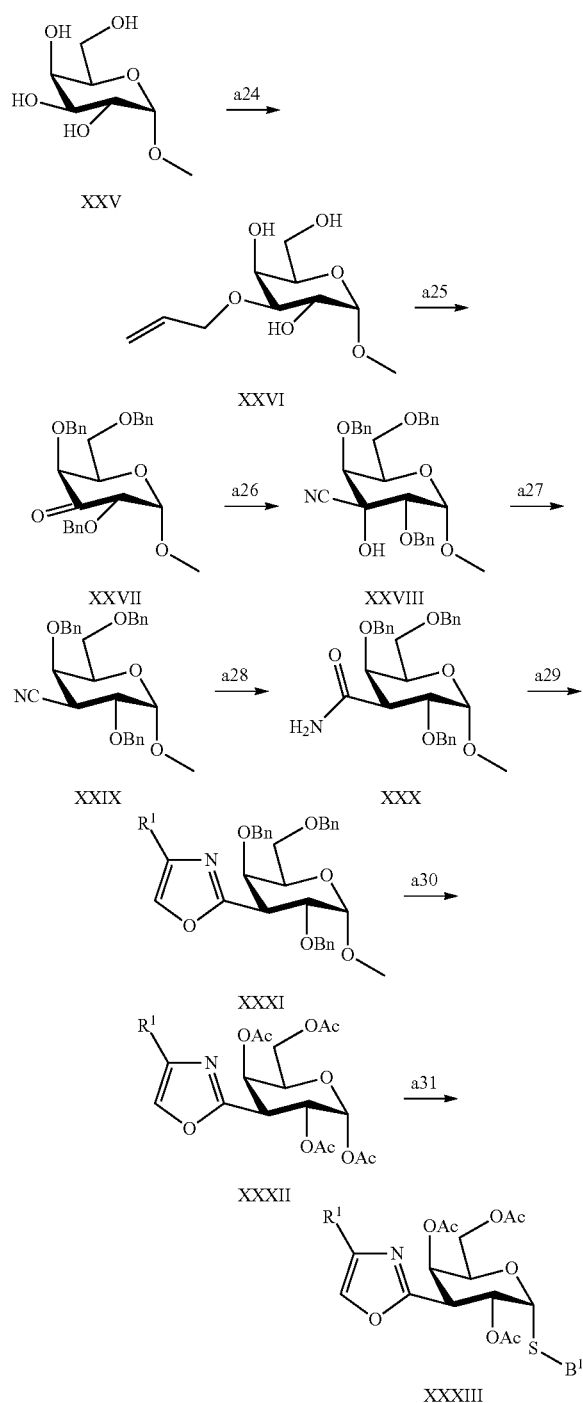

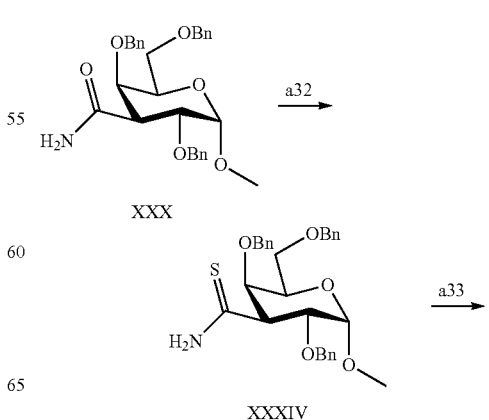

with Dess martin peroxinane in a solvent such as dichloromethane to give a compound of the formula XXVII.

a26) Reacting a compound of the formula XXVII with a cyanide reagent such as trimethylsilyl cyanide in the presence of AlCl$_3$ in a solvent such as DCM to give a compound of formula XXVIII.

a27) Reacting a compound of the formula XXVIII with O-phenyl chloromethanethioate in the presence of an organic bases 4-(dimethylamino)pyridine and triethylamine in a solvent such as acetonitrile to give a compound which is further reacted with 2,2'-azobis(2-methylpropionitrile and tris(trimethylsilyl)silane in a solvent such as toluene to give a compound of the formula XXIX.

a28) Reacting a compound of the formula XXIX was reacted with hydrogen peroxide in the presence of potassium carbonate in a solvent such as DMSO to give a compound of formula XXX.

a29) Reacting a compound of formula XXX with a compound of formula

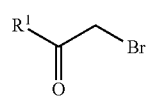

in the presence of silver trifluoromethanesulfonate in a solvent such as ethyl acetate to give a compound of formula XXXI.

A30) Reacting a compound of formula XXXI with hydrogen gas in the presence of Pd/C in a solvent such as methanol to give an intermediate compound which was further reacted with acetic anhydride in the presence of a base such as pyridine to give an intermediate compound which is further reacted with acetic anhydride in the presence of acetic acid and sulphuric acid to give a compound of the formula XXXII.

a31) Reacting a compound of the formula XXXII with a compound of the formula R$^1$—SH in the presence of boron trifluoride diethyl etherate in 1,2-dichloroethane to give a compound of formula XXXIII.

In a still further aspect the present invention relates to a process of preparing a compound of formula XXXVII or a pharmaceutically acceptable salt or solvate thereof comprising the step a32-a35 wherein R$^1$ and B$^1$ is defined as under formula 1;

a24) Reacting a compound of formula XXV with dibutyltinoxide in a solvent such as dry methanol at elevated temperatures followed by reaction with allylbromide in the presence of tetrabutylammoniumbromide in a solvent such as toluene to give a compound of formula XXVI.

a25) Reacting a compound of formula XXVI with benzylbromide in the presence of a base such as sodium hydride in a solvent such as DMF to give an intermediate compound which is reacted further with palladium(II)chloride in a solvent such as methanol to give another intermediate product which is reacted further

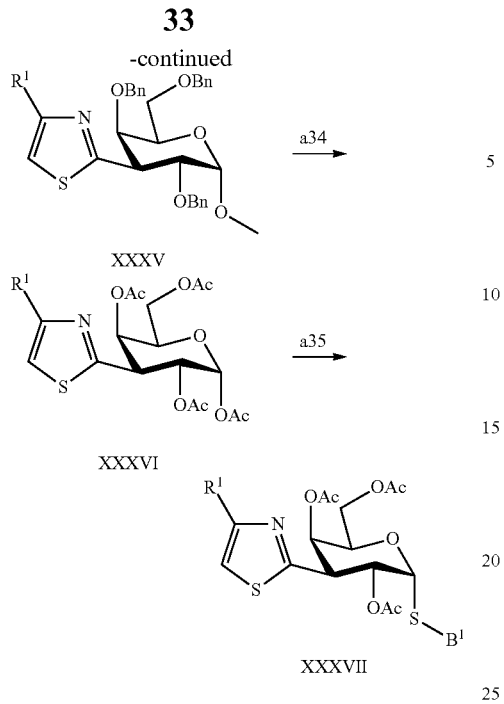

XXXV

XXXVI

XXXVII a32) Reacting a compound of formula XXX with lawessons reagent in THF to give a compound of the formula XXXIV.

a29) Reacting a compound of formula XXXIV with a compound of formula

in in a solvent such as ethanol to give a compound of formula XXXV.

A30) Reacting a compound of formula XXXV with trichloroborane n a solvent such as DCM to give an intermediate compound which was further reacted with acetic anhydride in the presence of a base such as pyridine to give an intermediate compound which is further reacted with acetic anhydride in the presence of acetic acid and sulphuric acid to give a compound of the formula XXXVI.

a31) Reacting a compound of the formula XXXVI with a compound of the formula $R^1$—SH in the presence of boron trifluoride diethyl etherate in 1,2-dichloroethane to give a compound of formula XXXVII.

In a still further aspect the present invention relates to a process of preparing a compound of formula XLII or a pharmaceutically acceptable salt or solvate thereof comprising the step a36-a40 wherein $R^1$ and $B^1$ is defined as under formula 1;

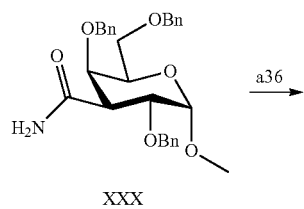

XXX

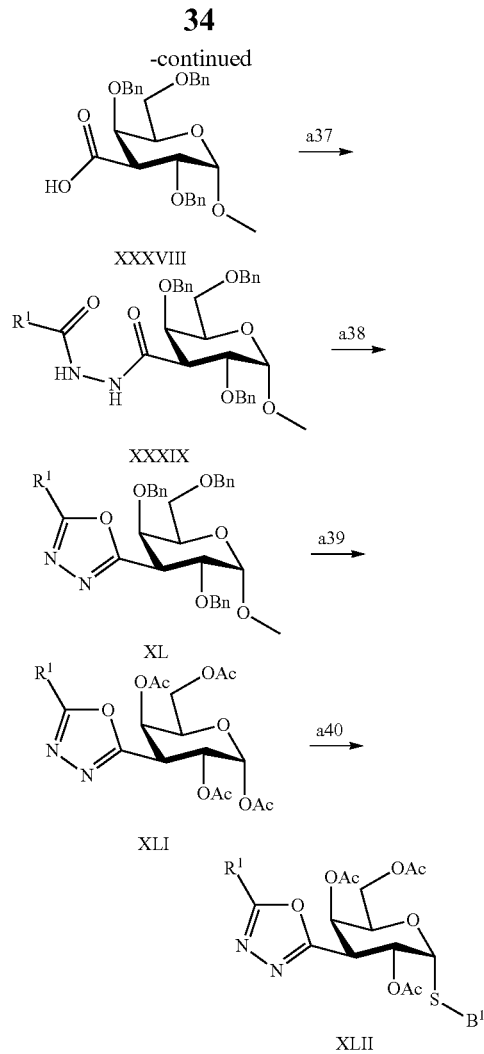

XXXVIII

XXXIX

XL

XLI

XLII a36) Reacting a compound of formula XXX with HCl followed by sodium nitrite in a solvent such as dioxane to give a compound of formula XXXVIII.

a37) Reacting a compound of formula XXXVIII a compound of the formula $R^1$—C(O)NHNH$_2$ using a reagent such as HATU in the presence of an organic base such as triethylamine to give a compound of formula XXXIX.

a38) Reacting a compound of formula XXXIX with Burgess reagent in a solvent mixture such as DMF/THF at elevated temperatures to give a compound of formula XL.

a39) Reacting a compound of formula XL with hydrogen in the presence of Pd/C in a solvent such as methanol to give an intermediate compound which was further reacted with acetic anhydride in the presence of a base such as pyridine to give an intermediate compound which is further reacted with acetic anhydride in the presence of acetic acid and sulphuric acid to give a compound of the formula XLI.

a40) Reacting a compound of the formula XLI with a compound of the formula $R^1$—SH in the presence of boron trifluoride diethyl etherate in 1,2-dichloroethane to give a compound of formula XLII.

In a still further aspect the present invention relates to a process of preparing a compound of the formula XLIV comprising step a41, wherein $B^1$ is defined as above under formula (1);

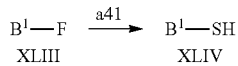

a41) Reacting a compound of the formula XLIII with Na$_2$S·10H$_2$O in the presence of a base such as NaOH in an inert solvent such as DMF to give a compound of formula XLIV.

It is understood that in any of the process steps a42-a45 below could be performed as part of the other processes above wherein B$^1$ is defined as substituent of the intermediates or products.

In a still further aspect the present invention relates to a process of preparing a compound of the formula XLVI comprising step a42, wherein B$^1$ is defined as above under formula (1);

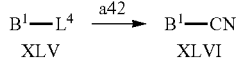

a42) Reacting a compound of the formula XLV, wherein L$^4$ is a leaving group such as bromine or iodine, with CuCN or zinc cyanide in an inert solvent such as dimethylformamide, optionally in the presence of a reagent such as tris(dibenzylideneacetone)dipalladium (0) and 1,1'-bis(diphenylphosphino)ferrocene at elevated temperatures, to give a compound of formula XLVI.

In a still further aspect the present invention relates to a process of preparing a compound of the formula XLVIII comprising step a43, wherein B$^1$ is defined as above under formula (1);

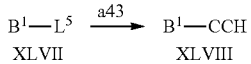

a43) Reacting a compound of the formula XLVII, wherein L$^5$ is a leaving group such as bromine or iodine, with an ethynyl reagent such as trimethylsilylacetylene. In the presence of a metallorganic reagents such as Pd(PPh$_3$)$_2$Cl$_2$ and CuI in a solvent such as THF to give a product which is optionally reacted further with TBAF to give a compound of the formula XLVIII.

In a still further aspect the present invention relates to a process of preparing a compound of the formula LX comprising step a44, wherein B1, R$^{6b}$, R$^{7b}$, R$^{12b}$, R$^{13b}$ is defined as above under formula (1);

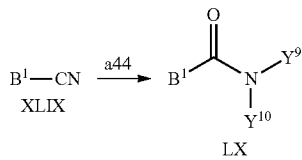

a44) Reacting a compound of the formula XLIX with a base such as sodium hydroxide to give an intermediate compound which could be reacted with an amide reagent such as HNR$^{6b}$R$^{7b}$ or HNR$^{12b}$R$^{13b}$ in the presence of a coupling reagent such as N-(3-dimethylaminopropyl)-N'-ethylcarbodiimide hydrochloride optionally in the presence of a reagent such as 1-hydroxybenzotriazole hydrate and an organic base such as triethyl amine in a solvent such as DMF to give a compound of formula LX wherein Y$^9$ is defined as R$^{6b}$ or R$^{12b}$ and Y$^{10}$ R$^{7b}$, R$^{13b}$.

In a still further aspect the present invention relates to a process of preparing a compound of the formula XLVI comprising step a45, wherein B$^1$ is defined as above under formula (1) Y$^{11}$, and Y$^{12}$ could together with a nitrogen form an N-(2-oxa)-6-azaspiro[3.3]heptanyl, L6 is a leaving group such as chloro, bromo or iodo.

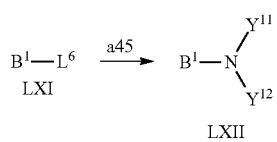

a45) Reacting a compound of formula LXI with a reagent such as HNY$^{11}$Y$^{12}$ in the presence of a base such as DIPEA in a solvent such as acetonitrile at elevated temperatures to give a compound of formula LXII.

In a still further aspect the present invention relates to a process of preparing a compound of the formula LXIV comprising step a46, wherein R$^1$ is defined as above under formula (1).

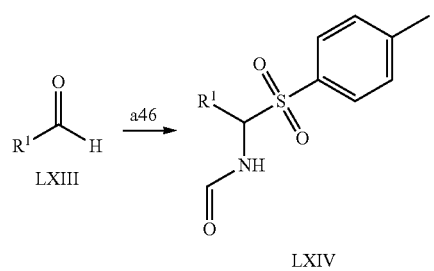

a46) Reacting p-toluenesulfinic acid sodium salt with concentrated HCl in a solvent mixture of water/tert-butyl methyl ether to give an intermediate product which is further reacted with LXIII in the presence of a reagents such as D(+)-10-camphorsulfonic acid and formamide in a solvent mixture such as toluene/MeCN to give a compound of formula LXIV.

In a still further aspect the present invention relates to a process of preparing a compound of the formula LXIV comprising step a47, wherein R$^1$ is defined as above under formula (1).

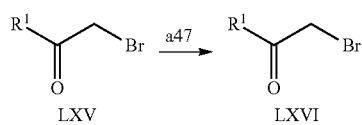

a47) Reacting a compound of formula LXV with tert-butyldimethylsilyl trifluoromethanesulfonate in the presence of triethylamine in a solvent such as DCM to give an intermediate product which is further reacted with and N-bromosuccinimide in a solvent such as ether to give a compound of the formula LXVI.

DETAILED DESCRIPTION

Figure 1:
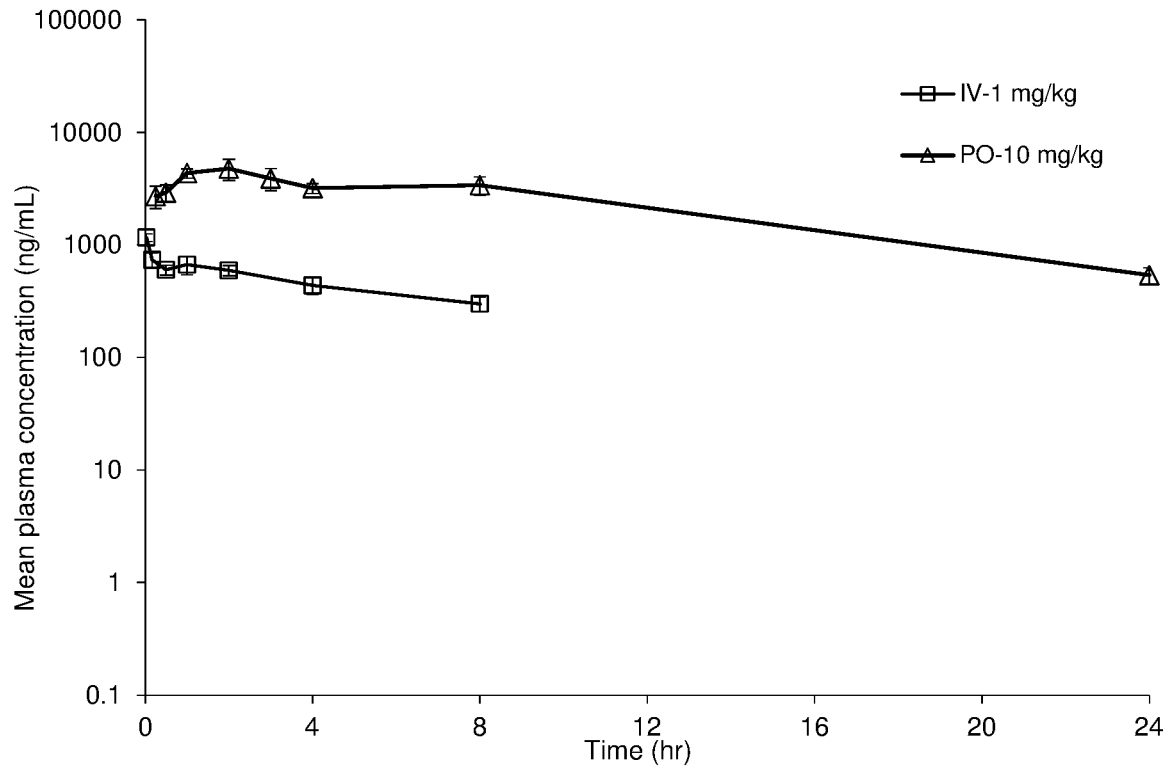
FIG. 1 compares the mean plasma levels after IV and PO administration

The present compounds of formula (1) differ from prior art compounds particularly in that the pyranose ring is α-D-galactopyranose. It is important to emphasize that alpha and beta anomers are very different isomers and it is by no means considered to be obvious to the skilled person to expect same or similar activity of both anomers. Consequently, alpha and beta anomers do not in general posses the same activity, and this is common knowledge to the skilled person. The compounds of the present invention are novel α-D-galactopyranose compounds that unexpectedly have shown very high affinity and specificity for galectin-3 and are considered novel potent drug candidates. Some of the novel α-D-galactopyranose compounds have galectin-1 affinity and some both galectin-1 and galectin-3 affinity and, as such have a broader disease treatment profile compared to selective galectin-1 inhibitors.

In broad aspect the present invention concerns a D-galactopyranose compound of formula (1)

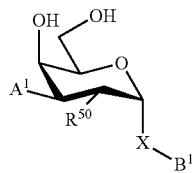

wherein
the pyranose ring is α-D-galactopyranose, and A1, X, $R^{50}$ and B1 are as defined above.

Preferably X is S.

Typically, Z is a pyrazolyl, preferably

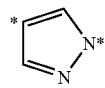

wherein the asterix on the carbon is linked to $R^1$ and the Asterix on the nitrogen is attached to the α-D-galactopyranose and X is S.

In another embodiment Z is selected from the group consisting of imidazole, such as 1,3-imidazol-2-yl; oxazolyl, such as oxazol-2-yl; oxadiazolyl; thiazolyl, such as thiazol-2-yl.

In one preferred embodiment $R^1$ is phenyl optionally substituted with a group selected from CN, OH, $NH_2$, F, Br, Cl, I, methyl optionally substituted with a fluorine (F), and $OCH_3$ optionally substituted with a F, and $SCH_3$ optionally substituted with a F. Typically, $R^1$ is phenyl substituted with one to three groups selected from F, Br, Cl, I, methyl.

In another preferred embodiment $R^1$ is

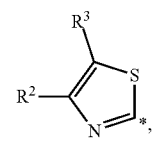

wherein $R^2$ is selected from the group consisting of OH, methyl and halogen, such as F, Cl and Br;
$R^3$ is selected from the group consisting of hydrogen, $C_{1-6}$ alkyl, such as methyl, and halogen. In one embodiment $R^2$ is halogen, such as Cl and $R^3$ is H.

In further preferred embodiment $R^1$ is

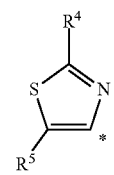

wherein
$R^4$ is selected from the group consisting of OH, $NH_2$ and halogen, such as F, Cl, and Br;
$R^5$ is selected from the group consisting of hydrogen, $C_{1-6}$ alkyl, such as methyl, and halogen. In one embodiment $R^4$ is H or OH and $R^5$ is H.

In further preferred embodiment $R^1$ is imidazolyl. In another preferred embodiment $R^1$ is oxadzolyl. In further preferred embodiment $R^1$ is pyrazolyl, optionally substituted with a $C_{1-3}$ alkyl, e.g. methyl. In a preferred embodiment B1 is a pyridinyl substituted with a group selected from a Cl; Br; $C_2$-alkynyl; CN; methyl; $CF_3$; pyridin; pyrimidin; oxazol; and thiazol.

In a further embodiment B1 is a pyridinyl substituted with a group selected from a Cl; Br; ethynyl; CN; methyl. In a still further embodiment B1 is a pyridinyl substituted with one or two selected from Cl; Br; ethynyl; CN; and methyl.

In a still further embodiment B1 is a phenyl substituted with a group selected from a halogen; and $C_{1-3}$ alkyl, optionally substituted with a F.

In a further embodiment B1 is a phenyl substituted with a group selected from the group consisting of Cl, CN, and $CONR^{6b}R^{7b}$, wherein $R^{6b}$ and $R^{7b}$ together with the nitrogen may form a heterocycloalkyl. In a still further embodiment B1 is a phenyl substituted with one or two of Cl, CN, and CO-azetidinyl.

In a further embodiment $R^{50}$ is selected from H, OH, $C_{1-4}$ alkyl, such as methyl, ethyl, or isopropyl, $C_{1-4}$ alkyl substituted with at least one from the group consisting of phenyl and phenyl substituted with one or more groups selected form OH and halogen.

In one embodiment $R^{50}$ is OH. In another embodiment $R^{50}$ is methoxy.

In a further embodiment the compound of formula (1) is selected from any one of:
3-Chlorophenyl 3-deoxy-3-[4-(3-fluorophenyl)-1H-1,2-pyrazol-1-yl]-1-thio-α-D-galactopyranoside,
5-Chloropyridin-3-yl 3-[4-(4-chloro-3,5-difluorophenyl)-1H-1,2-pyrazol-1-yl]-3-deoxy-1-thio-α-D-galactopyranoside,
5-Chloropyridin-3-yl 3-deoxy-3-[4-(3,4,5-trifluorophenyl)-1H-1,2-pyrazol-1-yl]-1-thio-α-D-galactopyranoside, and 5-Chloropyridin-3-yl 3-deoxy-3-[4-(3,5-difluoro-4-methylphenyl)-1H-1,2-pyrazol-1-yl]-1-thio-α-D-galactopyranoside.

In a still further embodiment the compound of formula (1) is selected from any one of:

3-Chlorophenyl 3-deoxy-3-[4-(3-fluorophenyl)-1H-1,2-pyrazol-1-yl]-1-thio-α-D-galactopyranoside, 5-Chloropyridin-3-yl 3-[4-(4-chloro-3,5-difluorophenyl)-1H-1,2-pyrazol-1-yl]-3-deoxy-1-thio-α-D-galactopyranoside, 5-Chloropyridin-3-yl 3-deoxy-3-[4-(3,4,5-trifluorophenyl)-1H-1,2-pyrazol-1-yl]-1-thio-α-D-galactopyranoside, 5-Chloropyridin-3-yl 3-deoxy-3-[4-(3,5-difluoro-4-methylphenyl)-1H-1,2-pyrazol-1-yl]-1-thio-α-D-galactopyranoside, 5-Bromopyridin-3-yl 3-deoxy-3-[4-(3,4,5-trifluorophenyl)-1H-1,2-pyrazol-1-yl]-1-thio-α-D-galactopyranoside, 5-Bromopyridin-3-yl 3-[4-(4-chloro-3,5-difluorophenyl)-1H-1,2-pyrazol-1-yl]-3-deoxy-1-thio-α-D-galactopyranoside, 5-Ethynylpyridin-3-yl 3-[4-(4-chloro-3,5-difluorophenyl)-1H-1,2-pyrazol-1-yl]-3-deoxy-1-thio-α-D-galactopyranoside, 5-Chloro-2-cyanophenyl 3-[4-(4-chloro-3,5-difluorophenyl)-1H-1,2-pyrazol-1-yl]-3-deoxy-1-thio-α-D-galactopyranoside, 2-(N-Azetidinyl-carbonyl)-5-chlorophenyl 3-[4-(4-chloro-3,5-difluorophenyl)-1H-1,2-pyrazol-1-yl]-3-deoxy-1-thio-α-D-galactopyranoside, 2-(N-Azetidinyl-carbonyl)-5-chlorophenyl 3-deoxy-3-[4-(3,4,5-trifluorophenyl)-1H-1,2-pyrazol-1-yl]-1-thio-α-D-galactopyranoside, 5-Chloro-2-cyanophenyl 3-deoxy-3-[4-(3,4,5-trifluorophenyl)-1H-1,2-pyrazol-1-yl]-1-thio-α-D-galactopyranoside, 5-Chloro-2-cyanopyridin-3-yl 3-deoxy-3-[4-(3,4,5-trifluorophenyl)-1H-1,2-pyrazol-1-yl]-1-thio-α-D-galactopyranoside, 5-Chloro-2-cyanopyridin-3-yl 3-[4-(4-chloro-3,5-difluorophenyl)-1H-1,2-pyrazol-1-yl]-3-deoxy-1-thio-α-D-galactopyranoside, 5-Chloro-2-methylpyridin-3-yl 3-deoxy-3-[4-(3,4,5-trifluorophenyl)-1H-1,2-pyrazol-1-yl]-1-thio-α-D-galactopyranoside, 5-Bromo-2-cyanopyridin-3-yl 3-deoxy-3-[4-(3,4,5-trifluorophenyl)-1H-1,2-pyrazol-1-yl]-1-thio-α-D-galactopyranoside, 2-Cyano-5-ethynylpyridin-3-yl 3-deoxy-3-[4-(3,4,5-trifluorophenyl)-1H-1,2-pyrazol-1-yl]-1-thio-α-D-galactopyranoside, 5-Chloropyridin-3-yl 3-[4-(4-chloro-3-fluorophenyl)-1H-1,2-pyrazol-1-yl]-3-deoxy-1-thio-α-D-galactopyranoside, 5-Chloropyridin-3-yl 3-deoxy-3-[4-(6-fluoropyridin-2-yl)-1H-1,2-pyrazol-1-yl]-1-thio-α-D-galactopyranoside, 5-Chloropyridin-3-yl 3-deoxy-3-[4-(5-fluoropyridin-2-yl)-1H-1,2-pyrazol-1-yl]-1-thio-α-D-galactopyranoside, 5-Chloropyridin-3-yl 3-deoxy-3-[4-(4-fluoropyridin-2-yl)-1H-1,2-pyrazol-1-yl]-1-thio-α-D-galactopyranoside, 5-Chloropyridin-3-yl 3-deoxy-3-[4-(1H-1,2-pyrazol-3-yl)-1H-1,2-pyrazol-1-yl]-1-thio-α-D-galactopyranoside, 5-Chloropyridin-3-yl 3-deoxy-3-[4-(1-methyl-1,2-pyrazol-3-yl)-1H-1,2-pyrazol-1-yl]-1-thio-α-D-galactopyranoside, 5-Chloropyridin-3-yl 3-deoxy-3-[4-(1H-imidazol-2-yl)-1H-1,2-pyrazol-1-yl]-1-thio-α-D-galactopyranoside, 5-Chloropyridin-3-yl 3-deoxy-3-[4-(oxazol-2-yl)-1H-1,2-pyrazol-1-yl]-1-thio-α-D-galactopyranoside, 5-Chloropyridin-3-yl 3-deoxy-3-[4-(thiazol-4-yl)-1H-1,2-pyrazol-1-yl]-1-thio-α-D-galactopyranoside, 5-Chloropyridin-3-yl 3-deoxy-3-[4-(thiazol-2-yl)-1H-1,2-pyrazol-1-yl]-1-thio-α-D-galactopyranoside, 5-Chloropyridin-3-yl 3-[4-(4-chlorothiazol-2-yl)-1H-1,2-pyrazol-1-yl]-3-deoxy-1-thio-α-D-galactopyranoside, 5-Bromopyridin-3-yl 3-[4-(4-chlorothiazol-2-yl)-1H-1,2-pyrazol-1-yl]-3-deoxy-1-thio-α-D-galactopyranoside, 5-Chloro-2-cyanophenyl 3-[4-(4-chlorothiazol-2-yl)-1H-1,2-pyrazol-1-yl]-3-deoxy-1-thio-α-D-galactopyranoside, 5-Chloro-2-cyanopyridin-3-yl 3-[4-(4-chlorothiazol-2-yl)-1H-1,2-pyrazol-1-yl]-3-deoxy-1-thio-α-D-galactopyranoside, 5-Chloropyridin-3-yl 3-deoxy-3-[4-(2-hydroxythiazol-4-yl)-1H-1,2-pyrazol-1-yl]-1-thio-α-D-galactopyranoside, 5-Chloropyridin-3-yl 3-deoxy-3-[4-(3,4,5-trifluorophenyl)-1H-1,2-pyrazol-1-yl]-2-O-methyl-1-thio-α-D-galactopyranoside, 5-Bromopyridin-3-yl 3-deoxy-3-[4-(3,4,5-trifluorophenyl)-1H-1,2-pyrazol-1-yl]-2-O-methyl-1-thio-α-D-galactopyranoside, 5-Ethynylpyridin-3-yl 3-deoxy-3-[4-(3,4,5-trifluorophenyl)-1H-1,2-pyrazol-1-yl]-2-O-methyl-1-thio-α-D-galactopyranoside, 5-Chloro-2-cyanopyridin-3-yl 3-deoxy-3-[4-(3,4,5-trifluorophenyl)-1H-1,2-pyrazol-1-yl]-2-O-methyl-1-thio-α-D-galactopyranoside, 5-Chloropyridin-3-yl 3-deoxy-3-[4-(3,4,5-trifluorophenyl)-1H-1,3-imidazol-1-yl]-1-thio-α-D-galactopyranoside, 5-Chloro-[3,3-bis(hydroxymethyl)azetidin-1-yl]pyridin-3-yl 3-deoxy-3-[4-(3,4,5-trifluorophenyl)-1H-1,2-pyrazol-1-yl]-1-thio-α-D-galactopyranoside, 5-Chloropyridin-3-yl 3-deoxy-3-[3-(3,4,5-trifluorophenyl)-1H-1,2-pyrazol-1-yl]-1-thio-α-D-galactopyranoside, 5-Bromo-2-cyanopyridin-3-yl 3-[5-(4-chlorothiazol-2-yl)-1-methyl-1H-1,2-pyrazol-3-yl]-3-deoxy-1-thio-α-D-galactopyranoside, 3,4-Dichlorophenyl 3-deoxy-3-[4-(3,4,5-trifluorophenyl)-oxazol-2-yl]-1-thio-α-D-galactopyranoside, 3,4-Dichlorophenyl 3-deoxy-3-[4-(3,4,5-trifluorophenyl)-thiazol-2-yl]-1-thio-α-D-galactopyranoside, 3,4-Dichlorophenyl 3-deoxy-3-[5-(3,4,5-trifluorophenyl)-1,3,4-oxadiazol-2-yl]-1-thio-α-D-galactopyranoside, 3,4-Dichlorophenyl 3-deoxy-3-[4-(2-hydroxythiazol-4-yl)-1H-1,2-pyrazol-1-yl]-2-O-methyl-1-thio-α-D-galactopyranoside, 5-Chloro-2-cyanophenyl 3-[4-(4-chloro-3,5-difluorophenyl)-1H-1,2-pyrazol-1-yl]-3-deoxy-2-O-methyl-1-thio-α-D-galactopyranoside, 5-Chloro-2-cyanophenyl 3-deoxy-3-[4-(3,4,5-trifluorophenyl)-1H-1,2-pyrazol-1-yl]-2-O-methyl-1-thio-α-D-galactopyranoside, and 5-Chloro-2-cyanophenyl 3-deoxy-3-[4-(2-hydroxythiazol-4-yl)-1H-1,2-pyrazol-1-yl]-2-O-methyl-1-thio-α-D-galactopyranoside.

In a still further embodiment the compound of formula (1) is selected from any one of:

3-Chlorophenyl 3-deoxy-3-[4-(3-fluorophenyl)-1H-1,2-pyrazol-1-yl]-1-thio-α-D-galactopyranoside, 5-Chloropyridin-3-yl 3-[4-(4-chloro-3,5-difluorophenyl)-1H-1,2-pyrazol-1-yl]-3-deoxy-1-thio-α-D-galactopyranoside, 5-Chloropyridin-3-yl 3-deoxy-3-[4-(3,4,5-trifluorophenyl)-1H-1,2-pyrazol-1-yl]-1-thio-α-D-galactopyranoside, 5-Chloropyridin-3-yl 3-deoxy-3-[4-(3,5-difluoro-4-methylphenyl)-1H-1,2-pyrazol-1-yl]-1-thio-α-D-galactopyranoside, 5-Bromopyridin-3-yl 3-deoxy-3-[4-(3,4,5-trifluorophenyl)-1H-1,2-pyrazol-1-yl]-1-thio-α-D-galactopyranoside,
5-Bromopyridin-3-yl 3-[4-(4-chloro-3,5-difluorophenyl)-1H-1,2-pyrazol-1-yl]-3-deoxy-1-thio-α-D-galactopyranoside,
5-Ethynylpyridin-3-yl 3-[4-(4-chloro-3,5-difluorophenyl)-1H-1,2-pyrazol-1-yl]-3-deoxy-1-thio-α-D-galactopyranoside,
5-Chloro-2-cyanophenyl 3-[4-(4-chloro-3,5-difluorophenyl)-1H-1,2-pyrazol-1-yl]-3-deoxy-1-thio-α-D-galactopyranoside,
2-(N-Azetidinyl-carbonyl)-5-chlorophenyl 3-[4-(4-chloro-3,5-difluorophenyl)-1H-1,2-pyrazol-1-yl]-3-deoxy-1-thio-α-D-galactopyranoside,
2-(N-Azetidinyl-carbonyl)-5-chlorophenyl 3-deoxy-3-[4-(3,4,5-trifluorophenyl)-1H-1,2-pyrazol-1-yl]-1-thio-α-D-galactopyranoside,
5-Chloro-2-cyanophenyl 3-deoxy-3-[4-(3,4,5-trifluorophenyl)-1H-1,2-pyrazol-1-yl]-1-thio-α-D-galactopyranoside,
5-Chloro-2-cyanopyridin-3-yl 3-deoxy-3-[4-(3,4,5-trifluorophenyl)-1H-1,2-pyrazol-1-yl]-1-thio-α-D-galactopyranoside,
5-Chloro-2-cyanopyridin-3-yl 3-[4-(4-chloro-3,5-difluorophenyl)-1H-1,2-pyrazol-1-yl]-3-deoxy-1-thio-α-D-galactopyranoside,
5-Chloro-2-methylpyridin-3-yl 3-deoxy-3-[4-(3,4,5-trifluorophenyl)-1H-1,2-pyrazol-1-yl]-1-thio-α-D-galactopyranoside,
5-Bromo-2-cyanopyridin-3-yl 3-deoxy-3-[4-(3,4,5-trifluorophenyl)-1H-1,2-pyrazol-1-yl]-1-thio-α-D-galactopyranoside,
2-Cyano-5-ethynylpyridin-3-yl 3-deoxy-3-[4-(3,4,5-trifluorophenyl)-1H-1,2-pyrazol-1-yl]-1-thio-α-D-galactopyranoside,
5-Chloropyridin-3-yl 3-[4-(4-chloro-3-fluorophenyl)-1H-1,2-pyrazol-1-yl]-3-deoxy-1-thio-α-D-galactopyranoside,
5-Chloropyridin-3-yl 3-deoxy-3-[4-(6-fluoropyridin-2-yl)-1H-1,2-pyrazol-1-yl]-1-thio-α-D-galactopyranoside,
5-Chloropyridin-3-yl 3-deoxy-3-[4-(5-fluoropyridin-2-yl)-1H-1,2-pyrazol-1-yl]-1-thio-α-D-galactopyranoside,
5-Chloropyridin-3-yl 3-deoxy-3-[4-(4-fluoropyridin-2-yl)-1H-1,2-pyrazol-1-yl]-1-thio-α-D-galactopyranoside,
5-Chloropyridin-3-yl 3-deoxy-3-[4-(1H-1,2-pyrazol-3-yl)-1H-1,2-pyrazol-1-yl]-1-thio-α-D-galactopyranoside,
5-Chloropyridin-3-yl 3-deoxy-3-[4-(1-methyl-1,2-pyrazol-3-yl)-1H-1,2-pyrazol-1-yl]-1-thio-α-D-galactopyranoside,
5-Chloropyridin-3-yl 3-deoxy-3-[4-(1H-imidazol-2-yl)-1H-1,2-pyrazol-1-yl]-1-thio-α-D-galactopyranoside,
5-Chloropyridin-3-yl 3-deoxy-3-[4-(oxazol-2-yl)-1H-1,2-pyrazol-1-yl]-1-thio-α-D-galactopyranoside,
5-Chloropyridin-3-yl 3-deoxy-3-[4-(thiazol-4-yl)-1H-1,2-pyrazol-1-yl]-1-thio-α-D-galactopyranoside,
5-Chloropyridin-3-yl 3-deoxy-3-[4-(thiazol-2-yl)-1H-1,2-pyrazol-1-yl]-1-thio-α-D-galactopyranoside,
5-Chloropyridin-3-yl 3-[4-(4-chlorothiazol-2-yl)-1H-1,2-pyrazol-1-yl]-3-deoxy-1-thio-α-D-galactopyranoside,
5-Bromopyridin-3-yl 3-[4-(4-chlorothiazol-2-yl)-1H-1,2-pyrazol-1-yl]-3-deoxy-1-thio-α-D-galactopyranoside,
5-Chloro-2-cyanophenyl 3-[4-(4-chlorothiazol-2-yl)-1H-1,2-pyrazol-1-yl]-3-deoxy-1-thio-α-D-galactopyranoside,
5-Chloro-2-cyanopyridin-3-yl 3-[4-(4-chlorothiazol-2-yl)-1H-1,2-pyrazol-1-yl]-3-deoxy-1-thio-α-D-galactopyranoside,
5-Chloropyridin-3-yl 3-deoxy-3-[4-(2-hydroxythiazol-4-yl)-1H-1,2-pyrazol-1-yl]-1-thio-α-D-galactopyranoside,
5-Chloropyridin-3-yl 3-deoxy-3-[4-(3,4,5-trifluorophenyl)-1H-1,2-pyrazol-1-yl]-2-O-methyl-1-thio-α-D-galactopyranoside,
5-Bromopyridin-3-yl 3-deoxy-3-[4-(3,4,5-trifluorophenyl)-1H-1,2-pyrazol-1-yl]-2-O-methyl-1-thio-α-D-galactopyranoside,
5-Ethynylpyridin-3-yl 3-deoxy-3-[4-(3,4,5-trifluorophenyl)-1H-1,2-pyrazol-1-yl]-2-O-methyl-1-thio-α-D-galactopyranoside,
5-Chloro-2-cyanopyridin-3-yl 3-deoxy-3-[4-(3,4,5-trifluorophenyl)-1H-1,2-pyrazol-1-yl]-2-O-methyl-1-thio-α-D-galactopyranoside,
5-Chloropyridin-3-yl 3-deoxy-3-[4-(3,4,5-trifluorophenyl)-1H-1,3-imidazol-1-yl]-1-thio-α-D-galactopyranoside,
5-Chloro-[3,3-bis(hydroxymethyl)azetidin-1-yl]pyridin-3-yl 3-deoxy-3-[4-(3,4,5-trifluorophenyl)-1H-1,2-pyrazol-1-yl]-1-thio-α-D-galactopyranoside,
5-Chloropyridin-3-yl 3-deoxy-3-[3-(3,4,5-trifluorophenyl)-1H-1,2-pyrazol-1-yl]-1-thio-α-D-galactopyranoside,
3,4-Dichlorophenyl 3-deoxy-3-[4-(3,4,5-trifluorophenyl)-oxazol-2-yl]-1-thio-α-D-galactopyranoside,
3,4-Dichlorophenyl 3-deoxy-3-[4-(3,4,5-trifluorophenyl)-thiazol-2-yl]-1-thio-α-D-galactopyranoside,
3,4-Dichlorophenyl 3-deoxy-3-[5-(3,4,5-trifluorophenyl)-1,3,4-oxadiazol-2-yl]-1-thio-α-D-galactopyranoside,
3,4-Dichlorophenyl 3-deoxy-3-[4-(2-hydroxythiazol-4-yl)-1H-1,2-pyrazol-1-yl]-2-O-methyl-1-thio-α-D-galactopyranoside,
5-Chloro-2-cyanophenyl 3-[4-(4-chloro-3,5-difluorophenyl)-1H-1,2-pyrazol-1-yl]-3-deoxy-2-O-methyl-1-thio-α-D-galactopyranoside,
5-Chloro-2-cyanophenyl 3-deoxy-3-[4-(3,4,5-trifluorophenyl)-1H-1,2-pyrazol-1-yl]-2-O-methyl-1-thio-α-D-galactopyranoside, and
5-Chloro-2-cyanophenyl 3-deoxy-3-[4-(2-hydroxythiazol-4-yl)-1H-1,2-pyrazol-1-yl]-2-O-methyl-1-thio-α-D-galactopyranoside.

As explained in the experimental section some of the prepared compounds of formula 1 wherein Z is pyrazol, X is S, $R^1$ is as defined above, $R^{51}$ is a selection of $R^{50}$ as defined above, and B1 is as defined above have high oral bioavailability and good CNS potential as evidenced by the data in the experimental section below.

In a particular aspect the present invention relates to a compound of formula 1A

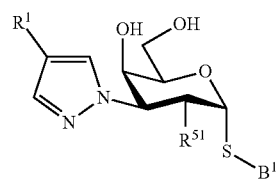

1A wherein
the pyranose ring is α-D-galactopyranose,
$R^1$ is selected from a) an aryl, such as phenyl or naphthyl, optionally substituted with a group selected from a halogen; CN; —COOH; —CONR$^{6a}$R$^{7a}$, wherein R$^{6a}$ and R$^{7a}$ are independently selected from H, C$_{1-3}$ alkyl, cyclopropyl, and iso-propyl, or R$^{6a}$ and R$^{7a}$ together with the nitrogen may form a heterocycloalkyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; $NR^{8a}R^{9a}$, wherein $R^{8a}$ and $R^{9a}$ are independently selected from H, $C_{1-3}$ alkyl and isopropyl; OH; and $R^{10a}$—CONH— wherein $R^{10a}$ is selected from $C_{1-3}$ alkyl and cyclopropyl; b) a heterocycle, such as heteroaryl or heterocycloalkyl, optionally substituted with a group selected from a halogen; a spiro heterocycle; CN; —COOH; —CONR$^{12a}$R$^{13a}$ wherein $R^{12a}$ and $R^{13a}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{14a}R^{15a}$, wherein $R^{14a}$ and $R^{15a}$ are independently selected from H, $C_{1-3}$ alkyl, cyclopropyl and isopropyl, C(=O)—$R^{21a}$, wherein $R^{21a}$ is selected from H and $C_{1-3}$ alkyl; OH; and $R^{16a}$—CONH— wherein $R^{16a}$ is selected from $C_{1-3}$ alkyl and cyclopropyl;

$B^1$ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and $R^{4b}$—CONH— wherein $R^{4b}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and $R^{5b}$—CONH— wherein $R^{5b}$ is selected from $C_{1-3}$ alkyl and cyclopropyl; b) an aryl, such as phenyl or naphthyl, optionally substituted with a group selected from a halogen; CN; $C_2$-alkynyl; —COOH; —CONR$^{6b}$R$^{7b}$, wherein $R^{6b}$ and $R^{7b}$ are independently selected from H, $C_{1-3}$ alkyl, cyclopropyl, and iso-propyl, or $R^{6b}$ and $R^{7b}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{8b}R^{9b}$, wherein $R^{8b}$ and $R^{9b}$ are independently selected from H, $C_{1-3}$ alkyl and isopropyl; OH; a heterocycle optionally substituted with a $C_{1-3}$ alkyl optionally substituted with a OH; and $R^{19b}$—CONH— wherein $R^{19b}$ is selected from $C_{1-3}$ alkyl and cyclopropyl; c) a $C_{5-7}$ cycloalkyl, optionally substituted with a substituent selected from a halogen, $C_2$-alkynyl, CN, methyl optionally substituted with a F, $OCH_3$ optionally substituted with a F, $OCH_2CH_3$ optionally substituted with a F, OH, and $R^{11b}$—CONH— wherein $R^{11b}$ is selected from $C_{1-3}$ alkyl and cyclopropyl; and d) a heterocycle, such as heteroaryl or heterocycloalkyl, optionally substituted with a group selected from a halogen; a spiro heterocycle, such as N-(2-oxa)-6-azaspiro[3.3]heptanyl; $C_2$-alkynyl; CN; —COOH; —CONR$^{12b}$R$^{13b}$, wherein $R^{12b}$ and $R^{13b}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{14b}R^{15b}$, wherein $R^{14b}$ and $R^{15b}$ are independently selected from H, $C_{1-3}$ alkyl and isopropyl; OH; a heterocycle optionally substituted with a $C_{1-3}$ alkyl optionally substituted with a OH; and $R^{16b}$—CONH— wherein $R^{16b}$ is selected from $C_{1-3}$ alkyl and cyclopropyl; e) a $C_{1-6}$ alkyl or branched $C_{3-6}$ alkyl; f) $C_{2-6}$ alkynyl;

$R^{51}$ is selected from the group consisting of a1) OH and, a2) $OC_{1-6}$ alkyl optionally substituted with one or more halogen, phenyl, phenyl substituted with one or more groups selected form OH and halogen, CN, $OR^{17b}$, $NR^{18b}R^{19b}$, and $CONH_2$, wherein $R^{17b}$ is selected from the group consisting of H, CN, a halogen, methyl optionally substituted with a F, $OCH_3$ optionally substituted with a F, $OCH_2CH_3$ optionally substituted with a F, OH, and $R^{29b}$—CONH— wherein $R^{29b}$ is selected from $C_{1-3}$ alkyl and cyclopropyl, $R^{18b}$ is selected from the group consisting of H, CN, a halogen, methyl optionally substituted with a F, $OCH_3$ optionally substituted with a F, $OCH_2CH_3$ optionally substituted with a F, OH, and $R^{21b}$—CONH— wherein $R^{21b}$ is selected from $C_{1-3}$ alkyl and cyclopropyl, and $R^{19b}$ is selected from the group consisting of H, CN, a halogen, methyl optionally substituted with a F, $OCH_3$ optionally substituted with a F, $OCH_2CH_3$ optionally substituted with a F, OH, and $R^{22b}$—CONH— wherein $R^{22b}$ is selected from $C_{1-3}$ alkyl and cyclopropyl; or a pharmaceutically acceptable salt or solvate thereof.

In an embodiment of formula 1A $R^1$ is selected from an aryl, such as phenyl or naphthyl, optionally substituted with a group selected from a halogen; CN; —COOH; —CONR$^{6a}$R$^{7a}$, wherein $R^{6a}$ and $R^{7a}$ are independently selected from H, $C_{1-3}$ alkyl, cyclopropyl, and iso-propyl, or $R^{6a}$ and $R^{7a}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{8a}R^{9a}$, wherein $R^{8a}$ and $R^{9a}$ are independently selected from H, $C_{1-3}$ alkyl and isopropyl; OH; and $R^{19a}$—CONH— wherein $R^{10a}$ is selected from $C_{1-3}$ alkyl and cyclopropyl. In a further embodiment of formula 1A $R^1$ is selected from a phenyl substituted with a group selected from a halogen. Typically, $R^1$ is selected from a phenyl substituted with two or more halogens, such as Cl or F, preferably in the meta and/or para position on the phenyl. The halogens should not be in the ortho position on the phenyl.

In an embodiment of formula 1A $B^1$ is selected from the group consisting of b) an aryl, such as phenyl or naphthyl, optionally substituted with a group selected from a halogen; CN; $C_2$-alkynyl; —COOH; —CONR$^{6b}$R$^{7b}$, wherein $R^{6b}$ and $R^{7b}$ are independently selected from H, $C_{1-3}$ alkyl, cyclopropyl, and iso-propyl, or $R^{6b}$ and $R^{7b}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{8b}R^{9b}$, wherein $R^{8b}$ and $R^{9b}$ are independently selected from H, $C_{1-3}$ alkyl and isopropyl; OH; a heterocycle optionally substituted with a $C_{1-3}$ alkyl optionally substituted with a OH; and $R^{19b}$—CONH— wherein $R^{10b}$ is selected from $C_{1-3}$ alkyl and cyclopropyl; and d) a heterocycle, such as heteroaryl or heterocycloalkyl, optionally substituted with a group selected from a halogen; a spiro heterocycle, such as N-(2-oxa)-6-azaspiro[3.3]heptanyl;

$C_2$-alkynyl; CN; —COOH; —CONR$^{12b}$R$^{13b}$, wherein R$^{12b}$ and R$^{13b}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; NR$^{14b}$R$^{15b}$, wherein R$^{14b}$ and R$^{15b}$ are independently selected from H, $C_{1-3}$ alkyl and isopropyl; OH; a heterocycle optionally substituted with a $C_{1-3}$ alkyl optionally substituted with a OH; and R$^{16b}$—CONH— wherein R$^{16b}$ is selected from $C_{1-3}$ alkyl and cyclopropyl. In a further embodiment of formula 1A B$^1$ is selected from a phenyl substituted with one or two substituents selected from halogen and CN, such as Cl and CN. Typically, B$^1$ is selected from a phenyl substituted with two substituents selected from Cl and CN, such as one Cl and one CN. In a still further embodiment of formula 1A B$^1$ is selected from a pyridyl substituted with one or two substituents selected from one or more of halogen, CN and ethynyl. Typically, B$^1$ is selected from a pyridyl substituted with one substituents selected from one or more of Br, Cl, CN and ethynyl. In another embodiment B$^1$ is selected from a pyridyl substituted with two substituents selected from one or more of Br, Cl, CN and ethynyl.

In an embodiment of formula 1A R$^{51}$ is selected from the group consisting of a1) OH and, a2) $OC_{1-6}$ alkyl optionally substituted with one or more halogen, phenyl, phenyl substituted with one or more groups selected form OH and halogen, CN, OR$^{17b}$, NR$^{18b}$R$^{19b}$, and CONH$_2$, wherein R$^{17b}$ is selected from the group consisting of H, CN, a halogen, methyl optionally substituted with a F, OCH$_3$ optionally substituted with a F, OCH$_2$CH$_3$ optionally substituted with a F, OH, and R$^{20b}$—CONH— wherein R$^{20b}$ is selected from $C_{1-3}$ alkyl and cyclopropyl, R$^{18b}$ is selected from the group consisting of H, CN, a halogen, methyl optionally substituted with a F, OCH$_3$ optionally substituted with a F, OCH$_2$CH$_3$ optionally substituted with a F, OH, and R$^{21b}$—CONH— wherein R$^{21b}$ is selected from $C_{1-3}$ alkyl and cyclopropyl, and R$^{19b}$ is selected from the group consisting of H, CN, a halogen, methyl optionally substituted with a F, OCH$_3$ optionally substituted with a F, OCH$_2$CH$_3$ optionally substituted with a F, OH, and R$^{22b}$—CONH— wherein R$^{22b}$ is selected from $C_{1-3}$ alkyl and cyclopropyl. In a further embodiment of formula 1A R$^{51}$ is selected from OH and $OC_{1-4}$ alkyl. Typically, R$^{51}$ is selected from OH and OCH$_3$.

The skilled person will understand that it may be necessary to adjust or change the order of steps in the processes a1 to a6, and such change of order is encompassed by the aspects of the process as described above in the reaction schemes and accompanying description of the process steps.

Furthermore, the skilled person will understand that the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g. t-butyldimethylsilyl, t-butyldipheylsilyl or trimethylsilyl), AcO(acetoxy), TBS(t-butyldimethylsilyl), TMS(trimethylsilyl), PMB (p-methoxybensyl), and tetrahydropyranyl. Suitable protecting groups for carboxylic acid include ($C_{1-6}$)-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbony 1 (Teoc). Suitable protecting groups for S include 5-C(=N)NH$_2$, TIPS.

The protection and deprotection of functional groups may take place before or after any reaction in the above-mentioned processes.

Furthermore the skilled person will appreciate, that, in order to obtain compounds of the invention in an alternative, and on some occasions more convenient manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

In a still further embodiment the compound (1) is on free form. "On free form" as used herein means a compound of formula (1), either an acid form or base form, or as a neutral compound, depending on the substitutents. The free form does not have any acid salt or base salt in addition. In one embodiment the free form is an anhydrate. In another embodiment the free form is a solvate, such as a hydrate.

In a further embodiment the compound of formula (1) is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "$C_{1-x}$ alkyl" as used herein means an alkyl group containing 1-x carbon atoms, e.g. $C_{1-5}$ or $C_{1-6}$, such as methyl, ethyl, propyl, butyl, pentyl or hexyl.

The term "$C_2$-alkynyl" as used herein means a —CCH group. Wherein the two carbon atoms are connected with a triple bond.

The term "branched $C_{3-6}$ alkyl" as used herein means a branched alkyl group containing 3-6 carbon atoms, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "$C_{5-7}$ cycloalkyl" as used herein means a cyclic alkyl group containing 5-7 carbon atoms, such as cyclopentyl, cyclohexyl, or cycloheptyl.

The term "Oxo" as used herein means an oxygen atom with double bonds, also indicated as =O.

The term "CN" as used herein means a nitril.

The term "a five or six membered heteroaromatic ring" as used herein means one five membered heteroaromatic ring or one six membered heteroaromatic ring. The five membered heteroaromatic ring contains 5 ring atoms of which one to four are heteroatoms selected from N, O, and S. The six membered heteroaromatic ring contains 6 ring atoms of which one to five are heteroatoms selected from N, O and S. Examples include thiophene, furan, pyran, pyrrole, imidazole, pyrazole, isothiazole, isooxazole, pyridine, pyrazine, pyrimidine and pyridazine. When such heteroaromatic rings are substituents they are termed thiophenyl, furanyl, pyranyl, pyrrolyl, imidazolyl, pyrazolyl, isothiazolyl, isooxazolyl, pyridinyl, pyrazinyl, pyrimidinyl and pyridazinyl. Also included are oxazoyl, thiazoyl, thiadiazoly, oxadiazoyl, and pyridonyl.

The term "a heterocycle, such as heteroaryl or heterocycloalkyl" as used herein means a heterocycle consisting of one or more 3-7 membered ring systems containing one or more heteroatoms and wherein such ring systems may optionally be aromatic. The term "a heteroaryl" as used herein means a mono or bicyclic aromatic ringsystem containing one or more heteroatoms, such as 1-10, e.g. 1-6, selected from O, S, and N, including but not limited to oxazolyl, oxadiazolyl, thiophenyl, thiadiazolyl, thiazolyl, pyridyl, pyrimidinyl, pyridonyl, pyrimidonyl, quinolinyl, azaquionolyl, isoquinolinyl, azaisoquinolyl, quinazolinyl, azaquinazolinyl, bensozaoyl, azabensoxazoyl, bensothiazoyl, or azabensothiazoyl. The term "a heterocycloalkyl" as used herein means a mono or bicyclic 3-7 membered alifatic heterocycle containing one or more heteroatoms, such as 1-7, e.g. 1-5, selected from O, S, and N, including but not limited to piperidinyl, tetrahydropyranyl, tetrahydrothipyranyl, or piperidonyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular, a human being, but it may also include animals, such as dogs, cats, cows, sheep and pigs.

The term "a therapeutically effective amount" of a compound of formula (1) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect, the present invention relates to a pharmaceutical composition comprising the compound of formula (1) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person skilled within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99% by weight of said at least one pharmaceutically acceptable adjuvant, diluent, excipient and/or carrier and from 1 to 99% by weight of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compounds as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The term "and/or" as used herein is intended to mean both alternatives as well as each of the alternatives individually. For instance, the expression "xxx and/or yyy" means "xxx and yyy"; "xxx"; or "yyy", all three alternatives are subject to individual embodiments.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context). This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention indiverse forms thereof.

Experimental Procedures (Evaluation of Kd Values)

The affinity of Example 1-45 for galectins were determined by a fluorescence anisotropy assay where the compound was used as an inhibitor of the interaction between galectin and a fluorescein tagged saccharide probe as described Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47, (Sorme et al., 2004) and Monovalent interactions of Galectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salomonsson et al., 2010).

| Example | Name | structure | Galectin-1 Kd (μM) | Galectin-3 Kd (μM) |
|---|---|---|---|---|
| 1 | 3-Chlorophenyl 3-deoxy-3-[4-(3-fluorophenyl)-1H-1,2-pyrazol-1-yl]-1-thio-α-D-galactopyranoside | 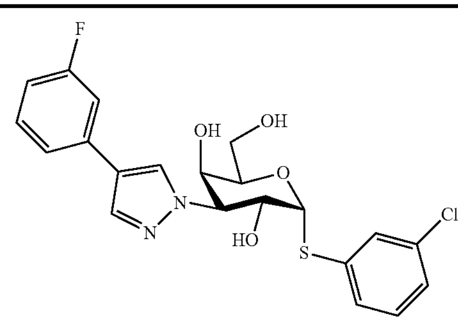 | 19.9 | 0.27 |
| 2 | 5-Chloropyridin-3-yl 3-[4-(4-chloro-3,5-difluorophenyl)-1H-1,2-pyrazol-1-yl]-3-deoxy-1-thio-α-D-galactopyranoside | 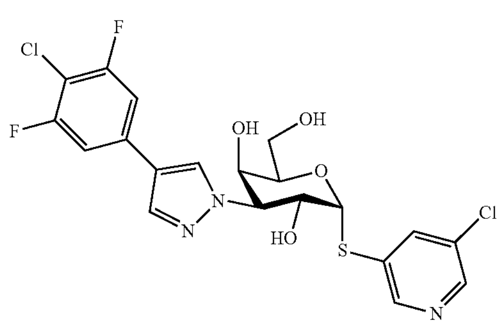 | 27.6 | 0.020 |

-continued

| Example | Name | structure | Galectin-1 Kd (μM) | Galectin-3 Kd (μM) |
|---|---|---|---|---|
| 3 | 5-Chloropyridin-3-yl 3-deoxy-3-[4-(3,4,5-trifluorophenyl)-1H-1,2-pyrazol-1-yl]-1-thio-α-D-galactopyranoside | 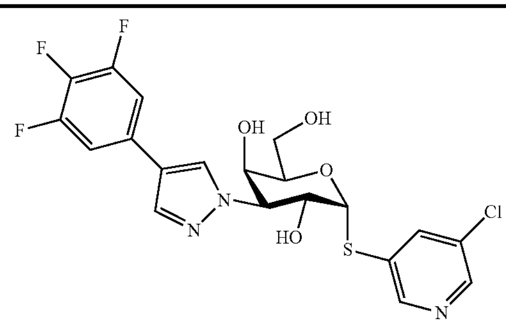 | 12.8 | 0.028 |
| 4 | 5-Chloropyridin-3-yl 3-deoxy-3-[4-(3,5-difluoro-4-methylphenyl)-1H-1,2-pyrazol-1-yl]-1-thio-α-D-galactopyranoside | 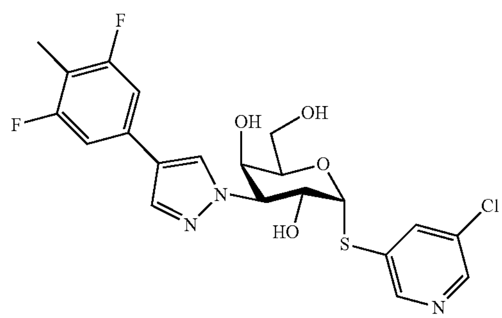 | 43 | 0.009 |
| 5 | 5-Bromopyridin-3-yl 3-deoxy-3-[4-(3,4,5-trifluorophenyl)-1H-1,2-pyrazol-1-yl]-1-thio-α-D-galactopyranoside | 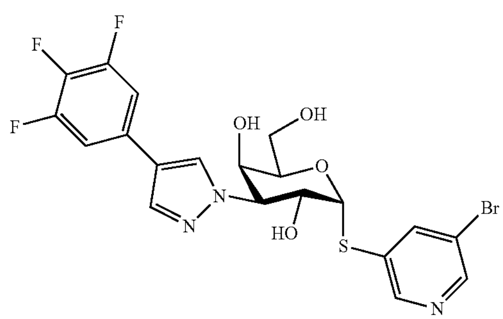 | 14.8 | 0.025 |
| 6 | 5-Bromopyridin-3-yl 3-[4-(4-chloro-3,5-difluorophenyl)-1H-1,2-pyrazol-1-yl]-3-deoxy-1-thio-α-D-galactopyranoside | 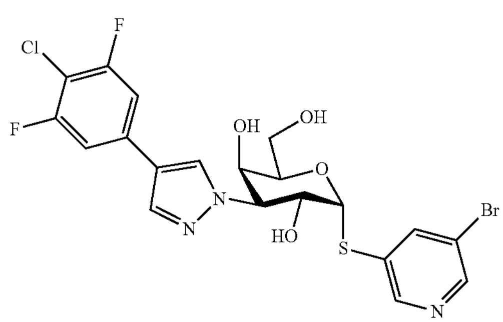 | 23 | 0.016 |
| 7 | 5-Ethynylpyridin-3-yl 3-[4-(4-chloro-3,5-difluorophenyl)-1H-1,2-pyrazol-1-yl]-3-deoxy-1-thio-α-D-galactopyranoside | 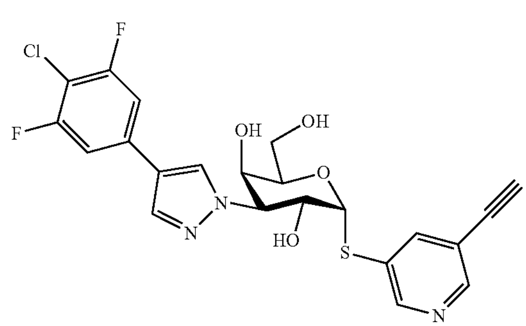 | 30 | 0.014 |

-continued

| Example | Name | structure | Galectin-1 Kd (μM) | Galectin-3 Kd (μM) |
|---|---|---|---|---|
| 8 | 5-Chloro-2-cyanophenyl 3-[4-(4-chloro-3,5-difluorophenyl)-1H-1,2-pyrazol-1-yl]-3-deoxy-1-thio-α-D-galactopyranoside | 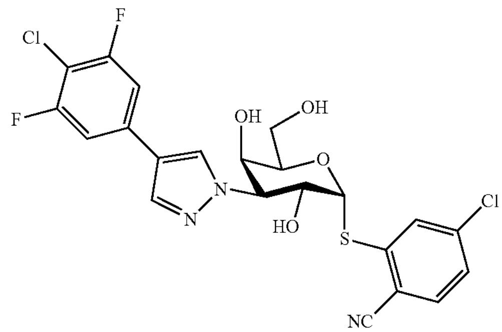 | 48 | 0.020 |
| 9 | 2-(N-Azetidinyl-carbonyl)-5-chlorophenyl 3-[4-(4-chloro-3,5-difluorophenyl)-1H-1,2-pyrazol-1-yl]-3-deoxy-1-thio-α-D-galactopyranoside | 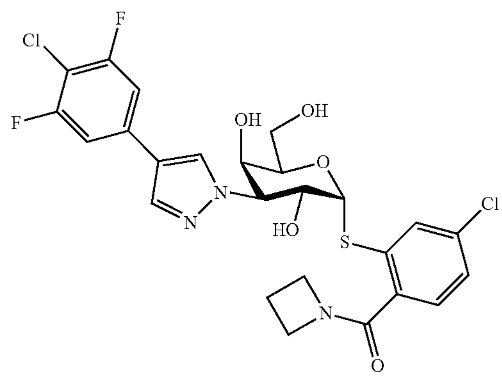 | 19.2 | 0.012 |
| 10 | 2-(N-Azetidinyl-carbonyl)-5-chlorophenyl 3-deoxy-3-[4-(3,4,5-trifluorophenyl)-1H-1,2-pyrazol-1-yl]-1-thio-α-D-galactopyranoside | 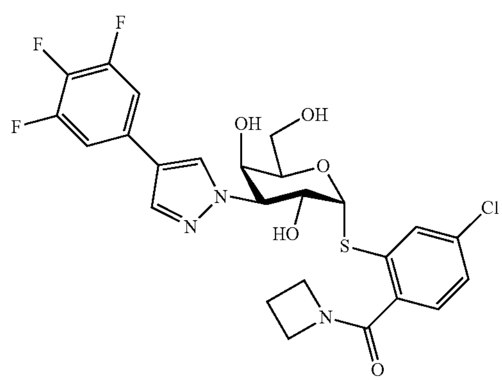 | 6.8 | 0.015 |
| 11 | 5-Chloro-2-cyanophenyl 3-deoxy-3-[4-(3,4,5-trifluorophenyl)-1H-1,2-pyrazol-1-yl]-1-thio-α-D-galactopyranoside | 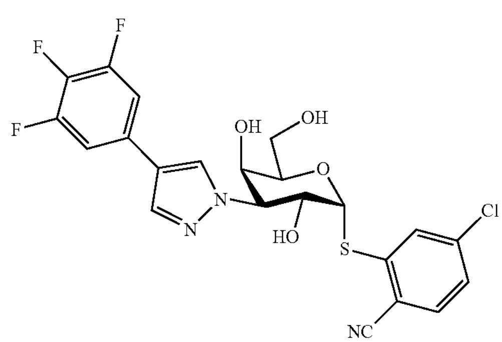 | 9.8 | 0.024 |

-continued

| Example | Name | structure | Galectin-1 Kd (μM) | Galectin-3 Kd (μM) |
|---|---|---|---|---|
| 12 | 5-Chloro-2-cyanopyridin-3-yl 3-deoxy-3-[4-(3,4,5-trifluorophenyl)-1H-1,2-pyrazol-1-yl]-1-thio-α-D-galactopyranoside | 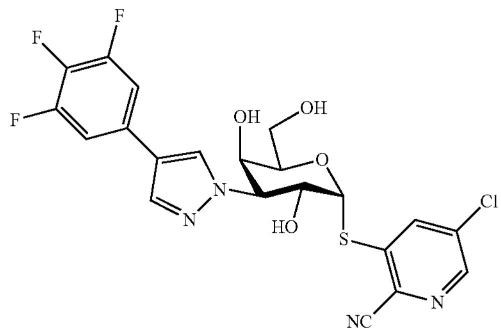 | 8.2 | 0.021 |
| 13 | 5-Chloro-2-cyanopyridin-3-yl 3-[4-(4-chloro-3,5-difluorophenyl)-1H-1,2-pyrazol-1-yl]-3-deoxy-1-thio-α-D-galactopyranoside | 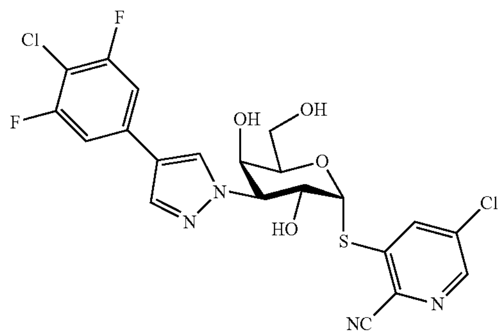 | 34 | 0.014 |
| 14 | 5-Chloro-2-methylpyridin-3-yl 3-deoxy-3-[4-(3,4,5-trifluorophenyl)-1H-1,2-pyrazol-1-yl]-1-thio-α-D-galactopyranoside | 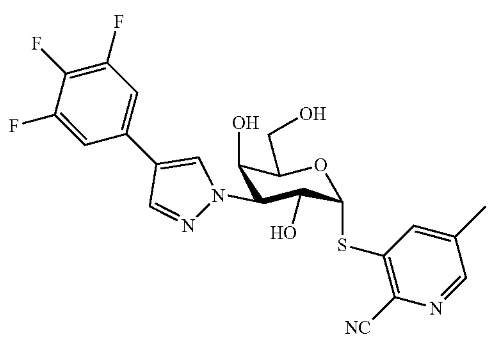 | 51 | 0.080 |
| 15 | 5-Bromo-2-cyanopyridin-3-yl 3-deoxy-3-[4-(3,4,5-trifluorophenyl)-1H-1,2-pyrazol-1-yl]-1-thio-α-D-galactopyranoside | 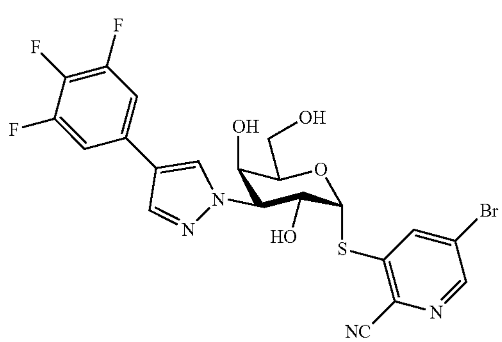 | 4.8 | 0.011 |

-continued

| Example | Name | structure | Galectin-1 Kd (μM) | Galectin-3 Kd (μM) |
|---|---|---|---|---|
| 16 | 2-Cyano-5-ethynylpyridin-3-yl 3-deoxy-3-[4-(3,4,5-trifluorophenyl)-1H-1,2-pyrazol-1-yl]-1-thio-α-D-galactopyranoside | 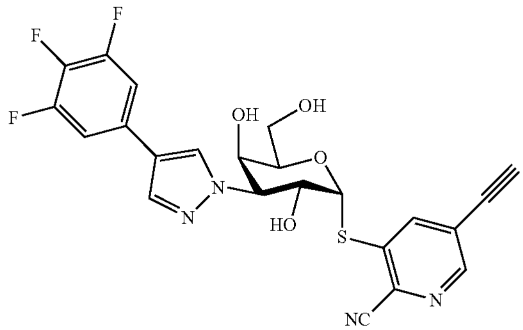 | 12.7 | 0.021 |
| 17 | 5-Chloropyridin-3-yl 3-[4-(4-chloro-3-fluorophenyl)-1H-1,2-pyrazol-1-yl]-3-deoxy-1-thio-α-D-galactopyranoside | 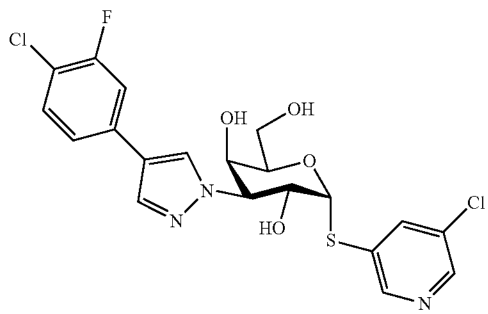 | 19.7 | 0.029 |
| 18 | 5-Chloropyridin-3-yl 3-deoxy-3-[4-(6-fluoropyridin-2-yl)-1H-1,2-pyrazol-1-yl]-1-thio-α-D-galactopyranoside | 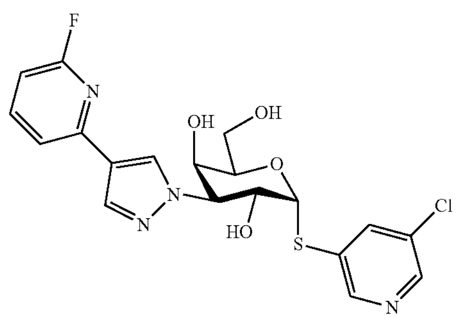 | 12.3 | 0.69 |
| 19 | 5-Chloropyridin-3-yl 3-deoxy-3-[4-(5-fluoropyridin-2-yl)-1H-1,2-pyrazol-1-yl]-1-thio-α-D-galactopyranoside | 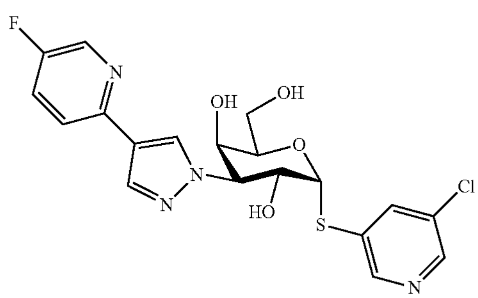 | 4.1 | 1.6 |
| 20 | 5-Chloropyridin-3-yl 3-deoxy-3-[4-(4-fluoropyridin-2-yl)-1H-1,2-pyrazol-1-yl]-1-thio-α-D-galactopyranoside | 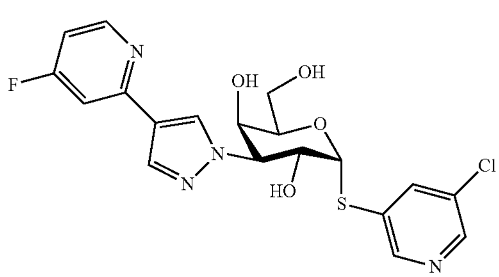 | 10.2 | 0.63 |

-continued

| Example | Name | structure | Galectin-1 Kd (µM) | Galectin-3 Kd (µM) |
|---|---|---|---|---|
| 21 | 5-Chloropyridin-3-yl 3-deoxy-3-[4-(1H-1,2-pyrazol-3-yl)-1H-1,2-pyrazol-1-yl]-1-thio-α-D-galactopyranoside | 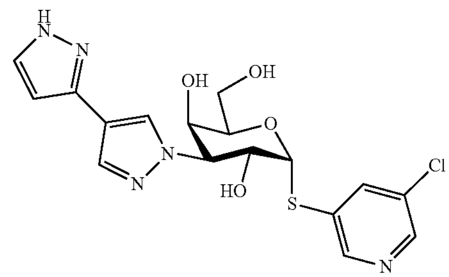 | 8.9 | 12.7 |
| 22 | 5-Chloropyridin-3-yl 3-deoxy-3-[4-(1-methyl-1,2-pyrazol-3-yl)-1H-1,2-pyrazol-1-yl]-1-thio-α-D-galactopyranoside | 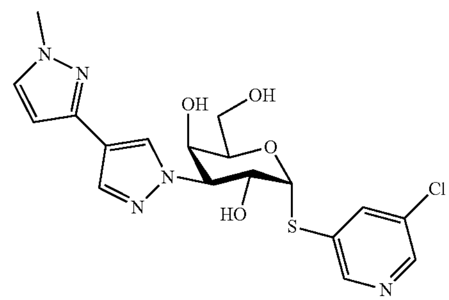 | 14.7 | 9.6 |
| 23 | 5-Chloropyridin-3-yl 3-deoxy-3-[4-(1H-imidazol-2-yl)-1H-1,2-pyrazol-1-yl]-1-thio-α-D-galactopyranoside | 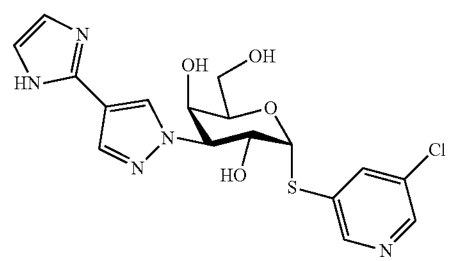 | 3.4 | 9 |
| 24 | 5-Chloropyridin-3-yl 3-deoxy-3-[4-(oxazol-2-yl)-1H-1,2-pyrazol-1-yl]-1-thio-α-D-galactopyranoside | 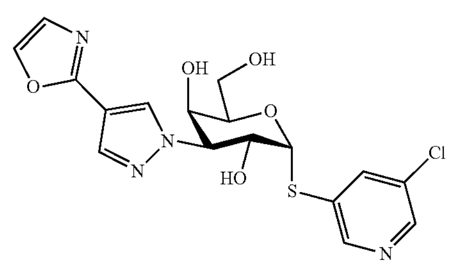 | 6.1 | 10.3 |
| 25 | 5-Chloropyridin-3-yl 3-deoxy-3-[4-(thiazol-4-yl)-1H-1,2-pyrazol-1-yl]-1-thio-α-D-galactopyranoside | 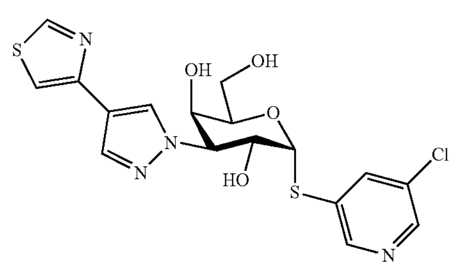 | 1.3 | 9.6 |

-continued

| Example | Name | structure | Galectin-1 Kd (μM) | Galectin-3 Kd (μM) |
|---|---|---|---|---|
| 26 | 5-Chloropyridin-3-yl 3-deoxy-3-[4-(thiazol-2-yl)-1H-1,2-pyrazol-1-yl]-1-thio-α-D-galactopyranoside | 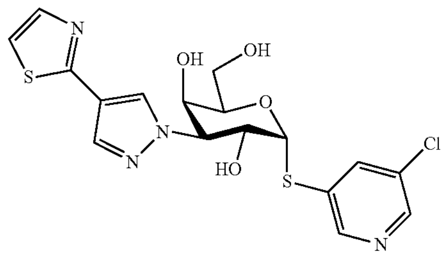 | 2.3 | 9.9 |
| 27 | 5-Chloropyridin-3-yl 3-[4-(4-chlorothiazol-2-yl)-1H-1,2-pyrazol-1-yl]-3-deoxy-1-thio-α-D-galactopyranoside | 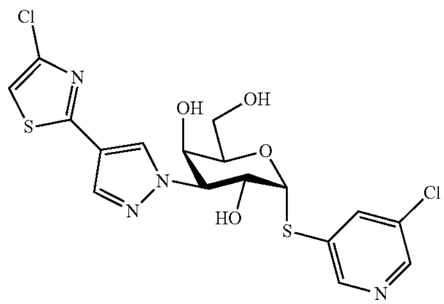 | 0.59 | 1.5 |
| 28 | 5-Bromopyridin-3-yl 3-[4-(4-chlorothiazol-2-yl)-1H-1,2-pyrazol-1-yl]-3-deoxy-1-thio-α-D-galactopyranoside | 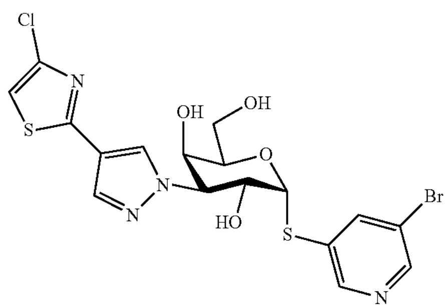 | 0.52 | 1.2 |
| 29 | 5-Chloro-2-cyanophenyl 3-[4-(4-chlorothiazol-2-yl)-1H-1,2-pyrazol-1-yl]-3-deoxy-1-thio-α-D-galactopyranoside | 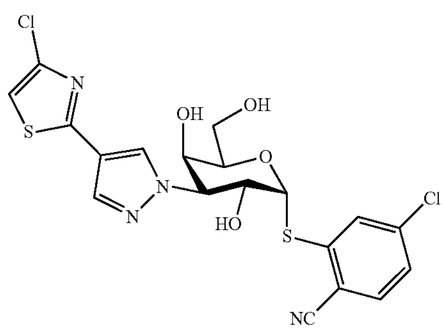 | 0.49 | 1.5 |
| 30 | 5-Chloro-2-cyanopyridin-3-yl 3-[4-(4-chlorothiazol-2-yl)-1H-1,2-pyrazol-1-yl]-3-deoxy-1-thio-α-D-galactopyranoside | 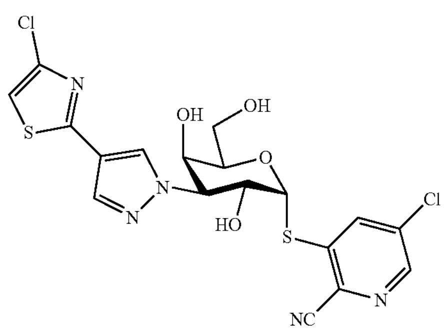 | 0.51 | 1.1 |

-continued

| Example | Name | structure | Galectin-1 Kd (μM) | Galectin-3 Kd (μM) |
|---|---|---|---|---|
| 31 | 5-Chloropyridin-3-yl 3-deoxy-3-[4-(2-hydroxythiazol-4-yl)-1H-1,2-pyrazol-1-yl]-1-thio-α-D-galactopyranoside | 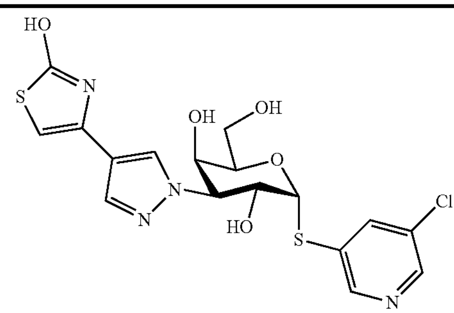 | 0.14 | 3.4 |
| 32 | 5-Chloropyridin-3-yl 3-deoxy-3-[4-(3,4,5-trifluorophenyl)-1H-1,2-pyrazol-1-yl]-2-O-methyl-1-thio-α-D-galactopyranoside | 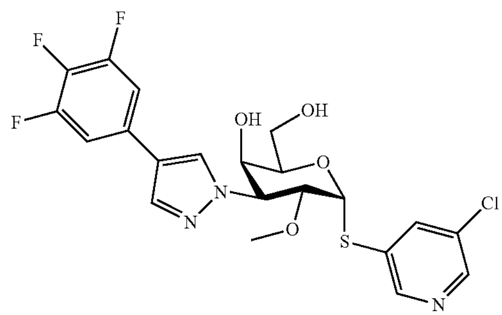 | 6.7 | 0.017 |
| 33 | 5-Bromopyridin-3-yl 3-deoxy-3-[4-(3,4,5-trifluorophenyl)-1H-1,2-pyrazol-1-yl]-2-O-methyl-1-thio-α-D-galactopyranoside | 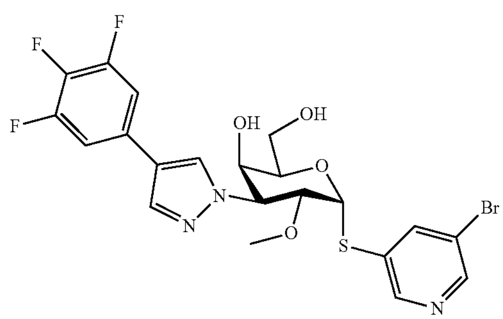 | 3.6 | 0.022 |
| 34 | 5-Ethynylpyridin-3-yl 3-deoxy-3-[4-(3,4,5-trifluorophenyl)-1H-1,2-pyrazol-1-yl]-2-O-methyl-1-thio-α-D-galactopyranoside | 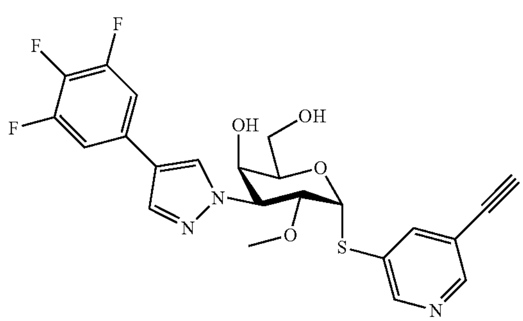 | 16.5 | 0.023 |
| 35 | 5-Chloro-2-cyanopyridin-3-yl 3-deoxy-3-[4-(3,4,5-trifluorophenyl)-1H-1,2-pyrazol-1-yl]-2-O-methyl-1-thio-α-D-galactopyranoside | 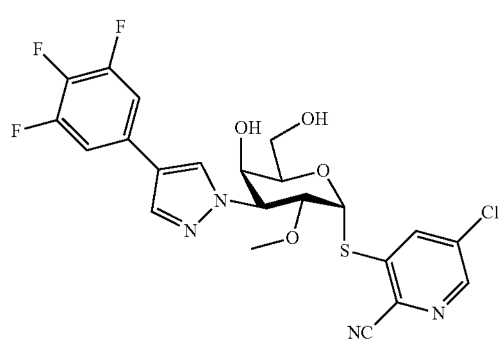 | 3.1 | 0.014 |

-continued

| Example | Name | structure | Galectin-1 Kd (μM) | Galectin-3 Kd (μM) |
|---|---|---|---|---|
| 36 | 5-Chloropyridin-3-yl 3-deoxy-3-[4-(3,4,5-trifluorophenyl)-1H-1,3-imidazol-1-yl]-1-thio-α-D-galactopyranoside | 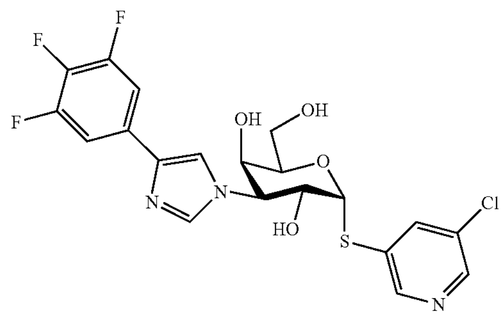 | 12.7 | 0.067 |
| 37 | 5-Chloro-[3,3-bis(hydroxymethyl)azetidin-1-yl]pyridin-3-yl 3-deoxy-3-[4-(3,4,5-trifluorophenyl)-1H-1,2-pyrazol-1-yl]-1-thio-α-D-galactopyranoside | 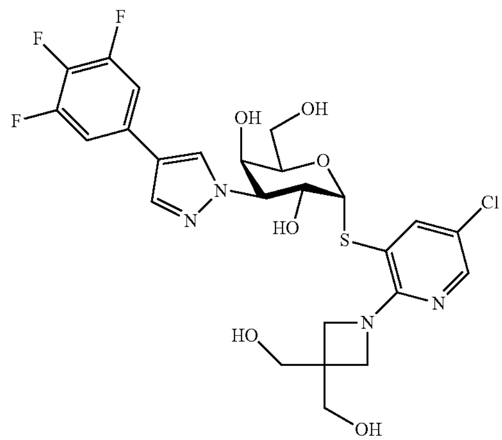 | 5.1 | 0.013 |
| 38 | 5-Chloropyridin-3-yl 3-deoxy-3-[3-(3,4,5-trifluorophenyl)-1H-1,2-pyrazol-1-yl]-2-O-methyl-1-thio-α-D-galactopyranoside | 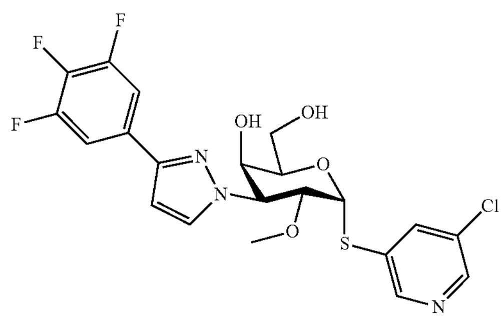 | 51 | 0.45 |
| 39 | 3,4-Dichlorophenyl 3-deoxy-3-[4-(3,4,5-trifluorophenyl)-oxazol-2-yl]-1-thio-α-D-galactopyranoside | 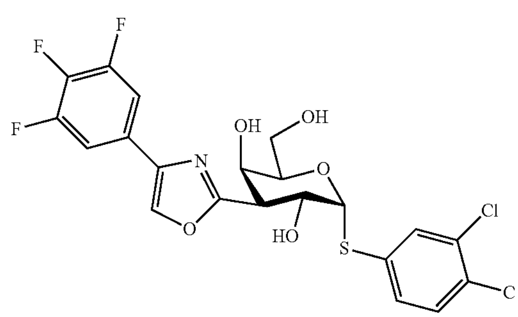 | >100 | 0.3 |

-continued

| Example | Name | structure | Galectin-1 Kd (μM) | Galectin-3 Kd (μM) |
|---|---|---|---|---|
| 40 | 3,4-Dichlorophenyl 3-deoxy-3-[4-(3,4,5-trifluorophenyl)-thiazol-2-yl]-1-thio-α-D-galactopyranoside | 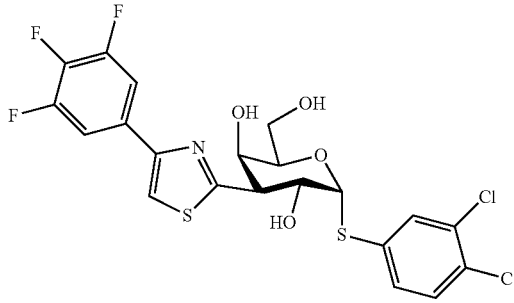 | >100 | 2 |
| 41 | 3,4-Dichlorophenyl 3-deoxy-3-[5-(3,4,5-trifluorophenyl)-1,3,4-oxadiazol-2-yl]-1-thio-α-D-galactopyranoside | 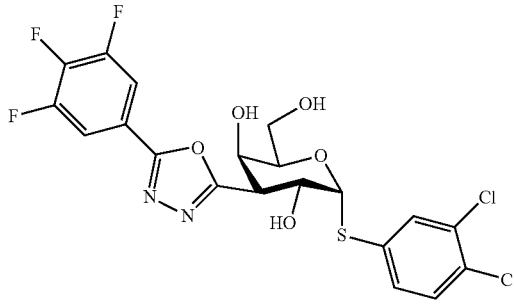 | >100 | 1.2 |
| 42 | 3,4-Dichlorophenyl 3-deoxy-3-[4-(2-hydroxythiazol-4-yl)-1H-1,2-pyrazol-1-yl]-2-O-methyl-1-thio-α-D-galactopyranoside | 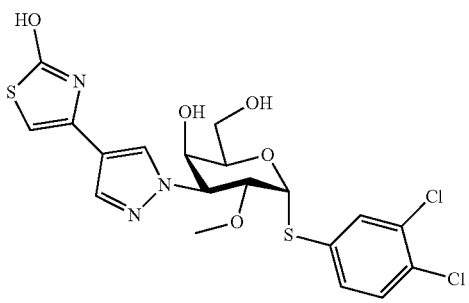 | 0.18 | 63 |
| 43 | 3,4-Dichlorophenyl 3-[4-(2-aminothiazol-4-yl)-1H-1,2-pyrazol-1-yl]-3-deoxy-2-O-methyl-1-thio-α-D-galactopyranoside | 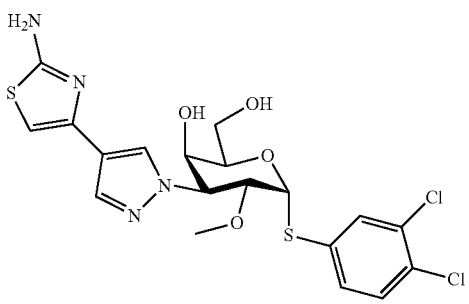 | 2.1 | 11 |
| 44 | 5-Chloro-2-cyanophenyl 3-[4-(4-chloro-3,5-difluorophenyl)-1H-1,2-pyrazol-1-yl]-3-deoxy-2-O-methyl-1-thio-α-D-galactopyranoside | 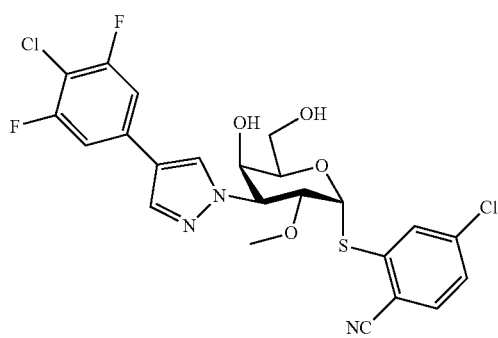 | 50 | 0.04 |

| Example | Name | structure | Galectin-1 Kd (μM) | Galectin-3 Kd (μM) |
|---|---|---|---|---|
| 45 | 5-Chloro-2-cyanophenyl 3-deoxy-3-[4-(3,4,5-trifluorophenyl)-1H-1,2-pyrazol-1-yl]-2-O-methyl-1-thio-α-D-galactopyranoside | 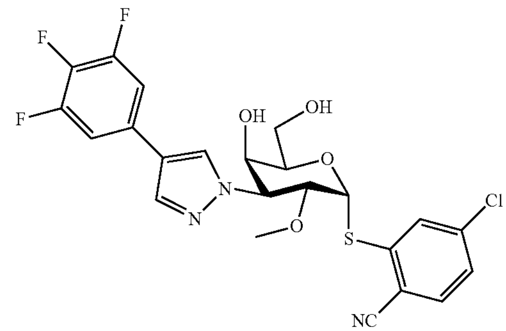 | 8.5 | 0.03 |

A group of the compounds in table above have potential to have good uptake over the intestine and good systemic and even CNS bioavailability upon oral treatment. These compounds are considered potential human drug candidates within CNS as treatment for e.g. neurodegenerative disorders such as dementia and Azheimers.

| Example | MDCK-MDR1 A > B Papp($10^{-6}$ cm/s) | MDCK-MDR1 A > B Papp($10^{-6}$ cm/s) |
|---|---|---|
| 2 | 25 | 50 |
| 3 | 14 | 39 |
| 6 | 18 | 52 |
| 12 | 12 | 51 |
| 15 | 12 | 53 |
| 17 | 28 | 49 |
| 32 | 30 | 33 |
| 33 | 34 | 23 |
| 34 | 35 | 37 |
| 35 | 23 | 35 |

Some of the potential CNS available compounds above, examples 2, 3, 6, 12, 15, 17, 32, 33, 34 and 35 were shown to have low or no efflux and high uptake in an in vitro cell model (see Hellinger, E.; Veszelka, S.; Toth, A. E.; Walter, F.; Kittel, A.; Bakk, M. L.; Tihanyi, K.; Hada, V.; Nakagawa, S.; Duy, T. D. H.; Niwa, M.; Deli, M. A.; Vastag, M. Comparison of Brain Capillary Endothelial Cell-Based and Epithelial (MDCK-MDR1, Caco-2, and VB-Caco-2) Cell-Based Surrogate Blood-Brain Barrier Penetration Models. Eur J Pharm Biopharm 2012, 82 (2), 340-351.) of passage over Blood Brain Barrier (BBB) predicting availability for these compounds in the CNS.

Figure 2:
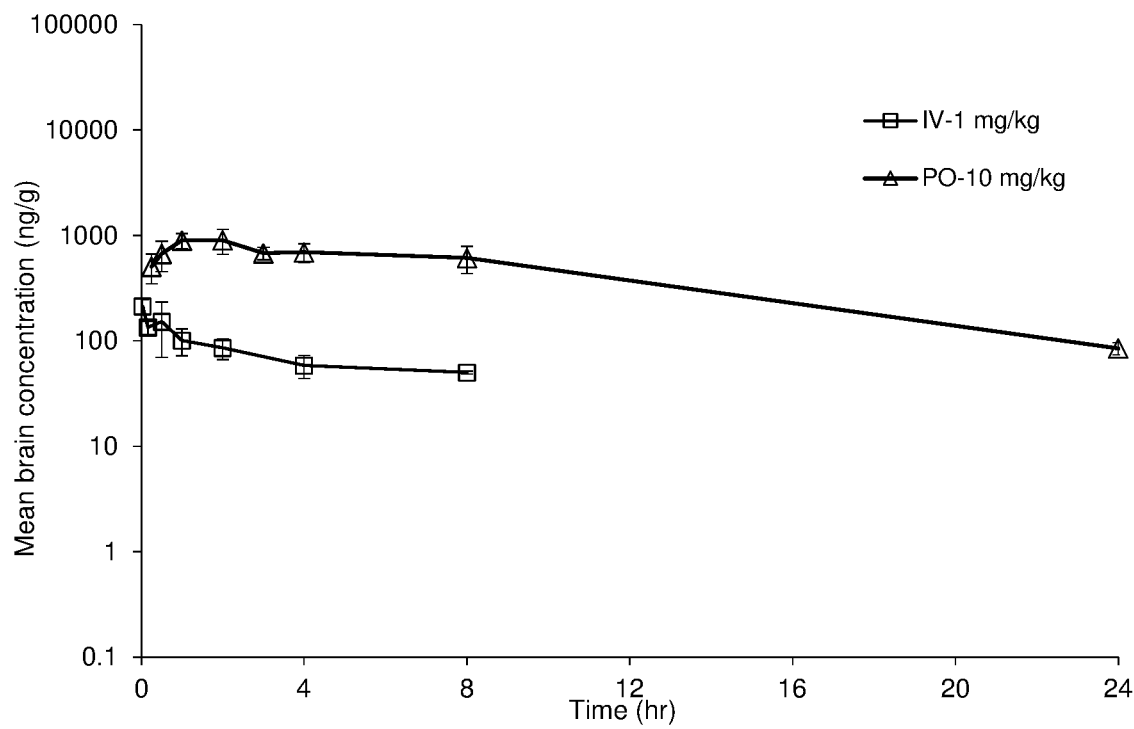
FIG. 2 compares the mean brain tissue concertation after IV and PO administration

In vivo mouse pharmacokinetic experiment for example 35 Dosing example 35 IV 1 mg/kg and PO 10 mg/kg results in excellent systemic bioavailability, FIG. 1. In addition, good exposure in brain is observed, FIG. 2. The ratio between exposure of example 35 in brain compared to plasma is determined to $AUC_{brain}/AUC_{plasma}=0.19$ after oral administration. (AUC=area under the curve)

SYNTHESIS OF EXAMPLES AND INTERMEDIATES

General Experimental

Nuclear Magnetic Resonance (NMR) spectra were recorded on a Varian instrument at 400 MHz or a 500 MHz Bruker Avance Neo 500 instrument, at 25° C.

Chemical shifts are reported in ppm (d) using the residual solvent as internal standard. Peak multiplicities are expressed as follow: s, singlet; d, doublet; dd, doublet of doublets; t, triplet; dt, doublet of triplet; q, quartet; m, multiplet; br s, broad singlet. LC-MS were acquired on an Agilent 1100 HPLC coupled with an Agilent MSD mass spectrometer operating in ES (+) ionization mode. Column Waters symmetry 2.1×30 mm C18 or Chromolith RP-18 2×50 mm Solvent A water+0.1% TFA and solvent B Acetonitrile+0.1% TFA. Wavelength 254 nm.

Preparative HPLC were acquired on a Gilson system. Flow: 15 ml/min Column: kromasil 100-5-C18 column Wavelength: 220 nm. Solvent A water+0.1% TFA and solvent B Acetonitrile+0.1% TFA.

The following abbreviations are used aq: aqueous
Calcd: Calculated
$CH_3CN$: Acetonitrile
CuI: Copper Iodide
DCM: Dichloromethane
DIPEA: Diisopropylethylamine
DMF: N,N-dimethylformamide
ESI-MS: Electrospray ionization mass spectrometry
$Et_3N$: Triethylamine
EtOAc: Ethylacetate
h: hour(s)
HATU: 1-[Bis(dimethylamino)methylene]-1H-1,2,3-triazolo[4,5-b]pyridinium 3-oxid hexafluorophosphate
HPLC: High performance liquid chromatography
LC: Liquid Chromatography
MeCN: Acetonitrile
mL: milliliter
MeOH: Methanol
MeOD: Deuterated methanol
min millimeter
mM millimolar
MS: Mass spectroscopy
nm: nanometer
NaI: Sodium Iodide
NaOMe: Sodium methoxide
$N_2$: Nitrogen gas
NMR: Nuclear magnetic resonance
Pd(dppf)$Cl_2$: [1,1'-bis(diphenylphosphino)ferrocene]dichloropalladium(II)
PE: petroleum ether
pH: acidity
Prep: Preparative rt: Room temperature
TBAF: Tetrabutylammonium fluoride
TFA: trifluoroacetic acid
THF: Tetrahydrofuran
UV: Ultraviolet
Å: Ångstrom The below example 1-45 where made from their respective intermediates 1-44

Example 1

3-Chlorophenyl 3-deoxy-3-[4-(3-fluorophenyl)-1H-1,2-pyrazol-1-yl]-1-thio-α-D-galactopyranoside

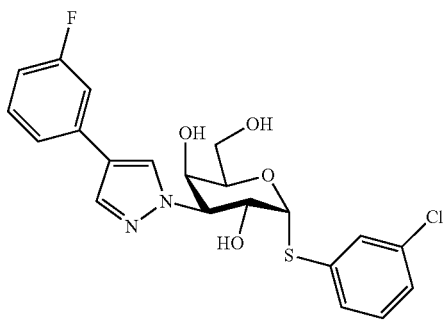

A solution of 3-chlorophenyl 3-(4-bromo-1H-1,2-pyrazol-1-yl)-3-deoxy-1-thio-α-D-galactopyranoside (30 mg, 0.069 mmol), (3-fluorophenyl)boronic acid (19 mg, 0.14 mmol), $K_2CO_3$ (38 mg, 0.28 mmol) and Pd(dppf)$Cl_2$ (7.6 mg, 0.010 mmol) in dioxane/water (1 mL, 2:1) was stirred 3 h at 60° C. The mixture was concentrated and purified by prep HPLC ($C_{18}$, $H_2O$/MeCN/0.1% TFA) to afford the title compound (5 mg, 16%). ESI-MS m/z calcd for [$C_{21}H_{20}ClFN_2O_4S$] [M+H]$^+$: 451.1; found: 450.7. $^1$H NMR (400 MHz, Methanol-d$_4$) δ 8.17 (s, 1H), 7.92 (s, 1H), 7.64 (s, 1H), 7.55-7.51 (m, 1H), 7.42-7.27 (m, 5H), 6.93 (t, J=7.8 Hz, 1H), 5.81 (d, J=5.4 Hz, 1H), 4.89-4.86 (m, 1H), 4.57 (dd, J=11.4, 2.7 Hz, 1H), 4.47 (t, J=6.1 Hz, 1H), 4.21 (d, J=1.9 Hz, 1H), 3.75 (dd, J=11.4, 5.8 Hz, 1H), 3.65 (dd, J=11.4, 6.6 Hz, 1H).

Example 2

5-Chloropyridin-3-yl 3-[4-(4-chloro-3,5-difluorophenyl)-1H-1,2-pyrazol-1-yl]-3-deoxy-1-thio-α-D-galactopyranoside

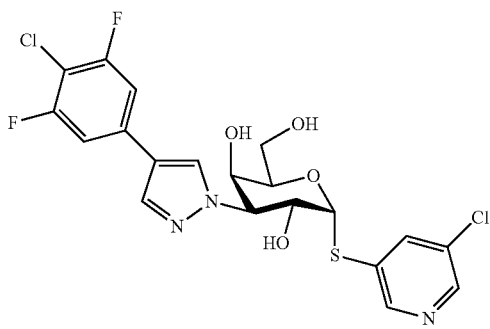

A solution of 5-chloropyridin-3-yl 3-(4-bromo-1H-1,2-pyrazol-1-yl)-3-deoxy-1-thio-α-D-galactopyranoside (49 mg, 0.11 mmol), (4-chloro-3,5-difluorophenyl)boronic acid (43 mg, 0.22 mmol), $K_2CO_3$ (78 mg, 0.56 mg) and Pd(dppf)$Cl_2$ (12 mg, 0.017 mmol) was dissolved in 1,4-dioxane/water (1 mL, 2:1) and stirred 4 h at 90° C. The mixture was partitioned between EtOAc and water and the organic phase was dried and concentrated. Purification of the residue by prep HPLC ($C_{18}$, $H_2O$/MeCN/0.1% TFA) afforded the title compound (5 mg, 9%). ESI-MS m/z calcd for [$C_{20}H_{17}Cl_2F_2N_3O_4S$] [M+H]$^+$: 504.0; found: 503.8. $^1$H NMR (400 MHz, Methanol-d$_4$) δ 8.64 (d, J=1.7 Hz, 1H), 8.47 (d, J=2.1 Hz, 1H), 8.24 (s, 1H), 8.20 (t, J=2.0 Hz, 1H), 7.97 (s, 1H), 7.38 (d, J=8.3 Hz, 2H), 5.91 (d, J=5.4 Hz, 1H), 4.91-4.86 (m, 1H), 4.61 (dd, J=11.3, 2.7 Hz, 1H), 4.43 (t, J=6.1 Hz, 1H), 4.19 (d, J=2.1 Hz, 1H), 3.76-3.65 (m, 2H).

Example 3

5-Chloropyridin-3-yl 3-deoxy-3-[4-(3,4,5-trifluorophenyl)-1H-1,2-pyrazol-1-yl]-1-thio-α-D-galactopyranoside

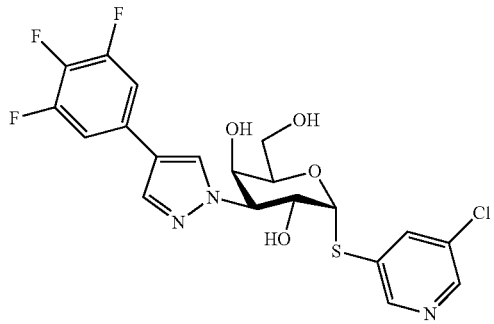

Pd(dppf)$Cl_2$ (18 mg, 0.024 mmol) was added to 5-chloropyridin-3-yl 2,4,6-tri-O-acetyl-3-(4-bromo-1H-1,2-pyrazol-1-yl)-3-deoxy-1-thio-α-D-galactopyranoside (90 mg, 0.16 mmol), (3,4,5-trifluorophenyl)boronic acid (56 mg, 0.32 mmol) and $K_2CO_3$ (177 mg, 1.28 mmol) in degassed water/dioxane (1:2, 1.5 mL). The mixture was stirred under argon for 3 h at 90° C. before it was cooled to ambient temperature. NaOH (3 M, 0.5 mL) was added and the mixture was stirred for 1 h. The mixture was diluted with water (10 mL) and extracted with DCM (3×10 mL). The organic phase was dried, concentrated and purified by prep HPLC ($C_{18}$, $H_2O$/MeCN/0.1 TFA) to afford the title compound (24 mg, 31%). ESI-MS m/z calcd for [$C_{20}H_{17}ClF_3N_3O_4S$] [M+H]$^+$: 488.1; found: 488.1. $^1$H NMR (400 MHz, Methanol-d4) δ 8.64 (d, J=1.6 Hz, 1H), 8.48 (d, J=2.1 Hz, 1H), 8.21 (t, J=1.8 Hz, 1H), 8.19 (s, 1H), 7.92 (s, 1H), 7.42-7.30 (m, 2H), 5.91 (d, J=5.4 Hz, 1H), 4.92-4.86 (m, 1H), 4.60 (dd, J=11.3, 2.6 Hz, 1H), 4.43 (t, J=6.0 Hz, 1H), 4.22-4.12 (m, 1H), 3.78-3.64 (m, 2H).

Example 4

5-Chloropyridin-3-yl 3-deoxy-3-[4-(3,5-difluoro-4-methylphenyl)-1H-1,2-pyrazol-1-yl]-1-thio-α-D-galactopyranoside

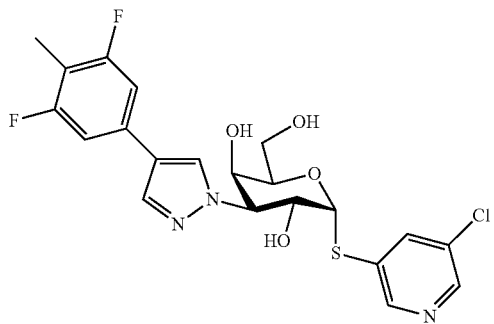

Pd(dppf)Cl$_2$ (16 mg, 0.021 mmol) was added to 5-chloropyridin-3-yl 2,4,6-tri-O-acetyl-3-(4-bromo-1H-1,2-pyrazol-1-yl)-3-deoxy-1-thio-α-D-galactopyranoside (80 mg, 0.14 mmol), 2-(3,5-difluoro-4-methylphenyl)-4,4,5,5-tetramethyl-1,3,2-dioxaborolane (59 mg, 0.23 mmol) and K$_2$CO$_3$ (157 mg, 1.14 mmol) in degassed water/dioxane (1:2, 1.5 mL). The mixture was stirred under argon for 3 h at 90° C. before it was cooled to ambient temperature. NaOH (3 M, 0.5 mL) was added and the mixture was stirred for 1 h. The mixture was diluted with water (10 mL) and extracted with DCM (3×10 mL). The organic phase was dried, concentrated and purified by prep HPLC (C$_{18}$, H$_2$O/MeCN/0.1% TFA) to afford the title compound (34 mg, 49%). ESI-MS m/z calcd for [C$_{21}$H$_{20}$ClF$_2$N$_3$O$_4$S] [M+H]$^+$: 484.1; found: 484.1. $^1$H NMR (400 MHz, Methanol-d$_4$) δ 8.64 (s, 1H), 8.47 (d, J=1.9 Hz, 1H), 8.20 (t, J=2.1 Hz, 1H), 8.16 (s, 1H), 7.91 (s, 1H), 7.16 (d, J=8.0 Hz, 2H), 5.91 (d, J=5.3 Hz, 1H), 4.92-4.85 (m, 1H), 4.59 (dd, J=11.3, 2.5 Hz, 1H), 4.43 (t, J=6.0 Hz, 1H), 4.22-4.16 (m, 1H), 3.77-3.64 (m, 2H), 2.17 (s, 3H).

Example 5

5-Bromopyridin-3-yl 3-deoxy-3-[4-(3,4,5-trifluorophenyl)-1H-1,2-pyrazol-1-yl]-1-thio-α-D-galactopyranoside

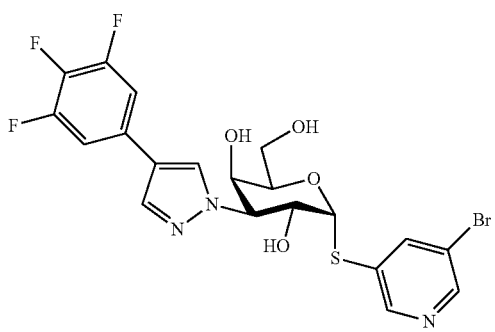

A nitrogen purged solution of 1,2,4,6-tetra-O-acetyl-3-(4-bromo-1H-1,2-pyrazol-1-yl)-3-deoxy-β-D-galactopyranoside (250 mg, 0.52 mmol), (3,4,5-trifluorophenyl)boronic acid (184 mg, 1.05 mmol), K$_2$CO$_3$ (434 mg, 3.14 mmol) and Pd(dppf)Cl$_2$ (58 mg, 0.079 mmol) in water/dioxane (1:2, 4 mL) was heated 20 min at 110° C. in a microwave reactor. The mixture was partitioned between EtOAc and water and the organic phase was dried, evaporated and purified by chromatography (SiO$_2$, PE/EtOAc). The obtained material and PCl$_5$ (52 mg, 0.25 mmol) were dissolved in DCM (1.5 mL) and BF$_3$OEt$_2$ (0.031 mL, 0.25 mmol) was added. The mixture was stirred 3 h at rt before it was diluted with DCM and washed with water and saturated aq NaHCO$_3$, dried and evaporated. The residue was dissolved with 5-bromopyridine-3-thiol (37 mg, 0.19 mmol) in DMF (1 mL). K$_2$CO$_3$ (53 mg, 0.39 mmol) was added and the mixture was stirred 18 h at rt. The mixture was diluted with EtOAc and washed with water and brine, the organic phase was dried and evaporated. The residue was stirred 1 h at rt in NaOMe (0.1 mL, 1M) and MeOH (1 mL). The reaction was quenched with acetic acid, concentrated and purified by prep HPLC (C$_{18}$, H$_2$O/MeCN/0.1% TFA) to afford the title compound (12 mg, 4%). ESI-MS m/z calcd for [C$_{20}$H$_{17}$BrF$_3$N$_3$O$_4$S] [M+H]$^+$: 532.0; found: 531.7. $^1$H NMR (400 MHz, Methanol-d$_4$) δ 8.68 (d, J=1.7 Hz, 1H), 8.57 (d, J=2.1 Hz, 1H), 8.33 (t, J=1.9 Hz, 1H), 8.19 (s, 1H), 7.92 (s, 1H), 7.37 (dd, J=9.1, 6.5 Hz, 2H), 5.89 (d, J=5.4 Hz, 1H), 4.90-4.86 (m, 1H), 4.59 (dd, J=11.3, 2.7 Hz, 1H), 4.43 (t, J=5.8 Hz, 1H), 4.19 (d, J=2.1 Hz, 1H), 3.74-3.67 (m, 2H).

Example 6

5-Bromopyridin-3-yl 3-[4-(4-chloro-3,5-difluorophenyl)-1H-1,2-pyrazol-1-yl]-3-deoxy-1-thio-α-D-galactopyranoside

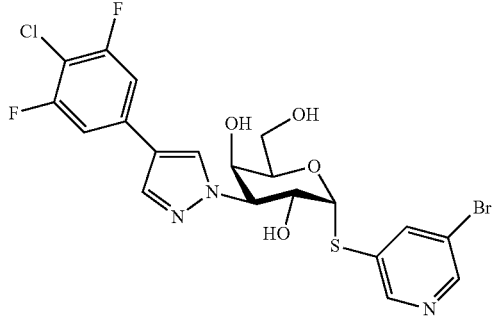

A solution of 2,4,6-tri-O-acetyl-3-[4-(4-chloro-3,5-difluorophenyl)-1H-1,2-pyrazol-1-yl]-3-deoxy-β-D-galactopyranosyl chloride (195 mg, 0.34 mmol), 5-bromopyridine-3-thiol (94 mg, 0.45 mmol) and Cs$_2$CO$_3$ (220 mg, 0.67 mmol) in DMF (2.0 mL) was stirred 20 h at rt. The mixture was partitioned between EtOAc and brine, the organic phase was dried, evaporated and the residue was purified by chromatography (SiO$_2$, PE/EtOAc). The obtained material was stirred 2 h at rt in MeOH (2.0 mL) and NaOMe (1 M, 1.0 mL). The reaction was neutralized with acetic acid (0.1 mL), evaporated, and the residue was purified by prep HPLC (C$_{18}$, H$_2$O/MeCN/0.1% TFA) to afford the title compound (49 mg, 26%). ESI-MS m/z calcd for [C$_{20}$H$_{17}$BrClF$_2$N$_3$O$_4$S] [M+H]$^+$: 548.0; found: 547.8. $^1$H NMR (400 MHz, Methanol-d4) δ 8.68 (d, J=1.9 Hz, 1H), 8.57 (d, J=2.1 Hz, 1H), 8.34 (t, J=2.0 Hz, 1H), 8.24 (d, J=0.6 Hz, 1H), 7.97 (d, J=0.6 Hz, 1H), 7.42-7.35 (m, 2H), 5.90 (d, J=5.4 Hz, 1H), 4.88 (dd, J=11.4, 5.4 Hz, 1H), 4.60 (dd, J=11.3, 2.8 Hz, 1H), 4.43

(t, J=6.3 Hz, 1H), 4.19 (d, J=1.7 Hz, 1H), 3.73 (dd, J=11.6, 5.3 Hz, 1H), 3.69 (dd, J=11.6, 6.9 Hz, 1H).

Example 7

5-Ethynylpyridin-3-yl 3-[4-(4-chloro-3,5-difluorophenyl)-1H-1,2-pyrazol-1-yl]-3-deoxy-1-thio-α-D-galactopyranoside

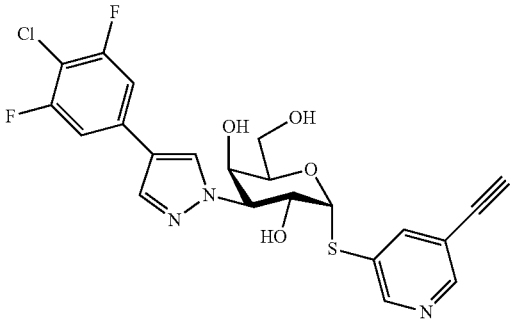

5-Bromopyridin-3-yl 3-[4-(4-chloro-3,5-difluorophenyl)-1H-1,2-pyrazol-1-yl]-3-deoxy-1-thio-α-D-galactopyranoside (25 mg, 0.045 mmol), Pd(PPh$_3$)$_2$Cl$_2$ (3.3 mg, 0.0045 mmol), CuI (1.0 mg, 0.0045 mol) were weighed into a flask and evacuated then flushed with nitrogen. THF (1.5 mL) and trimethylsilylacetylene (40 µL, 0.29 mmol) followed by Et$_3$N (0.2 mL) were added. The mixture was bubbled with nitrogen and then stirred 19 h at 50° C. The mixture was purified by passing through a silica column eluting with EtOAc, evaporated, and the residue was stirred 10 min at rt in THF (1.0 mL) and TBAF (1.0 mL, 1M in THF, 1.0 mmol). The mixture was partitioned between water and EtOAc and the organic phase was evaporated, and the residue was purified by prep HPLC (C$_{18}$, H$_2$O/MeCN/0.1 TFA) to afford the title compound (11 mg, 49%). ESI-MS m/z calcd for [C$_{22}$H$_{18}$ClF$_2$N$_3$O$_4$S] [M+H]$^+$: 494.1; found: 493.9. $^1$H NMR (400 MHz, Methanol-d$_4$) δ 8.83 (bs, 1H), 8.68 (bs, 1H), 8.25 (s, 1H), 8.22 (s, 1H), 7.97 (s, 1H), 7.39 (d, J=8.3 Hz, 2H), 5.90 (d, J=5.3 Hz, 1H), 4.88 (dd, J=11.3, 5.3 Hz, 1H), 4.61 (dd, J=11.3, 2.5 Hz, 1H), 4.44 (t, J=5.7 Hz, 1H), 4.20 (d, J=1.8 Hz, 1H), 3.87 (s, 1H), 3.72 (dd, J=11.5, 5.3 Hz, 1H), 3.68 (dd, J=11.5, 6.8 Hz, 1H).

Example 8

5-Chloro-2-cyanophenyl 3-[4-(4-chloro-3,5-difluorophenyl)-1H-1,2-pyrazol-1-yl]-3-deoxy-1-thio-α-D-galactopyranoside

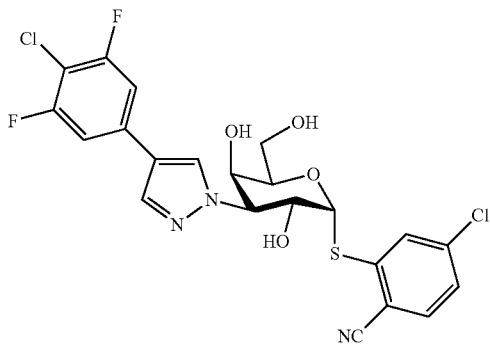

A solution of 2,4,6-tri-O-acetyl-3-[4-(4-chloro-3,5-difluorophenyl)-1H-1,2-pyrazol-1-yl]-3-deoxy-β-D-galactopyranosyl chloride (200 mg, 0.34 mmol), 4-chloro-2-sulfanylbenzonitrile (221 mg, 1.04 mmol) and Cs$_2$CO$_3$ (549 mg, 1.69 mmol) in DMF (2.0 mL) was stirred 40 h at 40° C. The mixture was partitioned between EtOAc and brine, the organic phase was dried and evaporated. The residue was stirred 18 h in pyridine (2.0 mL) and acetic anhydride (1.0 mL) before being concentrated and purified by chromatography (SiO$_2$, PE/EtOAc). The obtained material was stirred 3.5 h at rt in MeOH (4.0 mL) and NaOMe (1 M, 1.0 mL). The reaction was neutralized with acetic acid (0.1 mL), evaporated, and the residue was purified by prep HPLC (C$_{18}$, H$_2$O/MeCN/0.1% TFA) to afford the title compound (14 mg, 19%). ESI-MS m/z calcd for [C$_{22}$H$_{17}$Cl$_2$F$_2$N$_3$O$_4$S] [M+H]$^+$: 528.0; found: 527.8. $^1$H NMR (400 MHz, Methanol-d$_4$) δ 8.25 (s, 1H), 7.97 (s, 2H), 7.72 (d, J=8.4 Hz, 1H), 7.45 (dd, J=8.3, 2.0 Hz, 1H), 7.39 (d, J=8.3 Hz, 2H), 6.11 (d, J=5.4 Hz, 1H), 4.92 (dd, J=11.3, 5.4 Hz, 1H), 4.65 (dd, J=11.3, 2.7 Hz, 1H), 4.37 (t, J=6.2 Hz, 1H), 4.22 (d, J=2.0 Hz, 1H), 3.71 (dd, J=11.5, 5.6 Hz, 1H), 3.64 (dd, J=11.5, 6.7 Hz, 1H).

Example 9

2-(N-azetidinyl-carbonyl)-5-chlorophenyl 3-[4-(4-chloro-3,5-difluorophenyl)-1H-1,2-pyrazol-1-yl]-3-deoxy-1-thio-α-D-galactopyranoside

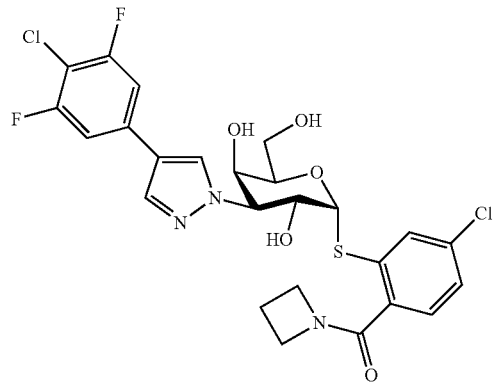

Pd(dppf)Cl$_2$ (23 mg, 0.03 mmol), (4-chloro-3,5-difluorophenyl)boronic acid (61 mg, 0.30 mmol) and K$_2$CO$_3$ (104 mg, 0.75 mmol) were weighed into a vial and flushed with nitrogen. A solution of 2-(N-azetidinyl-carbonyl)-5-chlorophenyl 3-(4-bromo-1H-1,2-pyrazol-1-yl)-3-deoxy-1-thio-α-D-galactopyranoside (78 mg, 0.15 mmol) in dioxane (2.0 mL) followed by water (0.5 mL) were added to the vial and degassed with nitrogen. The mixture was stirred 16 h at 80° C. and then partitioned between EtOAc and brine. The organic phase was evaporated, and purified by prep HPLC (C$_{18}$, H$_2$O/MeCN/0.1 TFA) to afford the title compound (4.3 g, 5%). ESI-MS m/z calcd for [C$_{25}$H$_{23}$Cl$_2$F$_2$N$_3$O$_5$S] [M+H]$^+$: 586.1; found: 586.0. $^1$H NMR (400 MHz, Methanol-d$_4$) δ 8.24 (s, 1H), 7.96 (s, 1H), 7.87 (d, J=1.9 Hz, 1H), 7.39 (m, 3H), 7.31 (d, J=8.2 Hz, 1H), 5.90 (d, J=5.4 Hz, 1H), 4.86 (dd, J=11.4, 5.4 Hz, 1H), 4.59 (dd, J=11.4, 2.7 Hz, 1H), 4.42 (t, J=6.1 Hz, 1H), 4.24-4.17 (m, 3H), 4.03 (t, J=7.7 Hz, 2H), 3.74 (dd, J=11.5, 5.5 Hz, 1H), 3.68 (dd, J=11.4, 6.7 Hz, 1H), 2.34 (p, J=7.7 Hz, 2H).

Example 10

2-(N-azetidinyl-carbonyl)-5-chlorophenyl 3-deoxy-3-[4-(3,4,5-trifluorophenyl)-1H-1,2-pyrazol-1-yl]-1-thio-α-D-galactopyranoside

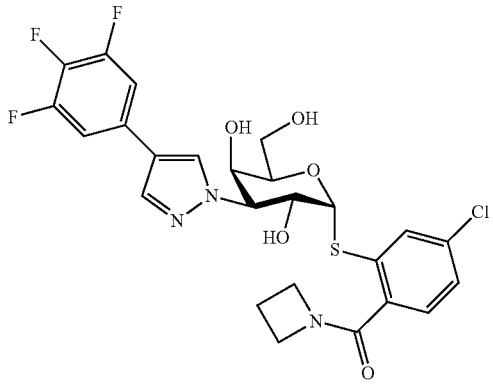

Pd(dppf)Cl$_2$ (20 mg, 0.026 mmol), (3,4,5-trifluorophenyl)boronic acid (47 mg, 0.26 mmol) and K$_2$CO$_3$ (90 mg, 0.65 mmol) were weighed into a vial and flushed with nitrogen. A solution of 2-(N-azetidinyl-carbonyl)-5-chlorophenyl 3-(4-bromo-1H-1,2-pyrazol-1-yl)-3-deoxy-1-thio-α-D-galactopyranoside (67 mg, 0.13 mmol) in dioxane (1.5 mL) followed by water (0.75 mL) were added to the vial and degassed with nitrogen. The mixture was stirred 18 h at 80° C. and was then partitioned between EtOAc and brine. The organic phase was evaporated, and the residue purified by chromatography (SiO$_2$, PE/EtOAc). The product was further purified by prep HPLC (C$_{18}$, H$_2$O/MeCN/0.1 TFA) to afford the title compound (7.8 g, 11%). ESI-MS m/z calcd for [C$_{25}$H$_{23}$ClF$_3$N$_3$O$_5$S] [M+H]$^+$: 570.1; found: 570.0. $^1$H NMR (400 MHz, Methanol-d$_4$) δ 8.19 (s, 1H), 7.92 (s, 1H), 7.87 (d, J=1.9 Hz, 1H), 7.42-7.33 (m, 3H), 7.31 (d, J=8.2 Hz, 1H), 5.90 (d, J=5.4 Hz, 1H), 4.87 (dd, J=11.2, 5.4 Hz, 1H), 4.58 (dd, J=11.4, 2.7 Hz, 1H), 4.42 (t, J=6.2 Hz, 1H), 4.24-4.16 (m, 3H), 4.03 (t, J=7.7 Hz, 2H), 3.74 (dd, J=11.5, 5.6 Hz, 1H), 3.68 (dd, J=11.4, 6.7 Hz, 1H), 2.34 (p, J=7.7 Hz, 2H).

Example 11

5-Chloro-2-cyanophenyl 3-deoxy-3-[4-(3,4,5-trifluorophenyl)-1H-1,2-pyrazol-1-yl]-1-thio-α-D-galactopyranoside

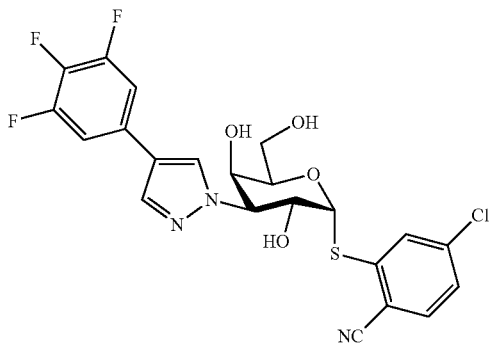

A nitrogen purged solution of 1,2,4,6-tetra-0-acetyl-3-deoxy-3-(4-iodo-1H-1,2-pyrazol-1-yl)-O-D-galactopyranoside (500 mg, 0.95 mmol), K$_2$CO$_3$ (659 mg, 4.77 mmol), (3,4,5-trifluorophenyl)boronic acid (252 mg, 1.43 mmol) and Pd(dppf)Cl$_2$ (105 mg, 0.14 mmol) in water/dioxane (1:2, 4.5 mL) was heated 1 h at 60° C. The mixture was partitioned between EtOAc and water and the organic phase was dried, evaporated and purified by chromatography (SiO$_2$, PE/EtOAc). The obtained material and PCl$_5$ (206 mg, 0.99 mmol) were dissolved in DCM (8 mL) and BF$_3$OEt$_2$ (0.12 mL, 0.99 mmol) was added. The mixture was stirred 5 h at rt before it was diluted with DCM and washed with water and saturated aq NaHCO$_3$, dried and evaporated. The residue was dissolved with 4-chloro-2-sulfanylbenzonitrile (161 mg, 0.95 mmol) in DMF (4 mL). K$_2$CO$_3$ (210 mg, 1.52 mmol) was added and the mixture was stirred 18 h at rt. The mixture was diluted with EtOAc and washed with water and brine, the organic phase was dried and evaporated. The residue was stirred 30 min at rt in NaOMe (0.5 mL, 1M) and MeOH (5 mL). The reaction was concentrated and purified by prep HPLC (C$_{18}$, H$_2$O/MeCN/0.1% TFA) to afford the title compound (31 mg, 6%). ESI-MS m/z calcd for [C$_{22}$H$_{17}$ClF$_3$N$_3$O$_4$S] [M+H]$^+$: 512.1; found: 512.3. $^1$H NMR (400 MHz, Methanol-d$_4$) δ 8.23-8.21 (m, 1H), 7.99 (d, J=2.0 Hz, 1H), 7.94 (d, J=0.7 Hz, 1H), 7.74 (d, J=8.3 Hz, 1H), 7.47 (dd, J=8.4, 2.0 Hz, 1H), 7.39 (dd, J=9.3, 6.5 Hz, 2H), 6.13 (d, J=5.4 Hz, 1H), 4.93 (dd, J=11.3, 5.4 Hz, 1H), 4.66 (dd, J=11.3, 2.8 Hz, 1H), 4.38 (t, J=6.3 Hz, 1H), 4.25-4.23 (m, 1H), 3.72 (dd, J=11.5, 5.6 Hz, 1H), 3.66 (dd, J=11.5, 6.7 Hz, 1H).

Example 12

5-Chloro-2-cyanopyridin-3-yl 3-deoxy-3-[4-(3,4,5-trifluorophenyl)-1H-1,2-pyrazol-1-yl]-1-thio-α-D-galactopyranoside

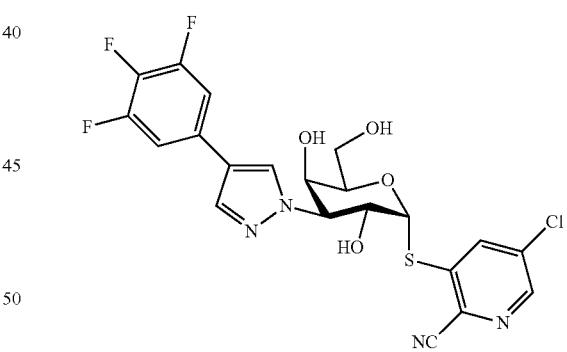

A nitrogen purged solution of 2-bromo-5-chloropyridin-3-yl 3-deoxy-3-[4-(3,4,5-trifluorophenyl)-1H-1,2-pyrazol-1-yl]-1-thio-α-D-galactopyranoside (60.0 mg, 0.11 mmol), zinc cyanide (12.4 mg, 0.11 mmol), 1,1'-bis(diphenylphosphino)ferrocene (4.8 mg, 0.0085 mmol), tris(dibenzylideneacetone)dipalladium(0) (4.8 mg, 0.0085 mmol) and Zn (3.5 mg, 0.053 mmol) in DMF (1 mL) was stirred 2 h at 100° C. The mixture was diluted with EtOAc, washed with water and brine. The organic phase was dried, concentrated and purified by prep HPLC (C$_{18}$, H$_2$O/MeCN/0.1% TFA) yielded the title compound (6 mg, 11%). ESI-MS m/z calcd for [C$_{21}$H$_{16}$ClF$_3$N$_4$O$_4$S] [M+H]$^+$: 513.1; found: 512.8, $^1$H NMR (400 MHz, Methanol-d$_4$) δ 8.55 (d, J=2.1 Hz, 1H), 8.43 (d, J=2.1 Hz, 1H), 8.20 (s, 1H), 7.92 (s, 1H), 7.40-7.33

(m, 2H), 6.21 (d, J=5.3 Hz, 1H), 4.93 (dd, J=11.3, 5.3 Hz, 1H), 4.66 (d, J=11.2 Hz, 1H), 4.31 (s, 1H), 4.20 (s, 1H), 3.68 (s, 1H), 3.66 (d, J=2.1 Hz, 1H).

Example 13

5-Chloro-2-cyanopyridin-3-yl 3-[4-(4-chloro-3,5-difluorophenyl)-1H-1,2-pyrazol-1-yl]-3-deoxy-1-thio-α-D-galactopyranoside

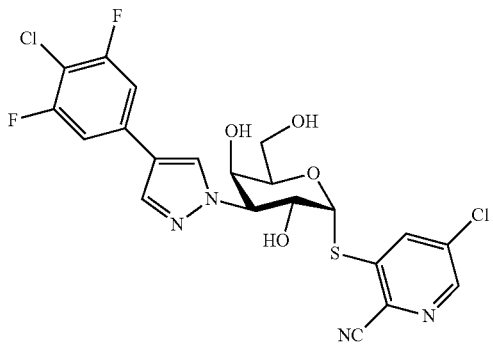

A nitrogen purged solution of 2-bromo-5-chloropyridin-3-yl 3-[4-(4-chloro-3,5-difluorophenyl)-1H-1,2-pyrazol-1-yl]-3-deoxy-1-thio-α-D-galactopyranoside (50 mg, 0.086 mmol), zinc cyanide (15.1 mg, 0.13 mmol), Zn (2.8 mg, 0.043 mmol), tris(dibenzylideneacetone)dipalladium(0) (3.9 mg, 0.0069 mmol) and 1,1'-bis(diphenylphosphino)ferrocene (3.9 mg, 0.0069 mmol) in DMF (2 mL) was stirred 20 h at 90° C. The mixture was diluted with EtOAc, washed with water and brine. The organic phase was dried, concentrated and purified by prep HPLC (C$_{18}$, H$_2$O/MeCN/0.1% TFA) yielded the title compound as a white solid (2.9 mg, 6%). ESI-MS m/z calcd for [C$_{21}$H$_{17}$Cl$_2$F$_2$N$_4$O$_4$S] [M+H]$^+$: 529.0; found: 528.7. $^1$H NMR (500 MHz, Methanol-d$_4$) δ 8.57 (d, J=2.1 Hz, 1H), 8.45 (d, J=2.1 Hz, 1H), 8.28 (s, 1H), 7.99 (s, 1H), 7.41 (d, J=8.3 Hz, 2H), 6.23 (d, J=5.3 Hz, 1H), 4.95 (dd, J=11.3, 5.4 Hz, 1H), 4.69 (dd, J=11.3, 2.7 Hz, 1H), 4.33 (t, J=6.0 Hz, 1H), 4.22 (s, 1H), 3.74-3.64 (m, 2H).

Example 14

5-Chloro-2-methylpyridin-3-yl 3-deoxy-3-[4-(3,4,5-trifluorophenyl)-1H-1,2-pyrazol-1-yl]-1-thio-α-D-galactopyranoside

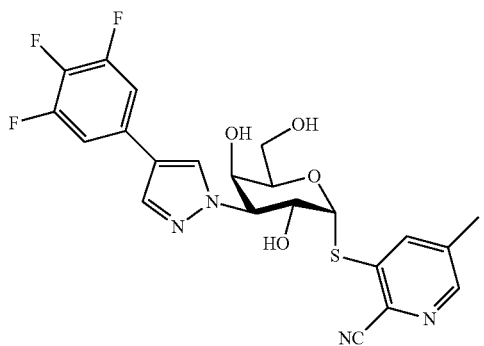

A nitrogen purged solution of 5-chloro-2-methylpyridin-3-yl 2,4,6-tri-O-acetyl-3-deoxy-3-(4-iodo-1H-1,2-pyrazol-1-yl)-1-thio-α-D-galactopyranoside (200 mg, 50% purity, 0.33 mmol), (3,4,5-trifluorophenyl)boronic acid (85.9 mg, 0.49 mmol), K$_2$CO$_3$ (225 mg, 1.63 mmol) and Pd(dppf)Cl$_2$ (35.7 mg, 0.049 mmol) in dioxane (4 mL) and water (2 mL) was stirred 6 h at 60° C. The mixture was concentrated, and the residue dissolved in MeOH (10 mL) and NaOMe (1 mL, 1 M). After stirring 1 h at rt the reaction was quenched with acetic acid (0.1 mL). The mixture was concentrated and purified by prep HPLC (C$_{18}$, H$_2$O/MeCN/0.1% TFA) to afford the title compound (6 mg, 4%) as a white solid. ESI-MS m/z calcd for [C$_{22}$H$_{20}$F$_3$N$_4$O$_4$S] [M+H]$^+$: 493.1; found: 492.9. $^1$H NMR (500 MHz, Methanol-d$_4$) δ 8.43 (s, 1H), 8.23-8.18 (m, 2H), 7.94 (s, 1H), 7.42-7.35 (m, 2H), 6.11 (d, J=5.4 Hz, 1H), 4.93 (dd, J=11.3, 5.4 Hz, 1H), 4.68 (dd, J=11.3, 2.7 Hz, 1H), 4.39 (t, J=6.1 Hz, 1H), 4.23 (d, J=2.1 Hz, 1H), 3.74-3.63 (m, 2H), 2.46 (s, 3H).

Example 15

5-Bromo-2-cyanopyridin-3-yl 3-deoxy-3-[4-(3,4,5-trifluorophenyl)-1H-1,2-pyrazol-1-yl]-1-thio-α-D-galactopyranoside

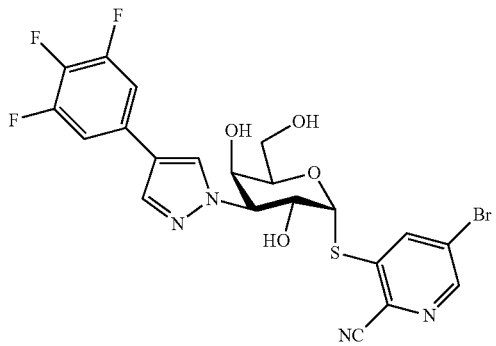

A solution of 5-bromo-2-cyanopyridin-3-yl 2,4,6-tri-O-acetyl-3-deoxy-3-[4-(3,4,5-trifluorophenyl)-1H-1,2-pyrazol-1-yl]-1-thio-α-D-galactopyranoside (453 mg, 0.66 mmol) in MeOH (12 mL), Et$_3$N (3 mL) and water (1 mL) was stirred 16 h at rt. The mixture was partitioned between EtOAc and water, the organic phase was dried and evaporated. The residue was recrystallized from EtOAc/PE (6 mL, 2:1) and the crystals were filtered off to afford the title compound (167 mg, 45%). The filtrate was concentrated and purified by prep HPLC (C$_{18}$, H$_2$O/MeCN/0.1 TFA) to afford the title compound (97 mg, 26%). ESI-MS m/z calcd for [C$_{21}$H$_{16}$BrF$_3$N$_4$O$_4$S] [M+H]$^+$: 557.0; found: 557.0. $^1$H NMR (400 MHz, Methanol-d$_4$) δ 8.67 (d, J=2.0 Hz, 1H), 8.60 (d, J=2.0 Hz, 1H), 8.22 (s, 1H), 7.95 (d, J=0.6 Hz, 1H), 7.39 (dd, J=9.3, 6.5 Hz, 2H), 6.21 (d, J=5.4 Hz, 1H), 4.95 (dd, J=11.3, 5.4 Hz, 1H), 4.68 (dd, J=11.3, 2.7 Hz, 1H), 4.33 (t, J=6.1 Hz, 1H), 4.22 (d, J=1.8 Hz, 1H), 3.74-3.65 (m, 2H).

Example 16

2-Cyano-5-ethynylpyridin-3-yl 3-deoxy-3-[4-(3,4,5-trifluorophenyl)-1H-1,2-pyrazol-1-yl]-1-thio-α-D-galactopyranoside

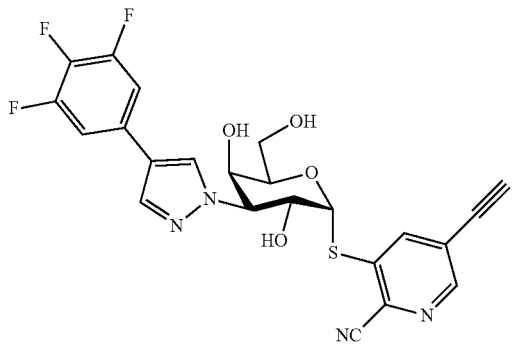

To a nitrogen purged solution of 5-bromo-2-cyanopyridin-3-yl 3-deoxy-3-[4-(3,4,5-trifluorophenyl)-1H-1,2-pyrazol-1-yl]-1-thio-α-D-galactopyranoside (100 mg, 0.18 mmol), bis(triphenylphosphine)palladium(II) chloride (6.3 mg, 0.0090 mmol) and CuI (1.7 mg, 0.0090 mmol) in THF (2.0 mL) trimethylsilylacetylene (35 µL, 0.25 mmol) was added followed by DIPEA (44 µL, 0.25 mmol). The mixture was stirred 20 h at 50° C., cooled to rt and TBAF (0.3 mL, 1 M in THF, 0.3 mmol) was added and the mixture was stirred 10 min at rt. The mixture was partitioned between EtOAc and water and the organic phase was dried and evaporated. The residue was purified by prep HPLC ($C_{18}$, $H_2O$/MeCN/0.1% TFA) to afford the title compound (39 mg, 43%). ESI-MS m/z calcd for [$C_{23}H_{17}F_3N_4O_4S$] [M+H]$^+$: 503.1; found: 503.1. $^1$H NMR (400 MHz, Methanol-$d_4$) δ 8.62 (d, J=1.8 Hz, 1H), 8.42 (d, J=1.8 Hz, 1H), 8.22 (s, 1H), 7.95 (s, 1H), 7.39 (dd, J=9.1, 6.6 Hz, 2H), 6.20 (d, J=5.4 Hz, 1H), 4.94 (dd, J=11.3, 5.4 Hz, 1H), 4.68 (dd, J=11.3, 2.7 Hz, 1H), 4.34 (t, J=6.1 Hz, 1H), 4.23 (d, J=2.0 Hz, 1H), 4.15 (s, 1H), 3.70 (dd, J=11.6, 5.2 Hz, 1H), 3.65 (dd, J=11.6, 6.9 Hz, 1H).

Example 17

5-Chloropyridin-3-yl 3-[4-(4-chloro-3-fluorophenyl)-1H-1,2-pyrazol-1-yl]-3-deoxy-1-thio-α-D-galactopyranoside

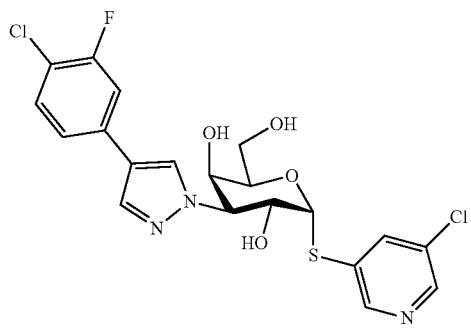

4-Bromo-1-chloro-2-fluorobenzene (13 µL, 0.10 mmol), 5-chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (45 mg, 0.052 mmol) and tetrakis(triphenylphosphine)palladium(0) (6.0 mg, 0.0052 mmol) were dissolved in a degassed mixture of toluene (0.5 mL), EtOH (0.1 mL) and aq $Na_2CO_3$ (52 µL, 2 M) and the resulting mixture was refluxed for 6 h. The mixture was concentrated, dissolved in MeOH (1.0 mL), $Et_3N$ (0.15 mL) and water (0.05 mL) and stirred 21 h at rt. The mixture was concentrated and purified by prep HPLC ($C_{18}$, $H_2O$/MeCN/0.1% TFA) to afford the title compound (3 mg, 12%). ESI-MS m/z calcd for [$C_{20}H_{18}Cl_2FN_3O_4S$] [M+H]$^+$: 486.0; found: 486.4. $^1$H NMR (400 MHz, Methanol-$d_4$) δ 8.64 (d, J=1.9 Hz, 1H), 8.47 (d, J=2.2 Hz, 1H), 8.23-8.15 (m, 2H), 7.93 (s, 1H), 7.49 (dd, J=10.6, 1.7 Hz, 1H), 7.46-7.42 (m, 1H), 7.40 (dd, J=8.4, 1.7 Hz, 1H), 5.91 (d, J=5.4 Hz, 1H), 4.92-4.85 (m, 1H), 4.60 (dd, J=11.4, 2.7 Hz, 1H), 4.43 (t, J=6.0 Hz, 1H), 4.20 (d, J=2.5 Hz, 1H), 3.77-3.69 (m, 2H).

Example 18

5-Chloropyridin-3-yl 3-deoxy-3-[4-(6-fluoropyridin-2-yl)-1H-1,2-pyrazol-1-yl]-1-thio-α-D-galactopyranoside

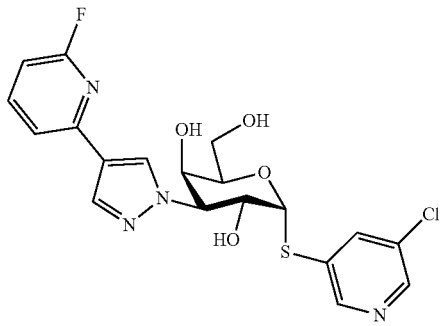

5-Chloropyridin-3-yl 2,4,6-tri-O-acetyl-3-deoxy-3-(4-iodo-1H-1,2-pyrazol-1-yl)-α-D-galactopyranoside (97 mg, 0.11 mmol), (6-fluoro-2-pyridyl)boronic acid (31 mg, 0.22 mmol) and Pd(dppf)$Cl_2$ (8.2 mg, 0.011 mmol) were dissolved in a degassed mixture of dioxane (1.0 mL), water (0.5 mL) and aq $Na_2CO_3$ (278 µL, 2 M). The mixture was stirred 17 h at 60° C. The mixture was filtered through celite, concentrated and the residue was dissolved in MeOH (1.0 mL), $Et_3N$ (0.15 mL) and water (0.05 mL) and stirred 5 h at rt. The mixture was filtered, concentrated and purified by prep HPLC ($C_{18}$, $H_2O$/MeCN/0.1 TFA) to afford the title compound (10 mg, 20%). ESI-MS m/z calcd for [$C_{19}H_{18}ClFN_4O_4S$] [M+H]$^+$: 453.1; found: 453.5. $^1$H NMR (500 MHz, Methanol-$d_4$) δ 8.66 (d, J=1.9 Hz, 1H), 8.49 (d, J=2.2 Hz, 1H), 8.38 (s, 1H), 8.23 (t, J=2.0 Hz, 1H), 8.11 (s, 1H), 7.91 (q, J=8.1 Hz, 1H), 7.58 (dd, J=7.5, 2.3 Hz, 1H), 6.85 (dd, J=8.1, 2.2 Hz, 1H), 5.94 (d, J=5.4 Hz, 1H), 4.91 (dd, J=11.4, 5.4 Hz, 1H), 4.65 (dd, J=11.3, 2.8 Hz, 1H), 4.45 (t, J=6.1 Hz, 1H), 4.22 (d, J=1.9 Hz, 1H), 3.77-3.69 (m, 2H).

Example 19

5-Chloropyridin-3-yl 3-deoxy-3-[4-(5-fluoropyridin-2-yl)-1H-1,2-pyrazol-1-yl]-1-thio-α-D-galactopyranoside

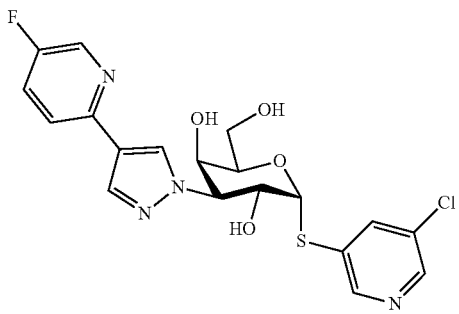

5-Chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (100 mg, 0.16 mmol), tetrakis(triphenylphosphine)palladium(0) (19 mg, 0.016 mmol) and 2-bromo-5-fluoro-pyridine (87 mg, 0.49 mmol) were dissolved in a degassed mixture of toluene (1.0 mL), EtOH (0.2 mL) and aq $Na_2CO_3$ (246 μL, 2 M) and the mixture was refluxed for 2 h. The mixture was cooled to rt and the organic phase was separated. The aqueous phase was extracted with EtOAc (2×1 mL) and the combined organic phases were dried and concentrated. The residue was dissolved in MeOH (1.0 mL), $Et_3N$ (0.15 mL) and water (0.05 mL) and stirred 17 h at 50° C. The mixture was filtered, concentrated and purified by prep HPLC ($C_{18}$, $H_2O$/MeCN/0.1% TFA) to afford the title compound (33 mg, 44%). ESI-MS m/z calcd for $[C_{19}H_{18}ClFN_4O_4S]$ $[M+H]^+$: 453.1; found: 453.0. $^1$H NMR (400 MHz, Methanol-d4) δ 8.64 (s, 1H), 8.50-8.45 (m, 1H), 8.44 (d, J=2.2 Hz, 1H), 8.36 (s, 1H), 8.20 (s, 1H), 8.08 (s, 1H), 7.80 (dd, J=8.8, 4.4 Hz, 1H), 7.70 (td, J=8.5, 2.7 Hz, 1H), 5.92 (d, J=5.3 Hz, 1H), 4.94-4.87 (m, 1H), 4.64 (dd, J=11.3, 2.4 Hz, 1H), 4.44 (t, J=5.9 Hz, 1H), 4.25-4.17 (m, 1H), 3.77-3.64 (m, 2H).

Example 20

5-Chloropyridin-3-yl 3-deoxy-3-[4-(4-fluoropyridin-2-yl)-1H-1,2-pyrazol-1-yl]-1-thio-α-D-galactopyranoside

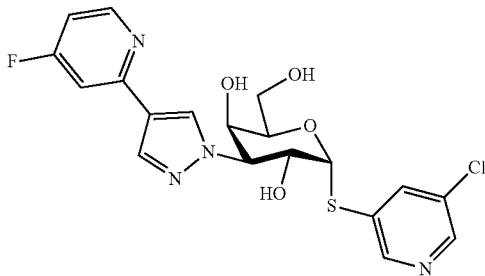

5-Chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (45 mg, 0.052 mmol), tetrakis(triphenylphosphine)palladium(0) (6.0 mg, 0.0052 mmol) and 2-bromo-4-fluoro-pyridine (35 μL, 0.33 mmol) were dissolved in a degassed mixture of toluene (1.0 mL), EtOH (0.2 mL) and aq $Na_2CO_3$ (167 μL, 3 M) and the mixture was refluxed for 20 h. The mixture was concentrated, dissolved in MeOH (1.0 mL), $Et_3N$ (0.15 mL) and water (0.05 mL) and stirred 24 h at rt. The mixture was concentrated and purified by prep HPLC ($C_{18}$, $H_2O$/MeCN/0.1% TFA) to afford the title compound (16 mg, 32%). ESI-MS m/z calcd for $[C_{19}H_{18}ClFN_4O_4S]$ $[M+H]^+$: 453.1; found: 453.5. $^1$H NMR (400 MHz, Methanol-d4) δ 8.64 (d, J=1.5 Hz, 1H), 8.59 (t, J=6.8 Hz, 1H), 8.55 (s, 1H), 8.47 (d, J=2.1 Hz, 1H), 8.20 (s, 1H), 8.19 (t, J=2.0 Hz, 1H), 7.81 (dd, J=9.7, 2.3 Hz, 1H), 7.34-7.26 (m, 1H), 5.91 (d, J=5.3 Hz, 1H), 4.90 (dd, J=11.3, 5.4 Hz, 1H), 4.68 (dd, J=11.3, 2.7 Hz, 1H), 4.45 (t, J=6.0 Hz, 1H), 4.22 (d, J=2.2 Hz, 1H), 3.77-3.66 (m, 2H).

Example 21

5-Chloropyridin-3-yl 3-deoxy-3-[4-(1H-1,2-pyrazol-3-yl)-1H-1,2-pyrazol-1-yl]-1-thio-α-D-galactopyranoside

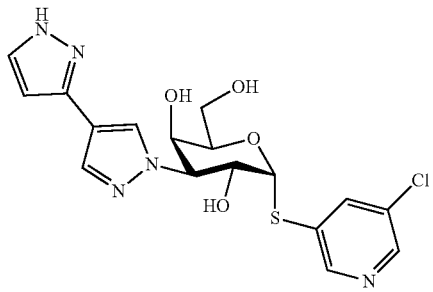

5-Chloropyridin-3-yl 2,4,6-tri-O-acetyl-3-deoxy-3-(4-iodo-1H-1,2-pyrazol-1-yl)-α-D-galactopyranoside (97 mg, 0.11 mmol), 1H-pyrazol-3-ylboronic acid (25 mg, 0.22 mmol) and Pd(dppf)$Cl_2$ (8.2 mg, 0.011 mmol) were dissolved in a degassed mixture of dioxane (1.0 mL), water (0.5 mL) and aq $Na_2CO_3$ (278 μL, 2 M). The mixture was stirred 17.5 h at 60° C. More 1H-pyrazol-3-ylboronic acid (25 mg, 0.22 mmol) was added and the mixture was stirred 23 h at 80° C. The mixture was concentrated and purified by prep HPLC ($C_{18}$, $H_2O$/MeCN/0.1% TFA). Further purification by chromatography ($SiO_2$, EtOAc/MeOH) afforded the title compound (7 mg, 15%). ESI-MS m/z calcd for $[C_{17}H_{18}ClN_5O_4S]$ $[M+H]^+$: 424.1; found: 424.5. $^1$H NMR (500 MHz, Methanol-d4) δ 8.65 (d, J=1.9 Hz, 1H), 8.47 (d, J=2.2 Hz, 1H), 8.20 (t, J=2.1 Hz, 1H), 8.14 (s, 1H), 7.89 (s, 1H), 7.67 (s, 1H), 6.50 (s, 1H), 5.91 (d, J=5.4 Hz, 1H), 4.92-4.87 (m, 1H), 4.62 (dd, J=11.7, 1.9 Hz, 1H), 4.46 (t, J=6.0 Hz, 1H), 4.22 (d, J=2.0 Hz, 1H), 3.74 (dd, J=11.6, 5.3 Hz, 1H), 3.71 (dd, J=11.6, 6.9 Hz, 1H).

Example 22

5-Chloropyridin-3-yl 3-deoxy-3-[4-(1-methyl-1,2-pyrazol-3-yl)-1H-1,2-pyrazol-1-yl]-1-thio-α-D-galactopyranoside

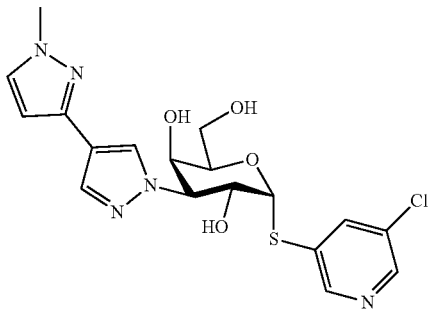

5-Chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (97 mg, 0.11 mmol), tetrakis(triphenylphosphine)palladium(0) (12.9 mg, 0.011 mmol) and 3-bromo-1-methylpyrazole (22.6 μL, 0.22 mmol) were dissolved in a degassed mixture of toluene (1.0 mL), EtOH (0.2 mL) and aq Na$_2$CO$_3$ (111 μL, 2 M) and the mixture was refluxed for 23 h. The mixture was concentrated, dissolved in MeOH (1.0 mL), Et$_3$N (0.15 mL) and water (0.05 mL) and stirred 23 h at rt. The mixture was concentrated and purified by prep HPLC (C$_{18}$, H$_2$O/MeCN/0.1 TFA) to afford the title compound (7.8 mg, 16%). ESI-MS m/z calcd for [C$_{18}$H$_{20}$ClN$_5$O$_4$S] [M+H]$^+$: 438.1; found: 438.5. $^1$H NMR (500 MHz, Methanol-d$_4$) δ 8.66 (d, J=1.9 Hz, 1H), 8.49 (d, J=2.2 Hz, 1H), 8.22 (t, J=2.1 Hz, 1H), 8.12 (s, 1H), 7.89-7.82 (m, 1H), 7.60 (d, J=2.2 Hz, 1H), 6.46 (d, J=2.3 Hz, 1H), 5.92 (d, J=5.3 Hz, 1H), 4.91-4.87 (m, 1H), 4.62 (dd, J=11.3, 2.7 Hz, 1H), 4.45 (t, J=6.1 Hz, 1H), 4.25-4.17 (m, 1H), 3.92 (s, 3H), 3.76-3.67 (m, 2H).

Example 23

5-Chloropyridin-3-yl 3-deoxy-3-[4-(1H-imidazol-2-yl)-1H-1,2-pyrazol-1-yl]-1-thio-α-D-galactopyranoside

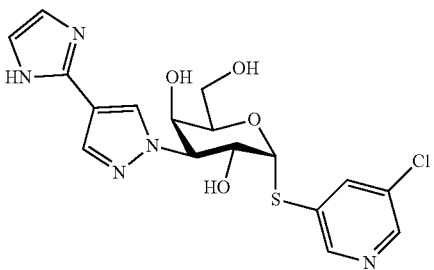

5-Chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (97 mg, 0.11 mmol), tetrakis(triphenylphosphine)palladium(0) (12.9 mg, 0.011 mmol) and 2-bromo-1H-imidazole (32.7 mg, 0.22 mmol) were dissolved in a degassed mixture of toluene (1.0 mL), EtOH (0.2 mL) and aq Na$_2$CO$_3$ (111 μL, 2 M) and the mixture was refluxed for 23 h. The mixture was concentrated, dissolved in MeOH (1.0 mL), Et$_3$N (0.15 mL) and water (0.05 mL) and stirred 23 h at rt. The mixture was concentrated and purified by prep HPLC (C$_{18}$, H$_2$O/MeCN/0.1% TFA) to afford the title compound (16 mg, 34%). ESI-MS m/z calcd for [C$_{17}$H$_{18}$ClN$_5$O$_4$S] [M+H]$^+$: 424.1; found: 424.5. $^1$H NMR (500 MHz, Methanol-d$_4$) δ 8.65 (d, J=1.8 Hz, 1H), 8.53 (s, 1H), 8.50 (d, J=2.2 Hz, 1H), 8.20 (t, J=2.1 Hz, 1H), 8.16-8.10 (m, 1H), 7.53 (s, 2H), 5.93 (d, J=5.3 Hz, 1H), 4.93-4.87 (m, 1H), 4.75 (dd, J=11.4, 2.8 Hz, 1H), 4.47 (t, J=6.0 Hz, 1H), 4.28-4.22 (m, 1H), 3.75 (dd, J=11.6, 5.4 Hz, 1H), 3.71 (dd, J=11.6, 6.9 Hz, 1H).

Example 24

5-Chloropyridin-3-yl 3-deoxy-3-[4-(oxazol-2-yl)-1H-1,2-pyrazol-1-yl]-1-thio-α-D-galactopyranoside

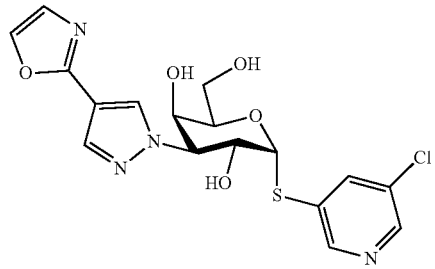

5-Chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (97 mg, 0.11 mmol), tetrakis(triphenylphosphine)palladium(0) (12.9 mg, 0.011 mmol) and 2-bromooxazole (32.9 mg, 0.22 mmol) were dissolved in a degassed mixture of toluene (1.0 mL), EtOH (0.2 mL) and aq Na$_2$CO$_3$ (111 μL, 2 M) and the mixture was refluxed for 23 h. The mixture was concentrated, dissolved in MeOH (1.0 mL), Et$_3$N (0.15 mL) and water (0.05 mL) and stirred 23 h at rt. The mixture was concentrated and purified by prep HPLC (C$_{18}$, H$_2$O/MeCN/0.1% TFA). Further purification by chromatography (SiO$_2$, EtOAc/MeOH) afforded the title compound (15.8 mg, 33%). ESI-MS m/z calcd for [C$_{17}$H$_{17}$ClN$_4$O$_5$S] [M+H]$^+$: 425.1; found: 425.5. $^1$H NMR (400 MHz, Methanol-d$_4$) δ 8.63 (d, J=1.8 Hz, 1H), 8.46 (d, J=2.2 Hz, 1H), 8.36 (s, 1H), 8.18 (t, J=2.1 Hz, 1H), 8.04 (s, 1H), 7.88 (s, 1H), 7.21 (s, 1H), 5.90 (d, J=5.3 Hz, 1H), 4.91-4.86 (m, 1H), 4.66 (dd, J=11.4, 2.8 Hz, 1H), 4.43 (t, J=6.2 Hz, 1H), 4.20 (d, J=1.9 Hz, 1H), 3.75-3.64 (m, 2H).

Example 25

5-Chloropyridin-3-yl 3-deoxy-3-[4-(thiazol-4-yl)-1H-1,2-pyrazol-1-yl]-1-thio-α-D-galactopyranoside

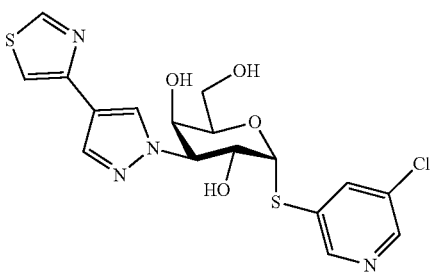

5-Chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (45 mg, 0.052 mmol), tetrakis(triphenylphosphine)palladium(0) (6.0 mg, 0.0052 mmol) and 4-bromothiazole (9.2 µL, 0.10 mmol) were dissolved in a degassed mixture of toluene (0.5 mL), EtOH (0.1 mL) and aq $Na_2CO_3$ (52 µL, 2 M) and the mixture was refluxed for 6 h. The mixture was concentrated, dissolved in MeOH (1.0 mL), $Et_3N$ (0.15 mL) and water (0.05 mL) and stirred overnight at rt. The mixture was concentrated and purified by prep HPLC ($C_{18}$, $H_2O$/MeCN/0.1 TFA) to afford the title compound (6.0 mg, 26%). ESI-MS m/z calcd for [$C_{17}H_{17}ClN_4O_4S_2$] [M+H]$^+$: 441.0; found: 441.5. $^1$H NMR (500 MHz, Methanol-$d_4$) δ 9.06 (d, J=2.0 Hz, 1H), 8.66 (d, J=1.8 Hz, 1H), 8.49 (d, J=2.1 Hz, 1H), 8.26 (s, 1H), 8.23 (t, J=2.1 Hz, 1H), 8.03-7.97 (m, 1H), 7.66 (d, J=2.0 Hz, 1H), 5.93 (d, J=5.4 Hz, 1H), 4.93-4.88 (m, 1H), 4.64 (dd, J=11.3, 2.7 Hz, 1H), 4.45 (t, J=6.1 Hz, 1H), 4.25-4.20 (m, 1H), 3.77-3.68 (m, 2H).

Example 26

5-Chloropyridin-3-yl 3-deoxy-3-[4-(thiazol-2-yl)-1H-1,2-pyrazol-1-yl]-1-thio-α-D-galactopyranoside

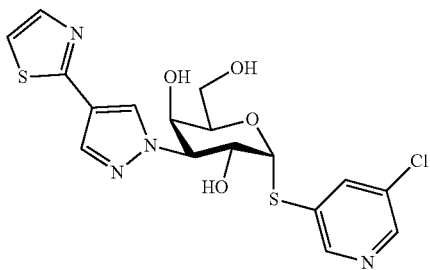

5-Chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (45 mg, 0.052 mmol), tetrakis(triphenylphosphine)palladium(0) (6.0 mg, 0.0052 mmol) and 2-bromothiazole (9.2 µL, 0.10 mmol) were dissolved in a degassed mixture of toluene (0.5 mL), EtOH (0.1 mL) and aq $Na_2CO_3$ (52 µL, 2 M) and the mixture was refluxed for 6 h. The mixture was concentrated, dissolved in MeOH (1.0 mL), $Et_3N$ (0.15 mL) and water (0.05 mL) and stirred overnight at rt. The mixture was concentrated and purified by prep HPLC ($C_{18}$, $H_2O$/MeCN/0.1% TFA) to afford the title compound (7.0 mg, 31%). ESI-MS m/z calcd for [$C_{17}H_{17}ClN_4O_4S_2$] [M+H]$^+$: 441.0; found: 441.0. $^1$H NMR (500 MHz, Methanol-$d_4$) δ 8.66 (d, J=1.9 Hz, 1H), 8.49 (d, J=2.2 Hz, 1H), 8.38 (s, 1H), 8.22 (t, J=2.1 Hz, 1H), 8.05 (d, J=0.6 Hz, 1H), 7.81 (d, J=3.4 Hz, 1H), 7.54 (d, J=3.4 Hz, 1H), 5.93 (d, J=5.4 Hz, 1H), 4.94-4.88 (m, 1H), 4.67 (dd, J=11.4, 2.8 Hz, 1H), 4.45 (t, J=6.3 Hz, 1H), 4.23 (d, J=1.8 Hz, 1H), 3.74 (dd, J=11.7, 5.4 Hz, 1H), 3.71 (dd, J=11.6, 7.0 Hz, 1H).

Example 27

5-Chloropyridin-3-yl 3-[4-(4-chlorothiazol-2-yl)-1H-1,2-pyrazol-1-yl]-3-deoxy-1-thio-α-D-galactopyranoside

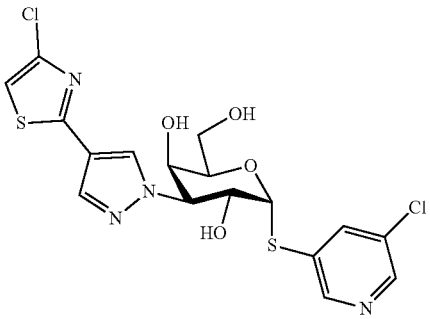

5-Chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (45 mg, 0.052 mmol), tetrakis(triphenylphosphine)palladium(0) (6.0 mg, 0.0052 mmol) and 2-bromo-4-chlorothiazole (21 mg, 0.10 mmol) were dissolved in a degassed mixture of toluene (0.5 mL), EtOH (0.1 mL) and aq $Na_2CO_3$ (52 µL, 2 M) and the mixture was refluxed for 16 h. The mixture was concentrated, dissolved in MeOH (1.0 mL), $Et_3N$ (0.15 mL) and water (0.05 mL) and stirred 3 h at rt. The mixture was concentrated and purified by prep HPLC ($C_{18}$, $H_2O$/MeCN/0.1% TFA) to afford the title compound (11 mg, 45%). ESI-MS m/z calcd for [$C_{17}H_{16}Cl_2N_4O_4S_2$] [M+H]$^+$: 475.0; found: 474.7. $^1$H NMR (500 MHz, Methanol-$d_4$) δ 8.63 (d, J=1.9 Hz, 1H), 8.46 (d, J=2.2 Hz, 1H), 8.35 (s, 1H), 8.18 (t, J=2.1 Hz, 1H), 8.02 (s, 1H), 7.30 (s, 1H), 5.90 (d, J=5.4 Hz, 1H), 4.91-4.85 (m, 1H), 4.64 (dd, J=11.3, 2.8 Hz, 1H), 4.43 (t, J=5.9 Hz, 1H), 4.20 (d, J=1.8 Hz, 1H), 3.72 (dd, J=11.6, 5.3 Hz, 1H), 3.68 (dd, J=11.6, 6.9 Hz, 1H).

Example 28

5-Bromopyridin-3-yl 3-[4-(4-chlorothiazol-2-yl)-1H-1,2-pyrazol-1-yl]-3-deoxy-1-thio-α-D-galactopyranoside

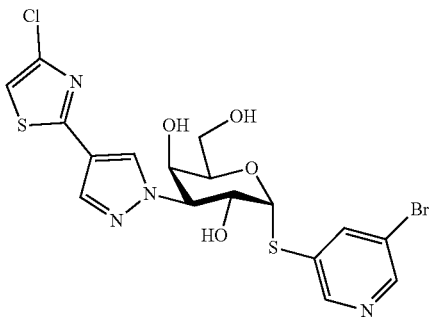

5-Bromopyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (189 mg, 0.29 mmol), tetrakis(triphenylphosphine)palladium(0) (33 mg, 0.029 mmol) and 2-bromo-4-chlorothiazole (115 mg, 0.58 mmol) were dissolved in a degassed mixture of toluene (2.0 mL), EtOH (0.4 mL) and aq $Na_2CO_3$ (217 μL, 2 M) and the mixture was refluxed for 19 h. The mixture was diluted with water (10 mL), filtered and extracted with EtOAc (2×10 mL). The combined organic phases were concentrated, and the residue was stirred 2 h at rt in MeOH (2 mL) and NaOMe (0.1 mL, 1 M). The reaction was quenched with acetic acid, concentrated and purified by prep HPLC ($C_{18}$, $H_2O$/MeCN/0.1 TFA) to afford the title compound (16 mg, 10%). ESI-MS m/z calcd for $[C_{17}H_{16}BrClN_4O_4S_2]$ $[M+H]^+$: 519.0; found: 518.8. $^1$H NMR (500 MHz, Methanol-$d_4$) δ 8.69 (d, J=1.7 Hz, 1H), 8.57 (d, J=1.9 Hz, 1H), 8.37 (s, 1H), 8.33 (t, J=1.9 Hz, 1H), 8.03 (s, 1H), 7.32 (s, 1H), 5.90 (d, J=5.4 Hz, 1H), 4.93-4.88 (m, 1H), 4.66 (dd, J=11.4, 2.7 Hz, 1H), 4.45 (t, J=6.2 Hz, 1H), 4.22 (d, J=2.0 Hz, 1H), 3.74 (dd, J=11.6, 5.3 Hz, 1H), 3.70 (dd, J=11.5, 6.9 Hz, 1H).

Example 29

5-Chloro-2-cyanophenyl 3-[4-(4-chlorothiazol-2-yl)-1H-1,2-pyrazol-1-yl]-3-deoxy-1-thio-α-D-galactopyranoside

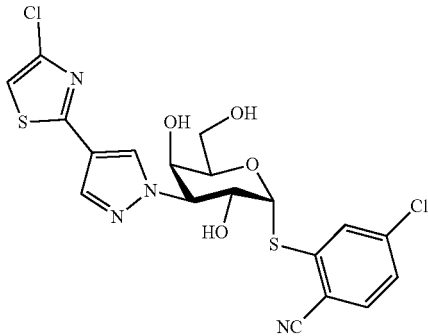

5-Chloro-2-cyanophenyl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (92 mg, 0.15 mmol), tetrakis(triphenylphosphine)palladium(0) (17 mg, 0.015 mmol) and 2-bromo-4-chlorothiazole (58 mg, 0.29 mmol) were dissolved in a degassed mixture of toluene (1.0 mL) and aq $Na_2CO_3$ (109 μL, 2 M) and the mixture was refluxed for 22 h. The mixture was diluted with water (2 mL), filtered and extracted with EtOAc (2×5 mL). The combined organic phases were concentrated, and the residue was stirred 1 h at rt in MeOH (1 mL) and NaOMe (15 μL, 1 M). The reaction was quenched with acetic acid, concentrated and purified by prep HPLC ($C_{18}$, $H_2O$/MeCN/0.1% TFA) to afford the title compound (12 mg, 13%). ESI-MS m/z calcd for $[C_{19}H_{16}Cl_2N_4O_4S_2]$ $[M+H]^+$: 499.0; found: 498.7. $^1$H NMR (500 MHz, Methanol-$d_4$) δ 8.38 (d, J=0.5 Hz, 1H), 8.04 (d, J=0.7 Hz, 1H), 7.99 (d, J=2.0 Hz, 1H), 7.75 (d, J=8.4 Hz, 1H), 7.48 (dd, J=8.4, 2.0 Hz, 1H), 7.32 (s, 1H), 6.13 (d, J=5.4 Hz, 1H), 4.94 (dd, J=11.4, 5.4 Hz, 1H), 4.71 (dd, J=11.4, 2.8 Hz, 1H), 4.39 (t, J=6.3 Hz, 1H), 4.27-4.22 (m, 1H), 3.72 (dd, J=11.5, 5.6 Hz, 1H), 3.65 (dd, J=11.5, 6.7 Hz, 1H).

Example 30

5-Chloro-2-cyanopyridin-3-yl 3-[4-(4-chlorothiazol-2-yl)-1H-1,2-pyrazol-1-yl]-3-deoxy-1-thio-α-D-galactopyranoside

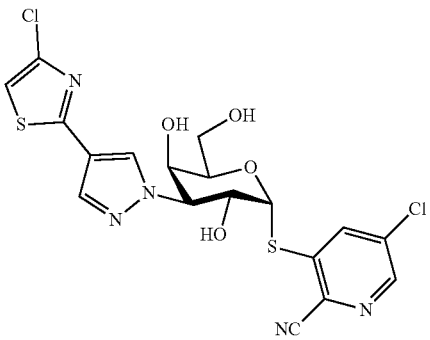

5-Chloro-2-cyanopyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (23 mg, 0.036 mmol), tetrakis(triphenylphosphine)palladium(0) (4.2 mg, 0.0036 mmol) and 2-bromo-4-chlorothiazole (14 mg, 0.073 mmol) were dissolved in a degassed mixture of toluene (0.25 mL), EtOH (0.05 mL) and aq $Na_2CO_3$ (27 μL, 2 M) and the mixture was refluxed for 10 h. The mixture was concentrated, dissolved in MeOH (1.0 mL), $Et_3N$ (0.15 mL) and water (0.05 mL) and stirred 1 h at rt. The mixture was concentrated and purified by prep HPLC ($C_{18}$, $H_2O$/MeCN/0.1% TFA) to afford the title compound (2.5 mg, 14%). ESI-MS m/z calcd for $[C_{18}H_{18}Cl_2N_5O_4S_2]$ $[M+H]^+$: 500.0; found: 499.8. $^1$H NMR (500 MHz, Methanol-$d_4$) δ 8.57 (d, J=2.1 Hz, 1H), 8.46 (d, J=2.1 Hz, 1H), 8.39 (s, 1H), 8.04 (s, 1H), 7.32 (s, 1H), 6.23 (d, J=5.4 Hz, 1H), 4.95 (dd, J=11.3, 5.4 Hz, 1H), 4.73 (dd, J=11.3, 2.8 Hz, 1H), 4.33 (t, J=6.2 Hz, 1H), 4.23 (d, J=2.0 Hz, 1H), 3.71-3.66 (m, 2H).

Example 31

5-Chloropyridin-3-yl 3-deoxy-3-[4-(2-hydroxythiazol-4-yl)-1H-1,2-pyrazol-1-yl]-1-thio-α-D-galactopyranoside

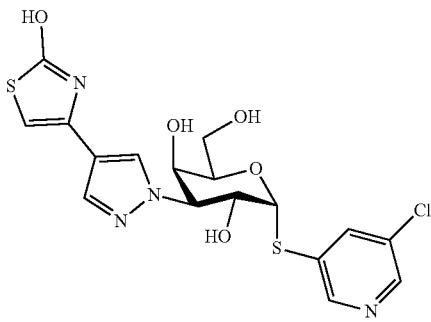

A solution of 5-chloropyridin-3-yl 2,4,6-tri-O-acetyl-3-deoxy-3-[4-(2-benzyloxythiazol-4-yl)-1H-1,2-pyrazol-1-yl]-1-thio-α-D-galactopyranoside (77 mg, 0.11 mmol) and palladium on carbon (10 mg, 0.094 mmol) in MeOH (1.0 mL) was subjected to hydrogen gas (1 atm). The mixture was heated 2 h at 50° C., cooled to rt and filtered. NaOMe (0.2 mL, 1 M) was added to the filtrate that was stirred 100 min at rt. Acetic acid (50 µL) was added and the mixture was concentrated and purified by prep HPLC ($C_{18}$, $H_2O$/MeCN/ 0.1% TFA) to afford the title compound (11 mg, 21%). ESI-MS m/z calcd for $[C_{17}H_{17}ClN_4O_5S_2]$ $[M+H]^+$: 457.0; found: 457.0. $^1$H NMR (400 MHz, Methanol-$d_4$) δ 8.62 (s, 1H), 8.45 (s, 1H), 8.17 (s, 1H), 8.09 (s, 1H), 7.82 (s, 1H), 6.34 (s, 1H), 5.89 (d, J=5.3 Hz, 1H), 4.85-4.78 (m, 1H), 4.59 (dd, J=11.3, 2.4 Hz, 1H), 4.42 (t, J=6.0 Hz, 1H), 4.22-4.12 (m, 1H), 3.77-3.63 (m, 2H).

Example 32

5-Chloropyridin-3-yl 3-deoxy-3-[4-(3,4,5-trifluorophenyl)-1H-1,2-pyrazol-1-yl]-2-O-methyl-1-thio-α-D-galactopyranoside

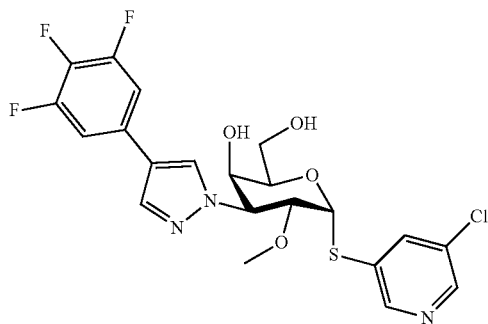

A solution of 5-chloropyridin-3-yl 3-deoxy-3-[4-(3,4,5-trifluorophenyl)-1H-1,2-pyrazol-1-yl]-1-thio-α-D-galactopyranos ide (183 mg, 0.38 mmol), benzaldehyde dimethylacetal (114 µL, 0.75 mmol) and p-toluenesulfonic acid monohydrate (30 mg, 0.14 mmol) in MeCN (2.0 mL) was stirred 72 h at rt. More benzaldehyde dimethylacetal (114 µL, 0.75 mmol) and p-toluenesulfonic acid monohydrate (30 mg, 0.14 mmol) was added and the mixture was stirred 1 h at rt. $Et_3N$ (100 µL, 0.73 mmol) followed by water and PE were added, the precipitate was isolated by filtration. The obtained solid was partitioned between EtOAc and saturated aq $NaHCO_3$, and the organic phase was evaporated and purified by chromatography ($SiO_2$, PE/EtOAc). The obtained material and NaH (60% in oil, 16 mg, 0.4 mmol) were stirred 5 min in DMF (2.0 mL) before iodomethane (17 µL, 0.27 mmol) was added. After stirring 30 min at rt water was added and the precipitate was isolated and triturated in MeOH. The obtained material was stirred 30 min at rt in 80% aq TFA (2.0 mL). Ice and PE were added, and the supernatant was decanted off. The residue was partitioned between EtOAc and water where pH was adjusted to approximately 7 using NaOH (1 M). The organic phase was dried, evaporated and purified by chromatography ($SiO_2$, PE/EtOAc). The product was triturated in PE/EtOAc (1:1) to afford the title compound (54 mg, 29%). ESI-MS m/z calcd for $[C_{21}H_{19}ClF_3N_3O_4S]$ $[M+H]^+$: 502.1; found: 502.1. $^1$H NMR (500 MHz, Methanol-$d_4$) δ 8.64 (d, J=1.9 Hz, 1H), 8.47 (d, J=2.2 Hz, 1H), 8.21 (s, 1H), 8.20 (t, J=2.1 Hz, 1H), 7.91 (s, 1H), 7.42-7.33 (m, 2H), 6.23 (d, J=5.1 Hz, 1H), 4.62 (dd, J=11.3, 2.7 Hz, 1H), 4.55 (dd, J=11.3, 5.2 Hz, 1H), 4.41 (t, J=6.2 Hz, 1H), 4.17 (d, J=1.8 Hz, 1H), 3.72 (dd, J=11.6, 5.3 Hz, 1H), 3.68 (dd, J=11.6, 6.9 Hz, 1H), 3.38 (s, 3H).

Example 33

5-Bromopyridin-3-yl 3-deoxy-3-[4-(3,4,5-trifluorophenyl)-1H-1,2-pyrazol-1-yl]-2-O-methyl-1-thio-α-D-galactopyranoside

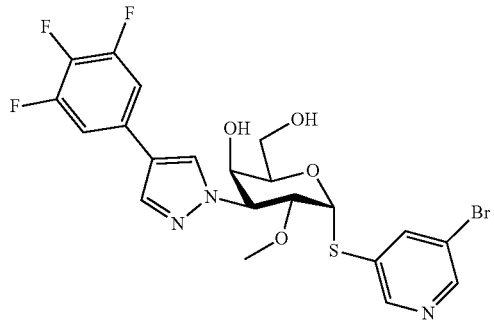

A solution of 5-bromopyridin-3-yl 3-deoxy-3-[4-(3,4,5-trifluorophenyl)-1H-1,2-pyrazol-1-yl]-1-thio-α-D-galactopyranoside (305 mg, 0.57 mmol), benzaldehyde dimethylacetal (182 µL, 1.2 mmol) and p-toluenesulfonic acid monohydrate (30 mg, 0.14 mmol) in MeCN (4.0 mL) was stirred 20 h at rt. $Et_3N$ (100 µL, 0.73 mmol) followed by water (2.0 mL) were added, the precipitate was isolated by filtration and the filter cake was washed with water and PE. The obtained solid and NaH (60% in oil, 30 mg, 0.71 mmol) were stirred 5 min in DMF (4.0 mL) before iodomethane (30 µL, 0.47 mmol) was added. After stirring 30 min at rt water was added and the precipitate was isolated by filtration. The precipitate was recrystallized in EtOAc/PE (1:2) and the crystals were isolated. The crystals were stirred 30 min at rt in 80% aq TFA (2.0 mL). Ice and PE were added, and the supernatant was decanted off. The residue was partitioned between EtOAc and water where pH was adjusted to approximately 7 using NaOH (1 M). The organic phase was dried, evaporated and purified by chromatography ($SiO_2$, PE/EtOAc) to afford the title compound (124 mg, 40%). ESI-MS m/z calcd for $[C_{21}H_{19}BrF_3N_3O_4S]$ $[M+H]^+$: 546.0; found: 546.0. $^1H$ NMR (400 MHz, Methanol-$d_4$) δ 8.68 (d, J=1.8 Hz, 1H), 8.56 (d, J=2.0 Hz, 1H), 8.34 (t, J=2.0 Hz, 1H), 8.21 (s, 1H), 7.91 (s, 1H), 7.38 (m, 2H), 6.21 (d, J=5.1 Hz, 1H), 4.62 (dd, J=11.3, 2.5 Hz, 1H), 4.54 (dd, J=11.3, 5.1 Hz, 1H), 4.41 (t, J=6.0 Hz, 1H), 4.17 (s, 1H), 3.75-3.63 (m, 2H), 3.38 (s, 3H).

Example 34

5-Ethynylpyridin-3-yl 3-deoxy-3-[4-(3,4,5-trifluorophenyl)-1H-1,2-pyrazol-1-yl]-2-O-methyl-1-thio-α-D-galactopyranoside

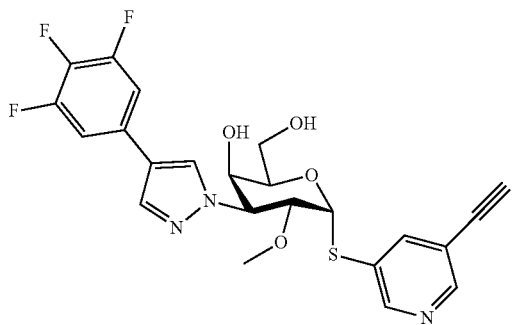

A solution of 5-bromopyridin-3-yl 3-deoxy-3-[4-(3,4,5-trifluorophenyl)-1H-1,2-pyrazol-1-yl]-2-O-methyl-1-thio-α-D-galactopyranoside (90 mg, 0.17 mmol) in THF (2.0 mL) was added to a mixture of CuI (2.0 mg, 0.0086 mmol) and bis(triphenylphosphine)palladium(II) chloride (6.3 mg, 0.0086 mmol) under nitrogen. DIPEA (41 µL, 0.23 mmol) followed by trimethylsilylacetylene (38 µL, 0.25 mmol) were added and the mixture was stirred 48 h at 50° C. The mixture was purified by chromatography (SiO$_2$, PE/EtOAc) and then triturated from PE/EtOAc (1:1). The obtained material was stirred 45 min in THF (2.0 mL) and TBAF (1.0 mL, 1 M in THF, 1.0 mmol). The mixture was partitioned between EtOAc, water and NaOH (1 mL, 1 M). The organic phase was dried, evaporated and purified by chromatography (SiO$_2$, PE/EtOAc) to afford the title compound (23 mg, 28%). ESI-MS m/z calcd for $[C_{23}H_{20}F_3N_3O_4S]$ $[M+H]^+$: 492.1; found: 492.1. $^1H$ NMR (500 MHz, Methanol-$d_4$) δ 8.69 (d, J=2.1 Hz, 1H), 8.54 (d, J=1.9 Hz, 1H), 8.21 (s, 1H), 8.19 (t, J=2.0 Hz, 1H), 7.91 (s, 1H), 7.43-7.34 (m, 2H), 6.19 (d, J=5.2 Hz, 1H), 4.62 (dd, J=11.3, 2.7 Hz, 1H), 4.54 (dd, J=11.3, 5.2 Hz, 1H), 4.42 (t, J=6.2 Hz, 1H), 4.18 (d, J=1.8 Hz, 1H), 3.71 (dd, J=11.5, 5.4 Hz, 1H), 3.66 (dd, J=11.5, 6.8 Hz, 1H), 3.38 (s, 3H).

Example 35

5-Chloro-2-cyanopyridin-3-yl 3-deoxy-3-[4-(3,4,5-trifluorophenyl)-1H-1,2-pyrazol-1-yl]-2-O-methyl-1-thio-α-D-galactopyranoside

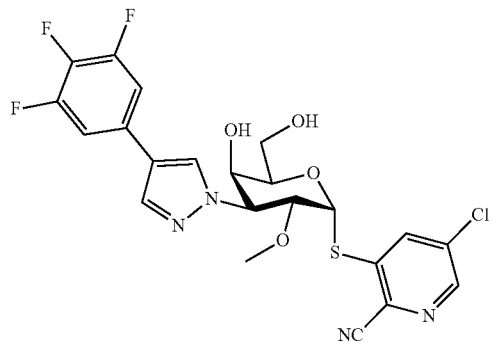

A nitrogen purged solution of 2-bromo-5-chloropyridin-3-yl 3-deoxy-3-[4-(3,4,5-trifluorophenyl)-1H-1,2-pyrazol-1-yl]-2-O-methyl-1-thio-α-D-galactopyranoside (124 mg, 0.21 mmol), 1,1'-bis(diphenylphosphino)ferrocene (9.6 mg, 0.017 mmol), zinc cyanide (25.1 mg, 0.21 mmol), tris(dibenzylideneacetone)dipalladium(0) (7.8 mg, 0.0085 mmol) and Zn (7.0 mg, 0.11 mmol) in DMF (2.77 mL) was stirred 1 h at 100° C. More zinc cyanide (25.1 mg, 0.21 mmol), Zn (7.0 mg, 0.11 mmol), 1,1'-bis(diphenylphosphino)ferrocene (9.6 mg, 0.017 mmol) and tris(dibenzylideneacetone)dipalladium(0) (7.8 mg, 0.0085 mmol) were added and the mixture was stirred 30 min at 100° C. The mixture was cooled to rt, diluted with EtOAc (30 mL), washed with water (5×30 mL) and brine (30 mL). The organic phase was dried, concentrated and purified by prep HPLC (C$_{18}$, H$_2$O/MeCN/0.1% TFA) to yield the title compound (22 mg, 20%). ESI-MS m/z calcd for $[C_{22}H_{18}ClF_3N_4O_4S]$ $[M+H]^+$: 527.1; found: 526.8, $^1H$ NMR (400 MHz, Methanol-$d_4$) δ 8.59 (d, J=2.1 Hz, 1H), 8.46 (d, J=2.1 Hz, 1H), 8.23 (s, 1H), 7.92 (s, 1H), 7.43-7.34 (m, 2H), 6.48 (d, J=5.1 Hz, 1H), 4.67 (dd, J=11.2, 2.6 Hz, 1H), 4.61 (dd, J=11.2, 5.1 Hz, 1H), 4.33 (t, J=6.0 Hz, 1H), 4.18 (d, J=1.9 Hz, 1H), 3.68 (d, J=6.0 Hz, 2H), 3.43 (s, 3H).

Example 36

5-Chloropyridin-3-yl 3-deoxy-3-[4-(3,4,5-trifluorophenyl)-1H-1,3-imidazol-1-yl]-1-thio-α-D-galactopyranoside

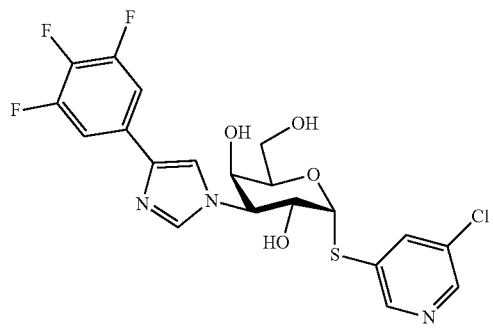

A solution of N-[p-tolylsulfonyl-(3,4,5-trifluorophenyl)methyl]formamide (54 mg, 0.16 mmol) in 1,2-dimethoxyethane (4.5 mL) was cooled to −10° C. To the solution phosphorus(V) oxychloride (36 µL, 0.39 mmol) was added followed by dropwise addition of Et₃N (0.11 mL, 0.79 mmol) in 1,2-dimethoxyethane (0.5 mL). The mixture reached rt in 1 h and was then stirred 2 h additionally at rt. The mixture was partitioned between water and EtOAc. The organic phase was washed with saturated aq NaHCO₃, dried and evaporated to afford crude 1,2,3-trifluoro-5-[isocyano(p-tolylsulfonyl)methyl]benzene. A solution of 5-chloropyridin-3-yl 3-amino-3-deoxy-1-thio-α-D-galactopyranoside (40 mg, 0.13 mmol), 2-oxoacetic acid (8.7 mg, 0.012 mmol) and K₂CO₃ (90 mg, 0.65 mmol) in DMF (0.6 mL) was stirred 2 h at rt. Afterwhich the crude 1,2,3-trifluoro-5-[isocyano(p-tolylsulfonyl)methyl]benzene dissolved in DMF (0.1 mL) was added and the resulting mixture was stirred 19 h at rt. The mixture was partitioned between water and EtOAc, the organic phase was dried and evaporated. The residue was purified by prep HPLC (C₁₈, H₂O/MeCN/0.1% TFA) to yield the title compound as a TFA salt (13 mg, 17%). ESI-MS m/z calcd for [C₂₀H₁₇ClF₃N₃O₄S] [M+H]⁺: 488.1; found: 488.1, ¹H NMR (500 MHz, Methanol-d₄) δ 9.00 (s, 1H), 8.67 (s, 1H), 8.53 (s, 1H), 8.19 (s, 1H), 8.16 (s, 1H), 7.59 (dd, J=8.3, 6.5 Hz, 2H), 5.94 (d, J=5.3 Hz, 1H), 4.86-4.83 (m, 1H), 4.74 (dd, J=11.3, 2.8 Hz, 1H), 4.45 (t, J=6.2 Hz, 1H), 4.23 (d, J=2.0 Hz, 1H), 3.78-3.70 (m, 2H).

Example 37

5-Chloro-[3,3-bis(hydroxymethyl)azetidin-1-yl]pyridin-3-yl 3-deoxy-3-[4-(3,4,5-trifluorophenyl)-1H-1,2-pyrazol-1-yl]-1-thio-α-D-galactopyranoside

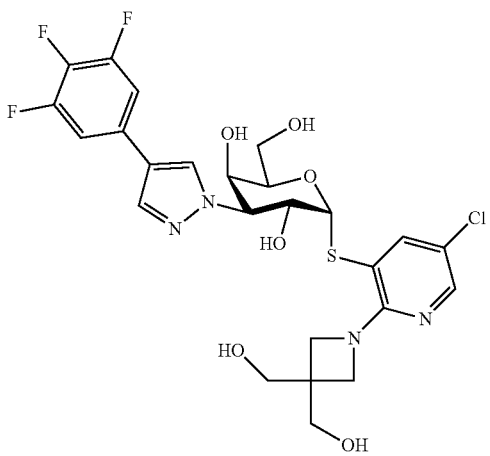

To a nitrogen purged solution of 5-chloro-2-{N-(2-oxa)-6-azaspiro[3.3]heptanyl}-pyridin-3-yl 3-(4-bromo-1H-1,2-pyrazol-1-yl)-3-deoxy-1-thio-α-D-galactopyranoside (42 mg, 0.079 mmol), Pd(dppf)Cl₂ (9.5 mg, 0.013 mmol) and K₂CO₃ (45 mg, 0.32 mmol) in dioxane (1.5 mL) and water (0.75 mL) (3,4,5-trifluorophenyl)boronic acid (24 mg, 0.13 mmol) was added and the mixture was stirred 18 h at 80° C. The mixture was filtered through silica, evaporated and purified by prep HPLC (C₁₈, H₂O/MeCN/0.1% TFA) to afford the title compound (1.1 mg, 2%). ESI-MS m/z calcd for [C₂₅H₂₆ClF₃N₄O₆S] [M+H]⁺: 586.1; found: 586.0. ¹H NMR (400 MHz, Methanol-d₄) δ 8.17 (s, 1H), 7.98 (s, 1H), 7.92 (s, 1H), 7.80 (s, 1H), 7.41-7.29 (m, 2H), 5.63 (d, J=5.2 Hz, 1H), 4.58 (d, J=9.3 Hz, 1H), 4.41 (t, J=6.2 Hz, 1H), 4.19 (s, 1H), 4.10 (d, J=8.6 Hz, 3H), 3.99 (d, J=8.8 Hz, 2H), 3.74 (s, 4H), 3.73-3.54 (m, 2H).

Example 38

5-Chloropyridin-3-yl 3-deoxy-3-[3-(3,4,5-trifluorophenyl)-1H-1,2-pyrazol-1-yl]-2-O-methyl-1-thio-α-D-galactopyranoside

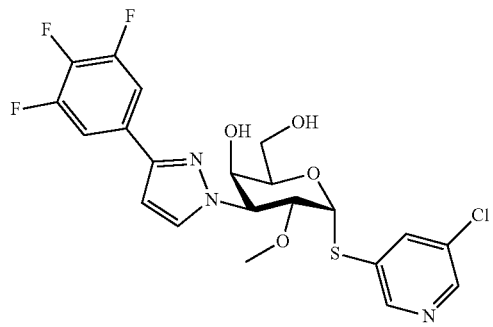

A nitrogen purged solution of 5-chloropyridin-3-yl 3-deoxy-3-(3-iodo-1H-1,2-pyrazol-1-yl)-2-O-methyl-1-thio-α-D-galactopyranoside (20 mg, 0.040 mmol), (3,4,5-trifluorophenyl)boronic acid (11 mg, 0.060 mmol), Pd(dppf)Cl₂ (4.4 mg, 0.0060 mmol) and K₂CO₃ (28 mg, 0.20 mmol) in dioxane (0.5 mL) and water (0.25 mL) was stirred 1 h at 60° C. The mixture was partitioned between EtOAc and water. The organic phase was dried, evaporated and purified by prep HPLC (C₁₈, H₂O/MeCN/0.1% TFA) to afford the title compound (12 g, 60%). ESI-MS m/z calcd for [C₂₁H₁₉ClF₃N₃O₄S] [M+H]⁺: 502.1; found: 502.1. ¹H NMR (500 MHz, Methanol-d₄) δ 8.66 (d, J=1.9 Hz, 1H), 8.49 (d, J=2.2 Hz, 1H), 8.24 (t, J=2.1 Hz, 1H), 7.82 (d, J=2.5 Hz, 1H), 7.61-7.54 (m, 2H), 6.73 (d, J=2.5 Hz, 1H), 6.24 (d, J=5.3 Hz, 1H), 4.65 (dd, J=11.3, 2.8 Hz, 1H), 4.54 (dd, J=11.3, 5.3 Hz, 1H), 4.41 (t, J=6.1 Hz, 1H), 4.21 (d, J=2.2 Hz, 1H), 3.75-3.66 (m, 2H), 3.37 (s, 3H).

Example 39

3,4-Dichlorophenyl 3-deoxy-3-[4-(3,4,5-trifluorophenyl)-oxazol-2-yl]-1-thio-α-D-galactopyranoside

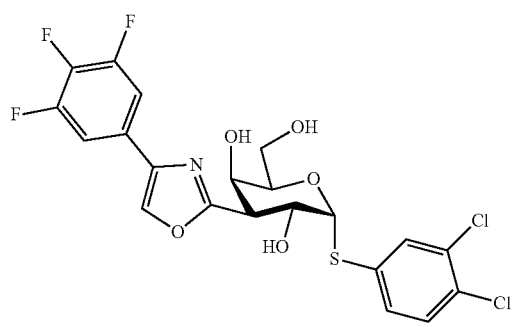

A solution of 3,4-dichlorophenyl 2,4-di-O-acetyl-3-deoxy-3-[4-(3,4,5-trifluorophenyl)-oxazol-2-yl]-1-thio-α-D- galactopyranoside (40 mg, 0.066 mmol) in MeOH (10 mL), Et$_3$N (0.184 mL) and water (0.5 mL) was stirred overnight at rt. The mixture was filtered and purified by prep HPLC (MeCN/H$_2$O (10 mmol/L NH$_4$HCO$_3$), X-Select10 μm 19*250 mm, 20 mL/min, UV 254) to afford the title compound (17 mg, 50%). ESI-MS m/z calcd for [C$_{21}$H$_{16}$Cl$_2$F$_3$NO$_5$S] [M+H]$^+$: 522.0; found: 522.0. $^1$H NMR (400 MHz, Methanol-d$_4$) δ 8.36 (s, 1H), 7.80 (d, J=2.0 Hz, 1H), 7.64-7.57 (m, 2H), 7.57-7.51 (m, 1H), 7.51-7.45 (m, 1H), 5.80 (d, J=5.2 Hz, 1H), 4.93-4.90 (m, 1H), 4.41 (t, J=6.4 Hz, 1H), 4.26-4.22 (m, 1H), 3.78-3.62 (m, 2H), 3.44 (dd, J=11.6, 2.8 Hz, 1H).

Example 40

3,4-Dichlorophenyl 3-deoxy-3-[4-(3,4,5-trifluorophenyl)-thiazol-2-yl]-1-thio-α-D-galactopyranoside

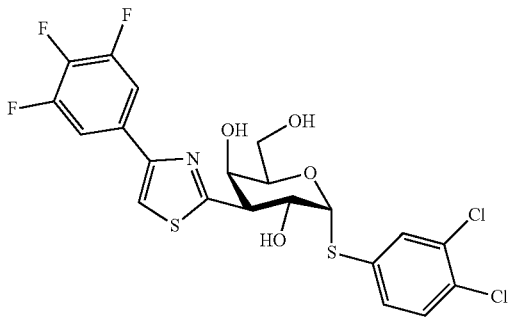

A solution of 3,4-dichlorophenyl 2,4-di-O-acetyl-3-deoxy-3-[4-(3,4,5-trifluorophenyl)-thiazol-2-yl]-1-thio-α-D-galactopyranoside (15 mg, 0.024 mmol) in MeOH (5 mL), Et$_3$N (0.10 mL) and water (0.5 mL) was stirred overnight at rt. The mixture was filtered and the filtrate was purified by prep HPLC (MeCN/H$_2$O (10 mmol/L NH$_4$HCO$_3$), X-Select10 μm 19*250 mm, 20 mL/min, UV 254) to afford the title compound (2.5 mg, 19%). ESI-MS m/z calcd for [C$_{21}$H$_{16}$Cl$_2$F$_3$NO$_4$S$_2$] [M+H]$^+$: 538.0; found: 538.0. $^1$H NMR (400 MHz, Methanol-d4) δ 7.90 (s, 1H), 7.81-7.70 (m, 3H), 7.54-7.42 (m, 2H), 5.76 (d, J=5.2 Hz, 1H), 4.66 (dd, J=11.6, 5.2 Hz, 1H), 4.42 (t, J=6.0 Hz, 1H), 4.26 (s, 1H), 3.77-3.65 (m, 2H), 3.61 (dd, J=11.6, 2.4 Hz, 1H).

Example 41

3,4-Dichlorophenyl 3-deoxy-3-[5-(3,4,5-trifluorophenyl)-1,3,4-oxadiazol-2-yl]-1-thio-α-D-galactopyranoside

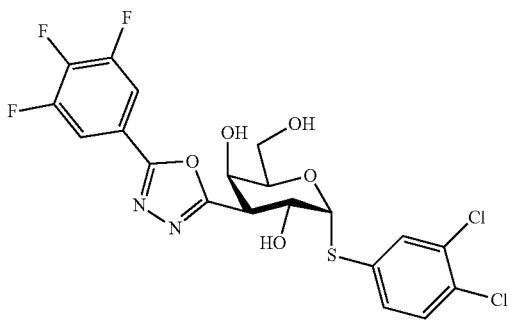

A solution of 3,4-dichlorophenyl 2,4-di-O-acetyl-3-deoxy-3-[(3,4,5-trifluorophenyl)-1,3,4-oxadiazol-2-yl]-1-thio-D-galactopyranoside (19 mg, 0.031 mmol) in MeOH (1 mL), Et$_3$N (0.5 mL) and water (0.25 mL) was stirred overnight at rt. The mixture was filtered and purified by prep HPLC (MeCN/H$_2$O (10 mmol/L NH$_4$HCO$_3$), X-Select10 μm 19*250 mm, 20 mL/min, UV 254). The product was further purified by preparative-SFC to afford the title compound (3.4 mg, 21%). ESI-MS m/z calcd for [C$_{20}$H$_{15}$Cl$_2$F$_3$N$_2$O$_5$S] [M+H]$^+$: 523.0; found: 523.0. $^1$H NMR (400 MHz, Methanol-d$_4$) δ 7.89-7.86 (m, 2H), 7.78 (d, J=2.0 Hz, 1H), 7.53-7.47 (m, 2H), 5.80 (d, J=5.2 Hz, 1H), 4.61 (s, 1H), 4.41 (t, J=6.0 Hz, 1H), 4.24 (s, 1H), 3.74-3.61 (m, 3H).

Example 42

3,4-Dichlorophenyl 3-deoxy-3-[4-(2-hydroxythiazol-4-yl)-1H-1,2-pyrazol-1-yl]-2-O-methyl-1-thio-α-D-galactopyranoside

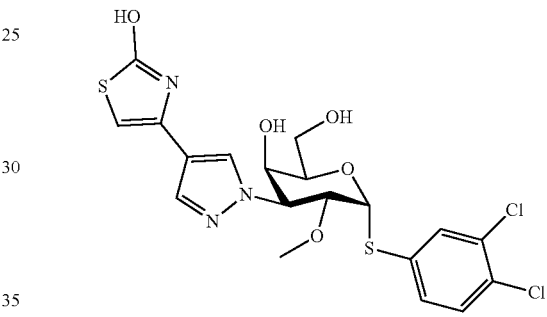

A solution of 3,4-dichlorophenyl 3-deoxy-3-(4-iodo-1H-1,2-pyrazol-1-yl)-2-O-methyl-1-thio-α-D-galactopyranoside (100 mg, 0.19 mmol), 2-(2-benzyloxythiazol-4-yl)-4,4,5,5-tetramethyl-1,3,2-dioxaborolane (112 mg, 0.28 mmol), and K$_2$CO$_3$ (130 mg, 0.94 mmol) in dioxane (1.5 mL) and water (0.75 mL) was degassed with nitrogen before Pd(dppf)Cl$_2$ (28 mg, 0.038 mmol) was added and the mixture stirred 1 h at 60° C. The mixture was partitioned between EtOAc and brine. The organic phase was dried, evaporated and purified by chromatography (SiO$_2$, PE/EtOAc). The obtained material was stirred 1 h in DCM (1.0 mL) and TFA (150 μL) at rt. The mixture was partitioned between EtOAc and saturated aq NaHCO$_3$. The organic phase was dried, evaporated and purified by chromatography (SiO$_2$, PE/EtOAc) to afford the title compound (28 mg, 29%). ESI-MS m/z calcd for [C$_{19}$H$_{19}$Cl$_2$N$_3$O$_5$S$_2$] [M+H]$^+$: 504.0; found: 504.0. $^1$H NMR (500 MHz, Methanol-d$_4$) δ 8.07 (s, 1H), 7.82-7.81 (m, 1H), 7.80 (d, J=2.1 Hz, 1H), 7.53 (dd, J=8.4, 2.1 Hz, 1H), 7.48 (d, J=8.4 Hz, 1H), 6.35 (s, 1H), 6.13 (d, J=5.2 Hz, 1H), 4.58 (m, 1H), 4.47 (dd, J=11.3, 5.3 Hz, 1H), 4.40 (t, J=6.2 Hz, 1H), 4.16 (d, J=1.9 Hz, 1H), 3.72 (dd, J=11.5, 5.5 Hz, 1H), 3.66 (dd, J=11.5, 6.7 Hz, 1H), 3.36 (s, 3H).

Example 43

3,4-Dichlorophenyl 3-[4-(2-aminothiazol-4-yl)-1H-1,2-pyrazol-1-yl]-3-deoxy-2-O-methyl-1-thio-α-D-galactopyranoside

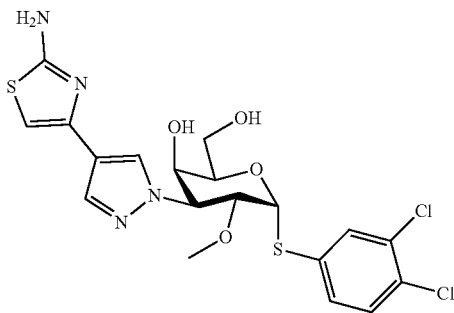

To an argon degassed solution of 3,4-dichlorophenyl 3-deoxy-3-(4-iodo-1H-1,2-pyrazol-1-yl)-1-thio-α-D-galactopyranos ide (39 mg, 0.073 mmol), [2-(tert-butoxycarbonylamino)thiazol-4-yl]boronic acid (18 mg, 0.073 mmol), tris(dibenzylideneacetone)dipalladium(0) (6.6 mg, 0.0073 mmol) and 1,1'-bis(diphenylphosphino)ferrocene (8.2 mg, 0.015 mmol) in dioxane (0.5 mL) $K_2CO_3$ (72.5 μL, 2 M, 0.15 mmol) and water (0.18 mL) were added and the mixture stirred 1 h at 60° C. The mixture was diluted with water and extracted trice with EtOAc. The organic phases were dried, evaporated and dissolved in DCM (1.0 mL) and TFA (1.0 mL). The mixture was stirred 1 h in at rt before being concentrated. The residue was purified by reverse phase chromatography ($C_{18}$, $H_2O$/MeCN/0.1 TFA) to afford the title compound (1.8 mg, 5%). ESI-MS m/z calcd for [$C_{19}H_{20}Cl_2N_4O_4S_2$] [M+H]$^+$: 503.0; found: 502.8. $^1$H NMR (500 MHz, Methanol-$d_4$) δ 8.18 (s, 1H), 7.89 (s, 1H), 7.82 (d, J=2.1 Hz, 1H), 7.55 (dd, J=8.4, 2.1 Hz, 1H), 7.50 (d, J=8.4 Hz, 1H), 6.82 (s, 1H), 6.15 (d, J=5.3 Hz, 1H), 4.63 (dd, J=11.3, 2.8 Hz, 1H), 4.50 (dd, J=11.3, 5.3 Hz, 1H), 4.43 (t, J=6.2 Hz, 1H), 4.20 (d, J=2.0 Hz, 1H), 3.74 (dd, J=11.5, 5.6 Hz, 1H), 3.69 (dd, J=11.5, 6.7 Hz, 1H), 3.38 (s, 3H).

Example 44

5-Chloro-2-cyanophenyl 3-[4-(4-chloro-3,5-difluorophenyl)-1H-1,2-pyrazol-1-yl]-3-deoxy-2-O-methyl-1-thio-α-D-galactopyranoside

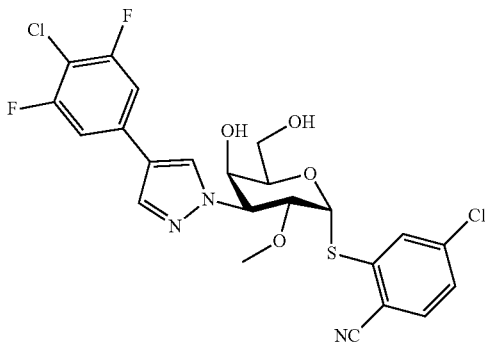

Pd(dppf)Cl$_2$ (6 mg, 0.0082 mmol), (4-chloro-3,5-difluorophenyl)boronic acid (15 mg, 0.076 mmol), 5-chloro-2-cyanophenyl 4,6-O-benzylidene-3-deoxy-3-(4-iodo-1H-1,2-pyrazol-1-yl)-2-O-methyl-1-thio-α-D-galactopyranoside (31 mg, 0.050 mmol) and $K_2CO_3$ (35 mg, 0.25 mmol) were weighed into a vial and flushed with nitrogen. Dioxane (2.0 mL) followed by water (1.0 mL) were added to the vial and degassed with nitrogen. The mixture was stirred 2 h at 60° C. and was then partitioned between EtOAc and brine. The organic phase was evaporated, and the residue purified by filtration through silica using EtOAc/DCM. The obtained material was stirred 20 min at rt in TFA/water (0.5 mL, 4:1). The mixture was neutralized with NaOH (1 M) and extracted twice with EtOAc. The combined organic phases were dried, evaporated and purified by prep HPLC ($C_{18}$, $H_2O$/MeCN/0.1 TFA). The product was further purified by chromatography ($SiO_2$, PE/EtOAc) to afford the title compound (6.0 mg, 22%). ESI-MS m/z calcd for [$C_{23}H_{19}Cl_2F_2N_3O_4S$] [M+H]$^+$: 542.0; found: 542.0. $^1$H NMR (500 MHz, Methanol-$d_4$) δ 8.28 (s, 1H), 7.99 (d, J=2.0 Hz, 1H), 7.96 (d, J=0.6 Hz, 1H), 7.75 (d, J=8.4 Hz, 1H), 7.49 (dd, J=8.4, 2.0 Hz, 1H), 7.40 (d, J=8.3 Hz, 2H), 6.38 (d, J=5.1 Hz, 1H), 4.66 (dd, J=11.3, 2.7 Hz, 1H), 4.60 (dd, J=11.3, 5.2 Hz, 1H), 4.38 (t, J=6.2 Hz, 1H), 4.20 (d, J=1.8 Hz, 1H), 3.70 (dd, J=11.5, 5.4 Hz, 1H), 3.64 (dd, J=11.5, 6.8 Hz, 1H), 3.43 (s, 3H).

Example 45

5-Chloro-2-cyanophenyl 3-deoxy-3-[4-(3,4,5-trifluorophenyl)-1H-1,2-pyrazol-1-yl]-2-O-methyl-1-thio-α-D-galactopyranoside

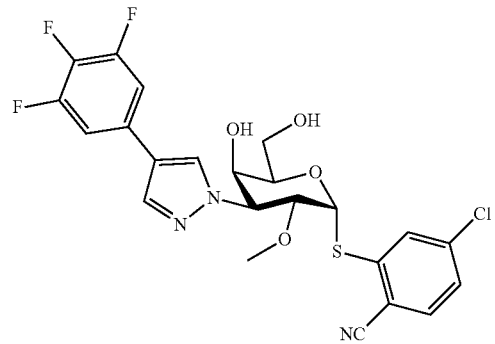

Pd(dppf)Cl$_2$ (6 mg, 0.0082 mmol), (4-chloro-3,5-difluorophenyl)boronic acid (15 mg, 0.076 mmol), 5-chloro-2-cyanophenyl 4,6-O-benzylidene-3-deoxy-3-(4-iodo-1H-1,2-pyrazol-1-yl)-2-O-methyl-1-thio-α-D-galactopyranoside (31 mg, 0.050 mmol) and $K_2CO_3$ (35 mg, 0.25 mmol) were weighed into a vial and flushed with nitrogen. Dioxane (2.0 mL) followed by water (1.0 mL) were added to the vial and degassed with nitrogen. The mixture was stirred 2 h at 60° C. and was then partitioned between EtOAc and brine. The organic phase was evaporated, and the residue purified by chromatography ($SiO_2$, PE/EtOAc). The obtained material was stirred 20 min at rt in TFA/water (0.5 mL, 4:1). The mixture was neutralized with NaOH (1 M) and extracted twice with EtOAc. The combined organic phases were dried, evaporated and purified by prep HPLC ($C_{18}$, $H_2O$/MeCN/0.1 TFA). The product was further purified by chromatography ($SiO_2$, PE/EtOAc) to afford the title compound (6.5 mg, 25%). ESI-MS m/z calcd for [$C_{23}H_{19}ClF_3N_3O_4S$] [M+H]+: 526.1; found: 526.1. $^1$H NMR (500 MHz, Methanol-$d_4$) δ 8.22 (s, 1H), 7.99 (d, J=2.0 Hz, 1H), 7.91 (s, 1H), 7.75 (d, J=8.4 Hz, 1H), 7.49 (dd, J=8.4, 2.0 Hz, 1H), 7.42-7.34 (m, 2H), 6.38 (d, J=5.1 Hz, 1H), 4.65 (dd, J=11.3, 2.7 Hz, 1H), 4.59 (dd, J=11.3, 5.2 Hz, 1H), 4.38 (t, J=6.1 Hz, 1H), 4.20 (d, J=1.8 Hz, 1H), 3.70 (dd, J=11.5, 5.4 Hz, 1H), 3.64 (dd, J=11.5, 6.8 Hz, 1H), 3.42 (s, 3H).

Intermediate 1

3-(4-Bromo-1H-pyrazol-1-yl)-3-deoxy-1,2:5,6-di-O-isopropylidene-α-D-galactofuranose

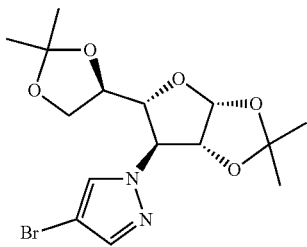

A solution of 1,2:5,6-di-O-isopropylidene-α-D-glucofuranose (5.00 g, 19.2 mmol) in DCM (100 mL) and pyridine (3.1 mL, 38.4 mmol) was cooled to 0° C. and trifluoromethanesulphonic anhydride (3.9 mL, 23.1 mmol) in DCM (20 mL) was added dropwise. After stirring 1 h at 10° C. the mixture was quenched by adding crushed ice. The mixture was partitioned between DCM and HCl (1 M), the organic phase was washed with saturated aq NaHCO$_3$, dried and concentrated. To the crude and Cs$_2$CO$_3$ (6.25 g, 19.2 mmol) in DMF (60 mL) 4-bromopyrazole (5.65 g, 38.4 mmol) was added. After stirring 18 h at rt ice was added to the mixture, the solids were filtered off and washed with 33% aq MeOH, then dried to afford the product (7.29 g, 97%). ESI-MS m/z calcd for [$C_{15}H_{21}BrN_2O_5$] [M+H]$^+$: 389.1; found: 388.8. $^1$H NMR (400 MHz, Chloroform-d) δ 7.53 (s, 1H), 7.52 (s, 1H), 5.98 (d, J=3.9 Hz, 1H), 4.90 (dd, J=3.9, 2.3 Hz, 1H), 4.68 (dd, J=6.7, 2.1 Hz, 1H), 4.34-4.22 (m, 2H), 4.06 (dd, J=8.3, 6.8 Hz, 1H), 3.89 (dd, J=8.3, 6.8 Hz, 1H), 1.64 (s, 3H), 1.45 (s, 3H), 1.39 (s, 3H), 1.38 (s, 3H).

1,2,4,6-Tetra-O-acetyl-3-(4-bromo-1H-1,2-pyrazol-1-yl)-3-deoxy-β-D-galactopyranoside

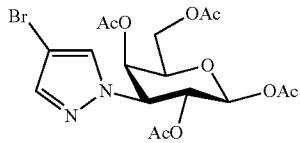

3-(4-Bromo-1H-pyrazol-1-yl)-3-deoxy-1,2:5,6-di-O-isopropylidene-α-D-galactofuranose (6.00 g, 15.4 mmol) was dissolved in TFA (24 mL) and water (96 mL) and stirred 3 h at rt. The mixture was evaporated using MeCN for azeotropic removal of water and TFA and finally treated in vacuum for 1 h. The crude was dissolved in EtOAc (30 mL). Et$_3$N (23.5 mL, 167 mmol) was added, temperature was maintained at 40° C. and acetic anhydride (13.3 mL, 139 mmol) was added at a rate to maintain the same temperature. The mixture was stirred at 40° C. for 6 h and at rt for 72 h, then cooled to 0° C. HCl (42 mL, 2 M, 84 mmol) was added slowly, the mixture was partitioned between EtOAc and water. The organic phase was washed with saturated aq NaHCO$_3$, then brine. The organic phase was evaporated, and the residue was stirred in EtOAc (10 mL) and PE (20 mL). The precipitate was isolated by filtration, washed with EtOAc/PE (1:4), dried, to afford the product (1.79 g, 27%). ESI-MS m/z calcd for [$C_{17}H_{21}BrN_2O_9$] [M-AcOH]$^+$: 417.0; found: 416.6. $^1$H NMR (400 MHz, Chloroform-d) δ 7.48 (s, 2H), 5.83-5.73 (m, 2H), 5.48 (d, J=2.9 Hz, 1H), 4.75 (dd, J=10.1, 3.0 Hz, 1H), 4.21-4.05 (m, 3H), 2.15 (s, 3H), 2.04 (s, 6H), 1.93 (s, 3H).

3-Chlorophenyl 3-(4-bromo-1H-1,2-pyrazol-1-yl)-3-deoxy-1-thio-α-D-galactopyranoside

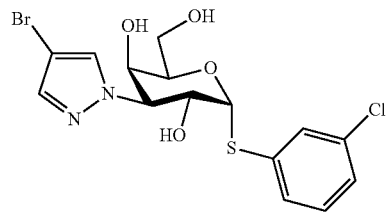

To a solution of 1,2,4,6-tetra-O-acetyl-3-(4-bromo-1H-1,2-pyrazol-1-yl)-3-deoxy-β-D-galactopyranoside (615 mg, 1.29 mmol) and PCl$_5$ (349 mg, 1.68 mmol) in DCM (8 mL), BF$_3$OEt$_2$ (0.26 mL, 2.15 mmol) was added and the resulting mixture was stirred 24 h at rt. The solution was washed with ice/water, the organic phase was washed with saturated aq NaHCO$_3$, dried and evaporated. The crude and 3-chlorobenzenethiol (0.12 mL, 1.00 mmol) were dissolved in DMF (5 mL), NaH (60% in oil, 77 mg, 2.00 mmol) was added and the mixture was stirred 3 h at rt. The mixture was diluted with EtOAc and washed twice with water and once with brine, the organic phase was dried, concentrated and purified by chromatography (SiO$_2$, PE/EtOAc) to afford a mixture of products. The mixture of products was stirred 1 h at rt in MeOH (4 mL) and NaOMe (1 M, 0.5 mL). The mixture was quenched with AcOH, concentrated and purified by HPLC (C$_{18}$, H$_2$O/MeCN/0.1 TFA) to afford the product (68 mg, 12%). ESI-MS m/z calcd for [$C_{15}H_{16}BrClN_2O_4S$] [M+H]$^+$: 435.0; found: 434.6. $^1$H NMR (400 MHz, Methanol-$d_4$) δ 7.86 (s, 1H), 7.62 (s, 1H), 7.54-7.49 (m, 2H), 7.33-7.27 (m, 2H), 5.77 (d, J=5.4 Hz, 1H), 4.77 (dd, J=11.4, 5.41H), 4.53 (dd, J=11.4, 2.8 Hz, 1H), 4.43 (t, J=6.0 Hz, 1H), 4.14 (d, J=2.2 Hz, 1H), 3.72 (dd, J=11.4, 5.8 Hz, 1H), 3.65 (dd, J=11.4, 6.5 Hz, 1H).

Intermediate 2

5-Chloropyridin-3-yl 3-(4-bromo-1H-1,2-pyrazol-1-yl)-3-deoxy-1-thio-α-D-galactopyranoside

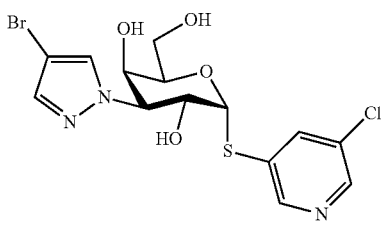

To a solution of 1,2,4,6-tetra-O-acetyl-3-(4-bromo-1H-1,2-pyrazol-1-yl)-3-deoxy-β-D-galactopyranoside (930 mg, 1.95 mmol) and PCl$_5$ (528 mg, 2.53 mmol) in DCM (15 mL) BF$_3$OEt$_2$ (0.31 mL, 2.53 mmol) was added and the resulting mixture was stirred 5 h at rt. The solution was washed with ice/water, the organic phase was washed with saturated aq NaHCO$_3$, dried and evaporated. The residue was dissolved with 5-chloropyridine-3-thiol (213 mg, 1.46 mmol) in DMF (7 mL), NaH (60% in oil, 112 mg, 2.92 mmol) was added and the mixture was stirred 16 h at rt. The mixture was diluted with EtOAc and washed twice with water and once with brine. The organic phase was dried, concentrated and purified by chromatography (SiO$_2$, PE/EtOAc). The obtained material was stirred 1 h at rt with NaOMe (0.5 mL, 1M) and MeOH (6 mL). The reaction was quenched with AcOH, evaporated and purified by HPLC (C$_{18}$, H$_2$O/MeCN/ 0.1% TFA) to afford the product (49 mg, 6%). ESI-MS m/z calcd for [C$_{14}$H$_{15}$BrClN$_3$O$_4$S] [M+H]$^+$: 436.0; found: 435.6. $^1$H NMR (400 MHz, Methanol-d$_4$) δ 8.63 (d, J=1.8 Hz, 1H), 8.47 (d, J=2.2 Hz, 1H), 8.20 (t, J=2.0 Hz, 1H), 7.87 (s, 1H), 7.53 (s, 1H), 5.88 (d, J=5.4 Hz, 1H), 4.80 (dd, J=11.3, 5.41H), 4.56 (dd, J=11.4, 2.7 Hz, 1H), 4.39 (t, J=6.0 Hz, 1H), 4.14 (d, J=2.0 Hz, 1H), 3.73-3.63 (m, 2H).

Intermediate 3

2,4,6-Tri-O-acetyl-3-(4-bromo-1H-1,2-pyrazol-1-yl)-3-deoxy-β-D-galactopyranosyl Chloride

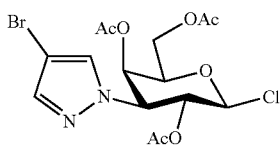

1,2,4,6-Tetra-O-acetyl-3-(4-bromo-1H-1,2-pyrazol-1-yl)-3-deoxy-β-D-galactopyranoside (2.0 g, 4.06 mmol) and PCl$_5$ (1.73 g, 8.12 mmol) were stirred in DCM (30 mL) and BF$_3$OEt$_2$ (0.65 mL, 5.30 mmol) was added. The mixture was stirred 4 h at rt, more BF$_3$OEt$_2$ (0.33 mL, 2.64 mmol) was added and continued stirring 2 h at rt. The mixture was partitioned between ice, water, NaOH (10 mL, 5M), and DCM, the organic phase was separated, dried and evaporated to afford the product (1.92 g, quant. yield). $^1$H NMR (400 MHz, Chloroform-d) δ 7.50 (s, 1H), 7.48 (s, 1H), 5.79 (dd, J=11.3, 8.5 Hz, 1H), 5.50 (d, J=3.1 Hz, 1H), 5.37 (d, J=8.5 Hz, 1H), 4.72 (dd, J=11.3, 3.2 Hz, 1H), 4.23-4.08 (m, 3H), 2.07 (s, 3H), 2.06 (s, 3H), 1.99 (s, 3H).

5-Chloropyridin-3-yl 2,4,6-tri-O-acetyl-3-(4-bromo-1H-1,2-pyrazol-1-yl)-3-deoxy-1-thio-α-D-galactopyranoside

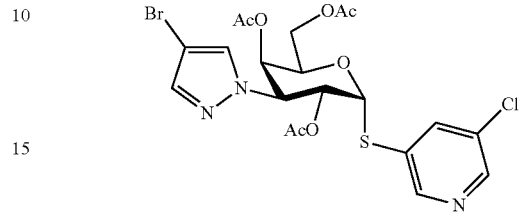

NaH (60% in oil, 50 mg, 1.31 mmol) was added to 2,4,6-tri-O-acetyl-3-(4-bromo-1H-1,2-pyrazol-1-yl)-3-deoxy-β-D-galactopyranosyl chloride (495 mg, 1.09 mmol) and 5-chloropyridine-3-thiol (159 mg, 1.09 mmol) in DMF (5 mL). The mixture was stirred 21 h at rt. More 5-chloropyridine-3-thiol (80 mg, 0.55 mmol) and NaH (60% in oil, 25 mg, 0.55 mmol) were added and the mixture was stirred for additionally 4 h before it was diluted with EtOAc (50 mL) and washed with water (5×50 mL) and brine (50 mL). The organic phase was dried, concentrated and purified by chromatography (SiO$_2$, PE/EtOAc) to afford the product (148 mg, 24%). ESI-MS m/z calcd for [C$_{20}$H$_{22}$BrClN$_3$O$_7$S] [M+H]$^+$: 562.0; found: 562.1. $^1$H NMR (400 MHz, Chloroform-d) δ 8.57 (s, 1H), 8.52 (s, 1H), 7.88 (s, 1H), 7.48 (s, 1H), 7.43 (s, 1H), 6.09 (d, J=5.1 Hz, 1H), 6.00-5.91 (m, 1H), 5.54 (s, 1H), 4.85 (d, J=11.9 Hz, 1H), 4.83-4.74 (m, 1H), 4.17-4.05 (m, 2H), 2.09-1.99 (m, 9H).

Intermediate 6

3-Deoxy-3-(4-iodo-1H-1,2-pyrazol-1-yl)-1,2:5,6-di-O-isopropylidene-α-D-galactofuranose

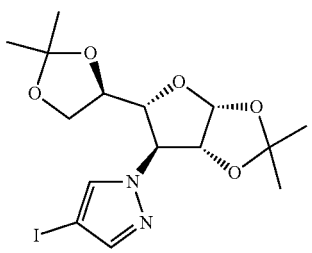

A solution of 1,2:5,6-di-O-isopropylidene-α-D-glucofuranose (12.54 g, 48.2 mmol) in DCM (150 mL) and pyridine (7.8 mL, 96.4 mmol) was cooled to 0° C. and trifluoromethanesulphonic anhydride (9.8 mL, 57.9 mmol) in DCM (30 mL) was added dropwise. After stirring 1 h at 10° C. the mixture was quenched by adding crushed ice. The mixture was partitioned between DCM and HCl (1 M), the organic phase was washed with saturated aq NaHCO$_3$, dried and concentrated. To a solution of the crude and Cs$_2$CO$_3$ (15.7 g, 48.2 mmol) in DMF (150 mL) 4-iodopyrazole (13.36 g, 67.5 mmol) was added. After stirring 2 h at rt ice was added to the mixture, the solids were filtered off and washed with 33% aq MeOH, then dried to afford the product (23.9 g, quantitative yield). ESI-MS m/z calcd for [C$_{15}$H$_{21}$IN$_2$O$_5$] [M+H]$^+$: 437.1; found: 436.9. $^1$H NMR (400 MHz, Chloroform-d) δ 7.58 (s, 1H), 7.54 (s, 1H), 5.98 (d, J=4.0 Hz, 1H), 4.89 (dd, J=3.9, 2.3 Hz, 1H), 4.71 (dd, J=6.7, 2.1 Hz, 1H), 4.31 (dd, J=6.7, 4.4 Hz, 1H), 4.29-4.22 (m, 1H), 4.05 (dd, J=8.3, 6.8 Hz, 1H), 3.88 (dd, J=8.3, 6.8 Hz, 1H), 1.64 (s, 3H), 1.45 (s, 3H), 1.38 (s, 6H).

1,2,4,6-Tetra-O-acetyl-3-deoxy-3-(4-iodo-1H-1,2-pyrazol-1-yl)-β-D-galactopyranoside

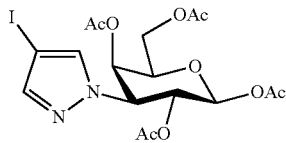

3-Deoxy-3-(4-iodo-1H-1,2-pyrazol-1-yl)-1,2:5,6-di-O-isopropylidene-α-D-galactofuranose (6.00 g, 15.4 mmol) was dissolved in TFA (40 mL) and water (100 mL) and stirred 1 h at rt. The mixture was evaporated using MeCN for azeotropic removal of water and TFA and finally treated in vacuum. The crude was dissolved in EtOAc (105 mL), Et$_3$N (105 mL) and acetic anhydride (53 mL, 560 mmol) were added and the mixture was stirred 20 h at rt. The mixture was cooled to 0° C. and EtOAc (200 mL) followed by HCl (280 mL, 2 M) were added slowly. The mixture was stirred 20 min, then filtered through celite. The organic phase was separated, washed with saturated aq NaHCO$_3$ and brine, dried and evaporated. The residue was filtered through silica using EtOAc/PE (1:1) and concentrated. The obtained syrup was dissolved in EtOAc (50 mL), and PE (80 mL) was added slowly, which resulted in crystallization. The crystals were isolated by filtration to afford the product (9.68 g, 58% purity, 38%). The filtrate was evaporated to afford more of the product (15.8 g, 65% purity, 62%). ESI-MS m/z calcd for [C$_{17}$H$_{21}$IN$_2$O$_9$] [M+H]$^+$: 525.0; found: 524.8. $^1$H NMR (400 MHz, Chloroform-d) δ 7.52 (s, 1H), 7.50 (s, 1H), 5.82-5.75 (m, 2H), 5.47 (d, J=3.1 Hz, 1H), 4.79 (m, 1H), 4.16-4.07 (m, 3H), 2.15 (s, 3H), 2.04 (s, 6H), 1.93 (s, 3H).

1,2,4,6-Tetra-O-acetyl-3-[4-(4-chloro-3,5-difluorophenyl)-1H-1,2-pyrazol-1-yl]-3-deoxy-β-D-galactopyranoside

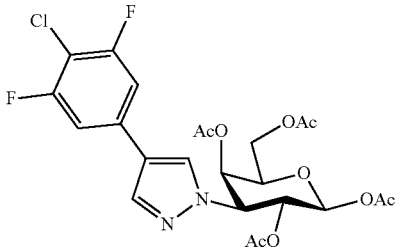

Pd(dppf)Cl$_2$ (582 mg, 0.76 mmol), 1,2,4,6-tetra-O-acetyl-3-deoxy-3-(4-iodo-1H-1,2-pyrazol-1-yl)-β-D-galactopyranoside (2.2 g, 3.78 mmol), K$_2$CO$_3$ (2.61 g, 18.9 mmol) and (4-chloro-3,5-difluorophenyl)boronic acid (994 mg, 4.9 mmol) were weighed into a flask and flushed with nitrogen. Dioxane (10 mL) followed by water (5.0 mL) were added to the flask and degassed with nitrogen. The mixture was stirred 1 h at 60° C. and then partitioned between EtOAc and brine. The organic phase was evaporated, and the residue purified by chromatography (SiO$_2$, PE/EtOAc) to afford the product (1.03 g, 77%). ESI-MS m/z calcd for [C$_{23}$H$_{23}$ClF$_2$N$_2$O$_9$] [M+H]$^+$: 545.1; found: 544.9. $^1$H NMR (400 MHz, Chloroform-d) δ 7.75 (s, 1H), 7.72 (s, 1H), 7.04 (d, J=7.9 Hz, 2H), 5.85 (bs, 2H), 5.55 (bs, 1H), 4.81 (bs, 1H), 4.21-4.07 (m, 3H), 2.17 (s, 3H), 2.02 (s, 3H), 1.93 (s, 3H).

2,4,6-Tri-O-acetyl-3-[4-(4-chloro-3,5-difluorophenyl)-1H-1,2-pyrazol-1-yl]-3-deoxy-β-D-galactopyranosyl chloride

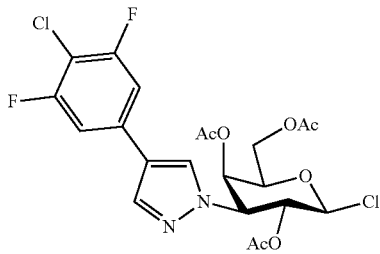

To a solution of 1,2,4,6-tetra-O-acetyl-3-[4-(4-chloro-3,5-difluorophenyl)-1H-1,2-pyrazol-1-yl]-3-deoxy-β-D-galactopyranoside (1.022 g, 1.87 mmol) and PCl$_5$ (996 mg, 4.7 mmol) in DCM (10 mL), BF$_3$OEt$_2$ (0.48 mL, 3.74 mmol) was added and the mixture was stirred 2.5 h at rt. The solution was partitioned between DCM and ice/water/NaOH (2 M). The organic phase was dried and evaporated to afford the product (1.34 g, quantitative yield). $^1$H NMR (400 MHz, Chloroform-d) δ 7.81 (bs, 2H), 7.04 (d, J=7.3 Hz, 2H), 5.86 (bs, 1H), 5.58 (s, 1H), 5.43 (bs, 1H), 4.91 (bs, 1H), 4.26-4.11 (m, 3H), 2.07 (s, 3H), 2.04 (s, 3H), 2.01 (s, 3H).

Intermediate 9

5-Chloro-2-cyanophenyl 3-(4-bromo-1H-1,2-pyrazol-1-yl)-3-deoxy-1-thio-α-D-galactopyranoside

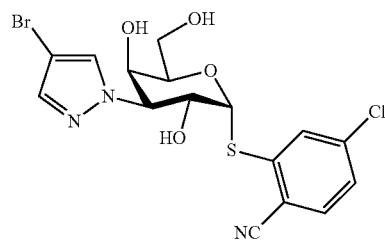

2,4,6-Tri-O-acetyl-3-(4-bromo-1H-1,2-pyrazol-1-yl)-3-deoxy-β-D-galactopyranosyl chloride (1.00 g, 1.32 mmol), 4-chloro-2-sulfanylbenzonitrile (314 mg, 1.85 mmol) and K$_2$CO$_3$ (360 mg, 2.6 mmol) were stirred 2 h at 60° C. in DMF (8.0 mL). The mixture was partitioned between EtOAc/water/HCl, the organic phase was collected, dried, and evaporated. The residue was purified by chromatography (SiO$_2$, PE/EtOAc) and the obtained material was stirred 18 h at rt in MeOH (4 mL) and NaOMe (1 M, 0.5 mL). The mixture was neutralized with acetic acid (60 µL), evaporated, and the residue was purified by prep HPLC (C$_{18}$, H₂O/MeCN/0.1 TFA) to afford the product (80 mg, 13%). ESI-MS m/z calcd for [C₁₆H₁₅BrClN₃O₄S] [M+H]⁺: 460.0; found: 459.7. ¹H NMR (400 MHz, Methanol-d₄) δ 7.97 (d, J=1.9 Hz, 1H), 7.88 (d, J=8.4 Hz, 1H), 7.53 (s, 1H), 7.45 (dd, J=8.4, 2.0 Hz, 1H), 6.07 (d, J=5.4 Hz, 1H), 4.84 (m, 1H), 4.61 (dd, J=11.4, 2.7 Hz, 1H), 4.33 (t, J=6.1 Hz, 1H), 4.17 (d, J=2.0 Hz, 1H), 3.68 (dd, J=11.4, 5.6 Hz, 1H), 3.61 (dd, J=11.4, 6.7 Hz, 1H).

2-(N-azetidinyl-carbonyl)-5-chlorophenyl 3-(4-bromo-1H-1,2-pyrazol-1-yl)-3-deoxy-1-thio-α-D-galactopyranoside

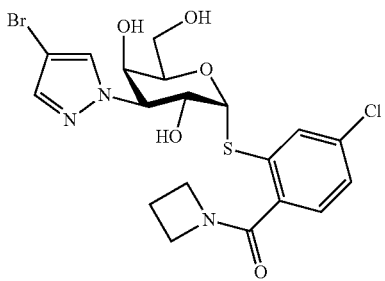

A mixture of 5-chloro-2-cyanophenyl 3-(4-bromo-1H-1,2-pyrazol-1-yl)-3-deoxy-1-thio-α-D-galactopyranoside (302 mg, 0.65 mmol) in EtOH (8.0 mL) and NaOH (3 M, 4.0 mL) was stirred 17 h at 50° C. The mixture was stirred 2 h at 70° C. before being concentrated and partitioned between EtOAc/water/HCl at pH 1-2. The organic phase was dried, evaporated, and the residue was purified by chromatography (SiO₂, PE/EtOAc). The obtained material, 1-hydroxybenzotriazole hydrate (147 mg, 0.93 mmol) and N-(3-dimethylaminopropyl)-N'-ethylcarbodiimide hydrochloride (183 mg, 0.93 mmol) were stirred in DMF (4 mL) and azetidine (91 μL, 1.24 mmol) was added followed by Et₃N (91 μL, 0.62 mmol). The mixture was stirred 18 h at rt, it was then partitioned between brine and EtOAc. The aqueous phase was extracted three times with EtOAc, and the combined organic phases were dried, evaporated, and purified by chromatography (SiO₂, EtOAc/MeOH) to give the product (157 mg, 49%). ESI-MS m/z calcd for [C₁₉H₂₁BrClN₃O₄S] [M+H]⁺: 518.0; found: 517.8. ¹H NMR (400 MHz, Methanol-d₄) δ 7.86 (s, 1H), 7.85 (d, J=1.8 Hz, 1H), 7.53 (s, 1H), 7.38 (dd, J=8.2, 1.8 Hz, 1H), 7.30 (d, J=8.2 Hz, 1H), 5.87 (d, J=5.4 Hz, 1H), 4.78 (dd, J=11.4, 5.4 Hz, 1H), 4.54 (dd, J=11.4, 2.7 Hz, 1H), 4.39 (t, J=6.1 Hz, 1H), 4.19 (d, J=7.8 Hz, 2H), 4.14 (d, J=2.5 Hz, 1H), 4.02 (d, J=7.7 Hz, 2H), 3.71 (dd, J=11.5, 5.5 Hz, 1H), 3.66 (dd, J=11.3, 6.8 Hz, 1H), 2.34 (p, J=7.7 Hz, 2H).

Intermediate 12

2-Bromo-5-chloro-pyridine-3-thiol

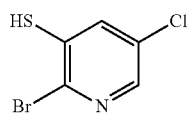

To an ice-cold solution of 2-bromo-5-chloro-3-fluoropyridine (2.00 g, 9.5 mmol) in DMF (10 mL) sodium hydrosulfide hydrate (682 mg, 8.5 mmol) was added. After 2 h at rt the mixture was partitioned between diethyl ether and HCl (0.5 M). The organic phase was extracted with NaOH (0.5 M). The aqueous phase was acidified with HCl (5 M) until a precipitate was formed. Filtration yielded the product (735 mg, 34%). ESI-MS m/z calcd for [C₅H₄BrClNS] [M+H]⁺: 223.9; found: 223.6. ¹H NMR (400 MHz, Chloroform-d) δ 8.12 (d, J=2.3 Hz, 1H), 7.64 (d, J=2.3 Hz, 1H), 4.04 (s, 1H).

2,4,6-Tri-O-acetyl-3-deoxy-3-(4-iodo-1H-1,2-pyrazol-1-yl)-β-D-galactopyranosyl Chloride

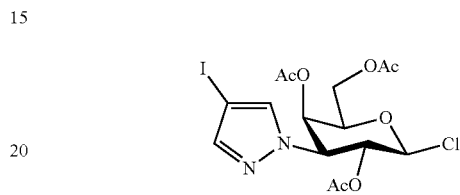

To a solution of 1,2,4,6-tetra-O-acetyl-3-deoxy-3-(4-iodo-1H-1,2-pyrazol-1-yl)-β-D-galactopyranoside (7.74 g, 14.7 mmol), PCl₅ (6.28 g, 29.5 mmol) in DCM (100 mL) and BF₃OEt₂ (3.95 mL, 29.5 mmol) was added. The mixture was stirred 4 h at rt and was then partitioned between ice/water and DCM, NaOH (85 mL, 2 M) was added and pH became approximately 5 during the washing. The organic phase was dried and evaporated to give the product (6.2 g, 60% purity), which was used without purification in subsequent steps.

2-Bromo-5-chloropyridin-3-yl 2,4,6-tri-O-acetyl-3-deoxy-3-(4-iodo-1H-1,2-pyrazol-1-yl)-1-thio-α-D-galactopyranoside

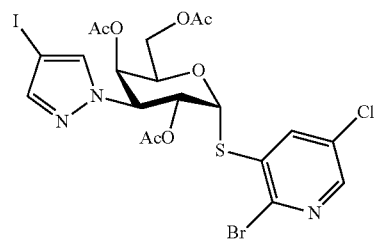

A solution of 2,4,6-tri-O-acetyl-3-deoxy-3-(4-iodo-1H-1,2-pyrazol-1-yl)-β-D-galactopyranosyl chloride (2.20 g, 60% purity, 2.63 mmol), 2-bromo-5-chloro-pyridine-3-thiol (710 mg, 3.16 mmol) and K₂CO₃ (729 mg, 5.27 mmol) in DMF (10 mL) was stirred 3 h at rt followed by 2 h at 50° C. The mixture was diluted with EtOAc and washed with water, NaOH (1 M) and brine. The organic phase was concentrated and purified by chromatography (SiO₂, PE/EtOAc) to yield the product (700 mg, 60% purity). ESI-MS m/z calcd for [C₂₀H₂₁BrClIN₃O₇S] [M+H]⁺: 687.9; found: 687.7. ¹H NMR (400 MHz, Chloroform-d) δ 8.23 (d, J=2.4 Hz, 1H), 7.88 (d, J=2.4 Hz, 1H), 7.53 (s, 1H), 7.48 (s, 1H), 6.24 (d, J=5.7 Hz, 1H), 6.02 (dd, J=11.8, 5.6 Hz, 1H), 5.56-5.51 (m, 1H), 4.93 (dd, J=11.8, 3.1 Hz, 1H), 4.73-4.67 (m, 1H), 4.18-4.04 (m, 2H), 2.05 (d, J=2.6 Hz, 3H), 2.01 (d, J=2.4 Hz, 3H), 1.97 (s, 3H).

2-Bromo-5-chloropyridin-3-yl 3-deoxy-3-[4-(3,4,5-trifluorophenyl)-1H-1,2-pyrazol-1-yl]-1-thio-α-D-galactopyranoside

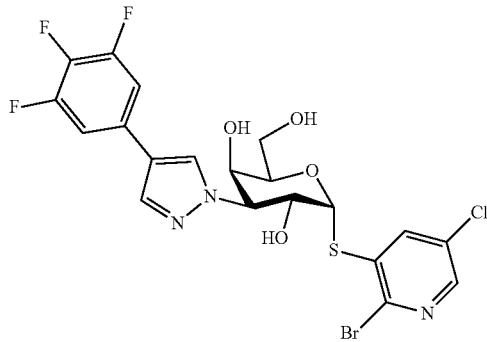

A solution of 2-bromo-5-chloropyridin-3-yl 2,4,6-tri-O-acetyl-3-deoxy-3-(4-iodo-1H-1,2-pyrazol-1-yl)-1-thio-α-D-galactopyranoside (700 mg, 60% purity, 1.0 mmol), Pd(dppf)Cl$_2$ (112 mg, 0.152 mmol), (3,4,5-trifluorophenyl)boronic acid (215 mg, 1.22 mmol) and K$_2$CO$_3$ (702 mg, 5.08 mmol) in dioxane (6 mL) and water (3 mL) was stirred 80 min at 60° C. followed by 16 h at rt. The mixture was concentrated and partitioned between EtOAc and water. The organic phase was washed with water and brine, dried and concentrated. The residue was purified by chromatography (SiO$_2$, PE/EtOAc) and the obtained material was dissolved in MeOH (20 mL) and NaOMe (2 mL, 1 M). After 1 h at rt the reaction was quenched with acetic acid (200 µL) and the mixture was concentrated. The residue was partitioned between EtOAc and water. The organic phase was washed with brine, dried and concentrated. Purification by prep HPLC (C$_{18}$, H$_2$O/MeCN/0.1% TFA) yielded the product (60 mg, 9%). ESI-MS m/z calcd for [C$_{20}$H$_{17}$BrClF$_3$N$_3$O$_4$S] [M+H]$^+$: 566.0; found: 565.8. $^1$H NMR (400 MHz, Methanol-d$_4$) δ 8.21-8.16 (m, 3H), 7.92 (s, 1H), 7.40-7.33 (m, 2H), 6.12 (d, J=5.5 Hz, 1H), 4.94 (dd, J=11.3, 5.5 Hz, 1H), 4.66 (dd, J=11.3, 2.7 Hz, 1H), 4.30 (t, J=6.1 Hz, 1H), 4.20 (d, J=2.1 Hz, 1H), 3.75-3.63 (m, 2H).

Intermediate 13

2-Bromo-5-chloropyridin-3-yl 3-[4-(4-chloro-3,5-difluorophenyl)-1H-1,2-pyrazol-1-yl]-3-deoxy-1-thio-α-D-galactopyranoside

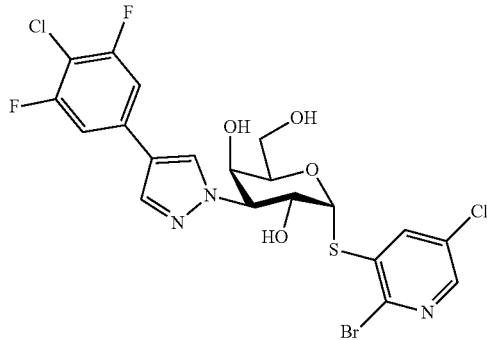

To a solution of 2,4,6-tri-O-acetyl-3-[4-(4-chloro-3,5-difluorophenyl)-1H-1,2-pyrazol-1-yl]-3-deoxy-β-D-galactopyranosyl chloride (270 mg, 0.52 mmol), 2-bromo-5-chloro-pyridine-3-thiol (291 mg, 1.30 mmol) in DMF (5 mL) Cs$_2$CO$_3$ (844 mg, 2.59 mmol) was added. After stirring 18 h at 40° C. more 2-bromo-5-chloro-pyridine-3-thiol (100 mg, 0.45 mmol) was added. After 6 h at 50° C. the mixture was diluted with EtOAc and washed with water and brine. The organic phase was dried, concentrated onto silica and purified by chromatography (SiO$_2$, PE/EtOAc). Further purification by prep HPLC (C$_{18}$, H$_2$O/MeCN/0.1% TFA) yielded the product (51 mg, 17%) as a white solid. ESI-MS m/z calcd for [C$_{20}$H$_{17}$BrCl$_2$F$_2$N$_3$O$_4$S] [M+H]$^+$: 581.9; found: 581.8. $^1$H NMR (500 MHz, Methanol-d$_4$) δ 8.28 (s, 1H), 8.23-8.19 (m, 2H), 7.99 (s, 1H), 7.41 (d, J=8.3 Hz, 2H), 6.14 (d, J=5.4 Hz, 1H), 4.96 (dd, J=11.3, 5.4 Hz, 1H), 4.69 (dd, J=11.3, 2.8 Hz, 1H), 4.32 (t, J=6.2 Hz, 1H), 4.22 (d, J=2.1 Hz, 1H), 3.77-3.64 (m, 2H).

Intermediate 14

3-Fluoro-5-methyl-pyridine-2-carbonitrile

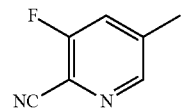

A nitrogen purged solution of 2-bromo-3-fluoro-5-methyl-pyridine (300 mg, 1.58 mmol), zinc cyanide (371 mg, 3.16 mmol), 1,1'-bis(diphenylphosphino)ferrocene (71 mg, 0.13 mmol), tris(dibenzylideneacetone)dipalladium(0) (72.6 mg, 0.13 mmol) and Zn (51 mg, 0.79 mmol) in DMF (5 mL) was stirred 16 h at 100° C. The mixture was removed from stirring and the solids were allowed to sink. The supernatant was partitioned between EtOAc and brine. The organic phase was washed with brine, dried, concentrated and purified by chromatography (SiO$_2$, PE/EtOAc) to yield the product (202 mg, 94%). $^1$H NMR (500 MHz, Chloroform-d) δ 8.37 (s, 1H), 7.44-7.36 (m, 1H), 2.48 (s, 3H).

5-Chloro-2-methylpyridin-3-yl 2,4,6-tri-O-acetyl-3-deoxy-3-(4-iodo-1H-1,2-pyrazol-1-yl)-1-thio-α-D-galactopyranoside

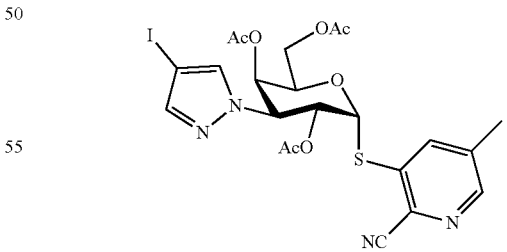

To a solution of 2,4,6-tri-O-acetyl-3-deoxy-3-(4-iodo-1H-1,2-pyrazol-1-yl)-β-D-galactopyranosyl chloride (420 mg, 60% purity, 0.84 mmol) in DMF (4 mL) potassium thioacetate (144 mg, 1.26 mmol) was added. After stirring 19 h at rt the mixture was diluted with EtOAc and washed with water and brine. The organic phase was dried, concentrated and purified by chromatography (SiO$_2$, PE/EtOAc). The obtained material was dissolved together with 3-fluoro-5-methyl-pyridine-2-carbonitrile (90.7 mg, 0.67 mmol) in DMF (2 mL) and diethylamine (114 µL, 1.11 mmol) was added. After 20 h at rt the mixture was diluted with EtOAc and washed with water and brine. The organic phase was dried, concentrated and purified by chromatography (SiO$_2$, PE/EtOAc) to yield the product (200 mg, 50% purity, 59%). ESI-MS m/z calcd for [C$_{22}$H$_{20}$F$_3$N$_4$O$_4$S] [M+H]$^+$: 615.0; found: 614.8.

Intermediate 15

5-Bromo-2-cyanopyridin-3-yl 2,4,6-tri-O-acetyl-3-deoxy-3-[4-(3,4,5-trifluorophenyl)-1H-1,2-pyrazol-1-yl]-1-thio-α-D-galactopyranoside

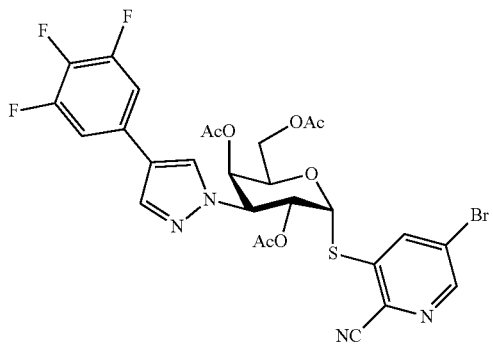

A nitrogen purged solution of 1,2,4,6-tetra-O-acetyl-3-deoxy-3-(4-iodo-1H-1,2-pyrazol-1-yl)-β-D-galactopyranoside (2.70 g, 5.15 mmol), K$_2$CO$_3$ (3.56 g, 25.8 mmol), (3,4,5-trifluorophenyl)boronic acid (1.36 g, 7.73 mmol) and Pd(dppf)Cl$_2$ (565 mg, 0.77 mmol) in water/dioxane (1:2, 22.5 mL) was heated 1 h at 60° C. The mixture was partitioned between EtOAc and water and the organic phase was dried, evaporated and purified by chromatography (SiO$_2$, PE/EtOAc). The obtained material and PCl$_5$ (1.17 g, 5.63 mmol) were dissolved in DCM (45 mL) and BF$_3$OEt$_2$ (0.80 mL, 6.50 mmol) was added. The mixture was stirred 5 h at rt before it was diluted with DCM and washed with water and saturated aq NaHCO$_3$, dried and evaporated. The residue was dissolved with potassium thioacetate (742 mg, 6.50 mmol) in DMF (20 mL) and the mixture was stirred 18 h at 30° C. The mixture was diluted with EtOAc and washed with water and brine. The organic phase was dried, evaporated and purified by chromatography (SiO$_2$, PE/EtOAc). The obtained material and 5-bromo-3-fluoropyridine-2-carbonitrile (750 mg, 3.73 mmol) were dissolved in DMF (8 mL) and diethylamine (0.72 mL, 7.00 mmol) was added and the mixture was stirred 2 h at rt. The mixture was partitioned between water and EtOAc, the organic phase was washed with water, dried and evaporated. The residue was purified by chromatography (SiO$_2$, PE/EtOAc) to afford the product (453 mg, 13%). ESI-MS m/z calcd for [C$_{27}$H$_{22}$BrF$_3$N$_4$O$_7$S] [M+H]$^+$: 683.0; found: 683.0. $^1$H NMR (400 MHz, Chloroform-d) δ 8.70 (d, J=2.0 Hz, 1H), 8.24 (d, J=2.0 Hz, 1H), 7.72 (s, 1H), 7.66 (s, 1H), 7.06 (dd, J=8.2, 6.4 Hz, 2H), 6.27 (d, J=5.6 Hz, 1H), 6.12 (dd, J=11.6, 5.6 Hz, 1H), 5.62 (d, J=2.4 Hz, 1H), 4.89 (dd, J=11.6, 3.0 Hz, 1H), 4.83-4.77 (m, 1H), 4.20-4.08 (m, 2H), 2.07 (s, 3H), 2.06 (s, 3H), 2.04 (s, 3H).

Intermediate 17

5-Chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside

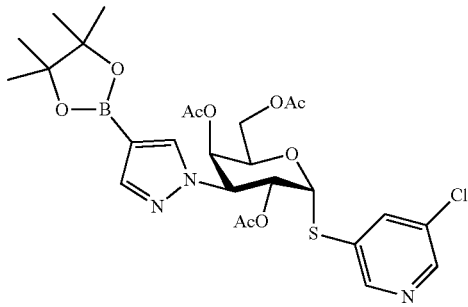

5-Chloropyridin-3-yl 2,4,6-tri-O-acetyl-3-(4-bromo-1H-1,2-pyrazol-1-yl)-3-deoxy-1-thio-α-D-galactopyranoside (428 mg, 0.76 mmol), Pd(dppf)Cl$_2$ (56 mg, 0.076 mmol), bis(pinacolato)diboron (579 mg, 2.28 mmol) and potassium acetate (373 mg, 3.80 mmol) were weighed into a vial and flushed with argon. Degassed DMSO (7.0 mL) was added to the vial and the mixture was stirred 17 h at 85° C. The mixture was diluted with EtOAc (100 mL) and washed with water (3×100 mL) and brine (100 mL). The organic phase was dried, evaporated, and purified by chromatography (SiO$_2$, PE/EtOAc) to afford the product (228 mg, 34%). ESI-MS m/z calcd for [C$_{26}$H$_{33}$BClN$_3$O$_9$S] [M+H]$^+$: 610.2; found: 610.0. $^1$H NMR (400 MHz, Chloroform-d) δ 8.58 (s, 1H), 8.52 (s, 1H), 7.93 (s, 1H), 7.77 (s, 1H), 7.70 (s, 1H), 6.16 (d, J=5.6 Hz, 1H), 5.97 (dd, J=11.7, 5.4 Hz, 1H), 5.54 (d, J=2.2 Hz, 1H), 4.91 (dd, J=11.7, 3.0 Hz, 1H), 4.82-4.77 (m, 1H), 4.19-4.11 (m, 1H), 4.08 (dd, J=11.5, 7.5 Hz, 1H), 2.04 (s, 3H), 2.03 (s, 3H), 1.99 (s, 3H), 1.32 (d, J=3.8 Hz, 12H).

Intermediate 18

5-Chloropyridin-3-yl 2,4,6-tri-O-acetyl-3-deoxy-3-(4-iodo-1H-1,2-pyrazol-1-yl)-β-D-galactopyranoside

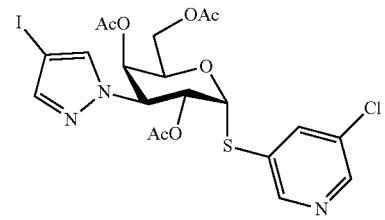

A solution of 2,4,6-tri-O-acetyl-3-deoxy-3-(4-iodo-1H-1,2-pyrazol-1-yl)-β-D-galactopyranosyl chloride (3.0 g, 60% purity, 3.59 mmol), 5-chloropyridine-3-thiol (1.05 g, 7.2 mmol) and Cs$_2$CO$_3$ (2.4 g, 7.2 mmol) in DMF (10.0 mL) was stirred 3 h at rt. The mixture was partitioned between EtOAc and brine, the organic phase was dried and evaporated. The residue was purified by chromatography (SiO$_2$, PE/EtOAc) to afford the product (1.48 g, 75% purity, 26%). ESI-MS m/z calcd for [C$_{20}$H$_{21}$ClIN$_3$O$_7$S] [M+H]$^+$: 610.0;

found: 609.8. ¹H NMR (400 MHz, Chloroform-d) δ 8.58 (s, 1H), 8.52 (s, 1H), 7.92 (s, 1H), 7.52 (s, 1H), 7.46 (s, 1H), 6.11 (d, J=5.6 Hz, 1H), 5.96 (dd, J=11.7, 5.5 Hz, 1H), 5.53 (d, J=2.9 Hz, 1H), 4.88 (dd, J=11.7, 3.1 Hz, 1H), 4.80-4.74 (m, 1H), 4.19-4.06 (m, 2H), 2.04 (s, 6H), 2.01 (s, 3H).

Intermediate 28

1,2,4,6-Tetra-O-acetyl-3-deoxy-3-[4-(4,4,5,5-tetramethyl-1,3,2-dioxaborolane-2-yl)-1H-1,2-pyrazol-1-yl]-β-D-galactopyranoside

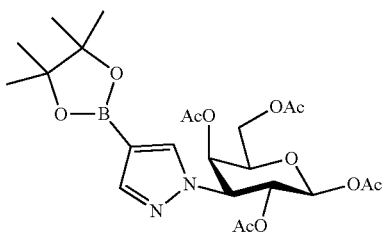

1,2,4,6-Tetra-O-acetyl-3-deoxy-3-(4-iodo-1H-1,2-pyrazol-1-yl)-β-D-galactopyranoside (5.243 g, 10.0 mmol), Pd(dppf)Cl₂ (732 mg, 1.00 mmol), bis(pinacolato)diboron (7.618 g, 30.0 mmol) and potassium acetate (4.907 g, 50.0 mmol) were dissolved in degassed DMF (100 mL) and the mixture was stirred 2 h at 60° C. The mixture was filtered through celite and concentrated to approximately 50 mL and diluted with PE/EtOAc (1:1, 500 mL). The solution was washed with water (3×500 mL) and brine (300 mL). The organic phase was dried, evaporated, and purified by chromatography (SiO₂, PE/EtOAc) to afford the product (4.22 g, 50% purity, 81%). ESI-MS m/z calcd for [C₂₃H₃₃BN₂O₁₁] [M+H]⁺: 525.2; found: 525.0. ¹H NMR (400 MHz, Chloroform-d) δ 7.76 (s, 1H), 7.73 (s, 1H), 5.88-5.78 (m, 2H), 5.47 (s, 1H), 4.88-4.77 (m, 1H), 4.24-4.07 (m, 3H), 2.15 (s, 3H), 2.03 (s, 6H), 1.90 (s, 3H), 1.35-1.22 (m, 12H).

2,4,6-Tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranosyl chloride

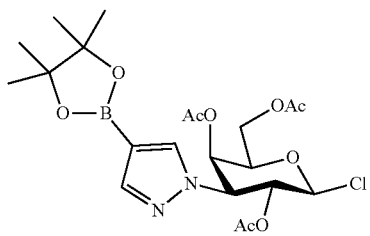

To a solution of 1,2,4,6-tetra-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (1.00 g, 50% purity, 1.19 mmol) and PCl₅ (794 mg, 3.81 mmol) in DCM (15.7 mL) BF₃OEt₂ (0.47 mL, 3.81 mmol) was added. The mixture was stirred 24 h at rt and was then poured on ice/DCM (1:1, 70 mL) and neutralized with NaOH (1 M). The organic phase was separated, and the aqueous phase was extracted with DCM (2×50 mL). The combined organic phases were washed with brine, dried and evaporated to give the product (1.01 g, 50% purity), which was used without purification in subsequent steps.

5-Bromopyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside

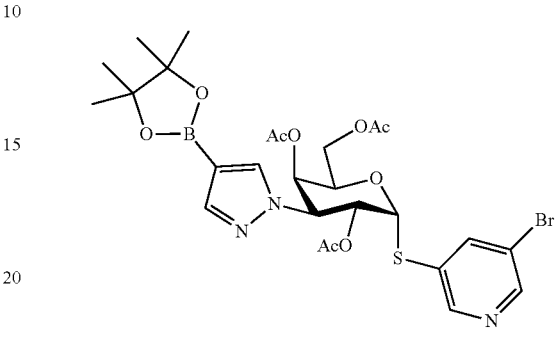

To a solution of 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranosyl chloride (500 mg, 50% purity, 1.00 mmol) and 5-bromopyridine-3-thiol (285 mg, 1.50 mmol) in DMF (8.1 mL) NaH (60% in oil, 76.5 mg, 2.00 mmol) was added and the mixture was stirred 21 h at rt. The mixture was diluted with EtOAc (100 mL) and washed with water (5×100 mL) and brine (100 mL). The organic phase was dried, evaporated and purified by chromatography (SiO₂, PE/EtOAc) to afford the product (189 mg, 20% purity, 29%). ESI-MS m/z calcd for [C₂₆H₃₃BBrN₃O₉S] [M+H]¹¹: 654.1; found: 654.0. ¹H NMR (500 MHz, Chloroform-d) δ 8.61 (d, J=2.0 Hz, 2H), 8.03 (t, J=1.8 Hz, 1H), 7.77 (s, 1H), 7.70 (s, 1H), 6.14 (d, J=5.5 Hz, 1H), 5.96 (dd, J=11.8, 5.6 Hz, 1H), 5.54 (d, J=2.6 Hz, 1H), 4.90 (dd, J=11.7, 3.2 Hz, 1H), 4.79 (t, J=6.4 Hz, 1H), 4.19-4.05 (m, 2H), 2.03 (s, 6H), 1.98 (s, 3H), 1.25 (s, 12H).

Intermediate 29

5-Chloro-2-cyanophenyl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside

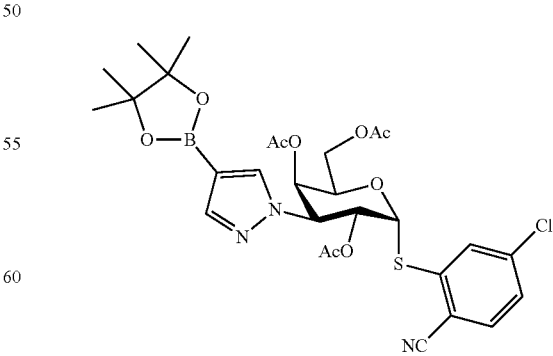

To a solution of 1,2,4,6-tetra-O-acetyl-3-deoxy-3-[4-(4,4,5,5-tetramethyl-1,3,2-dioxaborolane-2-yl)-1H-1,2-pyrazol-1-yl]-β-D-galactopyranoside (4.22 g, 50% purity, 8.05 mmol) and PCl₅ (3.35 g, 16.1 mmol) in DCM (66.2 mL) BF₃OEt₂ (1.99 mL, 16.1 mmol) was added. The mixture was stirred 1.5 h at rt and was then poured on ice and neutralized with NaOH (1 M). The organic phase was separated, and the aqueous phase was extracted with DCM (70 mL). The combined organic phases were dried and evaporated. The residue was dissolved in DMF (25 mL) and 4-chloro-2-sulfanylbenzonitrile (500 mg, 2.95 mmol) followed by NaH (60% in oil, 130 mg, 3.40 mmol) were added and the mixture was heated 1 h at 60° C. EtOAc (250 mL) was added and the mixture was washed with NaOH (0.1 M, 250 mL), water (3×250 mL) and brine (250 mL). The organic phase was dried, evaporated and purified by chromatography (SiO₂, PE/EtOAc) to afford the product (92 mg, 50% purity, 2%). ESI-MS m/z calcd for [C₂₈H₃₃BClN₃O₉S] [M+H]¹¹: 634.2; found: 634.0. ¹H NMR (400 MHz, Chloroform-d) δ 7.86 (s, 1H), 7.80 (s, 1H), 7.71 (s, 1H), 7.62 (d, J=8.2 Hz, 1H), 7.41 (d, J=8.3 Hz, 1H), 6.22 (d, J=5.4 Hz, 1H), 6.00 (dd, J=11.4, 5.6 Hz, 1H), 5.58-5.54 (m, 1H), 4.90 (dd, J=11.0, 3.1 Hz, 1H), 4.81 (t, J=4.3 Hz, 1H), 4.14-4.09 (m, 2H), 2.02 (s, 6H), 2.00 (s, 3H), 1.35-1.30 (m, 12H).

Intermediate 30

2-Bromo-5-chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside

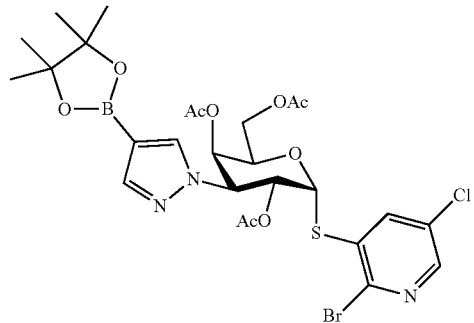

To a solution of 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranosyl chloride (500 mg, 50% purity, 1.00 mmol) and 2-bromo-5-chloropyridine-3-thiol (336 mg, 1.50 mmol) in DMF (8.1 mL) NaH (60% in oil, 76.5 mg, 2.00 mmol) was added and the mixture was heated 3 h at 50° C. The mixture was diluted with EtOAc (100 mL) and washed with water (5×100 mL) and brine (100 mL). The organic phase was dried, evaporated and purified by chromatography (SiO₂, PE/EtOAc) to afford the product (53 mg, 50% purity, 8%). ESI-MS m/z calcd for [C₂₆H₃₂BBrClN₃O₉S] [M+H]⁺: 688.1; found: 688.0. ¹H NMR (500 MHz, Chloroform-d) δ 8.23 (d, J=2.4 Hz, 1H), 7.91 (d, J=2.4 Hz, 1H), 7.79 (s, 1H), 7.73 (s, 1H), 6.29 (d, J=5.6 Hz, 1H), 6.04 (dd, J=11.8, 5.6 Hz, 1H), 5.56 (d, J=2.2 Hz, 1H), 4.98 (dd, J=11.7, 3.1 Hz, 1H), 4.76-4.69 (m, 1H), 4.17-4.09 (m, 2H), 2.05 (s, 3H), 2.01 (s, 3H), 1.98 (s, 3H), 1.34 (d, J=3.8 Hz, 12H).

5-Chloro-2-cyanopyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside

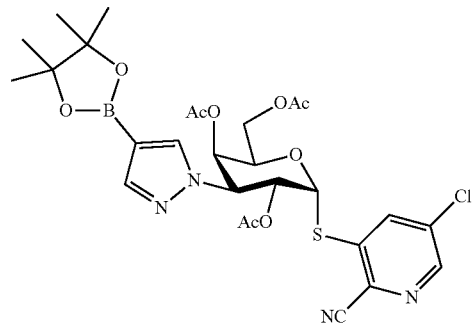

A solution of 2-bromo-5-chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (53 mg, 0.077 mmol), zinc cyanide (9.0 mg, 0.077 mmol), Zn (2.5 mg, 0.038 mmol), tris(dibenzylideneacetone)dipalladium(0) (2.8 mg, 0.0031 mmol) and 1,1'-bis(diphenylphosphino)ferrocene (3.5 mg, 0.0062 mmol) in argon purged DMF (1.0 mL) was stirred 3 h at 100° C. More zinc cyanide (4.5 mg, 0.038 mmol) was added and the mixture was stirred 2 h at 100° C. The mixture was diluted with EtOAc (10 mL), filtered through a plug of celite, washed with water (5×10 mL) and brine (10 mL). The organic phase was dried, concentrated and purified by chromatography (SiO₂, PE/EtOAc) to afford the product (23 mg, 40% purity, 47%). ESI-MS m/z calcd for [C₂₇H₃₂BClN₄O₉S] [M+H]⁺; 635.2; found: 634.9. ¹H NMR (500 MHz, Chloroform-d) δ 8.57 (s, 1H), 8.08 (s, 1H), 7.77 (s, 1H), 7.72 (s, 1H), 6.26 (d, J=4.9 Hz, 1H), 6.13-5.98 (m, 1H), 5.65-5.48 (m, 1H), 5.02-4.85 (m, 1H), 4.84-4.66 (m, 1H), 4.20-4.05 (m, 2H), 2.03 (s, 3H), 2.03 (s, 3H), 2.02 (s, 3H), 1.25 (s, 12H).

Intermediate 31

2-Benzyloxy-4-bromothiazole

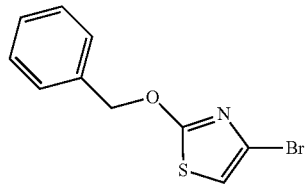 [SMILES: Brc1csc(OCc2ccccc2)n1]

Benzyl alcohol (2.00 g, 18.3 mmol) and NaH (60% in oil, 1.1 g, 27.5 mmol) were weighed into a bottle and THF (10 mL) was added. When the gas evolution ceased 2,4-dibromothiazole (3.25 g, 13.0 mmol) was added and the mixture was stirred 1 h at rt. The mixture was partitioned between diethyl ether and water. The organic phase was washed with brine, dried, evaporated and purified by chromatography (SiO₂, PE/EtOAc) to give the product (3.23 g, 92%). ¹H NMR (400 MHz, Chloroform-d) δ 7.49-7.34 (m, 5H), 6.62 (s, 1H), 5.46 (s, 2H).

5-Chloropyridin-3-yl 2,4,6-tri-O-acetyl-3-deoxy-3-[4-(2-benzyloxythiazol-4-yl)-1H-1,2-pyrazol-1-yl]-1-thio-α-D-galactopyranoside

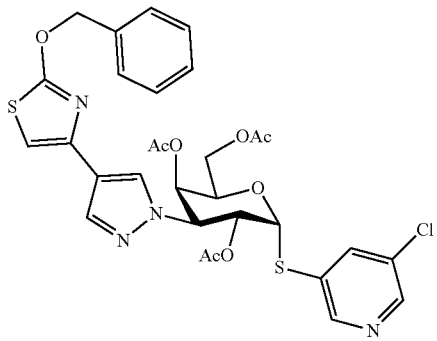

5-Chloropyridin-3-yl 2,4,6-tri-O-acetyl-3-deoxy-3-[4-(4,4,5,5-tetramethyl-1,3,2-dioxaborolane-2-yl)-1H-1,2-pyrazol-1-yl]-1-thio-α-D-galactopyranoside (100 mg, 0.16 mmol), tetrakis(triphenylphosphine)palladium(0) (19 mg, 0.016 mmol) and 2-benzyloxy-4-bromothiazole (133 mg, 0.49 mmol) were dissolved in a degassed mixture of toluene (1.0 mL), EtOH (0.2 mL) and aq $Na_2CO_3$ (246 µL, 2 M) and the resulting mixture was refluxed 2 h. The mixture was cooled to rt and the organic phase was separated. The aqueous phase was extracted with EtOAc (2×1 mL) and the combined organic phases were dried and concentrated. The residue was purified by chromatography ($SiO_2$, PE/EtOAc) to afford the product (77 mg, 70%). ESI-MS m/z calcd for $[C_{30}H_{29}ClN_4O_8S_2]$ $[M+H]^{11}$: 673.1; found: 673.2. $^1$H NMR (400 MHz, Chloroform-d) δ 8.58 (s, 1H), 8.52 (s, 1H), 7.89 (s, 1H), 7.79 (s, 1H), 7.76 (s, 1H), 7.51-7.45 (m, 2H), 7.45-7.35 (m, 3H), 6.59 (s, 1H), 6.13 (d, J=5.5 Hz, 1H), 6.00 (dd, J=11.6, 5.6 Hz, 1H), 5.59 (d, J=9.4 Hz, 1H), 5.48 (s, 1H), 4.91 (d, J=9.2 Hz, 1H), 4.85-4.77 (m, 1H), 4.18-4.06 (m, 2H), 2.04 (s, 6H), 2.01 (s, 3H).

Intermediate 35

2-Bromo-5-chloropyridin-3-yl 4,6-O-benzylidene-3-deoxy-3-[4-(3,4,5-trifluorophenyl)-1H-1,2-pyrazol-1-yl]-1-thio-α-D-galactopyranoside

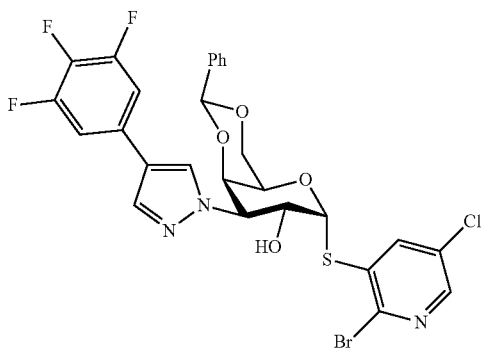

A solution of 2-bromo-5-chloropyridin-3-yl 3-deoxy-3-[4-(3,4,5-trifluorophenyl)-1H-1,2-pyrazol-1-yl]-1-thio-α-D-galactopyranoside (511 mg, 0.90 mmol), benzaldehyde dimethylacetal (176 µL, 1.17 mmol) and methanesulfonic acid (67 µL, 1.03 mmol) was stirred 30 min at rt before $Et_3N$ (200 µL) was added. The mixture was diluted with EtOAc (50 mL), washed with water (50 mL) and brine (50 mL), dried and concentrated. The residue was purified by chromatography ($SiO_2$, PE/EtOAc) to afford the product (158 mg, 27%). ESI-MS m/z calcd for $[C_{27}H_{20}BrClF_3N_3O_4S]$ $[M+H]^+$: 654.0; found: 653.8. $^1$H NMR (500 MHz, Chloroform-d) δ 8.19 (d, J=2.3 Hz, 1H), 7.92 (s, 1H), 7.78 (d, J=2.3 Hz, 1H), 7.77 (s, 1H), 7.47-7.38 (m, 5H), 7.09-7.02 (m, 2H), 6.51 (d, J=3.6 Hz, 1H), 5.59 (s, 1H), 4.99 (dd, J=11.0, 3.1 Hz, 1H), 4.77 (dd, J=11.0, 3.6 Hz, 1H), 4.57 (d, J=2.5 Hz, 1H), 4.42 (dd, J=12.8, 1.4 Hz, 1H), 4.24 (s, 1H), 4.19 (dd, J=12.9, 1.7 Hz, 1H).

2-Bromo-5-chloropyridin-3-yl 3-deoxy-3-[4-(3,4,5-trifluorophenyl)-1H-1,2-pyrazol-1-yl]-2-O-methyl-1-thio-α-D-galactopyranoside

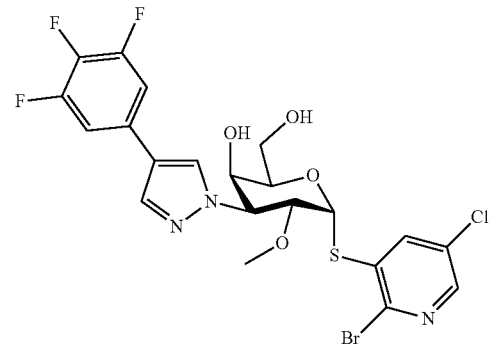

To a solution of 2-bromo-5-chloropyridin-3-yl 4,6-O-benzylidene-3-deoxy-3-[4-(3,4,5-trifluorophenyl)-1H-1,2-pyrazol-1-yl]-1-thio-α-D-galactopyranoside (158 mg, 0.24 mmol) in DMF (2.0 mL) NaH (60% in oil, 19 mg, 0.48 mmol) and iodomethane (22.5 µL, 0.36 mmol) were added and the mixture was stirred 30 min at rt. The mixture was diluted with EtOAc (10 mL), washed with water (5×10 mL) and brine (10 mL), dried and concentrated. The residue was stirred 20 min at rt in 80% aq TFA (0.83 mL). NaOH (10 mL, 1 M) was added and the mixture was extracted with EtOAc (2×10 mL). The combined organic phases were dried, concentrated and purified by chromatography ($SiO_2$, PE/EtOAc) to afford the product (124 mg, 84%). ESI-MS m/z calcd for $[C_{21}H_{18}BrClF_3N_3O_4S]$ $[M+H]^+$: 580.0; found: 579.7. $^1$H NMR (400 MHz, Methanol-$d_4$) δ 8.22 (s, 1H), 8.13 (d, J=2.4 Hz, 1H), 7.92 (s, 1H), 7.62 (d, J=2.4 Hz, 1H), 7.44-7.31 (m, 2H), 6.43 (d, J=5.2 Hz, 1H), 4.68 (dd, J=11.6, 2.6 Hz, 1H), 4.61 (dd, J=11.1, 5.1 Hz, 1H), 4.29 (t, J=6.1 Hz, 1H), 4.17 (s, 1H), 3.75 (d, J=6.1 Hz, 2H), 3.44 (s, 3H).

Intermediate 36

N-[p-Tolylsulfonyl-(3,4,5-trifluorophenyl)methyl]formamide

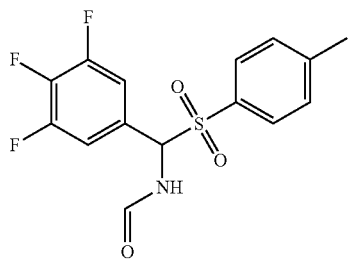 [SMILES: Cc1ccc(S(=O)(=O)C(NC=O)c2cc(F)c(F)c(F)c2)cc1]

To a solution of p-toluenesulfinic acid sodium salt (250 mg, 1.41 mmol) in water (1.67 mL) and tert-butyl methyl ether (0.83 mL) concentrated HCl (125 μL) was added dropwise and the mixture was stirred 10 min at rt. The mixture was diluted, and the phases were separated. The organic phase was washed with brine, dried and evaporated. The obtained material was dissolved together with 3,4,5-trifluorobenzaldehyde (150 mg, 0.94 mmol), D(+)-10-camphorsulfonic acid (22 mg, 0.094 mmol) and formamide (93 μL, 2.34 mmol) toluene/MeCN (2.0 mL, 1:1). After stirring 18 h at 60° C. the mixture was concentrated and purified by chromatography (SiO$_2$, PE/EtOAc) to afford the product (54 mg, 17%). ESI-MS m/z calcd for [C$_{15}$H$_{12}$F$_3$NO$_3$S] [M+Na]$^+$: 366.0; found: 366.0. $^1$H NMR (500 MHz, DMSO-d$_6$) δ 9.76 (d, J=10.7 Hz, 1H), 7.99 (s, 1H), 7.74 (d, J=8.2 Hz, 2H), 7.62 (dd, J=10.4, 4.8 Hz, 2H), 7.47 (d, J=8.0 Hz, 2H), 6.62 (d, J=10.6 Hz, 1H), 2.43 (s, 3H).

5-Chloropyridin-3-yl 3-amino-3-deoxy-1-thio-α-D-galactopyranoside

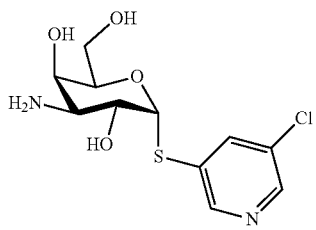

A solution of 5-chloropyridin-3-yl 2,4,6-tri-O-acetyl-3-azido-3-deoxy-1-thio-α-D-galactopyranoside (330 mg, 0.72 mmol) in MeOH (2 mL) and NaOMe (0.5 mL, 1 M) was stirred 3 h at rt. The mixture was quenched with acetic acid (0.1 mL), concentrated and partitioned between EtOAc and water. The organic phase was dried, evaporated and dissolved in MeOH (7 mL). 1,3-Propanedithiol (216 μL, 2.16 mmol) followed by Et$_3$N (301 μL, 2.16 mmol) were added and the mixture was stirred 18 h at rt. The mixture was concentrated and partitioned between EtOAc and water. The aqueous phase was evaporated to afford the product (169 mg, 77%). ESI-MS m/z calcd for [C$_{11}$H$_{15}$ClN$_2$O$_4$S] [M+H]$^+$: 307.0; found: 307.0. $^1$H NMR (500 MHz, Methanol-d$_4$) δ 8.59 (d, J=1.9 Hz, 1H), 8.44 (d, J=2.2 Hz, 1H), 8.14 (t, J=2.1 Hz, 1H), 5.72 (d, J=5.3 Hz, 1H), 4.28 (t, J=6.0 Hz, 1H), 4.08 (dd, J=10.6, 5.3 Hz, 1H), 3.96 (d, J=2.4 Hz, 1H), 3.75-3.66 (m, 2H), 2.92 (dd, J=10.6, 3.1 Hz, 1H).

Intermediate 37

2-Bromo-5-chloropyridin-3-yl 2,4,6-tri-O-acetyl-3-(4-bromo-1H-1,2-pyrazol-1-yl)-3-deoxy-1-thio-α-D-galactopyranoside

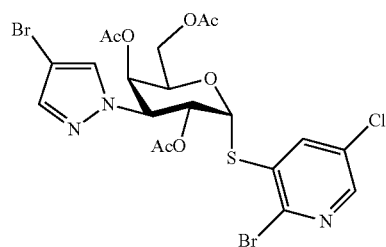

A solution of 2,4,6-tri-O-acetyl-3-(4-bromo-1H-1,2-pyrazol-1-yl)-3-deoxy-β-D-galactopyranosyl chloride (798 mg, 1.58 mmol), 2-bromo-5-chloropyridine-3-thiol (474 mg, 1.90 mmol) and K$_2$CO$_3$ (445 mg, 3.2 mmol) in DMF (4.0 mL) was stirred 19 h at rt. The mixture was partitioned between EtOAc and water. The organic phase was dried, concentrated and purified by chromatography (SiO$_2$, PE/EtOAc) to afford the product (234 mg, 23%). $^1$H NMR (400 MHz, Chloroform-d) δ 8.22 (d, J=2.3 Hz, 1H), 7.88 (d, J=2.3 Hz, 1H), 7.48 (s, 1H), 7.46 (d, J=3.3 Hz, 1H), 6.24 (d, J=5.6 Hz, 1H), 6.02 (dd, J=11.7, 5.6 Hz, 1H), 5.54 (s, 1H), 4.90 (dd, J=11.7, 3.0 Hz, 1H), 4.74-4.65 (m, 1H), 4.10 (m, 2H), 2.05 (s, 3H), 2.02 (s, 3H), 1.97 (s, 3H).

5-Chloro-2-{N-(2-oxa)-6-azaspiro[3.3]heptanyl}-pyridin-3-yl 3-(4-bromo-1H-1,2-pyrazol-1-yl)-3-deoxy-1-thio-α-D-galactopyranoside

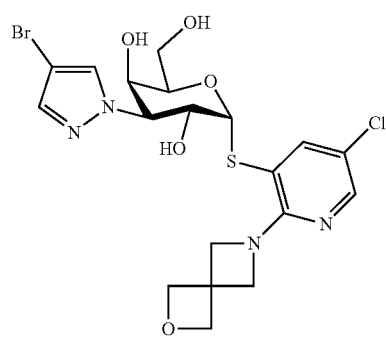

A solution of 2-bromo-5-chloropyridin-3-yl 2,4,6-tri-O-acetyl-3-(4-bromo-1H-1,2-pyrazol-1-yl)-3-deoxy-1-thio-α-D-galactopyranoside (100 mg, 0.15 mmol), DIPEA (0.29 mL, 2.25 mmol) and 2-oxa-6-azaspiro[3.3]heptane oxalate (73 mg, 0.5 mmol) in MeCN (2.0 mL) was stirred 3 h at 130° C. in a microwave reactor. The mixture was partitioned between EtOAc and water, and the organic phase was dried and evaporated. The obtained material was stirred 4 h at rt in MeOH (2.0 mL) and NaOMe (1.0 mL, 1 M). The mixture was neutralized with acetic acid (0.2 mL), concentrated and purified by prep HPLC (C$_{18}$, H$_2$O/MeCN/0.1% TFA) to afford the product (42 mg, 43%). ESI-MS m/z calcd for

[C$_{19}$H$_{22}$BrClN$_4$O$_5$S] [M+H]$^+$: 533.0; found: 533.0. $^1$H NMR (400 MHz, Methanol-d4) δ 7.99 (d, J=2.3 Hz, 1H), 7.96 (d, J=2.3 Hz, 1H), 7.86 (s, 1H), 7.54 (s, 1H), 5.62 (d, J=5.4 Hz, 1H), 4.83 (s, 4H), 4.78 (dd, J=11.4, 5.4 Hz, 1H), 4.61 (d, J=9.8 Hz, 2H), 4.54 (dd, J=11.4, 2.7 Hz, 1H), 4.49 (d, J=9.7 Hz, 2H), 4.36 (t, J=5.9 Hz, 1H), 4.13 (d, J=1.9 Hz, 1H), 3.72-3.60 (m, 2H).

Intermediate 38

3-Deoxy-3-(3-iodo-1H-1,2-pyrazol-1-yl)-1,2:5,6-di-O-isopropylidene-α-D-galactofuranose

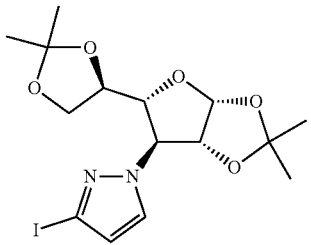

A solution of 1,2:5,6-di-O-isopropylidene-α-D-glucofuranose (5.00 g, 19.2 mmol) in DCM (100 mL) and pyridine (3.11 mL, 38.4 mmol) was cooled to 0° C. and trifluoromethanesulphonic anhydride (3.88 mL, 23.1 mmol) in DCM (15 mL) was added dropwise. After stirring 30 min at 10° C. the mixture was quenched by dropwise addition of HCl (1 M). The mixture was partitioned between DCM and HCl (1 M), the organic phase was washed with saturated aq NaHCO$_3$, dried and concentrated. Part of the obtained material (2.3 g, 5.86 mmol) and Cs$_2$CO$_3$ (1.91 g, 5.86 mmol) were dissolved in DMF (30 mL). To the solution 3-iodopyrazole (1.31 g, 6.74 mmol) was added and the mixture was stirred 20 h at rt. Ice was added and the solids were filtered off. The solids were purified by chromatography (SiO$_2$, PE/EtOAc) to afford the product (1.22 g, 48%). ESI-MS m/z calcd for [C$_{15}$H$_{21}$IN$_2$O$_5$] [M+H]$^+$: 437.1; found: 437.0. $^1$H NMR (500 MHz, Chloroform-d) δ 7.32 (d, J=2.3 Hz, 1H), 6.43 (d, J=2.3 Hz, 1H), 5.99 (d, J=4.0 Hz, 1H), 4.94 (dd, J=4.0, 2.4 Hz, 1H), 4.69 (dd, J=7.1, 2.4 Hz, 1H), 4.32 (dd, J=7.1, 4.1 Hz, 1H), 4.22 (td, J=6.8, 4.1 Hz, 1H), 4.04 (dd, J=8.3, 6.9 Hz, 1H), 3.89 (dd, J=8.3, 6.9 Hz, 1H), 1.63 (s, 3H), 1.44 (s, 3H), 1.38 (s, 3H), 1.37 (s, 3H).

1,2,4,6-Tetra-O-acetyl-3-deoxy-3-(3-iodo-1H-1,2-pyrazol-1-yl)-β-D-galactopyranoside

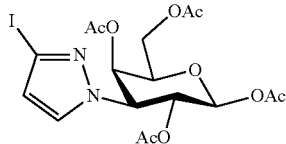

A solution of 3-deoxy-3-(3-iodo-1H-1,2-pyrazol-1-yl)-1,2:5,6-di-O-isopropylidene-α-D-galactofuranose (1.22 g, 2.79 mmol) in TFA/water (5 mL, 4:1) was stirred 1 h at rt. Water (2 mL) was added and the mixture was evaporated using MeCN for azeotropic removal of water and TFA. Finally, the residue was treated in vacuum. The crude was dissolved in EtOAc (8 mL) and Et$_3$N (4.57 mL, 33.5 mmol) followed by acetic anhydride (2.64 mL, 27.9 mmol) were added. The mixture was stirred 16 h at 30° C. The mixture was cooled to 0° C. and EtOAc (15 mL) followed by HCl (30 mL, 1 M) were added slowly. The mixture was stirred 20 min, then filtered through celite. The organic phase was separated, washed with saturated aq NaHCO$_3$ and brine, dried and evaporated. The residue was purified by chromatography (SiO$_2$, PE/EtOAc) to afford the product (1.135 g) as a furanoside/pyranoside mixture. The mixture was used without further purification in the next step. ESI-MS m/z calcd for [C$_{17}$H$_{21}$IN$_2$O$_9$] [M+H]$^+$: 525.0; found: 525.0.

5-Chloropyridin-3-yl 4,6-O-benzylidene-3-deoxy-3-(3-iodo-1H-1,2-pyrazol-1-yl)-1-thio-α-D-galactopyranoside

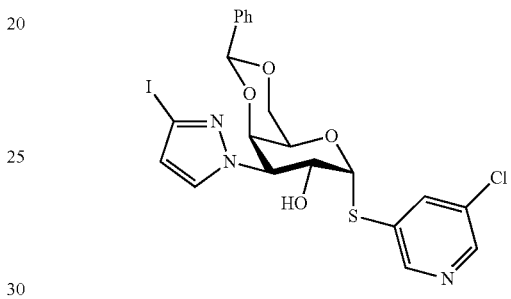

To a solution of 1,2,4,6-tetra-O-acetyl-3-deoxy-3-(3-iodo-1H-1,2-pyrazol-1-yl)-β-D-galactopyranoside (1.10 g, 2.10 mmol) and PCl$_5$ (568 mg, 2.73 mmol) in DCM (20 mL) boron trifluoride diethyl etherate (0.78 mL, 6.29 mmol) was added and the mixture was stirred 7 h at rt. The solution was diluted with DCM and washed with ice/water and saturated aq NaHCO$_3$. The organic phase was dried, evaporated and the residue was dissolved together with 5-chloropyridine-3-thiol (458 mg, 3.15 mmol) in DMF (10 mL). K$_2$CO$_3$ (580 mg, 4.20 mmol) was added and the mixture was stirred 16 h at rt. The mixture was diluted with EtOAc and washed twice with water and once with brine. The organic phase was dried, concentrated and purified by chromatography (SiO$_2$, PE/EtOAc). The obtained material was stirred 1 h at rt in MeOH (15 mL) and NaOMe (1 mL, 1 M). The reaction was quenched with dowex, filtered and the filtrate was evaporated. The obtained residue and p-toluenesulfonic acid monohydrate (58 mg, 0.30 mmol) were dissolved in MeCN (40 mL) and benzaldehyde dimethyl acetal (0.23 mL, 1.51 mmol) was added. The mixture was stirred 3 days at rt before more p-toluenesulfonic acid monohydrate (58 mg, 0.30 mmol) and benzaldehyde dimethyl acetal (0.23 mL, 1.51 mmol) were added and the mixture was stirred an additional 20 h at rt. Et$_3$N (0.14 mL mL, 1.01 mmol) was added and the mixture was concentrated. The residue was partitioned between EtOAc and saturated aq NaHCO$_3$. The organic phase was dried, evaporated and purified by chromatography (SiO$_2$, PE/EtOAc) to afford the product (226 mg, 19% yield). ESI-MS m/z calcd for [C$_{21}$H$_{19}$ClIN$_3$O$_4$S] [M+H]$^+$: 572.0; found: 572.0. $^1$H NMR (500 MHz, Chloroform-d) δ 8.57 (d, J=1.9 Hz, 1H), 8.46 (d, J=2.2 Hz, 1H), 7.90 (t, J=2.1 Hz, 1H), 7.52 (d, J=2.4 Hz, 1H), 7.43-7.35 (m, 6H), 6.49 (d, J=2.4 Hz, 1H), 5.96 (d, J=5.1 Hz, 1H), 5.54 (s, 1H), 4.92 (dd, J=11.3, 5.1 Hz, 1H), 4.78 (dd, J=11.3, 3.0 Hz, 1H), 4.52-4.48 (m, 1H), 4.30 (dd, J=12.7, 1.5 Hz, 1H), 4.15 (dd, J=12.4, 1.8 Hz, 1H).

5-Chloropyridin-3-yl 3-deoxy-3-(3-iodo-1H-1,2-pyrazol-1-yl)-2-O-methyl-1-thio-α-D-galactopyranoside

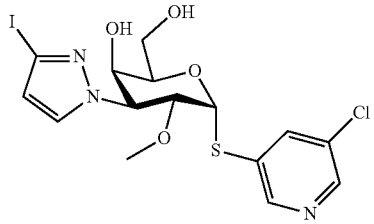

To a solution of 5-chloropyridin-3-yl 4,6-O-benzylidene-3-deoxy-3-(3-iodo-1H-1,2-pyrazol-1-yl)-1-thio-α-D-galactopyranoside (226 mg, 0.40 mmol) in DMF (5 mL) NaH (60% in oil, 30 mg, 0.79 mmol) followed by iodomethane (37 μL, 0.59 mmol) were added and the mixture was stirred 1 h at rt. The mixture was diluted with EtOAc, washed trice with water and the organic phase was dried and evaporated. The residue was stirred 3 h at 80° C. in acetic acid/water (5 mL, 9:1). The mixture was partitioned between EtOAc and water and the organic phase was washed with saturated aq NaHCO$_3$, dried and evaporated. The residue was stirred 1 h at rt in NaOMe (0.1 mL, 1 M) and MeOH (1.5 mL). The mixture was concentrated and purified by prep HPLC (C$_{18}$, H$_2$O/MeCN/0.1% TFA) to afford the product (145 mg, 74%). ESI-MS m/z calcd for [C$_{15}$H$_{17}$ClIN$_3$O$_4$S] [M+H]$^+$: 498.0; found: 498.0. $^1$H NMR (500 MHz, Chloroform-d) δ 8.64 (d, J=1.9 Hz, 1H), 8.48 (d, J=2.2 Hz, 1H), 8.22 (t, J=2.1 Hz, 1H), 7.65 (d, J=2.4 Hz, 1H), 6.50 (d, J=2.4 Hz, 1H), 6.21 (d, J=5.3 Hz, 1H), 4.61 (dd, J=11.3, 2.8 Hz, 1H), 4.47 (dd, J=11.3, 5.3 Hz, 1H), 4.37 (t, J=6.1 Hz, 1H), 4.12 (d, J=1.9 Hz, 1H), 3.71-3.63 (m, 2H), 3.36 (s, 3H).

Intermediate 39

2-Bromo-1-(3,4,5-trifluorophenyl)ethanone

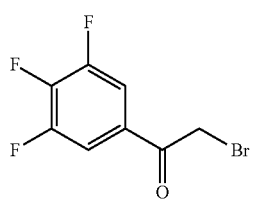 [SMILES: O=C(CBr)c1cc(F)c(F)c(F)c1]

To a solution of 1-(3,4,5-trifluorophenyl)ethanone (960 mg, 5.51 mmol) in DCM (50 mL) tert-butyldimethylsilyl trifluoromethanesulfonate (2.186 g, 8.27 mmol) and Et$_3$N (1.12 g, 11.0 mmol) were added and the mixture was stirred 1 h at rt. The mixture was partitioned between DCM (50 mL) and aq NaHCO$_3$ (60 mL). The organic phase was dried over Na$_2$SO$_4$ and concentrated. The residue was dissolved in THF (50 mL) and N-bromosuccinimide (981 mg, 5.51 mmol) and water (993 mg) were added. The mixture was stirred 15 min at rt before diethyl ether (100 mL) was added. The mixture was washed with water (80 mL), aq NaHCO$_3$ (60 mL) and brine (80 mL). The organic phase was dried over MgSO$_4$, concentrated and purified by chromatography (SiO$_2$, PE/EtOAc) to afford the product (800 mg, 57%). $^1$H NMR (400 MHz, CDCl$_3$) δ 7.72-7.57 (m, 2H), 4.35 (s, 2H).

Methyl 3-O-allyl-α-D-galactopyranoside

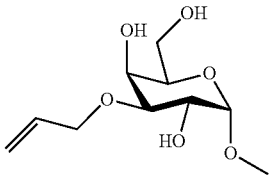

To a solution of methyl α-D-galactopyranoside (19.4 g, 100 mmol) in anhydrous methanol (200 mL) dibutyltin oxide (27.4 g, 110 mmol) was added and the mixture was refluxed 4 h. The mixture was concentrated. The dried residue was suspended in toluene (200 mL) and treated with allyl bromide (14.5 g, 120 mmol) and tetrabutylammonium bromide (32.2 g, 100 mmol). The suspension was stirred 18 h at 60° C. The mixture was evaporated and purified by chromatography (SiO$_2$, EtOAc) to afford the product (20 g, 85%). ESI-MS m/z calcd for [C$_{10}$H$_{18}$O$_6$] [M+NH$_4$]$^+$: 252.1; found:252.1.

Methyl 3-O-allyl-2,4,6-tri-O-benzyl-α-D-galactopyranoside

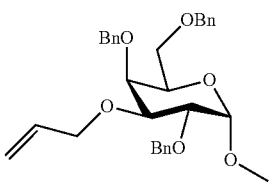

To a cooled (0° C.) solution of methyl 3-O-allyl-α-D-galactopyranoside (15 g, 64 mmol) in DMF (150 mL) NaH (60% in oil, 12.81 g, 320 mmol) was added. After 15 min, benzyl bromide (36.14 g, 0.21 mol) was added and the mixture was stirred 16 h at rt. EtOAc (600 mL) was added and the mixture was washed with HCl (400 mL, 1 M), water (400 mL) and brine. The organic phase was concentrated and was purified by chromatography (SiO$_2$, PE/EtOAc) to give the product (27 g, 84%). ESI-MS m/z calcd for [C$_{31}$H$_{36}$O$_6$] [M+NH$_4$]$^+$: 522.3; found: 522.2. $^1$H NMR (400 MHz, CDCl$_3$) δ 7.42-7.20 (m, 15H), 6.08-5.85 (m, 1H), 5.40-5.30 (m, 1H), 5.21-5.14 (m, 1H), 4.94 (d, J=11.5 Hz, 1H), 4.83 (d, J=12.1 Hz, 1H), 4.72-4.61 (m, 2H), 4.57 (d, J=11.5 Hz, 1H), 4.48 (d, J=11.8 Hz, 1H), 4.40 (d, J=11.8 Hz, 1H), 4.31-4.24 (m, 1H), 4.24-4.16 (m, 1H), 3.97 (dd, J=10.1, 3.7 Hz, 1H), 3.93-3.85 (m, 2H), 3.81 (dd, J=10.1, 2.8 Hz, 1H), 3.53 (d, J=6.4 Hz, 2H), 3.36 (s, 3H).

Methyl 2,4,6-tri-O-benzyl-α-D-galactopyranoside

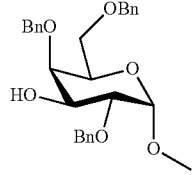

To a solution of methyl 3-O-allyl-2,4,6-tri-O-benzyl-α-D-galactopyranoside (23 g, 46 mmol) in MeOH (200 mL) palladium(II) chloride (840 mg, 4.73 mmol) was added and the mixture was stirred 16 h at rt. The mixture was concentrated and purified by chromatography (SiO$_2$, PE/EtOAc) to give the product (21 g, 91%). ESI-MS m/z calcd for [C$_{28}$H$_{32}$O$_6$] [M+NH$_4$]$^+$: 482.2; found: 482.2. $^1$H NMR (400 MHz, CDCl$_3$) δ 7.48-7.07 (m, 15H), 4.81 (d, J=11.6 Hz, 1H), 4.72-4.58 (m, 4H), 4.51 (d, J=11.8 Hz, 1H), 4.42 (d, J=11.8 Hz, 1H), 4.08-4.01 (m, 1H), 3.98-3.88 (m, 2H), 3.79 (dd, J=10.0, 3.5 Hz, 1H), 3.56 (d, J=6.5 Hz, 2H), 3.33 (s, 3H), 2.25 (d, J=3.9 Hz, 1H).

Methyl 2,4,6-tri-O-benzyl-α-D-xylo-hex-3-ulopyranoside

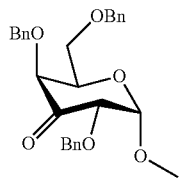

To a solution of methyl 2,4,6-tri-O-benzyl-α-D-galactopyranoside (11 g, 24 mmol) in DCM (120 mL) Dess-Martin Periodinane (15.06 g, 40 mmol) was added and the mixture was stirred 24 h at rt. The mixture was concentrated and purified by chromatography (SiO$_2$, PE/EtOAc) to give the product (10 g, 91%). ESI-MS m/z calcd for [C$_{28}$H$_{30}$O$_6$] [M+NH$_4$]$^+$: 480.2; found: 480.2. $^1$H NMR (400 MHz, CDCl$_3$) δ 7.38-7.17 (m, 15H), 5.01 (d, J=4.1 Hz, 1H), 4.80 (d, J=12.4 Hz, 1H), 4.64 (d, J=4.1 Hz, 1H), 4.58-4.44 (m, 3H), 4.41 (d, J=11.7 Hz, 1H), 4.30 (d, J=11.7 Hz, 1H), 4.15 (td, J=6.3, 1.6 Hz, 1H), 3.88 (d, J=1.7 Hz, 1H), 3.69 (dd, J=6.3, 1.2 Hz, 2H), 3.38 (s, 3H).

Methyl 2,4,6-tri-O-benzyl-3-C-cyano-α-D-gulopyranoside

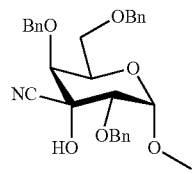

To a cooled (0° C.) solution of methyl 2,4,6-tri-O-benzyl-α-D-xylo-hex-3-ulopyranoside (1.29 g, 2.8 mmol) and trimethylsilyl cyanide (1.29 g, 13.0 mmol) in DCM (20 mL) AlCl$_3$ (1.15 g, 8.65 mmol) was added and the mixture was stirred 3 h at rt. NH$_4$Cl (aq, 100 mL) was added and the mixture was extracted with DCM. The organic phase was dried over Na$_2$SO$_4$, concentrated and purified by chromatography (SiO$_2$, PE/EtOAc) to give the product (1.5 g, 71%). ESI-MS m/z calcd for [C$_{29}$H$_{31}$NO$_6$] [M+NH$_4$]$^+$: 507.2; found: 507.2. $^1$H NMR (400 MHz, CDCl$_3$) δ 7.44-7.26 (m, 15H), 4.97 (d, J=10.5 Hz, 1H), 4.88 (d, J=11.8 Hz, 1H), 4.73 (d, J=11.9 Hz, 1H), 4.63 (d, J=3.8 Hz, 1H), 4.56 (d, J=10.5 Hz, 1H), 4.52 (d, J=11.9 Hz, 1H), 4.43 (d, J=11.9 Hz, 1H), 4.34 (s, 1H), 4.24 (t, J=6.7 Hz, 1H), 3.98 (d, J=3.8 Hz, 1H), 3.91 (s, 1H), 3.59-3.41 (m, 2H), 3.34 (s, 3H).

Methyl 2,4,6-tri-O-benzyl-3-C-cyano-3-O-phenoxythiocarbonyl-α-D-gulopyranoside

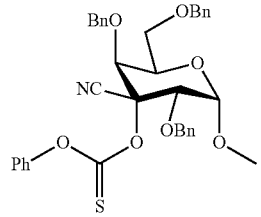

To a cooled (0° C.) solution of methyl 2,4,6-tri-O-benzyl-3-C-cyano-α-D-gulopyranoside (2.05 g, 4.19 mmol), Et$_3$N (424 mg, 4.19 mmol) and 4-(dimethylamino)pyridine (153 mg, 1.26 mmol) in MeCN (25 mL) 0-phenyl chloromethanethioate (1084 mg, 6.28 mmol) was added and the mixture was stirred overnight at rt. The mixture was concentrated and purified by chromatography (SiO$_2$, PE/EtOAc) to give the product (1.7 g, 65%). ESI-MS m/z calcd for [C$_{36}$H$_{35}$NO$_7$S] [M+H]$^+$: 626.2; found: 626.2. $^1$H NMR (400 MHz, CDCl$_3$) δ 7.54-7.22 (m, 18H), 7.20-7.06 (m, 2H), 5.08 (d, J=11.0 Hz, 1H), 5.01 (s, 1H), 4.97 (d, J=12.1 Hz, 1H), 4.84 (d, J=12.1 Hz, 1H), 4.66 (d, J=11.0 Hz, 1H), 4.53 (d, J=4.2 Hz, 1H), 4.44 (d, J=11.9 Hz, 1H), 4.34 (d, J=11.9 Hz, 1H), 4.23 (d, J=4.2 Hz, 1H), 4.16-4.05 (m, 1H), 3.43 (dd, J=9.5, 6.2 Hz, 1H), 3.38 (s, 3H), 3.29 (dd, J=9.5, 6.8 Hz, 1H).

Methyl 2,4,6-tri-O-benzyl-3-C-cyano-3-deoxy-α-D-galactopyranoside

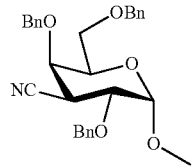

A solution of methyl 2,4,6-tri-O-benzyl-3-C-cyano-3-O-phenoxythiocarbonyl-α-D-gulopyranoside (1.7 g, 2.72 mmol), tris(trimethylsilyl)silane (1351 mg, 5.43 mmol) and 2,2'-azobis(2-methylpropionitrile) (446 mg, 2.72 mmol) in toluene (10 mL) was stirred 2 h at 100° C. under a nitrogen atmosphere. The mixture was concentrated and purified by chromatography (SiO$_2$, PE/EtOAc) to give the product (610 mg, 47%). ESI-MS m/z calcd for [C$_{29}$H$_{31}$NO$_5$] [M+NH$_4$]$^+$: 491.2; found: 491.3. $^1$H NMR (400 MHz, CDCl$_3$) δ 7.44-7.26 (m, 15H), 4.96 (d, J=10.8 Hz, 1H), 4.81 (d, J=12.0 Hz, 1H), 4.66 (d, J=11.6 Hz, 1H), 4.61-4.57 (m, 2H), 4.49 (d, J=11.6 Hz, 1H), 4.42 (d, J=12.0 Hz, 1H), 4.07-4.02 (m, 2H), 3.85 (t, J=6.4 Hz, 1H), 3.55-3.44 (m, 2H), 3.35 (s, 3H), 3.26 (dd, J=11.2, 2.4 Hz, 1H).

127

Methyl 2,4,6-tri-O-benzyl-3-C-carbamoyl-3-deoxy-α-D-galactopyranoside

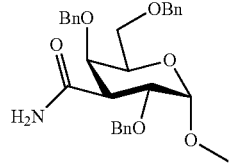

To a solution of methyl 2,4,6-tri-O-benzyl-3-C-cyano-3-deoxy-α-D-galactopyranoside (630 mg, 1.33 mmol) in DMSO (25 mL) $K_2CO_3$ (96 mg, 0.7 mmol) was added and the mixture was cooled to 0° C. Hydrogen peroxide (4 mL, 30 wt. % in $H_2O$) was added and the mixture was stirred 1 h at 30° C. The mixture was poured into water (150 mL) and the precipitate was collected and dissolved in EtOAc (100 mL). The mixture was washed with brine (80 mL), dried over $Na_2SO_4$ and concentrated to afford the product (500 mg, 77%). ESI-MS m/z calcd for $[C_{29}H_{33}NO_6]$ $[M+H]^+$: 492.2; found: 492.2. $^1H$ NMR (400 MHz, $CDCl_3$) δ 7.42-7.17 (m, 15H), 6.60 (s, 1H), 5.31 (s, 1H), 4.84 (d, J=3.2 Hz, 1H), 4.75 (d, J=11.1 Hz, 1H), 4.69 (d, J=11.5 Hz, 1H), 4.61 (d, J=11.5 Hz, 1H), 4.54 (d, J=11.8 Hz, 1H), 4.51-4.42 (m, 2H), 4.36 (s, 1H), 4.21 (dd, J=11.5, 3.3 Hz, 1H), 3.98 (t, J=6.5 Hz, 1H), 3.67-3.51 (m, 2H), 3.40 (s, 3H), 2.96 (dd, J=11.5, 2.5 Hz, 1H).

Methyl 2,4,6-tri-O-benzyl-3-deoxy-3-[4-(3,4,5-trifluorophenyl)-oxazol-2-yl]-α-D-galactopyranoside

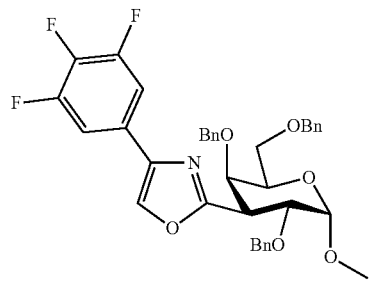

To a solution of methyl 2,4,6-tri-O-benzyl-3-C-carbamoyl-3-deoxy-α-D-galactopyranoside (110 mg, 0.22 mmol) in EtOAc (25 mL) silver trifluoromethanesulfonate (115 mg, 0.45 mmol) and 2-bromo-1-(3,4,5-trifluorophenyl)ethanone (113 mg, 0.45 mmol) were added and the mixture was stirred 16 h at 60° C. in the dark. The mixture was concentrated and purified by chromatography ($SiO_2$, PE/EtOAc) to give the product (60 mg, 42%). ESI-MS m/z calcd for $[C_{37}H_{34}F_3NO_6]$ $[M+H]^+$: 646.2; found: 646.2.

128

Methyl 2,4,6-tri-O-acetyl-3-deoxy-3-[4-(3,4,5-trifluorophenyl)-oxazol-2-yl]-α-D-galactopyranoside

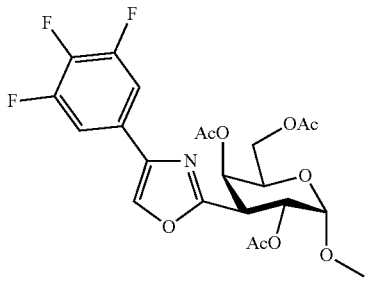

To a solution of methyl 2,4,6-tri-O-benzyl-3-deoxy-3-[4-(3,4,5-trifluorophenyl)-oxazol-2-yl]-α-D-galactopyranoside (1.00 g, 1.55 mmol) in MeOH (50 mL) Pd/C (5% Pd, 200 mg) was added and the mixture was stirred 48 h under a $H_2$ pressure at rt. The mixture was filtered, and the filtrate was concentrated. The residue was dissolved in pyridine (5 mL) and acetic anhydride (2 mL) was added. The mixture was stirred overnight at rt. The mixture was poured into water (100 mL) and extracted with EtOAc (2×100 mL). The organic layers were washed with water (50 mL), HCl (50 mL, 1M) and brine (50 mL), dried over $Na_2SO_4$, concentrated and purified by column chromatography (PE/EA=10/1~1/1, Silica-CS 4 g, 10 mL/min, silica gel, UV 254) to give the product (590 mg, 76%). ESI-MS m/z calcd for $[C_{22}H_{22}F_3NO_9]$ $[M+H]^+$: 502.1; found: 502.2. $^1H$ NMR (400 MHz, Chloroform-d) δ 7.81 (s, 1H), 7.32-7.27 (m, 2H), 5.62 (dd, J=12.0, 3.2 Hz, 1H), 5.50-5.46 (m, 1H), 5.08 (d, J=3.2 Hz, 1H), 4.31-4.23 (m, 1H), 4.21-4.04 (m, 2H), 3.87 (dd, J=12.0, 2.8 Hz, 1H), 3.48 (s, 3H), 2.06 (s, 3H), 2.00 (s, 3H), 1.97 (s, 3H).

Acetyl 2,4,6-tri-O-acetyl-3-deoxy-3-[4-(3,4,5-trifluorophenyl)-oxazol-2-yl]-α-D-galactopyranoside

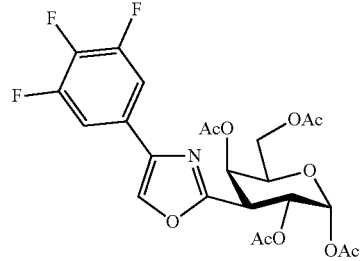

To a solution of methyl 2,4,6-tri-O-acetyl-3-deoxy-3-[4-(3,4,5-trifluorophenyl)-oxazol-2-yl]-α-D-galactopyranoside (560 mg, 1.12 mmol) in acetic anhydride (4 mL) and acetic acid (2 mL) $H_2SO_4$ (98.0%, 112 mg, 1.12 mmol) was added and the mixture was stirred overnight at rt. The mixture was poured into saturated aq $NaHCO_3$ (100 mL) and extracted with EtOAc (2×100 mL). The organic layers were washed with water (50 mL), brine (50 mL), dried over $Na_2SO_4$, concentrated and purified by column chromatography (PE/EA=10/1~1/1, Silica-CS 12 g, 20 mL/min, silica gel, UV 254) to give the product (400 mg, 68%). ESI-MS m/z calcd for $[C_{23}H_{22}F_3NO_{10}]$ $[M+H]^+$: 530.1; found: 530.2. $^1H$ NMR (400 MHz, Chloroform-d) δ 7.83 (s, 1H), 7.33-7.27 (m, 2H), 6.47 (d, J=3.2 Hz, 1H), 5.79 (dd, J=12.0, 3.2 Hz, 1H), 5.57-5.52 (m, 1H), 4.45-4.37 (m, 1H), 4.19-4.05 (m, 2H), 3.91-3.79 (m, 1H), 2.20 (s, 3H), 2.05 (s, 3H), 2.03 (s, 3H), 1.91 (s, 3H).

3,4-Dichlorophenyl 2,4-di-O-acetyl-3-deoxy-3-[4-(3,4,5-trifluorophenyl)-oxazol-2-yl]-1-thio-α-D-galactopyranoside

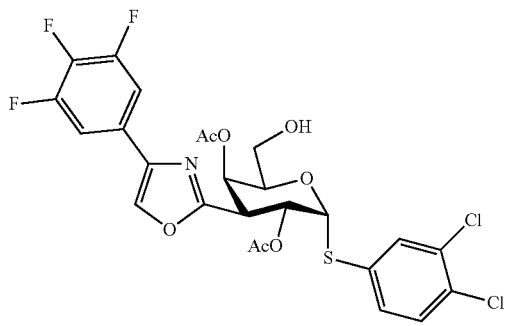

To a solution of acetyl 2,4,6-tri-O-acetyl-3-deoxy-3-[4-(3,4,5-trifluorophenyl)-oxazol-2-yl]-α-D-galactopyranoside (110 mg, 0.21 mmol) in 1,2-dichloroethane (10.0 mL) 3,4-dichlorobenzenethiol (446 mg, 2.49 mmol) and boron trifluoride diethyl etherate (0.256 mL, 2.08 mmol) were added and the mixture was stirred 16 h at 55° C. The mixture was poured into water (50 mL) and extracted with EtOAc (2×50 mL). The organic layers were washed with water (50 mL), brine (50 mL), dried over Na$_2$SO$_4$, concentrated and purified by column chromatography (PE/EA=10/1~1/1, Silica-CS 4 g, 10 mL/min, silica gel, UV 254) to give the product (40.0 mg, 32%). ESI-MS m/z calcd for [C$_{25}$H$_{20}$Cl$_2$F$_3$NO$_7$S] [M+H]$^+$: 606.0; found: 606.0. $^1$H NMR (400 MHz, Chloroform-d) δ 7.89 (s, 1H), 7.70-7.69 (m, 1H), 7.41-7.29 (m, 4H), 5.86 (d, J=5.2 Hz, 1H), 5.67-5.62 (m, 1H), 4.97-4.88 (m, 1H), 4.77-4.70 (m, 1H), 4.18-4.11 (m, 1H), 4.11-4.02 (m, 1H), 3.54 (dd, J=11.2, 2.8 Hz, 1H), 2.02 (s, 3H), 1.97 (s, 3H).

Intermediate 40

Methyl 2,4,6-tri-O-benzyl-3-C-carbamothioyl-3-deoxy-α-D-galactopyranoside

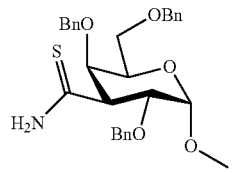

To a solution of methyl 2,4,6-tri-O-benzyl-3-C-carbamoyl-3-deoxy-α-D-galactopyranoside (1.00 g, 2.03 mmol) in THF (20.0 mL) Lawesson's reagent (823 mg, 2.03 mmol) was added and the mixture was stirred 2 h under reflux. The mixture was concentrated and purified by reversed-phase chromatography (MeCN/H$_2$O=1/20~3/1, C-18 column, 20 mL/min, UV 254) to give the product (600 mg, 58%). ESI-MS m/z calcd for [C$_{29}$H$_{33}$NO$_5$S] [M+H]$^+$: 508.2; found: 508.2. $^1$H NMR (400 MHz, Chloroform-d) δ 7.41-7.07 (m, 15H), 4.79 (d, J=3.2 Hz, 1H), 4.58 (dd, J=11.6, 2.8 Hz, 2H), 4.52-4.32 (m, 5H), 4.06-3.95 (m, 2H), 3.56-3.42 (m, 3H), 3.32 (s, 3H).

Methyl 2,4,6-tri-O-benzyl-3-deoxy-3-[4-(3,4,5-trifluorophenyl)-thiazol-2-yl]-α-D-galactopyranoside

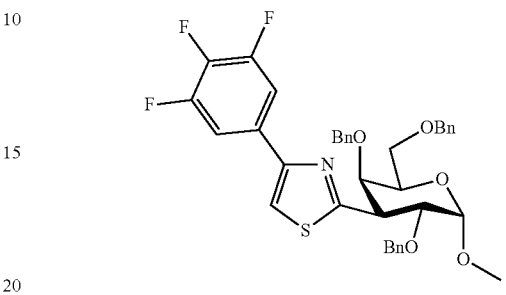

To a solution of methyl 2,4,6-tri-O-benzyl-3-C-carbamothioyl-3-deoxy-α-D-galactopyranoside (600 mg, 1.18 mmol) in EtOH (20.0 mL) 2-bromo-1-(3,4,5-trifluorophenyl)ethanone (598 mg, 2.36 mmol) was added and the mixture was refluxed 2 h. The mixture was concentrated and purified by column chromatography (PE/EA=10/1~5/1, Silica-CS 20 g, 20 mL/min, silica gel, UV 254) to give the product (670 mg, 86%). ESI-MS m/z calcd for [C$_{37}$H$_{34}$F$_3$NO$_5$S] [M+H]$^+$: 662.2; found: 662.2. $^1$H NMR (400 MHz, Chloroform-d) δ 7.50-7.38 (m, 2H), 7.34-7.08 (m, 14H), 7.01-6.94 (m, 2H), 4.70 (d, J=3.2 Hz, 1H), 4.58 (d, J=11.6 Hz, 1H), 4.53-4.45 (m, 2H), 4.40 (d, J=11.6 Hz, 1H), 4.30-4.01 (m, 5H), 3.86 (dd, J=11.6, 2.8 Hz, 1H), 3.59-3.46 (m, 2H), 3.34 (s, 3H).

Methyl 2,4,6-tri-O-acetyl-3-deoxy-3-[4-(3,4,5-trifluorophenyl)-thiazol-2-yl]-α-D-galactopyranoside

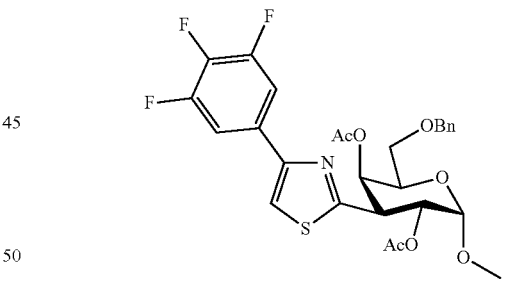

To a solution of methyl 2,4,6-tri-O-benzyl-3-deoxy-3-[4-(3,4,5-trifluorophenyl)-thiazol-2-yl]-α-D-galactopyranoside (450 mg, 0.68 mmol) in DCM (25 mL) trichloroborane (1 M in DCM, 10.2 mL) was added at −70° C. The mixture was slowly warmed to rt. After 2 hours, MeOH (5 mL) was added and the mixture was concentrated. The residue was dissolved in pyridine (3 mL) and acetic anhydride (1.5 mL) was added and the mixture was stirred overnight at rt. The mixture was poured into water (100 mL) and extracted with EtOAc (2×100 mL). The organic layers were washed with water (50 mL), HCl (1 M, 50 mL), brine (50 mL), dried over Na$_2$SO$_4$, concentrated and purified by column chromatography (PE/EA=10/1~1/1, Silica-CS 4 g, 10 mL/min, silica gel, UV 254) to afford the product (160 mg, 46%). ESI-MS m/z calcd for [C$_{22}$H$_{22}$F$_3$NO$_8$S] [M+H]$^+$: 518.1; found:

518.2. ¹H NMR (400 MHz, Chloroform-d) δ 7.50-7.36 (m, 2H), 7.33 (s, 1H), 5.60-5.46 (m, 2H), 5.00 (d, J=3.2 Hz, 1H), 4.27-4.20 (m, 1H), 4.13-3.97 (m, 3H), 3.42 (s, 3H), 2.00 (s, 3H), 1.92 (s, 3H), 1.89 (s, 3H).

Acetyl 2,4,6-tri-O-acetyl-3-deoxy-3-[4-(3,4,5-trifluorophenyl)-thiazol-2-yl]-α-D-galactopyranoside

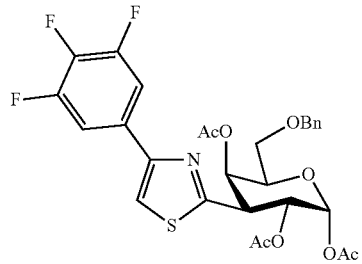

To a solution of methyl 2,4,6-tri-O-acetyl-3-deoxy-3-[4-(3,4,5-trifluorophenyl)-thiazol-2-yl]-α-D-galactopyranoside (160 mg, 0.31 mmol) in acetic anhydride (3 mL) and acetic acid (1 mL) H$_2$SO$_4$ (98.0%, 61.8 mg, 0.62 mmol) was added and the mixture was stirred overnight at rt. The mixture was poured into saturated aq NaHCO$_3$ (100 mL) and extracted with EtOAc (2×100 mL). The organic layers were washed with water (50 mL), brine (50 mL), dried over Na$_2$SO$_4$, concentrated and purified by column chromatography (PE/EA=10/1~1/1, Silica-CS 12 g, 20 mL/min, silica gel, UV 254) to give the product (100 mg, 59%). ESI-MS m/z calcd for [C$_{23}$H$_{22}$F$_3$NO$_9$S] [M+H]⁺: 546.1; found: 546.1. ¹H NMR (400 MHz, Chloroform-d) δ 7.57-7.42 (m, 2H), 7.40 (s, 1H), 6.46 (d, J=3.2 Hz, 1H), 5.77 (dd, J=12.0, 3.4 Hz, 1H), 5.66-5.62 (m, 1H), 4.47-4.43 (m, 1H), 4.22-4.12 (m, 1H), 4.11-4.01 (m, 2H), 2.21 (s, 3H), 2.06 (s, 3H), 2.02 (s, 3H), 1.91 (s, 3H).

3,4-Dichlorophenyl 2,4-di-O-acetyl-3-deoxy-3-[4-(3,4,5-trifluorophenyl)-thiazol-2-yl]-1-thio-α-D-galactopyranoside

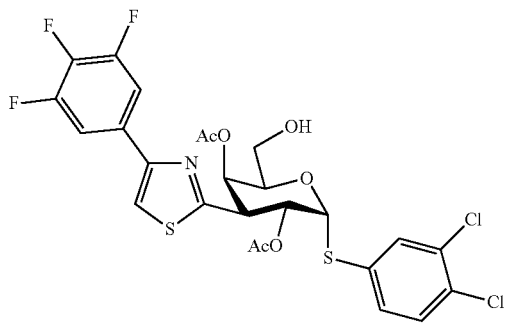

To a solution of acetyl 2,4,6-tri-O-acetyl-3-deoxy-3-[4-(3,4,5-trifluorophenyl)-thiazol-2-yl]-α-D-galactopyranoside (100 mg, 0.18 mmol) in 1,2-dichloroethane (10.0 mL) 3,4-dichlorobenzenethiol (263 mg, 1.47 mmol) and boron trifluoride diethyl etherate (0.226 mL, 1.83 mmol) were added and the mixture was stirred 16 h at 55° C. The mixture was poured into water (50 mL) and extracted with EtOAc (2×50 mL). The organic layers were washed with water (50 mL), brine (50 mL), dried over Na$_2$SO$_4$, concentrated and purified by column chromatography (PE/EA=10/1~1/1, Silica-CS 4 g, 10 mL/min, silica gel, UV 254) to give the product (20 mg, 12%). ESI-MS m/z calcd for [C$_{25}$H$_{20}$Cl$_2$F$_3$NO$_6$S$_2$] [M+H]⁺: 622.0; found: 622.0. ¹H NMR (400 MHz, Chloroform-d) δ 7.72-7.69 (m, 1H), 7.49-7.45 (m, 2H), 7.42-7.37 (m, 3H), 5.87 (d, J=5.2 Hz, 1H), 5.69-5.64 (m, 1H), 4.97-4.88 (m, 1H), 4.81-4.76 (m, 1H), 4.23-4.11 (m, 2H), 3.70 (dd, J=11.2, 2.8 Hz, 1H), 2.03 (s, 3H), 1.98 (s, 3H).

Intermediate 41

Methyl 2,4,6-tri-O-benzyl-3-C-carboxy-3-deoxy-α-D-galactopyranoside

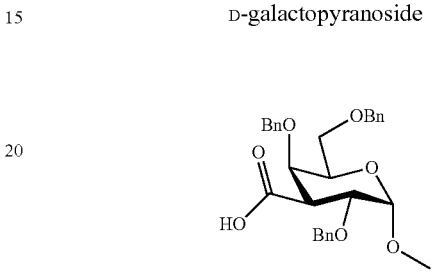

To a cooled (0° C.) solution of methyl 2,4,6-tri-O-benzyl-3-C-carbamoyl-3-deoxy-α-D-galactopyranoside (1.20 g, 2.44 mmol) in dioxane (18 mL) concentrated hydrochloric acid (2.03 mL, 2.44 mmol) was added dropwise, followed by portionwise addition of solid sodium nitrite (1.68 g, 2.44 mmol). The mixture was stirred 3 h at rt before being poured into ice/water (30 mL) and extracted with DCM (2×20 mL). The combined organic layers were dried over MgSO$_4$ and evaporated to give the product (1.10 g, 92%). ESI-MS m/z calcd for [C$_{29}$H$_{32}$O$_7$] [M+NH$_4$]⁺: 510.2; found: 510.4. ¹H NMR (400 MHz, Chloroform-d) δ 7.28-7.13 (m, 15H), 4.67 (d, J=11.6 Hz, 1H), 4.56-4.33 (m, 6H), 4.14-4.11 (m, 2H), 3.89 (t, J=6.8 Hz, 1H), 3.50-3.40 (m, 2H), 3.26 (s, 3H), 3.03 (dd, J=11.2, 2.8 Hz, 1H).

Methyl 2,4,6-tri-O-benzyl-3-C-[2-(3,4,5-trifluorophenyl)carbohydrazide]-3-deoxy-α-D-galactopyranoside

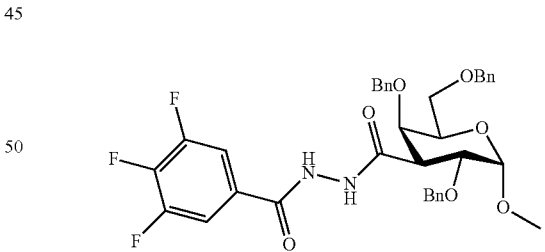

To a solution of methyl 2,4,6-tri-O-benzyl-3-C-carboxy-3-deoxy-α-D-galactopyranoside (1.10 g, 2.23 mmol) in DCM (15 mL) HATU (1.02 g, 2.68 mmol), Et$_3$N (1.25 mL, 8.93 mmol) and 3,4,5-trifluorobenzohydrazide (510 mg, 2.68 mmol) were added and the mixture was stirred 3 h under a nitrogen atmosphere at rt. The mixture was poured into water (20 mL) and extracted with DCM (2×20 mL). The organic layers were washed with water (50 mL), brine (50 mL), dried over Na$_2$SO$_4$, concentrated and purified by column chromatography (PE/EA=1/1~0/1, Silica-CS 20 g, 20 mL/min, silica gel, UV254) to give the product (1.04 g, 63%). ESI-MS m/z calcd for [C$_{36}$H$_{35}$F$_3$N$_2$O$_7$] [M+H]⁺:

665.2; found: 665.3. ¹H NMR (400 MHz, Chloroform-d) δ 9.41 (d, J=5.6 Hz, 1H), 8.57 (d, J=5.6 Hz, 1H), 7.40-7.14 (m, 17H), 4.73-4.59 (m, 4H), 4.48-4.35 (m, 3H), 4.28-4.20 (m, 2H), 3.89 (t, J=6.8 Hz, 1H), 3.54-3.44 (m, 2H), 3.29 (s, 3H), 3.04 (dd, J=11.2, 2.4 Hz, 1H).

Methyl 2,4,6-tri-O-benzyl-3-deoxy-3-[4-(3,4,5-trifluorophenyl)-1,3,4-oxadiazol-2-yl]-α-D-galactopyranoside

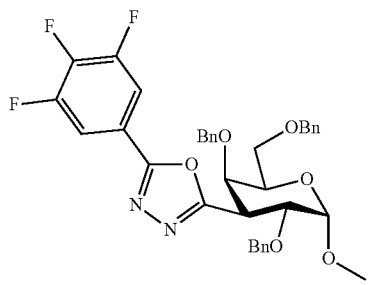

To a solution of methyl 2,4,6-tri-O-benzyl-3-C-[2-(3,4,5-trifluorophenyecarbohydrazide]-3-deoxy-α-D-galactopyranoside (1.04 g, 1.56 mmol) in DMF (10 mL) and THF (1 mL) Burgess Reagent (1.49 g, 6.26 mmol) was added and the mixture was stirred 90 min at 125° C. in a microwave reactor. The mixture was concentrated and purified by column chromatography (PE/EA=2:1, Silica-CS 12 g, 20 mL/min, silica gel, UV 254) to give the product (610 mg, 60%). ESI-MS m/z calcd for [C₃₆H₃₃F₃N₂O₆] [M+H]⁺: 647.2; found: 647.3. ¹H NMR (400 MHz, Chloroform-d) δ 7.37-6.90 (m, 17H), 4.70 (d, J=3.6 Hz, 1H), 4.55-4.27 (m, 6H), 4.06-4.04 (m, 2H), 3.94 (d, J=11.6 Hz, 1H), 3.78 (dd, J=11.6, 2.8 Hz, 1H), 3.58-3.49 (m, 2H), 3.36 (s, 3H).

Methyl 2,4,6-tri-O-acetyl-3-deoxy-3-[4-(3,4,5-trifluorophenyl)-1,3,4-oxadiazol-2-yl]-α-D-galactopyranoside

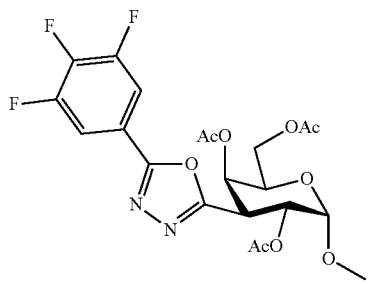

To a solution of methyl 2,4,6-tri-O-benzyl-3-deoxy-3-[4-(3,4,5-trifluorophenyl)-1,3,4-oxadiazol-2-yl]-α-D-galactopyranoside (610 mg, 0.94 mmol) in MeOH (10 mL) Pd/C (5% Pd, 150 mg) was added and the mixture was stirred 48 h under a H₂ pressure at rt. The mixture was filtered, and the filtrate was concentrated. The residue was dissolved in pyridine (5 mL) and acetic anhydride (2 mL) was added and the mixture was stirred overnight at rt. The mixture was poured into water (10 mL) and extracted with EtOAc (2×100 mL). The organic layers were washed with water (20 mL), HCl (20 mL, 1M) and brine (20 mL), dried over Na₂SO₄, concentrated and purified by column chromatography (PE/EA=10/1~1/1, Silica-CS 4 g, 10 mL/min, silica gel, UV 254) to give the product (320 mg, 68%). ESI-MS m/z calcd for [C₂₁H₂₁F₃N₂O₉] [M+NH₄]⁺: 520.1; found: 520.1. ¹H NMR (400 MHz, Chloroform-d) δ 7.66 (t, J=7.2 Hz, 2H), 5.64 (dd, J=12.0, 3.6 Hz, 1H), 5.48 (s, 1H), 5.11 (d, J=3.2 Hz, 1H), 4.31-4.28 (m, 1H), 4.18-4.09 (m, 2H), 4.01 (dd, J=11.6, 2.8 Hz, 1H), 3.49 (s, 3H), 2.07 (s, 3H), 2.04 (s, 3H), 1.99 (s, 3H).

Acetyl 2,4,6-tri-O-acetyl-3-deoxy-3-[4-(3,4,5-trifluorophenyl)-1,3,4-oxadiazol-2-yl]-α-D-galactopyranoside

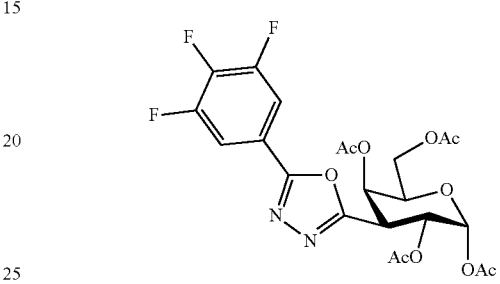

To a solution of methyl 2,4,6-tri-O-acetyl-3-deoxy-3-[4-(3,4,5-trifluorophenyl)-1,3,4-oxadiazol-2-yl]-α-D-galactopyranoside (320 mg, 0.64 mmol) in acetic anhydride (2.5 mL) and acetic acid (1 mL) H₂SO₄ (98.0%, 63.7 mg, 0.64 mmol) was added and the mixture was stirred overnight at rt. The mixture was poured into saturated aq NaHCO₃ (30 mL) and extracted with EtOAc (2×30 mL). The organic layers were washed with water (50 mL), brine (50 mL), dried over Na₂SO₄, concentrated and purified by column chromatography (PE/EA=10/1~3/1, Silica-CS 12 g, 20 mL/min, silica gel, UV 254) to give the product (230 mg, 68%). ESI-MS m/z calcd for [C₂₂H₂₁F₃N₂O₁₀] [M+H]⁺: 531.1; found: 531.1. ¹H NMR (400 MHz, Chloroform-d) δ 7.68-7.65 (m, 2H), 6.49 (d, J=3.2 Hz, 1H), 5.81 (dd, J=12.4, 3.6 Hz, 1H), 5.55 (s, 1H), 4.46-4.42 (m, 1H), 4.18-4.08 (m, 2H), 4.01 (dd, J=12.0, 2.4 Hz, 1H), 2.20 (s, 3H), 2.06 (s, 3H), 2.05 (s, 3H), 1.94 (s, 3H).

3,4-Dichlorophenyl 2,4-di-O-acetyl-3-deoxy-3-[4-(3,4,5-trifluorophenyl)-1,3,4-oxadiazol-2-yl]-1-thio-D-galactopyranoside

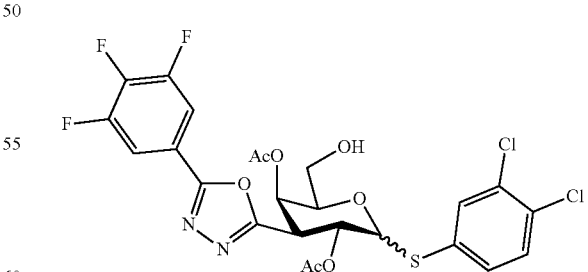

To a cooled (0° C.) solution of acetyl 2,4,6-tri-O-acetyl-3-deoxy-3-[4-(3,4,5-trifluorophenyl)-1,3,4-oxadiazol-2-yl]-α-D-galactopyranoside (110 mg, 0.21 mmol) and 3,4-dichlorobenzenethiol (186 mg, 1.04 mmol) in 1,2-dichloroethane (5.0 mL) boron trifluoride diethyl etherate (0.256 mL, 2.07 mmol) was added and the mixture was stirred 16 h at 50° C.

The mixture was poured into water (20 mL) and extracted with EtOAc (2×20 mL). The organic layers were washed with water (20 mL), brine (20 mL), dried over Na$_2$SO$_4$, concentrated and purified by column chromatography (PE/EA=10/1~1/1, Silica-CS 4 g, 10 mL/min, silica gel, UV 254) to give the product (19 mg, 15%). ESI-MS m/z calcd for [C$_{24}$H$_{19}$Cl$_2$F$_3$N$_2$O$_7$S] [M+H]$^+$: 607.0; found: 607.0.

Intermediate 42

2-(2-Benzyloxythiazol-4-yl)-4,4,5,5-tetramethyl-1,3,2-dioxaborolane

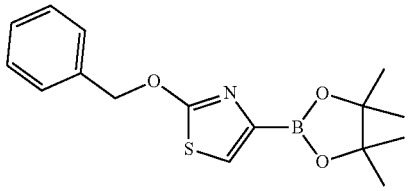 [SMILES: CC1(C)OB(c2csc(OCc3ccccc3)n2)OC1(C)C]

2-Benzyloxy-4-bromothiazole (1.00 g, 3.7 mmol), potassium acetate (1.1 g, 11.1 mmol) and bis(pinacolato)diboron (1.92 g, 7.4 mmol) were suspended in dioxane (10 mL), degassed with nitrogen, and (2-dicyclohexylphosphino-2',4',6'-triisopropyl-1,1'-biphenyl)[2-(2'-amino-1,1'-biphenyl)]palladium(II) methanesulfonate (156 mg, 0.19 mmol) and potassium tert-butoxide (21 mg, 0.19 mmol) were added. The mixture was stirred 10 h at 80° C. and was then partitioned between EtOAc and brine. The organic phase was dried, evaporated and purified by chromatography (SiO$_2$, PE/EtOAc) to give the product (1.00 g, 85%). $^1$H NMR (500 MHz, Chloroform-d) δ 7.46-7.33 (m, 6H), 5.54 (s, 2H), 1.36 (s, 12H).

3,4-Dichlorophenyl 3-deoxy-3-(4-iodo-1H-1,2-pyrazol-1-yl)-1-thio-α-D-galactopyranoside

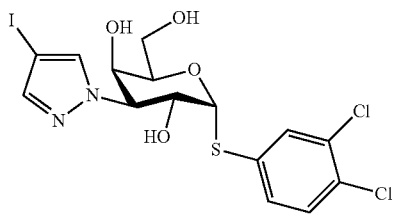

A solution of 2,4,6-tri-O-acetyl-3-deoxy-3-(4-iodo-1H-1,2-pyrazol-1-yl)-β-D-galactopyranosyl chloride (3.17 g, 4.00 mmol), 3,4-dichlorobenzenethiol (0.64 mL, 4.8 mmol) and Cs$_2$CO$_3$ (1.63 g, 5.00 mmol) in DMF (25 mL) was stirred 20 h at rt. The mixture was partitioned between EtOAc and brine, and the organic phase was dried, concentrated and purified by chromatography (SiO$_2$, PE/EtOAc). The obtained material was stirred 3 h at rt in MeOH (30 mL) and NaOMe (2.0 mL, 1 M). The mixture was neutralized with dowex, filtered, evaporated and purified by chromatography (SiO$_2$, PE/EtOAc) to yield the product (1.31 g, 63%). ESI-MS m/z calcd for [C$_{15}$H$_{15}$Cl$_2$IN$_2$O$_4$S] [M+H]+: 516.9; found: 516.9. $^1$H NMR (400 MHz, Methanol-d$_4$) δ 7.86 (s, 1H), 7.77 (d, J=2.0 Hz, 1H), 7.56 (s, 1H), 7.51 (dd, J=8.4, 2.0 Hz, 1H), 7.46 (d, J=8.4 Hz, 1H), 5.79 (d, J=5.4 Hz, 1H), 4.78 (dd, J=11.4, 5.4 Hz, 1H), 4.55 (dd, J=11.4, 2.8 Hz, 1H), 4.40 (t, J=6.1 Hz, 1H), 4.13 (d, J=1.9 Hz, 1H), 3.73-3.63 (m, 2H).

3,4-Dichlorophenyl 3-deoxy-3-(4-iodo-1H-1,2-pyrazol-1-yl)-2-O-methyl-1-thio-α-D-galactopyranoside

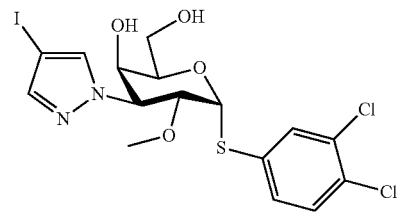

To a solution of 3,4-dichlorophenyl 3-deoxy-3-(4-iodo-1H-1,2-pyrazol-1-yl)-1-thio-α-D-galactopyranoside (1.313 g, 2.5 mmol) in MeCN (30 mL) benzaldehyde dimethylacetal (0.57 mL, 3.75 mmol) and p-toluenesulfonic acid monohydrate (50 mg, 0.26 mmol) were added and the mixture was stirred 1 h at rt. Et$_3$N (0.5 mL) was added followed by water (5 mL) and the mixture was stirred 15 min at rt. The formed precipitate was isolated by filtration, washed with PE, then washed with 33% aq MeOH and dried. The obtained material was dissolved in DMF (10 mL) and NaH (60% in oil, 155 mg, 3.86 mmol) followed by iodomethane (0.24 mL, 3.86 mmol) were added. After stirring 1 h at rt MeOH (20 mL) and water (5 mL) were added. The precipitate was isolated by filtration, washed with 50% aq MeOH, and dried. The obtained material was stirred 30 min at rt in 80% aq TFA (15 mL) and was then partitioned between EtOAc and water. The organic phase was washed NaOH (5 M, 40 mL), dried, and evaporated to obtain a white solid that was triturated in PE to give the product (828 mg, 61%). ESI-MS m/z calcd for [C$_{16}$H$_{17}$Cl$_2$IN$_2$O$_4$S] [M+H]$^+$: 530.9; found: 530.9. $^1$H NMR (400 MHz, Methanol-d$_4$) δ 7.87 (s, 1H), 7.79 (d, J=2.0 Hz, 1H), 7.54 (s, 1H), 7.52 (dd, J=8.4, 2.1 Hz, 1H), 7.47 (d, J=8.4 Hz, 1H), 6.10 (d, J=5.3 Hz, 1H), 4.58 (dd, J=11.2, 2.7 Hz, 1H), 4.45 (dd, J=11.3, 5.3 Hz, 1H), 4.38 (t, J=6.1 Hz, 1H), 4.11 (d, J=2.2 Hz, 1H), 3.70 (dd, J=11.5, 5.6 Hz, 1H), 3.65 (dd, J=11.5, 6.7 Hz, 1H), 3.34 (s, 3H).

Intermediate 43 tert-Butyl N-(4-bromothiazol-2-yl)carbamate

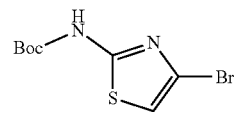

An argon degassed solution of 2,4-dibromothiazole (972 mg, 4.00 mmol), tert-butyl carbamate (515 mg, 4.40 mmol), tris(dibenzylideneacetone)dipalladium(0) (69 mg, 0.12 mmol), 4,5-bis(diphenylphosphino)-9,9-dimethylxanthene (93 mg, 0.16 mmol) and Cs$_2$CO$_3$ (2.61 g, 8.00 mmol) in dioxane (13 mL) was stirred 24 h at 85° C. The mixture was cooled to rt, filtered through a plug of celite and concentrated. The residue was purified by chromatography (SiO$_2$, PE/EtOAc) to give the product (113 mg, 8%). $^1$H NMR (500 MHz, Methanol-d$_4$) δ 6.95 (s, 1H), 1.54 (s, 9H).

[2-(tert-Butoxycarbonylamino)thiazol-4-yl]boronic Acid

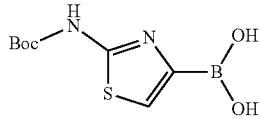 [SMILES: CC(C)(C)OC(=O)Nc1nc(B(O)O)cs1]

To an argon degassed solution of (2-dicyclohexylphosphino-2',4',6'-triisopropyl-1,1'-biphenyl)[2-(2'-amino-1,1'-biphenyl)]palladium(II) methanesulfonate (3.8 mg, 0.0045 mmol) and potassium tert-butoxide (0.5 mg, 0.0045 mmol) in dioxane (0.5 mL) tert-butyl N-(4-bromothiazol-2-yl)carbamate (50 mg, 0.15 mmol), potassium acetate (44 mg, 0.45 mmol) and bis(pinacolato)diboron (76 mg, 0.30 mmol) were added and the mixture was stirred 19.5 h at 80° C. More (2-dicyclohexylphosphino-2',4',6'-triisopropyl-1,1'-biphenyl) [2-(2'-amino-1,1'-biphenyl)]palladium(II) methanesulfonate (1.8 mg, 0.0021 mmol) and potassium tert-butoxide (0.24 mg, 0.0021 mmol) were added and the mixture was stirred 24 h at 80° C. The mixture was cooled to rt, filtered through a plug of celite and evaporated. The residue was added to a plug of silica, washed with EtOAc and eluted with MeOH/AcOH (20:1) to give the product (20 mg, 55%). $^1$H NMR (500 MHz, Methanol-$d_4$) δ 6.75 (s, 1H), 1.55 (s, 9H).

Intermediate 44

5-Chloro-2-cyanophenyl 2,4,6-tri-O-acetyl-3-deoxy-3-(4-iodo-1H-1,2-pyrazol-1-yl)-1-thio-α-D-galactopyranoside

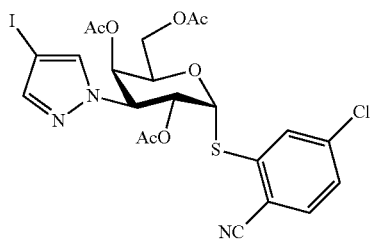

A solution of 2,4,6-tri-O-acetyl-3-deoxy-3-(4-iodo-1H-1,2-pyrazol-1-yl)-β-D-galactopyranosyl chloride (2.83 g, 3.56 mmol), 4-chloro-2-sulfanylbenzonitrile (950 mg, 3.92 mmol) and Cs$_2$CO$_3$ (1.74 g, 5.34 mmol) in DMF (9.0 mL) was stirred 16 h at rt. The mixture was partitioned between EtOAc and brine, and the organic phase was dried, concentrated and purified by chromatography (SiO$_2$, PE/EtOAc) to yield the product (686 mg, 30%). ESI-MS m/z calcd for [C$_{22}$H$_{21}$ClIN$_3$O$_7$S] [M+H]$^+$: 634.0; found: 634.0. $^1$H NMR (500 MHz, Methanol-$d_4$) δ 7.72 (d, J=2.0 Hz, 1H), 7.63 (d, J=8.3 Hz, 1H), 7.52 (s, 1H), 7.47 (s, 1H), 7.41 (dd, J=8.3, 2.0 Hz, 1H), 6.18 (d, J=5.6 Hz, 1H), 5.99 (dd, J=11.8, 5.6 Hz, 1H), 5.55-5.53 (m, 1H), 4.88 (dd, J=11.8, 3.1 Hz, 1H), 4.79 (t, J=6.6 Hz, 1H), 4.16-4.05 (m, 2H), 2.04 (s, 3H), 2.03 (s, 3H), 2.01 (s, 3H).

5-Chloro-2-cyanophenyl 4,6-O-benzylidene-3-deoxy-3-(4-iodo-1H-1,2-pyrazol-1-yl)-2-O-methyl-1-thio-α-D-galactopyranoside

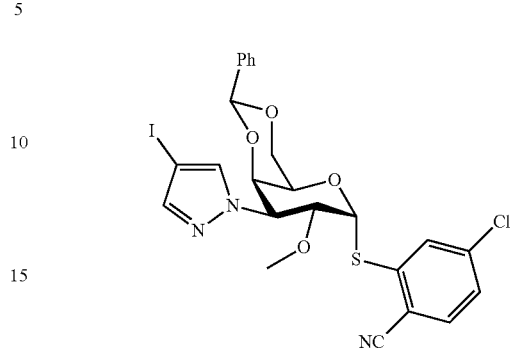

A solution of 5-chloro-2-cyanophenyl 2,4,6-tri-O-acetyl-3-deoxy-3-(4-iodo-1H-1,2-pyrazol-1-yl)-1-thio-α-D-galactopyranoside (686 mg, 1.08 mmol) in MeOH (25 mL) and NaOMe (2.0 mL, 1 M) was stirred 2 h at rt. The mixture was neutralized with dowex, filtered and evaporated. Water was added and the precipitate was isolated by filtration, washed with 33% aq MeOH and dried. The obtained material was dissolved in MeCN (8 mL) and benzaldehyde dimethylacetal (0.17 mL, 1.1 mmol) and p-toluenesulfonic acid monohydrate (50 mg, 0.26 mmol) were added. The mixture was stirred 16 h at rt before Et$_3$N (70 µL) was added followed by water (3 mL). The formed precipitate was isolated by filtration, washed with 33% aq MeOH and dried. The obtained material was stirred in DMF (2.0 mL) and NaH (60% in oil, 50 mg, 1.25 mmol) followed by iodomethane (60 µL, 0.93 mmol) were added. After stirring 3 h at rt the mixture was poured onto ice and HCl (1 M). The precipitate was isolated by filtration, washed with 33% aq MeOH, dried and purified by chromatography (SiO$_2$, PE/EtOAc) to give the product (63 mg, 17%). ESI-MS m/z calcd for [C$_{24}$H$_{21}$ClN$_3$O$_4$S] [M+H]$^+$: 610.0; found: 610.0. $^1$H NMR (500 MHz, Methanol-$d_4$) δ 7.74 (d, J=1.9 Hz, 1H), 7.69 (s, 1H), 7.63 (d, J=8.3 Hz, 1H), 7.58 (s, 1H), 7.46-7.34 (m, 6H), 6.19 (d, J=5.2 Hz, 1H), 5.53 (s, 1H), 4.92 (dd, J=11.3, 3.1 Hz, 1H), 4.50 (dd, J=11.3, 5.2 Hz, 1H), 4.46 (d, J=2.5 Hz, 1H), 4.35 (s, 1H), 4.24 (dd, J=12.8, 1.5 Hz, 1H), 4.13 (dd, J=12.8, 1.7 Hz, 1H), 3.39 (s, 3H).

REFERENCES

Aits S, Kricker J, Liu B, Ellegaard A M, Hämälistö S, Tvingsholm S, Corcelle-Termeau E, Høgh S, Farkas T, Holm Jonassen A, Gromova I, Mortensen M, Jäättelä M. (2015) Sensitive detection of lysosomal membrane permeabilization by lysosomal galectin puncta assay Autophagy. 2015; 11(8):1408-24.

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. Infect. Immun. Vol. 69: 832-837.

Arthur C M, Baruffi M D, Cummings R D, Stowell S R. (2015) Evolving mechanistic insights into galectin functions. Methods Mol Biol. 1207:1-35.

Helen Blanchard, Khuchtumur Bum-Erdene, Mohammad Hussaini Bohari & Xing Yu (2016) Galectin-1 inhibitors and their potential therapeutic applications: a patent review, Expert Opinion on Therapeutic Patents, 26:5, 537-554, DOI: 10.1517/13543776.2016.1163338

Blidner A G, Méndez-Huergo S P, Cagnoni A J, Rabinovich G A. (2015) Re-wiring regulatory cell networks in immunity by galectin-glycan interactions. FEBS Lett. 2015 Sep. 6. pii: S0014-5793(15)00807-8.

Chen, W.-S., Leffler H., Nilsson, U. J., Panjwani, N. (2012). Targeting Galectin-1 and Galectin-3 Attenuates VEGF-A-induced Angiogenesis; Mol. Biol. Cell (suppl), Abstract No. 2695.

Cooper, D. N.; Massa, S. M.; Barondes, S. H. (1991) Endogenous muscle lectin inhibits myoblast adhesion to laminin. The Journal of Cell Biology 115, 1437-1448.

Cumpstey, I., Carlsson, S., Leffler, H. and Nilsson, U. J. (2005) Synthesis of a phenyl thio-ß-D-galactopyranoside library from 1,5-difluoro-2,4-dinitrobenzene: discovery of efficient and selective monosaccharide inhibitors of galectin-7. Org. Biomol. Chem. 3: 1922-1932.

Cumpstey, I., Sundin, A., Leffler, H. and Nilsson, U. J. (2005) $C_2$-Symmetrical thiodigalactoside bis-benzamido derivatives as high-affinity inhibitors of galectin-3: Efficient lectin inhibition through double arginine—arene interactions. Angew. Chem. Int. Ed. 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. Chem. Eur. J. 14: 4233-4245.

Delaine, T., Cumpstey, I., Ingrassia, L., Le Mercier, M., Okechukwu, P., Leffler, H., Kiss, R., and Nilsson, U. J. (2008). Galectin-Inhibitory Thiodigalactoside Ester Derivatives Have Anti-Migratory Effects in Cultured Lung and Prostate Cancer Cells. J Med Chem 51; 8109-8114.

Demotte, N., Wieers, G., van der Smissen, P., Moser, M., Schmidt, C., Thielemans, K., et al., (2010). Cancer Res. 70; 7476-7488.

Dings, R. P. M.; Miller, M. C.; Nesmelova, I.; Astorgues-Xerri, L.; Kumar, N.; Serova, M.; Chen, X.; Raymond, E.; Hoye, T. R.; Mayo, K. H. Journal of medicinal . . . 2012, 55, 5121-5129.

Ebrahim A H, Alalawi Z, Mirandola L, Rakhshanda R, Dahlbeck S, Nguyen D, Jenkins M1, Grizzi F, Cobos E, Figueroa J A, Chiriva-Internati M (2014 Galectins in cancer: carcinogenesis, diagnosis and therapy. Ann Transl Med. 2014 September; 2(9):88.

Elola M T, Blidner A G, Ferragut F, Bracalente C, Rabinovich G A. (2015) Assembly, organization and regulation of cell-surface receptors by lectin-glycan complexes. Biochem J. 2015 Jul. 1; 469(1):1-16.

Farkas, I.; Szabó, I. F.; Bognár, R.; Anderle, D. Carbohydr. Res. 1976, 48, 136-138.

Giguère, D.; Bonin, M.-A.; Cloutier, P.; Patnam, R.; St-Pierre, C.; Sato, S.; Roy, R. Bioorganic & Medicinal Chemistry 2008, 16, 7811-7823.

Giguére, D.; André, S.; Bonin, M.-A.; Bellefleur, M.-A.; Provencal, A.; Cloutier, P.; Pucci, B.; Roy, R.; Gabius, H.-J. Bioorganic & Medicinal Chemistry 2011, 19, 3280-3287.

Giguere, D., Patnam, R., Bellefleur, M.-A., St.-Pierre, C., Sato, S., and Roy, R. (2006). Carbohydrate triazoles and isoxazoles as inhibitors of galectins-1 and -3. Chem Commun: 2379-2381.

Glinsky, G. V., Price, J. E., Glinsky, V. V., Mossine, V. V., Kiriakova, G., and Metcalf, J. B. (1996). Cancer Res 56: 5319-5324.

Glinsky, V. V., Kiriakova, G., Glinskii, O. V., Mossine, V. V., Mawhinney, T. P., Turk, J. R., Glinskii, A. B., Huxley, V. H., Price, J. E., and Glinsky, G. V. (2009). Synthetic Galectin-3 Inhibitor Increases Metastatic Cancer Cell Sensitivity to Taxol-Induced Apoptosis In Vitro and In Vivo. Neoplasia 11; 901-909.

van Hattum, H.; Branderhorst, H. M.; Moret, E. E.; Nilsson, U. J.; Leffler, H.; Pieters, R. J. J. Med. Chem. 2013, 56, 1350-1354. Huflejt, M. E. and Leffler, H. (2004) Galectin-4 in normal tissues and cancer. Glycoconj. J. 20: 247-255.

Hockl P F, Wolosiuk A, Pérez-Sáez JM1, Bordoni AV2, Croci DO3, Toum-Terrones Y2, Soler-Illia GJ4, Rabinovich GA5. Glyco-nano-oncology: Novel therapeutic opportunities by combining small and sweet. Treatment of cancer Pharmacol Res. 2016 Feb. 4. pii: S1043-6618(16) 00042-6. doi: 10.1016/j.phrs.2016.02.005. [Epub ahead of print]

Ingrassia et al. (2006) A Lactosylated Steroid Contributes in Vivo Therapeutic Benefits in Experimental Models of Mouse Lymphoma and Human Glioblastoma. J. Med. CHem. 49: 1800-1807.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast Cancer. Clin. Cancer Res. 9: 2374-2383.

Kathiriya, J. J. et al. Galectin-1 inhibition attenuates profibrotic signaling in hypoxia-induced pulmonary fibrosis. Cell Death Discovery 3, 17010-13 (2017).

Kouo, T., Huang, L., Pucsek, A. B., Cao, M., Solt, S., Armstrong, T., Jaffee, E. (2015) Cancer Immonol. Res. 3: 412-23

Leffler, H. and Barondes, S. H. (1986) Specificity of binding of three soluble rat lung lectins to substituted and unsubstituted mammalian beta-galactosides. J. Biol. Chem. 261: 10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. Glycoconj. J. 19: 433-440.

Leffler, H., editor, (2004b) Special Issue on Galectins. Glycoconj. J. 19: 433-638.

Lepur A, Salomonsson E, Nilsson U J, Leffler H. (2012) Ligand induced galectin-3 protein self-association. J Biol Chem. 2012 Jun. 22; 287(26):21751-6.

Lin, C.-I., Whang, E. E., Donner, D. B., Jiang, X., Price, B. D., Carothers, A. M., Delaine, T., Leffler, H., Nilsson, U. J., Nose, V., et al. (2009). Galectin-3 Targeted Therapy with a Small Molecule Inhibitor Activates Apoptosis and Enhances Both Chemosensitivity and Radiosensitivity in Papillary Thyroid Cancer. Mol Cancer Res 7: 1655-1662.

MacKinnon, A. C., Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. J. Immun. 180; 2650-2658.

Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1 driven lung fibrosis by Galectin-3. Am. J. Resp. Crit. Care Med., in press.

Massa, S. M., Cooper, D. N. W., Leffler, H., Barondes, S. H. (1993) L-29, an endogenous lectin, binds to glycoconjugate ligands with positive cooperativity. *Biochemistry* 32: 260-267.

Melero, I., Berman, D. M., Aznar, M. A., Korman, A. J., Gracia, J. L. P., Haanen, J. (2015) *Nature Reviews Cancer,* 15: 457-472

Partridge, E. A., Le Roy, C., Di Guglielmo, G. M., Pawling, J., Cheung, P., Granovsky, M., Nabi, I. R., Wrana, J. L., and Dennis, J. W. (2004). Regulation of cytokine receptors by Golgi N-glycan processing and endocytosis. *Science* 306: 120-124.

Perillo, N. L.; Pace, K. E.; Seilhamer, J. J.; Baum, L. G. Nature 1995, 378, 736-739.

Pienta, K. J., Naik, H., Akhtar, A., Yamazaki, K., Replogle, T. S., Lehr, J., Donat, T. L., Tait, L., Hogan, V., and Raz, A. (1995). Inhibition of spontaneous metastasis in a rat prostate cancer model by oral administration of modified citrus pectin. *J Natl Cancer Inst* 87, 348-353.

Poirier, F. Roles of galectins in vivo. Biochem. Soc. Symp. 2002:95-103.

Ramos-Soriano, J.; Niss, U.; Angulo, J.; Angulo, M.; Moreno-Vargas, A. J.; Carmona, A. T.; Ohlson, S.; Robina, I. Chem. Eur. J. 2013, 19, 17989-18003.

Ruvolo, P. P. *Biochim. Biophys Acta.* Molecular cell research (2015) E-pub ahead of print, title: Galectin-3 as a guardian of the tumor microenvironment, published on-line 8 Apr. 2015: (http://www.sciencedirect.com/science/article/pii/S0167488915002700), Salameh, B. A., Leffler, H. and Nilsson, U. J. (2005) *Bioorg. Med. Chem. Lett.* 15: 3344-3346.

Salameh, B. A., Cumpstey, I., Sundin, A., Leffler, H., and Nilsson, U. J. (2010). 1H-1,2,3-Triazol-1-yl thiodigalactoside derivatives as high affinity galectin-3 inhibitors. *Bioorg Med Chem* 18: 5367-5378.

Salomonsson, E., Larumbe, A., Tejler, J., Tullberg, E., Rydberg, H., Sundin, A., Khabut, A., Frejd, T., Lobsanov, Y. D., Rini, J. M., Nilsson, U. J., and Leffler, H (2010). Monovalent interactions of galectin-1. *Biochemistry* 49: 9518-9532.

Sörme, P., Qian, Y., Nyholm, P.-G., Leffler, H., Nilsson, U. J. (2002) Low micromolar inhibitors of galectin-3 based on 3'-derivatization of N-acetyllactosamine *ChemBioChem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., Magnusson, B.-G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Tejler, J.; Tullberg, E.; Frejd, T.; Leffler, H.; Nilsson, U. J. Carbohydrate Research 2006, 341, 1353-1362.

Tejler, J.; Salameh, B.; Leffler, H.; Nilsson, U. J. Org. Biomol. Chem. 2009, 7, 3982. Thijssen, V. L., Poirer, F., Baum, L. G., and Griffioen, A. W. (2007). Galectins in the tumor endothelium: opportunities for combined cancer therapy. *Blood* 110: 2819-2827.

Toscano, M. A., Bianco, G. A., Ilarregui, J. M., Croci, D. O., Correale, J., Hernandez, J. D., Zwirner, N. W., Poirier, F., Riley, E. M., Baum, L. G., et al. (2007). Differential glycosylation of TH1, TH2 and TH-17 effector cells selectively regulates susceptibility to cell death. *Nat Immunol* 8: 825-834.

We claim:
1. A D-galactopyranose compound of formula (1)

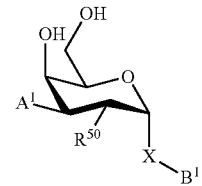

wherein
the pyranose ring is α-D-galactopyranose,
$A^1$ is $R^1$—Z,
wherein
Z is a five membered heterocycle having at least one heteroatom selected from O, S, and N, except 1,2,3-triazole and is attached to the α-D-galactopyranose;
$R^1$ is selected from a) an aryl, optionally substituted with a group selected from a halogen; CN; —COOH; —CONR$^{6a}$R$^{7a}$, wherein R$^{6a}$ and R$^{7a}$ are independently selected from H, $C_{1-3}$ alkyl, cyclopropyl, and isopropyl, or R$^{6a}$ and R$^{7a}$ together with the nitrogen may form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; NR$^{8a}$R$^{9a}$, wherein R$^{8a}$ and R$^{9a}$ are independently selected from H, $C_{1-3}$ alkyl and isopropyl; OH; and R$^{10a}$—CONH— wherein R$^{10a}$ is selected from $C_{1-3}$ alkyl and cyclopropyl; and b) a heterocycle, optionally substituted with a group selected from a halogen; a spiro heterocycle; CN; —COOH; —CONR$^{12a}$R$^{13a}$, wherein R$^{12a}$ and R$^{13a}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; NR$^{14a}$R$^{15a}$, wherein R$^{14a}$ and R$^{15a}$ are independently selected from H, $C_{1-3}$ alkyl, and cyclopropyl; C(=O)—R$^{21a}$, wherein R$^{21a}$ is selected from H and $C_{1-3}$ alkyl; OH; and R$^{16a}$—CONH— wherein R$^{16a}$ is selected from $C_{1-3}$ alkyl and cyclopropyl;
X is selected from S, SO, $SO_2$, O, C=O, and CR$^{2b}$R$^{3b}$ wherein R$^{2b}$ and R$^{3b}$ are independently selected from hydrogen, OH, or halogen;
$B^1$ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and R$^{4b}$—CONH— wherein R$^{4b}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and R$^{5b}$—CONH— wherein R$^{5b}$ is selected from $C_{1-3}$ alkyl and cyclopropyl; b) an aryl, optionally substituted with a group selected from a halogen; CN; a spiro heterocycle; $C_2$-alkynyl; —COOH; —CONR$^{6b}$R$^{7b}$, wherein R$^{6b}$ and R$^{7b}$ are independently selected from H, $C_{1-3}$ alkyl, cyclopropyl, and iso-propyl, or R$^{6b}$ and R$^{7b}$ together with the nitrogen may form a heterocycloalkyl; $C_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$^{8b}$R$^{9b}$, wherein R$^{8b}$ and R$^{9b}$ are independently selected from H, $C_{1-3}$ alkyl and isopropyl; OH; a heterocycle optionally substituted with a $C_{1-3}$ alkyl optionally substituted with a OH; and R$^{10b}$—CONH— wherein R$^{10b}$ is selected from $C_{1-3}$ alkyl and cyclopropyl; c) a $C_{5-7}$ cycloalkyl, optionally substituted with a substituent selected from a halogen, $C_2$-alkynyl, CN, methyl optionally substituted with a F, OCH$_3$ optionally substituted with a F, OCH$_2$CH$_3$ optionally substituted with a F, OH, and R$^{11b}$—CONH— wherein R$^{11b}$ is selected from $C_{1-3}$ alkyl and cyclopropyl; d) a heterocycle, optionally substituted with a group selected from a halogen; a spiro heterocycle; $C_2$-alkynyl; CN; —COOH; —CONR$^{12b}$R$^{13b}$, wherein R$^{12b}$ and R$^{13b}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$^{14b}$R$^{15b}$, wherein R$^{14b}$ and R$^{15b}$ are independently selected from H, $C_{1-3}$ alkyl and isopropyl; OH; a heterocycle optionally substituted with a $C_{1-3}$ alkyl optionally substituted with a OH; and R$^{16b}$—CONH— wherein R$^{16b}$ is selected from $C_{1-3}$ alkyl and cyclopropyl; e) a $C_{1-6}$ alkyl or branched $C_{3-6}$ alkyl; and f) $C_{2-6}$ alkynyl;

$R^{50}$ is selected from the group consisting of a) H, b) OH, c) OC$_{1-6}$ alkyl optionally substituted with one or more halogen, phenyl, phenyl substituted with one or more groups selected form OH and halogen, CN, OR$^{17b}$, NR$^{18b}$R$^{19b}$, and CONH$_2$, wherein R$^{17b}$ is selected from the group consisting of H, CN, a halogen, methyl optionally substituted with a F, OCH$_3$ optionally substituted with a F, OCH$_2$CH$_3$ optionally substituted with a F, OH, and R$^{20b}$—CONH— wherein R$^{20b}$ is selected from $C_{1-3}$ alkyl and cyclopropyl, R$^{18b}$ is selected from the group consisting of H, CN, a halogen, methyl optionally substituted with a F, OCH$_3$ optionally substituted with a F, OCH$_2$CH$_3$ optionally substituted with a F, OH, and R$^{21b}$—CONH— wherein R$^{21b}$ is selected from $C_{1-3}$ alkyl and cyclopropyl, and R$^{19b}$ is selected from the group consisting of H, CN, a halogen, methyl optionally substituted with a F, OCH$_3$ optionally substituted with a F, OCH$_2$CH$_3$ optionally substituted with a F, OH, and R$^{22b}$—CONH— wherein R$^{22b}$ is selected from $C_{1-3}$ alkyl and cyclopropyl, d) branched OC$_{3-6}$ alkyl optionally substituted with one or more halogen, CN, OR$^{23b}$, NR$^{24b}$R$^{25b}$, and CONH$_2$, wherein R$^{23b}$ is selected from the group consisting of H, CN, a halogen, methyl optionally substituted with a F, OCH$_3$ optionally substituted with a F, OCH$_2$CH$_3$ optionally substituted with a F, OH, and R$^{26b}$—CONH— wherein R$^{26b}$ is selected from $C_{1-3}$ alkyl and cyclopropyl, R$^{24b}$ is selected from the group consisting of H, CN, a halogen, methyl optionally substituted with a F, OCH$_3$ optionally substituted with a F, OCH$_2$CH$_3$ optionally substituted with a F, OH, and R$^{27b}$—CONH— wherein R$^{27b}$ is selected from $C_{1-3}$ alkyl and cyclopropyl, and R$^{25b}$ is selected from the group consisting of H, CN, a halogen, methyl optionally substituted with a F, OCH$_3$ optionally substituted with a F, OCH$_2$CH$_3$ optionally substituted with a F, OH, and R$^{28}$—CONH— wherein R$^{28}$ is selected from $C_{1-3}$ alkyl and cyclopropyl, and e) cyclic OC$_{3-6}$ alkyl optionally substituted with one or more halogen, CN, OR$^{29}$, NR$^{30}$R$^{31}$ or CONH$_2$, wherein R$^{29}$ is selected from the group consisting of H, CN, a halogen, methyl optionally substituted with a F, OCH$_3$ optionally substituted with a F, OCH$_2$CH$_3$ optionally substituted with a F, OH, and R$^{32}$—CONH— wherein R$^{32}$ is selected from $C_{1-3}$ alkyl and cyclopropyl, R$^{30}$ is selected from the group consisting of H, CN, a halogen, methyl optionally substituted with a F, OCH$_3$ optionally substituted with a F, OCH$_2$CH$_3$ optionally substituted with a F, OH, and R$^{33}$—CONH— wherein R$^{33}$ is selected from $C_{1-3}$ alkyl and cyclopropyl, and R$^{31}$ is selected from the group consisting of H, CN, a halogen, methyl optionally substituted with a F, OCH$_3$ optionally substituted with a F, OCH$_2$CH$_3$ optionally substituted with a F, OH, and R$^{34}$—CONH— wherein R$^{34}$ is selected from $C_{1-3}$ alkyl and cyclopropyl; or a pharmaceutically acceptable salt or solvate thereof.

2. The compound of claim 1 wherein Z is selected from 1,2,4-triazolyl, oxazolyl, isoxazolyl, oxadiazolyl, dioxolyl, dithiolyl, thiazolyl, isothiazolyl, furanyl, thiophen, pyrrolyl, imidazolyl, or pyrazolyl.

3. The compound of claim 1 wherein Z is

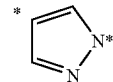

wherein the asterix on the carbon is linked to R$^1$ and the Asterix on the nitrogen is attached to the α-D-galactopyranose.

4. The compound of claim 1 wherein R$^1$ is phenyl optionally substituted with a group selected from CN, OH, NH$_2$, F, Br, Cl, I, methyl optionally substituted with a fluorine (F), OCH$_3$ optionally substituted with a F, and SCH$_3$ optionally substituted with a F.

5. The compound of claim 1 wherein R$^1$ is selected from a five or six membered heteroaromatic ring, optionally substituted with a group selected from Br; F; Cl; I; OH; CN; NR$^{14a}$R$^{15a}$, wherein R$^{14a}$ and R$^{15a}$ are independently selected from H, $C_{1-3}$ alkyl, and cyclopropyl; C(=O)—R$^{21a}$, wherein R$^{21a}$ is selected from H and $C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; OC$_{1-3}$ alkyl optionally substituted with a F; and SC$_{1-3}$ alkyl optionally substituted with a F.

6. The compound of claim 5 wherein R$^1$ is a pyridinyl, optionally substituted with a group selected from OH, NH$_2$, CN, Br, Cl, I, F, methyl optionally substituted with a F, OCH$_3$ optionally substituted with a F, and SCH$_3$ optionally substituted with a F; or a pyrimidyl, optionally substituted with a group selected from H, CN, Br, Cl, I, F, methyl optionally substituted with a F, OCH$_3$ optionally substituted with a F, and SCH$_3$ optionally substituted with a F.

7. The compound of claim 1 wherein $R^1$ is a five or six membered heteroaromatic ring selected from the group consisting of pyrazolyl, imidazolyl, oxazolyl, and formulas 2 to 9, wherein the asterix * indicates the carbon atom of the heteroaromatic ring that is covalently attached to the Z substituent:

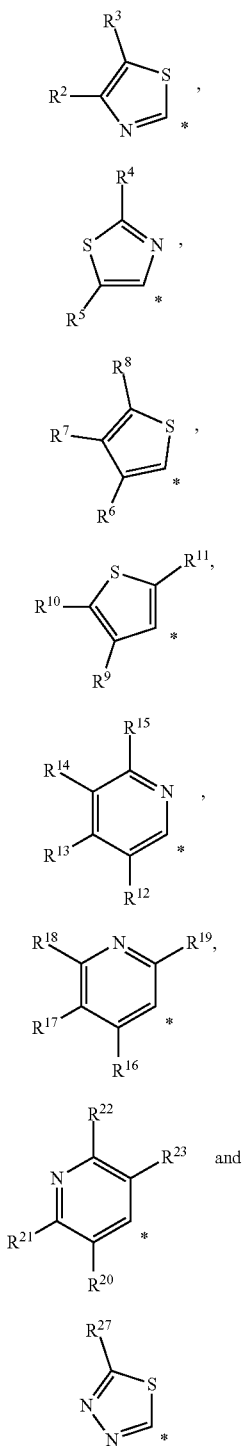

wherein $R^2$ to $R^{23}$ and $R^{27}$ are independently selected from H; halogen; OH; CN; SH; S—$C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; $OC_{1-3}$ alkyl optionally substituted with a F; $NR^{24}R^{25}$, wherein $R^{24}$ is selected from H, and $C_{1-3}$ alkyl, and $R^{25}$ is selected from H, $C_{1-3}$ alkyl, and $COR^{26}$, wherein $R^{26}$ is selected from H, and $C_{1-3}$ alkyl.

8. The compound of claim 7 wherein $R^1$ is selected from the group consisting of

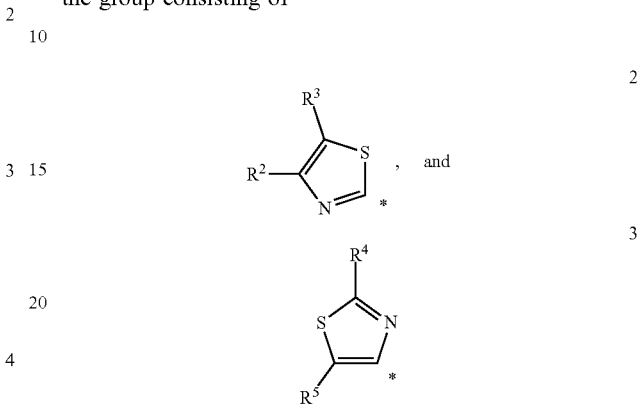

wherein $R^2$ is selected from the group consisting of OH, methyl and halogen;
$R^3$ is selected from the group consisting of hydrogen, $C_{1-6}$ alkyl and halogen;
$R^4$ is selected from the group consisting of OH, $NH_2$ and halogen;
$R^5$ is selected from the group consisting of hydrogen, $C_{1-6}$ alkyl and halogen.

9. The compound of claim 1 wherein X is selected from S, SO, $SO_2$, and O.

10. The compound of claim 1 wherein B1 is selected from a heteroaryl, optionally substituted with a group selected from a halogen; CN; ethynyl; methyl optionally substituted with a F; and a heterocycle optionally substituted with a $C_{1-3}$ alkyl optionally substituted with a OH.

11. The compound of claim 10 wherein B1 is selected from a pyridinyl, optionally substituted with a group selected from a Cl, Br, CN, methyl, $CF_3$, azetidinyl; azetidinyl substituted with a $CH_2OH$, pyridinyl, pyrimidinyl, oxazolyl, and thiazolyl.

12. The compound of claim 1 wherein B1 is selected from a phenyl, optionally substituted with a group selected from a halogen, CN, $C_{1-3}$ alkyl, optionally substituted with a F, and $CONR^{6b}R^{7b}$, wherein $R^{6b}$ and $R^{7b}$ are independently selected from H, $C_{1-3}$ alkyl, cyclopropyl, and iso-propyl, or $R^{6b}$ and $R^{7b}$ together with the nitrogen may form a heterocycloalkyl.

13. The compound of claim 1 wherein $R^{50}$ is selected from H, OH, $OC_{1-6}$ alkyl, $C_{1-4}$ alkyl, and $C_{1-4}$ alkyl substituted with at least one from the group consisting of phenyl and phenyl substituted with one or more groups selected from OH and halogen.

14. The compound of claim 1 selected from the group consisting of:
3-Chlorophenyl 3-deoxy-3-[4-(3-fluorophenyl)-1H-1,2-pyrazol-1-yl]-1-thio-α-D-galactopyranoside,
5-Chloropyridin-3-yl 3-[4-(4-chloro-3,5-difluorophenyl)-1H-1,2-pyrazol-1-yl]-3-deoxy-1-thio-α-D-galactopyranoside,
5-Chloropyridin-3-yl 3-deoxy-3-[4-(3,4,5-trifluorophenyl)-1H-1,2-pyrazol-1-yl]-1-thio-α-D-galactopyranoside, 5-Chloropyridin-3-yl 3-deoxy-3-[4-(3,5-difluoro-4-methylphenyl)-1H-1,2-pyrazol-1-yl]-1-thio-α-D-galactopyranoside, 5-Bromopyridin-3-yl 3-deoxy-3-[4-(3,4,5-trifluorophenyl)-1H-1,2-pyrazol-1-yl]-1-thio-α-D-galactopyranoside, 5-Bromopyridin-3-yl 3-[4-(4-chloro-3,5-difluorophenyl)-1H-1,2-pyrazol-1-yl]-3-deoxy-1-thio-α-D-galactopyranoside, 5-Ethynylpyridin-3-yl 3-[4-(4-chloro-3,5-difluorophenyl)-1H-1,2-pyrazol-1-yl]-3-deoxy-1-thio-α-D-galactopyranoside, 5-Chloro-2-cyanophenyl 3-[4-(4-chloro-3,5-difluorophenyl)-1H-1,2-pyrazol-1-yl]-3-deoxy-1-thio-α-D-galactopyranoside, 2-(N-Azetidinyl-carbonyl)-5-chlorophenyl 3-[4-(4-chloro-3,5-difluorophenyl)-1H-1,2-pyrazol-1-yl]-3-deoxy-1-thio-α-D-galactopyranoside, 2-(N-Azetidinyl-carbonyl)-5-chlorophenyl 3-deoxy-3-[4-(3,4,5-trifluorophenyl)-1H-1,2-pyrazol-1-yl]-1-thio-α-D-galactopyranoside, 5-Chloro-2-cyanophenyl 3-deoxy-3-[4-(3,4,5-trifluorophenyl)-1H-1,2-pyrazol-1-yl]-1-thio-α-D-galactopyranoside, 5-Chloro-2-cyanopyridin-3-yl 3-deoxy-3-[4-(3,4,5-trifluorophenyl)-1H-1,2-pyrazol-1-yl]-1-thio-α-D-galactopyranoside, 5-Chloro-2-cyanopyridin-3-yl 3-[4-(4-chloro-3,5-difluorophenyl)-1H-1,2-pyrazol-1-yl]-3-deoxy-1-thio-α-D-galactopyranoside, 5-Chloro-2-methylpyridin-3-yl 3-deoxy-3-[4-(3,4,5-trifluorophenyl)-1H-1,2-pyrazol-1-yl]-1-thio-α-D-galactopyranoside, 5-Bromo-2-cyanopyridin-3-yl 3-deoxy-3-[4-(3,4,5-trifluorophenyl)-1H-1,2-pyrazol-1-yl]-1-thio-α-D-galactopyranoside, 2-Cyano-5-ethynylpyridin-3-yl 3-deoxy-3-[4-(3,4,5-trifluorophenyl)-1H-1,2-pyrazol-1-yl]-1-thio-α-D-galactopyranoside, 5-Chloropyridin-3-yl 3-[4-(4-chloro-3-fluorophenyl)-1H-1,2-pyrazol-1-yl]-3-deoxy-1-thio-α-D-galactopyranoside, 5-Chloropyridin-3-yl 3-deoxy-3-[4-(6-fluoropyridin-2-yl)-1H-1,2-pyrazol-1-yl]-1-thio-α-D-galactopyranoside, 5-Chloropyridin-3-yl 3-deoxy-3-[4-(5-fluoropyridin-2-yl)-1H-1,2-pyrazol-1-yl]-1-thio-α-D-galactopyranoside, 5-Chloropyridin-3-yl 3-deoxy-3-[4-(4-fluoropyridin-2-yl)-1H-1,2-pyrazol-1-yl]-1-thio-α-D-galactopyranoside, 5-Chloropyridin-3-yl 3-deoxy-3-[4-(1H-1,2-pyrazol-3-yl)-1H-1,2-pyrazol-1-yl]-1-thio-α-D-galactopyranoside, 5-Chloropyridin-3-yl 3-deoxy-3-[4-(1-methyl-1,2-pyrazol-3-yl)-1H-1,2-pyrazol-1-yl]-1-thio-α-D-galactopyranoside, 5-Chloropyridin-3-yl 3-deoxy-3-[4-(1H-imidazol-2-yl)-1H-1,2-pyrazol-1-yl]-1-thio-α-D-galactopyranoside, 5-Chloropyridin-3-yl 3-deoxy-3-[4-(oxazol-2-yl)-1H-1,2-pyrazol-1-yl]-1-thio-α-D-galactopyranoside, 5-Chloropyridin-3-yl 3-deoxy-3-[4-(thiazol-4-yl)-1H-1,2-pyrazol-1-yl]-1-thio-α-D-galactopyranoside, 5-Chloropyridin-3-yl 3-deoxy-3-[4-(thiazol-2-yl)-1H-1,2-pyrazol-1-yl]-1-thio-α-D-galactopyranoside, 5-Chloropyridin-3-yl 3-[4-(4-chlorothiazol-2-yl)-1H-1,2-pyrazol-1-yl]-3-deoxy-1-thio-α-D-galactopyranoside, 5-Bromopyridin-3-yl 3-[4-(4-chlorothiazol-2-yl)-1H-1,2-pyrazol-1-yl]-3-deoxy-1-thio-α-D-galactopyranoside, 5-Chloro-2-cyanophenyl 3-[4-(4-chlorothiazol-2-yl)-1H-1,2-pyrazol-1-yl]-3-deoxy-1-thio-α-D-galactopyranoside, 5-Chloro-2-cyanopyridin-3-yl 3-[4-(4-chlorothiazol-2-yl)-1H-1,2-pyrazol-1-yl]-3-deoxy-1-thio-α-D-galactopyranoside, 5-Chloropyridin-3-yl 3-deoxy-3-[4-(2-hydroxythiazol-4-yl)-1H-1,2-pyrazol-1-yl]-1-thio-α-D-galactopyranoside, 5-Chloropyridin-3-yl 3-deoxy-3-[4-(3,4,5-trifluorophenyl)-1H-1,2-pyrazol-1-yl]-2-O-methyl-1-thio-α-D-galactopyranoside, 5-Bromopyridin-3-yl 3-deoxy-3-[4-(3,4,5-trifluorophenyl)-1H-1,2-pyrazol-1-yl]-2-O-methyl-1-thio-α-D-galactopyranoside, 5-Ethynylpyridin-3-yl 3-deoxy-3-[4-(3,4,5-trifluorophenyl)-1H-1,2-pyrazol-1-yl]-2-O-methyl-1-thio-α-D-galactopyranoside, 5-Chloro-2-cyanopyridin-3-yl 3-deoxy-3-[4-(3,4,5-trifluorophenyl)-1H-1,2-pyrazol-1-yl]-2-O-methyl-1-thio-α-D-galactopyranoside, 5-Chloropyridin-3-yl 3-deoxy-3-[4-(3,4,5-trifluorophenyl)-1H-1,3-imidazol-1-yl]-1-thio-α-D-galactopyranoside, 5-Chloro-[3,3-bis(hydroxymethyl) azetidin-1-yl]pyridin-3-yl 3-deoxy-3-[4-(3,4,5-trifluorophenyl)-1H-1,2-pyrazol-1-yl]-1-thio-α-D-galactopyranoside, 5-Chloropyridin-3-yl 3-deoxy-3-[3-(3,4,5-trifluorophenyl)-1H-1,2-pyrazol-1-yl]-1-thio-α-D-galactopyranoside, 3,4-Dichlorophenyl 3-deoxy-3-[4-(3,4,5-trifluorophenyl)-oxazol-2-yl]-1-thio-α-D-galactopyranoside, 3,4-Dichlorophenyl 3-deoxy-3-[4-(3,4,5-trifluorophenyl)-thiazol-2-yl]-1-thio-α-D-galactopyranoside, 3,4-Dichlorophenyl 3-deoxy-3-[5-(3,4,5-trifluorophenyl)-1,3,4-oxadiazol-2-yl]-1-thio-α-D-galactopyranoside, 3,4-Dichlorophenyl 3-deoxy-3-[4-(2-hydroxythiazol-4-yl)-1H-1,2-pyrazol-1-yl]-2-O-methyl-1-thio-α-D-galactopyranoside, 5-Chloro-2-cyanophenyl 3-[4-(4-chloro-3,5-difluorophenyl)-1H-1,2-pyrazol-1-yl]-3-deoxy-2-O-methyl-1-thio-α-D-galactopyranoside, 5-Chloro-2-cyanophenyl 3-deoxy-3-[4-(3,4,5-trifluorophenyl)-1H-1,2-pyrazol-1-yl]-2-O-methyl-1-thio-α-D-galactopyranoside, and 5-Chloro-2-cyanophenyl 3-deoxy-3-[4-(2-hydroxythiazol-4-yl)-1H-1,2-pyrazol-1-yl]-2-O-methyl-1-thio-α-D-galactopyranoside; or a pharmaceutically salt or solvate thereof.

15. A pharmaceutical composition comprising the compound of claim 1 and optionally a pharmaceutically acceptable additive.

16. A method for treatment of a disorder relating to the binding of a galectin-3 to a ligand in a mammal, wherein a therapeutically effective amount of at least one compound according to claim 1 is administered to a mammal in need of said treatment, wherein said disorder is selected from the group consisting of inflammation; Inflammation induced thrombosis; Atopic dermatitis; Acute coronary syndrome; fibrosis selected from the group consisting of pulmonary fibrosis, liver fibrosis, kidney fibrosis, ophthalmological fibrosis and fibrosis of the skin and heart; local fibrosis; fibrotic complications of therapies selected from the group consisting of coronary stents, bile duct stents, cerebral artery stents, and ureter stents; scleroderma; scarring; keloid formation; covid-19; acute lung injury; ARDS; viral pneumonitis, aberrant scar formation; surgical adhesions; septic shock; cancer selected from the group consisting of colorectal cancer, pancreatic cancer, gastric cancer, biliary tract cancer, lung cancers, mesothelioma, breast cancer, ovarian cancer, uterine cancer, cancer of the cervix uteri, cancer of the salpingx, medulloblastomao, glioma, meningioma, sarcomas of the bones and muscles, leukemias and lymphomas; transplant rejection; metastasising cancers; ageing; Dementia; Alzheimers; TGFbeta driven bone disease; Pulmonary hypertension; autoimmune diseases selected from the group consisting of psoriasis, rheumatoid arthritis, Rheumatoid lung, Crohn's disease, ulcerative colitis, ankylosing spondylitis, and systemic lupus erythematosus; viral infections selected from the group consisting of influenza virus, HIV, Herpes virus, Coronaviruses, and Hepatitis C; metabolic disorders; heart disease; heart failure; pathological angiogenesis; and eye diseases selected from age-related macular degeneration and corneal neovascularization; atherosclerosis; metabolic diseases; diabetes; type I diabetes; type 2 diabetes; insulin resistens; obesity; Marfans syndrome; Loeys-Dietz syndrome; nephropathy; Diastolic HF; fibrotic lung complications of aPD1 and other CPI therapies; asthma and other interstitial lung diseases; liver disorders selected from non-alcoholic steatohepatitis and non-alcoholic fatty liver disease; and uterine disease selected from uterine fibroids and uterine or cervical fibrosis.

\* \* \* \* \*